(12) United States Patent
Schann et al.

US008962627B2

(10) Patent No.: US 8,962,627 B2
(45) Date of Patent: Feb. 24, 2015

(54) OXIME DERIVATIVES AND THEIR USE AS ALLOSTERIC MODULATORS OF METABOTROPIC GLUTAMATE RECEPTORS

(75) Inventors: Stephan Schann, Illkirch (FR);
Stanislas Mayer, Eschau (FR);
Christophe Morice, Widensolen (FR);
Bruno Giethlen, Altorf (FR)

(73) Assignee: Prestwick Chemical, Inc., Illkirch Graffenstaden (FR)

( * ) Notice: Subject to any disclaimer, the term of this patent is extended or adjusted under 35 U.S.C. 154(b) by 166 days.

(21) Appl. No.: 13/505,235

(22) PCT Filed: Oct. 29, 2010

(86) PCT No.: PCT/EP2010/066537
§ 371 (c)(1),
(2), (4) Date: Jul. 17, 2012

(87) PCT Pub. No.: WO2011/051478
PCT Pub. Date: May 5, 2011

(65) Prior Publication Data
US 2012/0277212 A1    Nov. 1, 2012

(30) Foreign Application Priority Data
Oct. 30, 2009  (EP) .................................. 09360049

(51) Int. Cl.
| | | |
|---|---|---|
| A01N 43/58 | (2006.01) | |
| A01N 43/60 | (2006.01) | |
| A61K 31/50 | (2006.01) | |
| A61K 31/495 | (2006.01) | |
| A01N 43/90 | (2006.01) | |
| A61K 31/519 | (2006.01) | |
| A01N 43/42 | (2006.01) | |
| A61K 31/44 | (2006.01) | |
| C07D 487/00 | (2006.01) | |
| C07D 231/46 | (2006.01) | |
| C07D 471/00 | (2006.01) | |
| C07D 513/02 | (2006.01) | |
| C07D 515/02 | (2006.01) | |
| C07D 311/68 | (2006.01) | |
| C07D 405/04 | (2006.01) | |
| C07D 405/14 | (2006.01) | |
| C07D 471/04 | (2006.01) | |
| C07D 487/04 | (2006.01) | |
| C07D 495/04 | (2006.01) | |
| C07D 513/04 | (2006.01) | |
| C07D 519/00 | (2006.01) | |

(52) U.S. Cl.
CPC ............ *C07D 311/68* (2013.01); *C07D 405/04* (2013.01); *C07D 405/14* (2013.01); *C07D 471/04* (2013.01); *C07D 487/04* (2013.01); *C07D 495/04* (2013.01); *C07D 513/04* (2013.01); *C07D 519/00* (2013.01)

USPC ........ 514/249; 514/259.1; 514/301; 544/281; 544/349; 546/114

(58) Field of Classification Search
None
See application file for complete search history.

(56) References Cited

U.S. PATENT DOCUMENTS

| 4,065,467 A | 12/1977 | Doria et al. .................... 549/403 |
| 4,777,252 A | 10/1988 | Slusarchyk et al. .......... 540/363 |
| 2003/0109574 A1 | 6/2003 | Komata et al. ................ 514/456 |
| 2004/0198750 A1 | 10/2004 | Green et al. ............... 514/260.1 |

FOREIGN PATENT DOCUMENTS

| EP | 0 787 723 | 8/1997 |
| WO | WO 2004/052869 | 6/2004 |
| WO | WO 2004/092154 | 10/2004 |
| WO | WO 2009/010454 | 1/2009 |
| WO | WO 2009/010455 | 1/2009 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Battaglia et al., "Pharmacological Activation of mGlu4 Metabotripic Glutamate Receptors Reduces Nigrostriatal Degeneration in Mice Treated with 1-Methyl-4-Phenyl-1,2,3,6-Tetrahydropyridine", *J. Neurosci*, 26(27):7222-7229, 2006.
Boldyrev and Johnson, "Homocysteine and its Derivatives as Possible Modulators of Neuronal and Non-Neuronal Cell Glutamate Receptors in Alzheimer's Disease", *J. Alzheimers Dis.*, 11(2):219-228, 2007.
Brauner-Osborne et al., "Ligands for Glutamate Receptors: Design and Therapeutic Prospects", *J. Med. Chem.*, 43(14):2609-2645, 2000.
Bridges and Lindsley, "G-Protein-Coupled Receptors: From Classical Modes of Modulation to Allosteric Mechanisms", *ACS Chem Biol*, 3(9):530-541, 2008.
Bruno et al., "Metabotopic Glutamate Receptor Subtypes as Targets for Neuroprotective Drugs", *J. Cereb. Blood Flow Metab.*, 21(9):1013-1033, 2001.

(Continued)

*Primary Examiner* — Jeffrey H Murray
(74) *Attorney, Agent, or Firm* — Fulbright & Jaworski LLP

(57) ABSTRACT

The present invention provides new oxime derivatives of the general formula (I), pharmaceutical compositions containing them and their use for the treatment and/or prophylaxis of conditions associated with altered glutamatergic signalling and/or functions, and/or conditions which can be affected by alteration of glutamate level or signalling in mammals. This invention further provides new oxime derivatives of the general formula (I) consisting of modulators of nervous system receptors sensitive to glutamate, which makes them particularly suitable for the treatment and/or prophylaxis of acute and chronic neurological and/or psychiatric disorders. In particular embodiments, the new oxime derivatives of the invention are modulators of metabotropic glutamate receptors (mGluRs). The invention further provides positive allosteric modulators of mGluRs and more specifically positive alSosteric modulators of mGluR4.

17 Claims, 2 Drawing Sheets

(56) References Cited

OTHER PUBLICATIONS

Chang et al., "Metabotropic Glutamate Receptor 4 Expression in colorectal Carcinoma and Its Prognostic Significance", *Cli. Cancer Res.*, 11(9) :3288-3295, 2005.
Conn and Pin, "Pharmacology and Functions of Metabotropic Glutamate Receptors", *Annu. Rev. Pharmacol. Toxicol.*, 37:205-237, 1997.
Conn et al., "Metabotropic Glutamate Receptors in the Basal Ganglia Motor Circuit", *Nat. Rev. Neuroscience*, 6(10) :787-798, 2005.
Conn et al., "Activation of metabotropic glutamate receptors as a novel approach for treatment of schizophrenia", *Trends Pharmacol. Sci.*, 30(1) :25-31, 2009.
Cryan et al., "Antidepressant and anziolytic-like effects in mice lacking the group III metabotropic glutamate receptor mGluR7", *Eur. J. Neurosc.*, 17(11) :2409-2417, 2003.
Engers et al., "Synthesis and Evaluation of a Series of Heterobiarylamides That Are Centrally Penetrant Metabotropic Glutamate Receptor 4 (mGluR4) Positive Allosteric Modulators (PAMs)", *J. Med Chem.*, 52:4115-4118, 2009.
Eschle et al., "Behavioral Comparison of Sucrose and L-2-Amino-4-Phosphonobutyrate (L-AP4) Tastes in Rats: Does L-AP4 Have a Sweet Taste?", *Neuroscience*, 155(2) :522-529, 2008.
Broekkamp et al., "Major Tranquillizers Can Be Distinguished From Minor Tranquilizers on the Basis of Effects on Marble Burying and Swim-Induced Grooming in Mice", *Eur. J. Pharmacol.*, 126:223-229, 1986.
Flor et al., "Molecular Cloning, Functional Expression and Pharmacological Characterization of the Human Metabotropic Glutamate Receptor Type 4", *Neuropharmacology*, 34 :149-155, 1995.
Goudet et al., "Group III metabotropic glutamate receptors inhibit hyperalgesia in animal models of inflammation and neuropathic pain", *Pain*, 137(1) :112-124, 2008.
Iacovelli et al., "Pharmacological Activation of mGlu4 Metabotropic Glutamate Receptors Inhibits the Growth of Medulloblastomas", *J. Neurosci.*, 26(32) :8388-8397, 2006.
Ferreira et al., "Sythesis of Beta-Substituted Alanines via Michael addition of nucleophiles to dehydroalanine derivatives", *J. Chem. Soc.*, Perkin trans 1, pp. 3317-3324, 2000.
Pires et al., "Acute effects of selective serotonin reuptake inhibitors on neuroleptic-induced catalepsy in mice", *J. Med. And Biol. Res.*, 38:1867-1872, 2005.
Costantino et al., "1-Benzopyran-4-one Antioxidants as Aldose Reductase Inhibitors", *J. Med. Chem.*, 42(11) :1881-1893, 1999.
Menichincheri et al., "Catecholic Flavonoids Acting as Telomerase Inhibitors", *J. Med. Chem.*, 47 :6466-6475, 2004.
Ares et al., "A Convenient Large-Scale Synthesis of 5-Methoxyflavone and Its Application to Analog Preparation", *J. Org. Chem.*, 68 :7903-7905, 1993.
Taki et al., "Emission Ratiometric Imaging of Intracellular Zing: Design of a Benzoxazole Fluorescent Sensor and Its Application in Two-Photon Microscopy", *JACS*, 126 (3) :712-713, 2004.
Klak et al., "Combined administration of PHCCC, a positive allosteric modulator of mGlu4 receptors and ACPT-1, mGlu III receptor agonist evokes antidepresant-like effects in rats", *Amino Acids*, 32(2) :169-172, 2006.
Konieczny et al., "LY354740, a group II metabotropic glutamate receptor agonist with potential antiparkinsonian properties in rats", *Naunyn-Schmiederbergs Arch. Pharmacol.*, 358(4):500-502, 1998.
Lopez et al., "Functional interaction between adenosine A2A and group III metabotropic glutamate receptors to reduce parkinsonian symptoms in rats", *Neuropharmacology*, 55(4) :483-490, 2008.
Maj et al., "(-)-PHCCC, a positive allosteric modulator of mGluR4: characterization , mechanism of action, and neuroprotection", *Neuropharmacology*, 45(7):895-903, 2003.
Makoff et al., "Molecular characterization and localization of human metabotropic glutamate receptor type 4", *Brain Res. Mol. Brain Res.*, 37 :239-248, 1996.
Marino et al., "Allosteric modulation of group III metabotropic glutamate receptor 4: A potential approach to Parkinson's disease treatment", *Proc. Natl. Acad. Sci. USA*, 100(23) :13668-13673, 2003.
Mathiesen et al., "Positive allosteric modulation of the human metabotropic glutamate receptor 4 (hmGluR4) by SIB-1893 and MPEP", *Br. J. Pharmacol.*, 138(6) :1026-1030, 2003.
Mattson, "Exciotoxic and Excitoprotective mechanisms: Abundant Targest for Prevention and Treatment of Neurodegenerative Disorders", *Neuromolecular Med.*, 3(2):65-94, 2003.
Meli et al., "Acitvation of mGluI but not mGlu5 metabotropic glutamate receptors contributes to postischemic neuronal injury in vitro and in vivo", *Pharmacol. Biochem. Behav.*, 73(2) :439-446, 2002.
Niswender et al., "Positive allosteric modulators of the metabotropic glutamate receptor subtype 4 (mGluR4): Part I. Discovery of pyrazolo[3,4-d]pyrimidines as novel mGluR4 positive allosteric modulators", *Bioorg. Med. Chem. Lett.*, 18(2):5626-5630, 2008.
Niswender et al., "Discovery, characterization, and antiparkinsonian effect of novel positive allosteric modulators of metabotropic glutamate receptor 4", *Mol. Pharmacol.*, 74(5) :1345-1358, 2008.
Palucha et al., "Group III mGlu receptor agonists produce anxiolytic- and antidepressant-like effects after central administration in rats", *Neuropharmacology*, 46(2) :151-159, 2004.
Palucha et al., "Metabotropic glutamate receptor ligands as possible anxiolytic and antidepressant drugs", *Pharmacol. Ther.*, 115(1) :116-147, 2007.
Palucha-Poniewiera et al., "Peripheral administration of groiup III mGlu Receptor agonist ACPT-I exerts potential antipsychotic effects in rodents", *Neuropharmacology*, 55(4):517-524, 2008.
Pessimissis et al., "The Glutamatergic system Expression in Human PC-3 and LNCaP Prostate Cancer Cells", *Anitcancer Res.*, 29(1) :371-377, 2009.
Pilc et al., "Multiple MPEP administration evoke anxiolytic- and antidepressant-like effects in rats", *Neuropharmacology*, 43(2) :181-187, 2002.
Pin and Acher, "The Metabotropic Glutamate Receptors: Structure, Activation Mechanism and Pharmacology", *Curr. Drug Targets CNS Neurol. Disord.*, 1(3):297-317, 2002.
Schoepp et al., "Pharmacological agents acting at subtypes of metabotropic glutamate receptors", *Neuropharmacology*, 38(10):1431-1476, 1999.
Shiozaki et al., "Actions of adenosine A2A receptor antagonist KW-6002 on drug-induced catalepsy and hypokinesia caused by reserpine or MPTP", *Psychopharmacology*, 147:90-95, 1999.
Stachowicz et al., "Anxiolytic-like effects of PHCCC, an allosteric modulator of mGlu4 receptors, in rats", *Eur. J. Pharmacol.*, 498(1-3) :153-156, 2004.
Stephans and Yamamoto, "Methamphetamine-Induced Neurotoxicity: roles for Glutamate and Dopamine Efflux", *Synapse*, 17(3):203-209, 1994.
Tanabe et al., "A Family Metabotropic Glutamate Receptors", *Neuron.*, 8 :169-179, 1992.
Uehara et al., "Metabotropic Glutamate Receptor Type 4 Is Involved in Autoinhibitory Cascade for Glucagon Secretion by alpha-Cells of Islet of Langerhans", *Diabetes*, 53(4) :998-1006, 2004.
Vernon et al., "Selective Activation of Group III Metabotropic Glutamate Receptors by L-(+)-2-Amino-4-phosphonobutryic Acid Protects the Nigrostriatal System against 6-Hydroxydopamine Toxicity in Vivo", *J. Pharmacol. Exp. Ther.*, 320(1) :397-409, 2007.
Vernon et al., "Additive neuroprotection by metabotropic glutamate receptor subtype-selective ligands in a rat Parkinson's model", *Neuroreport*, 19(4) :475-478, 2008.
Williams et al, "Positive allosteric modulators of the metabotropic glutamate receptor subtype 4 (mGluR4). Part II: Challenges in hit-to-lead", *Bioorg. Med. Chem. Lett.*, 19(3):962-966, 2009.
Wu et al., "Group III human metabotropic glutamate receptors 4, 7 and 8: Molecular cloning, functional expression, and comparison of pharmacological properties in RGT cells", *Brain Res. Mol. Brain Res.*, 53 :88-97, 1998.
Zhang et al., "Effects of Activation of Group III Metabotropic glutamate Receptors on Spinal Synaptic Transmission in a Rat Model of Neuropathic Pain", *Neuroscience*, 158(2) :875-874, 2009.
International Search Report issued in PCT Application No. PCT/EP2010/066537, mailed Feb. 11, 2011.

* cited by examiner

OXIME DERIVATIVES AND THEIR USE AS ALLOSTERIC MODULATORS OF METABOTROPIC GLUTAMATE RECEPTORS

This application is a national phase application under 35 U.S.C. §371 of International Application No. PCT/EP2010/066537 filed 29 Oct. 2010, which claims priority to European Application No. 09360049.2 filed 30 Oct. 2009. The entire contents of each of the above-referenced applications is specifically incorporated herein by reference without disclaimer.

The present invention provides new oxime derivatives of the general formula (I), pharmaceutical compositions containing them and their use for the treatment and/or prophylaxis of conditions associated with altered glutamatergic signalling and/or functions, and/or conditions which can be affected by alteration of glutamate level or signalling in mammals. This invention further provides new oxime derivatives of the general formula (I) consisting of modulators of nervous system receptors sensitive to glutamate, which makes them particularly suitable for the treatment and/or prophylaxis of acute and chronic neurological and/or psychiatric disorders. In particular embodiments, the new oxime derivatives of the invention are modulators of metabotropic glutamate receptors (mGluRs). The invention further provides positive allosteric modulators of mGluRs and more specifically positive allosteric modulators of mGluR4.

Glutamatergic pathways have been shown to be clearly involved in the physiopathology of a number of neuronal damages and injuries. Many nervous system disorders including epilepsy and chronic or acute degenerative processes such as for example Alzheimer's disease, Huntington's disease, Parkinson's disease and amyotrophic lateral sclerosis (Mattson M P., *Neuromolecular Med.*, 3(2), 65-94, 2003), but also AIDS-induced dementia, multiple sclerosis, spinal muscular atrophy, retinopathy, stroke, ischemic, hypoxia, hypoglycaemia and various traumatic brain injuries, involve neuronal cell death caused by imbalanced levels of glutamate. It has also been shown that drug-induced neurotoxicity, for example neurotoxic effects of methamphetamine (METH) on striatal dopaminergic neurons, could actually be mediated by over-stimulation of the glutamate receptors (Stephans S E and Yamamoto B K, *Synapse* 17(3), 203-9, 1994). Antidepressant and anxiolytic-like effects of compounds acting on glutamate have also been observed on mice, suggesting that glutamatergic transmission is implicated in the pathophysiology of affective disorders such as major depression, schizophrenia and anxiety (Palucha A et al., *Pharmacol. Ther.* 115(1), 116-47, 2007; Cryan J F at al., *Eur. J. Neurosc.* 17(11), 2409-17, 2003; Conn P J at al., *Trends Pharmacol. Sci.* 30(1), 25-31, 2009). Consequently, any compound able to modulate glutamatergic signalling or function would constitute a promising therapeutic compound for many disorders of the nervous system.

Moreover, compounds modulating glutamate level or signalling may be of great therapeutic value for diseases and/or disorders not directly mediated by glutamate levels and/or glutamate receptors malfunctioning, but which could be affected by alteration of glutamate levels or signaling.

In the central nervous system (CNS), L-glutamate (Glu) is the main excitatory neurotransmitter and is referred to as an excitatory amino-acid (EAA), and gamma-aminobutyric acid (GABA) is the main inhibitory neurotransmitter. The balance between excitation and inhibition is of utmost importance to CNS functions, and dysfunctions of either of the two can be related to various neurological disorders.

Glutamate is ubiquitously distributed in the nervous system in high concentrations, especially in the brain and spinal cord of mammals, where it is working at a variety of excitatory synapses being thereby involved in virtually all physiological functions such as motor control, vision, central control of heart, processes of learning and memory. However, a large number of studies have established that cellular communication involving glutamate can also lead to a mechanism of cell destruction. This combination of neuroexcitatory activities and neurotoxic properties is called excitotoxicity.

Glutamate operates through two classes of receptors (Bräuner-Osborne H at al., *J. Med. Chem.* 43(14), 2609-45, 2000). The first class of glutamate receptors is directly coupled to the opening of cation channels in the cellular membrane of the neurons. Therefore they are called ionotropic glutamate receptors (IGluRs). The IGluRs are divided in three subtypes, which are named according to the depolarizing action of their selective agonists: N-methyl-D-aspartate (NMDA), α-amino-3-hydroxy-5-methylisoxazole-4-propionic acid (AMPA), and kainic acid (KA). The second class of glutamate receptor consists of G-protein coupled receptors (GPCRs) called metabotropic glutamate receptors (mGluRs). These mGluRs are localized both pre- and post-synaptically. They are coupled to multiple second messenger systems and their role is to regulate the activity of the ionic channels or enzymes producing second messengers via G-proteins binding the GTP (Conn P J and Pin J P., *Annu. Rev. Pharmacol. Toxicol.*, 37, 205-37, 1997). Although they are generally not directly involved in rapid synaptic transmission, the mGluRs modulate the efficacy of the synapses by regulating either the post-synaptic channels and their receptors, or the pre-synaptic release or recapture of glutamate. Therefore, mGluRs play an important role in a variety of physiological processes such as long-term potentiation and long-term depression of synaptic transmission, regulation of baroreceptive reflexes, spatial learning, motor learning, and postural and kinetic integration.

To date, eight mGluRs have been cloned and classified in three groups according to their sequence homologies, pharmacological properties and signal transduction mechanisms. Group I is constituted of mGluR1 and mGluR5, group II of mGluR2 and mGluR3 and group III of mGluR4, mGluR6, mGluR7 and mGluR8 (Pin J P and Acher F., *Curr. Drug Targets CNS Neurol. Disord.*, 1(3), 297-317, 2002; Schoepp D D at al., *Neuropharmacology*, 38(10), 1431-76, 1999).

mGluRs modulators can be classified in two families depending on their site of interaction with the receptor (see Bräuner-Osborne H et al., *J. Med. Chem.* 43(14), 2609-45, 2000 for review). The first family consists in orthosteric modulators (or competitive modulators) able to interact with the glutamate binding-site of the mGluRs, which is localized in the large extra-cellular N-terminal part of the receptor (about 560 amino acids). Therefore, they are glutamate analogs and constitute a highly polar family of ligand. Examples of orthosteric modulators are S-DHPG or LY-367385 for group I mGluRs, LY-354740 or (2R-4R)-APDC for group II mGluRs and ACPT-I or L-AP4 for group III mGluRs. The second family of mGluRs modulators consists in allosteric modulators that interact with a different site from the extracellular active site of the receptor (see Bridges T M et al., *ACS Chem Biol*, 3(9), 530-41, 2008 for review). Their action results in a modulation of the effects induced by the endogenous ligand glutamate. Examples of such allosteric modulators are Ro-674853, MPEP or JNJ16259685 for group I mGluRs and CBiPES, LY181837 or LY487379 for group II mGluRs.

For groups III mGluRs, examples of allosteric modulators were so far described for the mGluR subtype 4 (mGluR4). PHCCC, MPEP and SIB1893 (Maj M at al., *Neuropharma-* cology, 45(7), 895-903, 2003; Mathiesen J M at al., *Br. J. Pharmacol.* 138(6), 1026-30, 2003) were the first ones described in 2003. More recently, more potent positive allosteric modulators were reported in the literature (Niswender C M et al., *Mol. Pharmacol.* 74(5), 1345-58, 2008; Niswender C M at al., *Bioorg. Med. Chem. Lett,* 18(20), 5626-30, 2008; Williams R et al., *Bioorg. Med. Chem. Lett.* 19(3), 962-6, 2009; Engers D W et al., *J. Med. Chem. May* 27, 2009) and in two patent publications describing families of amido and heteroaromatic compounds (WO 2009/010454 and WO 2009/010455).

Numerous studies have already described the potential applications of mGluR modulators in neuroprotection (see Bruno V et al., *J. Cereb. Blood Flow Metab.,* 21(9), 1013-33, 2001 for review). For instance, antagonist compounds of group I mGluRs showed interesting results in animal models for anxiety and postischemic neuronal injury (Pilc A et al., *Neuropharmacology,* 43(2), 181-7, 2002; Meli E et al., *Pharmacol. Biochem. Behav.,* 73(2), 439-46, 2002), agonists of group II mGluRs showed good results in animal models for Parkinson and anxiety (Konieczny J et al., *Naunyn-Schmiederbergs Arch. Pharmacol.,* 358(4), 500-2, 1998).

Group III mGluR modulators showed positive results in several animal models of schizophrenia (Palucha-Poniewiera A et al., *Neuropharmacology,* 55(4), 517-24, 2008) and chronic pain (Goudet C et al., *Pain,* 137(1), 112-24, 2008; Zhang H M et al., *Neuroscience,* 158(2), 875-84, 2009).

Group III mGluR were also shown to exert the excitotoxic actions of homocysteine and homocysteic acid contributing to the neuronal pathology and immunosenescence that occur in Alzheimer Disease (Boldyrev A A and Johnson P, *J. Alzheimers Dis.* 11(2), 219-28, 2007).

Moreover, group III mGluR modulators showed promising results in animal models of Parkinson and neurodegeneration (Conn P J et al., *Nat. Rev. Neuroscience,* 6(10), 787-98, 2005 for review; Vernon A C et al., *J. Pharmacol. Exp. Ther.,* 320(1), 397-409, 2007; Lopez S et al., *Neuropharmacology,* 55(4), 483-90, 2008; Vernon A C et al, *Neuroreport,* 19(4), 475-8, 2008). It was further demonstrated with selective ligands that the mGluR subtype implicated in these antiparkinsonian and neuroprotective effects was mGluR4 (Marino M J et al., *Proc. Natl. Acad. Sci. USA* 100(23), 13668-73, 2003; Battaglia G et al., *J. Neurosci.* 26(27), 7222-9, 2006; Niswender C M et al., *Mol. Pharmacol.* 74(5), 1345-58, 2008).

mGluR4 modulators were also shown to exert anxiolytic activity (Stachowicz K et al., *Eur. J. Pharmacol.,* 498(1-3), 153-6, 2004) and anti-depressive actions (Palucha A et al., *Neuropharmacology* 46(2), 151-9, 2004; Klak K et al., *Amino Acids* 32(2), 169-72, 2006).

In addition, mGluR4 were also shown to be involved in glucagon secretion inhibition (Uehara S., *Diabetes* 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (Pessimissis N et al., *Anticancer Res.* 29(1), 371-7, 2009) or colorectal carcinoma (Chang H J et al., *Cli. Cancer Res.* 11(9), 3288-95, 2005) and its activation with PHCCC was shown to inhibit growth of medulloblastomas (Iacovelli L et al., *J. Neurosci.* 26(32) 8388-97, 2006), mGluR4 modulators may therefore have also potential role for the treatment of cancers.

Finally, receptors of the umami taste expressed in taste tissues were shown to be variants of the mGluR4 receptor (Eschle B K., *Neuroscience,* 155(2), 522-9, 2008). As a consequence, mGluR4 modulators may also be useful as taste agents, flavour agents, flavour enhancing agents or food additives.

Chromone-derived core structures for pharmaceutically active compounds were described in the patent application WO 2004/092154. In the latter application, they are disclosed as inhibitors of protein kinases.

EP-A-0 787 723 relates to specific cyclopropachromencarboxylic acid derivatives which are said to have mGluR antagonistic activity.

The present invention relates to compounds of the general formula (I):

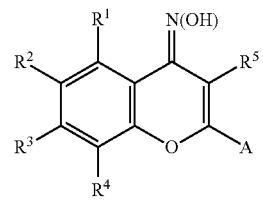

and pharmaceutically acceptable salts, solvates and prodrugs thereof.

$R^1$, $R^2$, $R^3$, and $R^4$ each independently represent a -L-R group.

L represents a bond, a $C_1$-$C_{10}$ alkylene, a $C_2$-$C_{10}$ alkenylene, or a $C_2$-$C_{10}$ alkynylene, wherein said alkylene, said alkenylene or said alkynylene is optionally substituted with one or more groups independently selected from halogen, —$CF_3$, —CN, —OH, or —$NH_2$, and further wherein one or more —$CH_2$— units comprised in said alkylene, said alkenylene or said alkynylene are each optionally replaced by a group independently selected from —O—, —$NR^{11}$—, —CO—, —S—, —SO—, or —$SO_2$—.

R is selected from hydrogen, $C_1$-$C_{10}$ alkyl, halogen, optionally substituted aryl, optionally substituted heteroaryl, optionally substituted cycloalkyl, optionally substituted heterocycloalkyl, —$NR^{11}R^{12}$, —$OR^{11}$, —$SR^{11}$, —$SOR^{11}$, —$SO_2R^{11}$, —$CF_3$, or —CN, wherein said optionally substituted aryl, said optionally substituted heteroaryl, said optionally substituted cycloalkyl, or said optionally substituted heterocycloalkyl may be substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, or -$L^1$-$R^{13}$.

$R^{11}$ and $R^{12}$ are each independently selected from hydrogen, optionally substituted $C_1$-$C_{10}$ alkyl, optionally substituted aryl, optionally substituted heteroaryl, optionally substituted cycloalkyl, optionally substituted heterocycloalkyl, or —$CF_3$, wherein said optionally substituted alkyl, said optionally substituted aryl, said optionally substituted heteroaryl, said optionally substituted cycloalkyl, or said optionally substituted heterocycloalkyl may be substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to.

$L^1$ is selected from a bond, $C_1$-$C_{10}$ alkylene, $C_2$-$C_{10}$ alkenylene, or $C_2$-$C_{10}$ alkynylene, wherein one or two —$CH_2$— units comprised in said alkylene, said alkenylene or said alkynylene are each optionally replaced by a group independently selected from —O—, —NH—, —N($C_1$-$C_4$ alkyl)-, —CO—, —S—, —SO— or —$SO_2$—.

$R^{13}$ is selected from hydrogen, $C_1$-$C_4$ alkyl, halogen, optionally substituted phenyl, optionally substituted heteroaryl, optionally substituted cycloalkyl, optionally substituted heterocycloalkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —SH, —S($C_1$-$C_4$ alkyl), —$CF_3$, or —CN, wherein said optionally substituted phenyl, said optionally substituted heteroaryl, said optionally substituted cycloalkyl, or said optionally substituted heterocycloalkyl may be substituted with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to.

$R^5$ is selected from hydrogen, $C_1$-$C_4$ alkyl, halogen, —$CF_3$, —CN, —OH, —O($C_1$-$C_4$ alkyl), —COOH, —COO($C_1$-$C_4$ alkyl), —$CONH_2$, —CONH($C_1$-$C_4$ alkyl), —CON($C_1$-$C_4$ alkyl)($C_1$-$C_4$ alkyl), wherein the two $C_1$-$C_4$ alkyl moieties of said —CON($C_1$-$C_4$ alkyl)($C_1$-$C_4$ alkyl) are optionally mutually linked to form a ring together with the nitrogen atom which they are attached to, —$NH_2$, —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to.

A is a bicyclic moiety corresponding to formula (II):

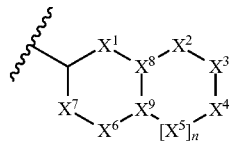

which may be saturated or unsaturated, and wherein:
n is 0 or 1;
$X^1$ to $X^6$ are each independently selected from N, N($R^{x1}$), C($R^{x2}$), C($R^{x2}$)($R^{x3}$), O, S, S(O), S(O)$_2$, or C(O);
$X^7$ is N or N($R^{x1}$);
any of groups $X^1$ to $X^7$ containing a nitrogen atom may form an N-oxide group;
$X^8$ and $X^9$ are each independently selected from N, C, or C($R^{x2}$);
each $R^{x1}$ is independently selected from hydrogen, $C_1$-$C_4$ alkyl, —OH, —O($C_1$-$C_4$ alkyl), or —($C_1$-$C_4$ alkylene)-phenyl; and
each $R^{x2}$ and each $R^{x3}$ is independently selected from hydrogen, $C_1$-$C_4$ alkyl, halogen, —$CF_3$, —CN, —OH, —O($C_1$-$C_4$ alkyl), —COOK, —COO($C_1$-$C_4$ alkyl), —$CONH_2$, —CONH($C_1$-$C_4$ alkyl), —CON($C_1$-$C_4$ alkyl)($C_1$-$C_4$ alkyl), —$NH_2$, —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) or of said —CON($C_1$-$C_4$ alkyl)($C_1$-$C_4$ alkyl) are optionally mutually linked to form a ring together with the nitrogen atom which they are attached to.

In this description, the bicyclic ring system of formula (I) including the O-heteroatom and the oxime group, to which the substituents $R^1$ to $R^5$ and A are attached, is also referred to as "chromone moiety".

Thus, the present invention relates to new oxime derivatives of the general formula (I) as described and defined herein and pharmaceutically acceptable salts, solvates and prodrugs thereof, pharmaceutical compositions containing any of the aforementioned entities and their use for the treatment and/or prophylaxis of conditions associated with altered glutamatergic signalling and/or functions, and/or conditions which can be affected by alteration of glutamate level or signalling in mammals. It further relates to a method of treating and/or preventing conditions associated with altered glutamatergic signalling and/or functions, and/or conditions which can be affected by alteration of glutamate level or signalling in a mammal. Accordingly, the present invention provides a method of treating and/or preventing a disease or disorder, in particular a condition associated with altered glutamatergic signalling and/or functions, and/or a condition which can be affected by alteration of glutamate level or signalling, the method comprising the administration of a compound of the general formula (I) as described and defined herein, or a pharmaceutically acceptable salt, solvate or prodrug thereof, or a pharmaceutical composition comprising any of the aforementioned entities, to a subject (preferably, a mammal; more preferably, a human) in need of such treatment or prevention. In further embodiments the compounds of the general formula (I) are modulators of mGluRs of the nervous system. In preferred embodiments the compounds of the invention are allosteric modulators of the mGluRs and in a most preferred embodiment they are positive allosteric modulators of mGluR4.

The conditions associated with altered glutamatergic signalling and/or functions, and/or conditions which can be affected by alteration of glutamate level or signalling, and which can be treated and/or prevented with the compounds or the pharmaceutical compositions according to the invention, include in particular: epilepsy, including newborn, infantile, childhood and adult syndromes, partial (localization-related) and generalized epilepsies, with partial and generalized, convulsive and non-convulsive seizures, with and without impairment of consciousness, and status epilepticus; Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Motor neuron disease or amyotrophic lateral sclerosis (ALS); Other neurodegenerative and/or hereditary disorders of the nervous system, including spinocerebrellar degenerations such as Friedrich's ataxia and other hereditary cerebellar ataxias, predominantly spinal muscular atrophies, hereditary neuropathies, and phakomatoses; Disorders of the peripheral nervous system, including trigeminal neuralgia, facial nerve disorders, disorders of the other cranial nerves, nerve root and plexus disorders, mononeuritis such as carpal tunnel syndrome and sciatica, hereditary and idiopathic peripheral neuropathies, inflammatory and toxic neuropathies; Multiple sclerosis and other demyelinating diseases of the nervous system; Infantile cerebral palsy (spastic), monoplegic, paraplegic or tetraplegic; Hemiplegia and hemiparesis, flaccid or spastic, and other paralytic syndromes; Cerebrovascular disorders, including subarachnoid hemorrhage, intracerebral hemorrhage, occlusion and stenosis of precerebral arteries, occlusion of cerebral arteries including thrombosis and embolism, brain ischemia, stroke, transient ischemic attacks, atherosclerosis, cerebrovascular dementias, aneurysms, cerebral deficits due to cardiac bypass surgery and grafting; Migraine, including classical migraine and variants such as cluster headache; Headache; Myoneural disorders including myasthenia gravis, acute muscle spasms, myopathies including muscular dystrophies, mytotonias and familial periodic paralysis; Disorders of the eye and visual pathways, including retinal disorders, and visual disturbances; Intracranial trauma/injury and their sequels; Trauma/injury to nerves and spinal cord and their sequels; Poisoning and toxic effects of nonmedicinal substances; Accidental poisoning by drugs, medicinal substances and biologicals acting on the central, peripheral and autonomic system; Neurological and psychiatric adverse effects of drugs, medicinal and biological substances; Disturbance of sphincter control and sexual function; Mental disorders usually diagnosed in infancy, childhood or adolescence, including: mental retardation, learning disorders, motor skill disorders, communication disorders, pervasive developmental disorders, attention deficit and disruptive behaviour disorders, feeding and eating disorders, TIC disorders, elimination disorders; Delirium and other cognitive disorders; Substance related disorders including: alcohol-related disorders, nicotine-related disorders, disorders related to cocaine, opioids, cannabis, hallucinogens and other drugs; Schizophrenia and other psychotic disorders; Mood disorders, including depressive disorders and bipolar disorders; Anxiety disorders, including panic disorders, phobias, obsessive-compulsive disorders, stress disorders, generalized anxiety disorders; Eating disorders, including anorexia and bulimia; Sleep disorders, including dyssomnias (insomnia, hypersomnia, narcolepsy, breathing related sleep disorder) and parasomnias; Medication-induced movement disorders (including neuroleptic-induced parkinsonism and tardive dyskinesia); Endocrine and metabolic diseases including diabetes, disorders of the endocrine glands, hypoglycaemia; Acute and chronic pain; Nausea and vomiting; Irritable bowel syndrome; or cancers.

In particular, the conditions associated with altered glutamatergic signalling and/or functions, and/or conditions which can be affected by alteration of glutamate level or signalling to be treated and/or prevented by the compounds or the pharmaceutical compositions according to the invention, include: Dementias and related diseases, including dementias of the Alzheimer's type (DAT), Alzheimer's disease, Pick's disease, vascular dementias, Lewy-body disease, dementias due to metabolic, toxic and deficiency diseases (including alcoholism, hypothyroidism, and vitamin B12 deficiency), AIDS-dementia complex, Creutzfeld-Jacob disease and atypical subacute spongiform encephalopathy; Parkinsonism and movement disorders, including Parkinson's disease, multiple system atrophy, progressive supranuclear palsy, corticobasal degeneration, hepatolenticular degeneration, chorea (including Huntington's disease and hemiballismus), athetosis, dystonias (including spasmodic torticollis, occupational movement disorder, Gilles de la Tourette syndrome), tardive or drug induced dyskinesias, tremor and myoclonus; Acute and chronic pain; Anxiety disorders, including panic disorders, phobias, obsessive-compulsive disorders, stress disorders and generalized anxiety disorders; Schizophrenia and other psychotic disorders; Mood disorders, including depressive disorders and bipolar disorders; Endocrine and metabolic diseases including diabetes, disorders of the endocrine glands and hypoglycaemia; or cancers.

The present invention further provides a method for identifying an agent that binds to metabotropic glutamate receptor 4 (mGluR4), or in other words for determining the capability of one or more test agent(s) to bind to the receptor, comprising the following steps: (a) contacting mGluR4 with a compound of the present invention which is labeled, preferably radio-Labeled or fluorescence-labeled, under conditions that permit binding of the compound to mGluR4, thereby generating a bound, labeled compound; (b) detecting a signal that corresponds to the amount of the bound, labeled compound in the absence of test agent; (c) contacting the bound, labeled compound with a test agent; (d) detecting a signal that corresponds to the amount of the bound labeled compound in the presence of test agent; and (e) comparing the signal detected in step (d) to the signal detected in step (b) to determine whether the test agent binds to mGluR4. As will be understood, a substantially unchanged signal detected in step (d) in comparison with the signal detected in step (b) indicates that the test agent does not bind to the receptor, or binds to the receptor less strongly than the compounds according to the invention. A decreased or increased signal detected in step (d) in comparison with the signal detected in step (b) indicates that the test agent binds to the receptor. Thus, agents that bind to mGluR4 can be identified among the test agents employed in the above method. It will further be understood that it is preferred to remove unbound labeled compounds, e.g. in a washing step, before carrying out steps (b) and (d).

The mGluR4 which is used in the above method may be a human form (Flor P J, Lukic S, Rüegg D, Leonhardt T, Knöpfel T, Kuhn R. 1995. *Neuropharmacology.* 34:149-155. Makoff A, Lelchuk R, Oxer M, Harrington K, Emson P. 1996. *Brain Res. Mol. Brain. Res.* 37:239-248. Wu 5, Wright R A, Rockey P K, Burgett S G, Arnold J S, Rosteck P R Jr, Johnson B G, Schoepp D D, Belagaje R M. 1998. *Brain Res. Mot. Brain Res.* 53:88-97.), e.g. a protein of the accession number NP_000832 or a protein having at least 80% (preferably, at least 90%; more preferably, at least 95%; even more preferably, at least 99%) amino acid identity to said protein of the accession number NP_000832, or a non-human form, including e.g. a mouse form or rat form (Tanabe Y, Masu M, Ishii T, Shigemoto R, Nakanishi S. 1992. *Neuron.* 8:169-179.), or a homolog thereof found in a different species (e.g. in a different mammalian species), or a mutein of any of the aforementioned entities which mutein retains the mGluR4 activity. Said mutain can preferably be obtained by substitution, insertion, addition and/or deletion of one or more (such as, e.g., 1 to 20, including 1 to 10 or 1 to 3) amino acid residues of said aforementioned entities. The mGluR4 used in the above method may also be a functional fragment of any of the aforementioned entities (including said muteins), i.e. a fragment which retains the mGluR4 activity of the respective aforementioned entity or, in other words, a fragment having essentially the same biological activity (i.e., at least about 60% activity, preferably at least about 70% activity, more preferably at least about 80% activity, even more preferably at least about 90% activity) as the respective aforementioned entity. A person skilled in the art is readily in a position to determine whether mGluR4 activity is retained using techniques known in the art, e.g. knock-out and rescue experiments. Furthermore, the mGluR4 used in the above method may also be a compound comprising any one or more of the aforementioned entities (including, without limitation, a protein of the accession number NP_000832, a protein having at least 80% amino acid identity to said protein of the accession number NP_000832, or a functional fragment thereof), wherein the mGluR4 activity is retained. Preferably, the mGluR4 used in the above method is a human form.

The compounds of the general formula (I) will be described in more detail in the following:

$R^1$, $R^2$, $R^3$, and $R^4$ each independently represent a -L-R group.

L represents a bond, $C_1$-$C_{10}$ alkylene, $C_2$-$C_{10}$ alkenylene, or $C_2$-$C_{10}$ alkynylene. Said alkylene, said alkenylene or said alkynylene is optionally substituted with one or more (such as, e.g., one, two, three, or four) groups independently selected from halogen, —$CF_3$, —CN, —OH, or —$NH_2$.

Moreover, one or more (such as, e.g., one, two, three, or four), preferably one or two, more preferably one, —$CH_2$— units comprised in said alkylene, said alkenylene or said alkynylene are each optionally replaced by a group independently selected from: —O—, —$NR^{11}$—, —CO—, —S—, —SO—, or —$SO_2$—. This includes the option that the replacing groups —$NR^{11}$— and —CO— are combined, in any order, to form an amide group. Otherwise, if more than one —$CH_2$— unit is replaced, it is preferred that these —$CH_2$— units are non-adjacent. Preferably, no —$CH_2$— unit, one —$CH_2$— unit or two —$CH_2$— units are each replaced by a group independently selected from —O—, —$NR^{11}$—, —CO—, or —S—. More preferably, no —$CH_2$— unit is replaced or one —$CH_2$— unit or two —$CH_2$— units are each replaced by a group independently selected from —O—, —$NR^{11}$—, or —S—. Even more preferably, no —$CH_2$— unit is replaced or one or two —$CH_2$— units are each replaced by —O—.

More preferably, L is a bond, $C_1$-$C_6$ alkylene, $C_2$-$C_6$ alkenylene, or $C_2$-$C_6$ alkynylene, wherein one or two —$CH_2$— units comprised in said alkylene, said alkenylene or said alkynylene are each optionally replaced by a group independently selected from —O—, —$NR^{11}$—, —CO—, or —S—.

Even more preferably, L is a bond, $C_1$-$C_6$ alkylene, $C_2$-$C_6$ alkenylene, or $C_2$-$C_6$ alkynylene, wherein one or two —$CH_2$— units comprised in said alkylene, said alkenylene, or said alkynylene are each optionally replaced by —O—.

Most preferably, L is a bond or $C_1$-$C_6$ alkylene, wherein one or two —$CH_2$— units comprised in said alkylene are each optionally replaced by —O—.

R is selected from hydrogen, $C_1$-$C_{10}$ alkyl, halogen, optionally substituted aryl, optionally substituted heteroaryl, optionally substituted cycloalkyl, optionally substituted heterocycloalkyl, —$NR^{11}R^{12}$, —$OR^{11}$, —$SR^{11}$, —$SOR^{11}$, —$SO_2R^{11}$, —$CF_3$, or —CN, wherein said optionally substituted aryl, said optionally substituted heteroaryl, said optionally substituted cycloalkyl, or said optionally substituted heterocycloalkyl may be substituted with one or more (such as, e.g., one, two, three, or four), preferably one or two, substituent groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to, or -L-$R^{13}$. Said substituent groups are preferably selected from $C_1$-$C_4$ alkyl, —($C_1$-$C_4$ alkylene)-OH, alkylene)-O—($C_1$-$C_4$ alkyl), —OH, —O($C_1$-$C_4$ alkyl), —O—($C_1$-$C_4$ alkylene)-O—($C_1$-$C_4$ alkyl), —$NH_2$, —NH($C_1$-$C_4$ alkyl), —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, —$CF_3$, or halogen, and more preferably selected from $C_1$-$C_4$ alkyl, —($C_1$-$C_4$ alkylene)-OH, —($C_1$-$C_4$ alkylene)-O—($C_1$-$C_4$ alkyl), —O($C_1$-$C_4$ alkyl), —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, or halogen, Said halogen may, for example, be selected from fluoro, chloro, bromo, or iodo.

Preferably, R is selected from: hydrogen; optionally substituted aryl; optionally substituted heteroaryl having 5 or 6 ring atoms, wherein 1, 2, or 3 ring atoms are each independently selected from O, S, or N and the other ring atoms are carbon atoms; optionally substituted heterocycloalkyl having 3 to 10 ring atoms, wherein one or more (such as, e.g., one, two, or three) ring atoms are each independently selected from O, S, or N and the other ring atoms are carbon atoms; —NH($C_1$-$C_4$ alkyl); —N($C_1$-$C_4$ alkyl)($C_1$-$C_4$ alkyl); or —O($C_1$-$C_4$ alkyl), Said aryl may, for example, be a phenyl. Said heteroaryl may, for example, be selected from pyridinyl, thienyl, furyl, pyrrolyl, imidazolyl, pyrazolyl, pyrazinyl, pyrimidinyl, pyridazinyl, oxazolyl, isoxazolyl, or furazanyl. Said heterocycloalkyl may, for example, be selected from tetrahydrofuranyl, piperidinyl, piperazinyl, pyrrolidinyl, imidazolidinyl, morpholinyl, pyrazolidinyl, tetrahydrothienyl, oxazolidinyl, isoxazolidinyl, aziridinyl, azetidinyl, octahydroquinolinyl, octahydroisoquinolinyl, azepanyl, diazepanyl, oxazepanyl or 2-oxa-5-aza-bicyclo[2.2.1]hept-5-yl.

More preferably, R is selected from: hydrogen; optionally substituted phenyl; optionally substituted heteroaryl having 5 or 6 ring atoms, wherein 1, 2, or 3 ring atoms are each independently selected from O, S, or N and the other ring atoms are carbon atoms; —O($C_1$-$C_4$ alkyl); or optionally substituted heterocycloalkyl having 3 to 10 ring atoms, wherein one or more ring atoms are each independently selected from O, S, or N and the other ring atoms are carbon atoms.

Even more preferably, R is selected from: hydrogen; optionally substituted phenyl; optionally substituted heteroaryl having 5 or 6 ring atoms, wherein 1, 2, or 3 ring atoms are each independently selected from O, S, or N and the other ring atoms are carbon atoms; or optionally substituted heterocycloalkyl having 5 to 7 ring atoms, wherein one or two ring atoms are each independently selected from N or O and the other ring atoms are carbon atoms.

As is apparent from the above, preferred combinations -L-R are those wherein L is a bond, $C_1$-$C_6$ alkylene, $C_2$-$C_6$ alkenylene, or $C_2$-$C_6$ alkynylene, wherein one or two —$CH_2$— units comprised in said alkylene, said alkenylene, or said alkynylene are each optionally replaced by —O—, and preferably L is a bond or $C_1$-$C_6$ alkylene, wherein one or two —$CH_2$— units comprised in said alkylene are each optionally replaced by —O—, and further wherein R is selected from hydrogen, optionally substituted phenyl, optionally substituted heteroaryl having 5 or 6 ring atoms, wherein 1, 2, or 3 ring atoms are each independently selected from O, S, or N and the other ring atoms are carbon atoms; or optionally substituted heterocycloalkyl having 5 to 7 ring atoms, wherein one or two ring atoms are each independently selected from N or O and the other ring atoms are carbon atoms. Said optionally substituted phenyl, said optionally substituted heteroaryl having 5 or 6 ring atoms, or said optionally substituted heterocycloalkyl having 5 to 7 ring atoms may be substituted with one or more, preferably one or two, groups independently selected from $C_1$-$C_4$ alkyl, —($C_1$-$C_4$ alkylene)-OH, —($C_1$-$C_4$ alkylene)-O—($C_1$-$C_4$ alkyl), —OH, —O($C_1$-$C_4$ alkyl), —O—($C_1$-$C_4$ alkylene)-O—($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, —$CF_3$, or halogen, and more preferably selected from $C_1$-$C_4$ alkyl, —($C_1$-$C_4$ alkylene)-OH, —($C_1$-$C_4$ alkylene)-O—($C_1$-$C_4$ alkyl), —O($C_1$-$C_4$ alkyl), —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, or halogen.

Exemplary preferred -L-R groups encompassed by the above preferred definition are independently selected from: hydrogen; $C_1$-$C_4$ alkyl; —($C_1$-$C_3$ alkylene)-O—($C_1$-$C_2$ alkyl); —($C_2$-$C_4$ alkynylene)-phenyl; —OH; —O($C_1$-$C_4$ alkyl); —O($C_1$-$C_2$ alkylene)-O—($C_1$-$C_2$ alkyl); —($C_1$-$C_4$ alkylene)-morpholinyl; —O($C_1$-$C_4$ alkylene)-phenyl; —O($C_1$-$C_4$ alkylene)-imidazolyl; —O($C_1$-$C_4$ alkylene)-pyrrolidinyl; —O($C_1$-$C_4$ alkylene)-piperidinyl; —O($C_1$-$C_4$ alkylene)-morpholinyl; —O($C_1$-$C_4$ alkylene)-pyridinyl; —O($C_1$-$C_4$ alkylene)-oxazepanyl; —O($C_1$-$C_4$ alkylene)-(2-oxa-5-aza-bicyclo[2.2.1]hept-5-yl); —O($C_1$-$C_4$ alkylene)-piperazinylene-($C_1$-$C_4$ alkyl); or —O($C_1$-$C_4$ alkylene)-diazepanylene-($C_1$-$C_4$ alkyl); wherein the phenyl, imidazolyl, pyrrolidinyl, piperidinyl, morpholinyl, pyridinyl, oxazepanyl, 2-oxa-5-aza-bicyclo[2.2.1]hept-5-yl, piperazinylene, and diazepanylene moieties are each optionally substituted with one or more, preferably one or two, groups independently selected from halogen, —$CF_3$, $C_1$-$C_4$ alkyl, —($C_1$-$C_4$ alkylene)-OH, —($C_1$-$C_4$ alkylene)-O—($C_1$-$C_4$ alkyl), —OH, —O($C_1$-$C_4$ alkyl), —O—($C_1$-$C_4$ alkylene)-O—($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, more preferably selected from halogen, $C_1$-$C_4$ alkyl, —($C_1$-$C_4$ alkylene)-OH, —($C_1$-$C_4$ alkylene)-O—($C_1$-$C_4$ alkyl), —O($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to.

Moreover, in particularly preferred embodiments, either $R^1$ to $R^4$ are all hydrogen, or one of $R^1$ to $R^4$ is a -L-R group other than hydrogen as defined above and the other ones of $R^1$ to $R^4$ are hydrogen. In this latter preferred embodiment, the -L-R group other than hydrogen is in particular one of $R^2$ and $R^3$, and more preferably $R^2$.

Accordingly, in one preferred embodiment $R^1$ and $R^4$ are each hydrogen, one of $R^2$ and $R^3$ (preferably $R^3$) is hydrogen, and the other one of $R^2$ and $R^3$ (preferably $R^2$) is selected from: hydrogen; $C_1$-$C_4$ alkyl; —($C_1$-$C_3$ alkylene)-O—($C_1$-$C_2$ alkyl); —($C_2$-$C_4$ alkynylene)-phenyl; —OH; —O($C_1$-$C_4$ alkyl); —O($C_1$-$C_2$ alkylene)-O—($C_1$-$C_2$ alkyl); —($C_1$-$C_4$ alkylene)-morpholinyl; —O($C_1$-$C_4$ alkylene)-phenyl; —O($C_1$-$C_4$ alkylene)-imidazolyl; —O($C_1$-$C_4$ alkylene)-pyrrolidinyl; —O($C_1$-$C_4$ alkylene)-piperidinyl; —O($C_1$-$C_4$ alkylene)-morpholinyl; —O($C_1$-$C_4$ alkylene)-pyridinyl; —O($C_1$-$C_4$ alkylene)-oxazepanyl; —O($C_1$-$C_4$ alkylene)-(2-oxa-5-aza-bicyclo[2.2.1]hept-5-yl); —O($C_1$-$C_4$ alkylene)-piperazinylene-($C_1$-$C_4$ alkyl); or —O($C_1$-$C_4$ alkylene)-diazepanylene-($C_1$-$C_4$ alkyl); wherein the phenyl, imidazolyl, pyrrolidinyl, piperidinyl, morpholinyl, pyridinyl, oxazepanyl, 2-oxa-5-aza-bicyclo[2.2.1]hept-5-yl, piperazinylene, and diazepanylene moieties are each optionally substituted with one or more, preferably one or two, groups independently selected from halogen, —$CF_3$, $C_1$-$C_4$ alkyl, —($C_1$-$C_4$ alkylene)-OH, —($C_1$-$C_4$ alkylene)-O—($C_1$-$C_4$ alkyl), —OH, —O($C_1$-$C_4$ alkyl), —O—($C_1$-$C_4$ alkylene)-O—($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, more preferably selected from halogen, $C_1$-$C_4$ alkyl, —($C_1$-$C_4$ alkylene)-OH, —($C_1$-$C_4$ alkylene)-O—($C_1$-$C_4$ alkyl), —O($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to. In one aspect of this embodiment, one of $R^2$ and $R^3$ (preferably $R^3$) is hydrogen, and the other one of $R^2$ and $R^3$ (preferably $R^2$) is not hydrogen.

$R^{11}$ and $R^{12}$ are each independently selected from hydrogen, optionally substituted $C_1$-$C_{10}$ alkyl, optionally substituted aryl, optionally substituted heteroaryl, optionally substituted cycloalkyl, optionally substituted heterocycloalkyl, or —$CF_3$, wherein said optionally substituted alkyl, said optionally substituted aryl, said optionally substituted heteroaryl, said optionally substituted cycloalkyl, or said optionally substituted heterocycloalkyl may be substituted with one or more, preferably one or two, more preferably one, groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to. It is preferred that the aforementioned groups are unsubstituted. Preferably, $R^{11}$ and $R^{12}$ are each independently selected from hydrogen, or $C_1$-$C_4$ alkyl.

$L^1$ is selected from a bond, $C_1$-$C_{10}$ alkylene, $C_2$-$C_{10}$ alkenylene, or $C_2$-$C_{10}$ alkynylene, wherein one or two —$CH_2$— units comprised in said alkylene, said alkenylene or said alkynylene are each optionally replaced by a group independently selected from —O—, —NH—, —N($C_1$-$C_4$ alkyl)-, —CO—, —S—, —SO— or —$SO_2$—. This includes the option that the replacing group —NH— or the replacing group —N($C_1$-$C_4$ alkyl)- is combined with the replacing group —CO—, in any order, to form an amide group. Otherwise, if more than one —$CH_2$— unit is replaced, it is preferred that these —$CH_2$— units are non-adjacent.

Preferably, $L^1$ is selected from a bond, $C_1$-$C_6$ alkylene, $C_2$-$C_6$ alkenylene, or $C_2$-$C_6$ alkynylene, wherein one or two —$CH_2$— units comprised in said alkylene, said alkenylene or said alkynylene are each optionally replaced by a group independently selected from —O—, —NH—, —CO—, or —S—.

More preferably, $L^1$ is selected from a bond, $C_1$-$C_6$ alkylene, $C_2$-$C_6$ alkenylene, or $C_2$-$C_6$ alkynylene, wherein one or two —$CH_2$— units comprised in said alkylene, said alkenylene or said alkynylene are each optionally replaced by a group independently selected from —O—, —NH—, or —S—.

Even more preferably, $L^1$ is a bond, $C_1$-$C_6$ alkylene, $C_2$-$C_6$ alkenylene, or $C_2$-$C_6$ alkynylene, wherein one or two —$CH_2$— units comprised in said alkylene, said alkenylene or said alkynylene are each optionally replaced by —O—.

Most preferably, $L^1$ is a bond or $C_1$-$C_6$ alkylene, wherein one or two —$CH_2$— units comprised in said alkylene are each optionally replaced by —O—.

$R^{13}$ is selected from hydrogen, $C_1$-$C_4$ alkyl, halogen, optionally substituted phenyl, optionally substituted heteroaryl, optionally substituted cycloalkyl, optionally substituted heterocycloalkyl, —$NH_2$, —NH($C_1$-$C_4$ alkyl), —N($C_1$-$C_4$ alkyl)($C_1$-$C_4$ alkyl), —OH, —O($C_1$-$C_4$ alkyl), —SH, —S($C_1$-$C_4$ alkyl), —$CF_3$, or —CN, wherein said optionally substituted phenyl, said optionally substituted heteroaryl, said optionally substituted cycloalkyl, or said optionally substituted heterocycloalkyl may be substituted with one or more, preferably one or two, more preferably one, groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to.

Preferably, $R^{13}$ is selected from hydrogen, $C_1$-$C_4$ alkyl, halogen, optionally substituted phenyl, optionally substituted heteroaryl, optionally substituted cycloalkyl, optionally substituted heterocycloalkyl, —NH($C_1$-$C_4$ alkyl), —N($C_1$-$C_4$ alkyl)($C_1$-$C_4$ alkyl), —O($C_1$-$C_4$ alkyl), —S($C_1$-$C_4$ alkyl), —$CF_3$, or —CN.

More preferably, $R^{13}$ is selected from: hydrogen; $C_1$-$C_4$ alkyl; halogen; optionally substituted phenyl; optionally substituted heteroaryl having 5 or 6 ring atoms, wherein 1, 2, or 3 ring atoms are each independently selected from O, S, or N and the other ring atoms are carbon atoms; cycloalkyl having 3 to 7 ring atoms; optionally substituted heterocycloalkyl having 3 to 10 ring atoms, wherein one or more (such as, e.g., one, two, or three) ring atoms are each independently selected from O, S, or N and the other ring atoms are carbon atoms; —NH($C_1$-$C_4$ alkyl); —N($C_1$-$C_4$ alkyl)($C_1$-$C_4$ alkyl); —O($C_1$-$C_4$ alkyl); —S($C_1$-$C_4$ alkyl); —$CF_3$; or —CN.

Even more preferably, $R^{13}$ is selected from: hydrogen; —O($C_1$-$C_4$ alkyl); optionally substituted phenyl; optionally substituted heteroaryl having 5 or 6 ring atoms, wherein 1, 2, or 3 ring atoms are each independently selected from O, S, or N and the other ring atoms are carbon atoms; or optionally substituted heterocycloalkyl having 3 to 10 ring atoms, wherein one or more ring atoms are each independently selected from O, S, or N and the other ring atoms are carbon atoms.

$R^5$ is selected from hydrogen, $C_1$-$C_4$ alkyl, halogen, —$CF_3$, —CN, —OH, —O($C_1$-$C_4$ alkyl), —COOH, —COO($C_1$-$C_4$ alkyl), —$CONH_2$, —CONH($C_1$-$C_4$ alkyl), —CON($C_1$-$C_4$ alkyl)($C_1$-$C_4$ alkyl) wherein the two $C_1$-$C_4$ alkyl moieties of said —CON($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to, —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to. Said halogen may, for example, be selected from fluoro, chloro, bromo, or iodo. Preferably, $R^5$ is selected from hydrogen, $C_1$-$C_4$ alkyl, halogen, —$CF_3$, —CN, —OH, or —O($C_1$-$C_4$ alkyl). More preferably, $R^5$ is selected from hydrogen or $C_1$-$C_4$ alkyl. Even more preferably, $R^5$ is hydrogen.

A is a bicyclic moiety corresponding to formula (II):

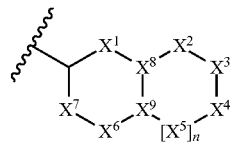

which may be saturated or unsaturated, i.e. one or more double bonds may be present in one or both rings formed by $X^1$ to $X^9$. This includes the option that one or both rings formed by $X^1$ to $X^9$ are aromatic.

n is 0 or 1.

$X^1$ to $X^6$ are each independently selected from N, N($R^{x1}$), C($R^{x2}$), C($R^{x2}$)($R^{x3}$), O, S, S(O), S(O)$_2$, or C(O). Preferably, $X^1$ to $X^6$ are each independently selected from N, N($R^{x1}$), C($R^{x2}$), C($R^{x2}$)($R^{x3}$), S or O.

$X^7$ is N or N($R^{x1}$).

Included is furthermore the option that any of groups $X^1$ to $X^7$ containing a nitrogen atom can form an N-oxide group.

$X^8$ and $X^9$ are each independently selected from N, C, or C($R^{x2}$).

Each $R^{x1}$ is independently selected from hydrogen, $C_1$-$C_4$ alkyl, —OH, —O($C_1$-$C_4$ alkyl), or —($C_1$-$C_4$ alkylene)-phenyl. Preferably, each $R^{x1}$ is independently selected from hydrogen, or $C_1$-$C_4$ alkyl.

Each $R^{x2}$ and each $R^{x3}$ is independently selected from hydrogen, $C_1$-$C_4$ alkyl, halogen, —$CF_3$, —CN, —OH, —O($C_1$-$C_4$ alkyl), —COOH, —COO($C_1$-$C_4$ alkyl), —$CONH_2$, —CONH($C_1$-$C_4$ alkyl), —CON($C_1$-$C_4$ alkyl)($C_1$-$C_4$ alkyl), —$NH_2$, —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) or of said —CON($C_1$-$C_4$ alkyl)($C_1$-$C_4$ alkyl) are optionally mutually linked to form a ring (such as, e.g., a pyrrolidinyl ring or a piperidinyl ring) together with the nitrogen atom which they are attached to. Preferably, each $R^{x2}$ and each $R^{x3}$ is independently selected from hydrogen, $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to. More preferably, each $R^{x2}$ and each $R^{x3}$ is independently selected from hydrogen, $C_1$-$C_4$ alkyl, halogen, —$CF_3$, —OH, or —O($C_1$-$C_4$ alkyl).

As will be understood, the bicyclic moiety corresponding to formula (II) is linked to the remainder of the compound of general formula (I) by the interrupted bond shown in formula (II), i.e. ⌇. As will further be understood, the absence or the presence of one or two substituents $R^{x1}$, $R^{x2}$ and $R^{x3}$ in the groups $X^1$ to $X^9$ will depend on the presence and the position of double bonds in the bicyclic ring system of formula (II).

In preferred embodiments, one or two of the groups $X^1$ to $X^6$, $X^8$ and $X^9$ are each independently selected from N, N($R^{x1}$), O, S, S(O), or S(O)$_2$ (preferably, selected from N, N($R^{x1}$), S or O) in the case of $X^1$ to $X^6$ and from N in the case of $X^8$ and $X^9$, respectively, and the remaining groups $X^1$ to $X^6$, $X^8$ and $X^9$ are each independently selected from C($R^{x2}$) or C($R^{x2}$)($R^{x3}$) in the case of $X^1$ to $X^6$ and from C or C($R^{x2}$) in the case of $X^8$ and $X^9$, respectively. Accordingly, in one embodiment one or two of the groups $X^1$ to $X^6$ are each independently selected from N, N($R^{x1}$), O, or S, the remaining groups $X^1$ to $X^6$ are each independently selected from C($R^{x2}$) or C($R^{x2}$)($R^{x3}$), and $X^8$ and $X^9$ are each independently selected from C or C($R^{x2}$); alternatively, in another embodiment one or none of the groups $X^1$ to $X^6$ is selected from N, N($R^{x1}$), O, or S, the remaining groups $X^1$ to $X^6$ are each independently selected from C($R^{x2}$) or C($R^{x2}$)($R^{x3}$), one of $X^8$ and $X^9$ is N, and the other one of $X^8$ and $X^9$ is C or C($R^{x2}$).

In further preferred embodiments, one or two of the groups $X^1$ to $X^6$, $X^8$ and $X^9$ are each independently selected from N, N($R^{x1}$) or S in the case of $X^1$ to $X^6$ and from N in the case of $X^8$ and $X^9$, respectively, and the remaining groups $X^1$ to $X^6$, $X^8$ and $X^9$ are each independently selected from C($R^{x2}$) or C($R^{x2}$)($R^{x3}$) in the case of $X^1$ to $X^6$ and from C or C($R^{x2}$) in the case of $X^8$ and $X^9$, respectively. Accordingly, in one embodiment one or two of $X^1$ to $X^6$ are each independently selected from N, $N(R^{x1})$ or S, the remaining groups $X^1$ to $X^6$ are each independently selected from $C(R^{x2})$ or $C(R^{x2})(R^{x3})$, and $X^8$ and $X^9$ are each independently selected from C or $C(R^{x2})$; alternatively, in another embodiment one or none of the groups $X^1$ to $X^6$ is selected from N, $N(R^{x1})$ or S, the remaining groups $X^1$ to $X^6$ are each independently selected from $C(R^{x2})$ or $C(R^{x2})(R^{x3})$, one of $X^8$ and $X^9$ is N, and the other one of $X^8$ and $X^9$ is C or $C(R^{x2})$.

It is preferred that A is a bicyclic moiety corresponding to formula (II) as described and defined herein above, wherein the first ring of the bicyclic moiety (i.e. the ring which is linked to the remainder of the compound of general formula (I)) is aromatic, and it is more preferred that A is a bicyclic moiety corresponding to formula (II) as described and defined herein above, wherein the two rings of the bicyclic moiety form an aromatic ring system.

It is particularly preferred that A is one of the following groups:

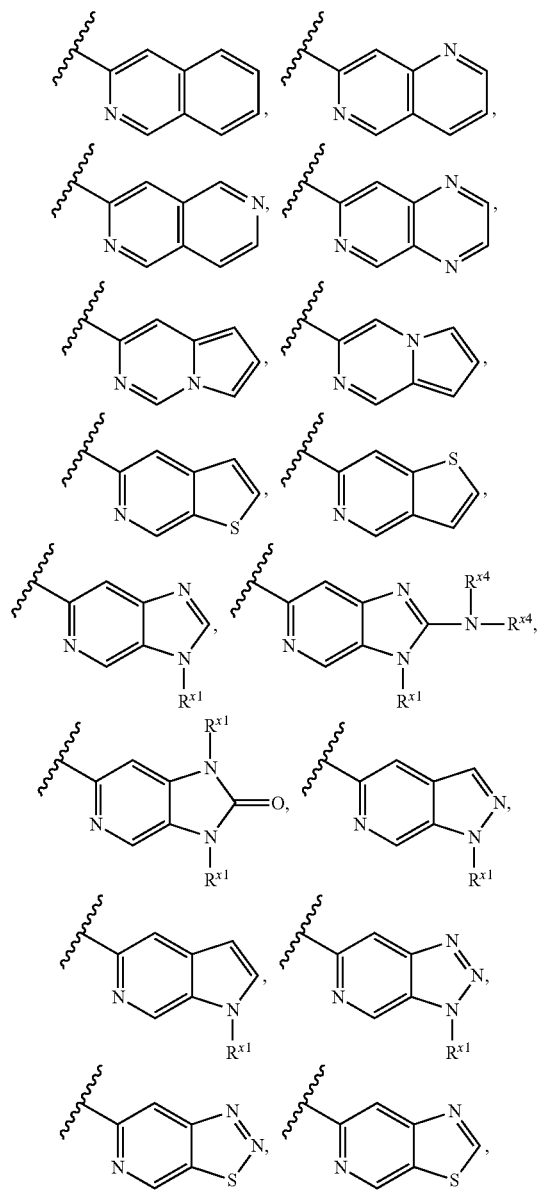

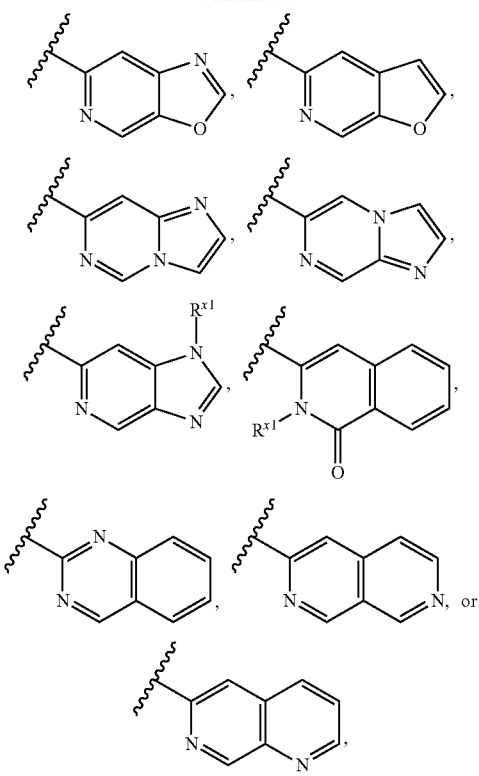

each of which may optionally be substituted on ring carbon atoms with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, and preferably selected from $C_1$-$C_4$ alkyl, halogen, —OH, or —O($C_1$-$C_4$ alkyl). Furthermore, each $R^{x1}$ (if present) is independently selected from hydrogen, $C_1$-$C_4$ alkyl, —OH, or —O($C_1$-$C_4$ alkyl), and preferably selected from hydrogen or $C_1$-$C_4$ alkyl. Each $R^{x4}$ (if present) is independently selected from hydrogen or $C_1$-$C_4$ alkyl, or the two groups $R^{x4}$ (if present) are each independently $C_1$-$C_4$ alkyl and are mutually linked to form a ring (such as, e.g., a pyrrolidinyl ring or a piperidinyl ring) together with the nitrogen atom which they are attached to. It is preferred that the above depicted optionally substituted groups are unsubstituted and $R^{x1}$ (if present) is hydrogen.

More preferably, A is one of the following groups:

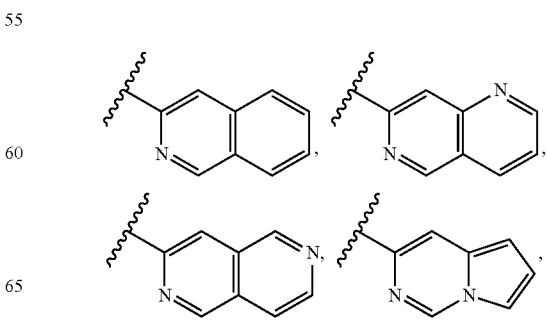

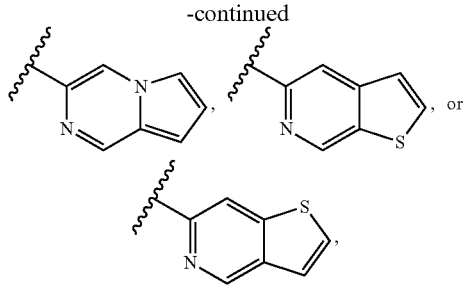

each of which may optionally be substituted on ring carbon atoms with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, and preferably selected from $C_1$-$C_4$ alkyl, halogen, —OH, or —O($C_1$-$C_4$ alkyl). It is preferred that the above depicted optionally substituted groups are unsubstituted.

Even more preferably, A is one of the following groups:

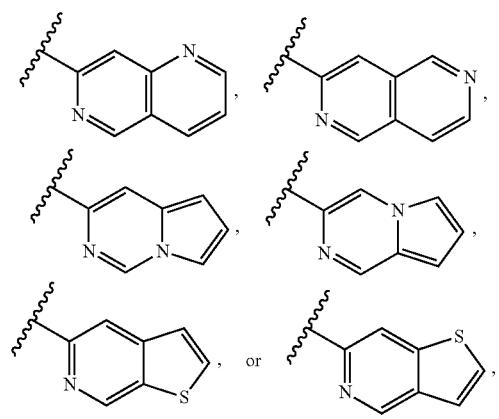

each of which may optionally be substituted on ring carbon atoms with one or more groups independently selected from $C_1$-$C_4$ alkyl, halogen, —$CF_3$, —CN, —OH, —O($C_1$-$C_4$ alkyl), —$NH_2$, —NH($C_1$-$C_4$ alkyl), or —N($C_1$-$C_4$ alkyl)($C_1$-$C_4$ alkyl) wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to, and preferably selected from $C_1$-$C_4$ alkyl, halogen, —OH, or —O($C_1$-$C_4$ alkyl). It is preferred that the above depicted optionally substituted groups are unsubstituted.

It is particularly preferred that the compound of the general formula (I) is selected from:
2-isoquinolin-3-yl-chromen-4-one oxime;
7-bromo-2-isoquinolin-3-yl-chromen-4-one oxime;
7-bromo-2-isoquinolin-3-yl-6-methyl-chromen-4-one oxime;
6-bromo-2-isoquinolin-3-yl-chromen-4-one oxime;
2-isoquinolin-3-yl-6-methyl-chromen-4-one oxime;
6-fluoro-2-isoquinolin-3-yl-chromen-4-one oxime;
6,8-diffluoro-2-isoquinolin-3-yl-chromen-4-one oxime;
8-chloro-2-isoquinolin-3-yl-chromen-4-one oxime;
4-fluoro-2-isoquinolin-3-yl-chromen-4-one-(Z)-oxime;
2-isoquinolin-3-yl-6-trifluoromethoxy-chromen-4-one oxime;
2-isoquinolin-3-yl-6-trifluoromethyl-chromen-4-one oxime;
2-(7-fluoro-isoquinolin-3-yl)-chromen-4-one oxime;
2-(7-methoxy-isoquinolin-3-yl)-chromen-4-one oxime;
2-(6,7-dimethoxy-isoquinolin-3-yl)-chromen-4-one oxime;
2-(6-methyl-isoquinolin-3-yl)-chromen-4-one oxime;
2-(7-chloro-isoquinolin-3-yl)-chromen-4-one oxime;
2-(5-bromo-isoquinolin-3-yl)-chromen-4-one oxime;
2-(5-hydroxy-isoquinolin-3-yl)-chromen-4-one oxime;
2-(5-methoxy-isoquinolin-3-yl)-chromen-4-one oxime;
2-isoquinolin-3-yl-7-phenylethynyl-chromen-4-one oxime;
2-isoquinolin-3-yl-7-((E)-styryl)-chromen-4-one oxime;
2-isoquinolin-3-yl-7-phenethyl-chromen-4-one oxime;
7-ethynyl-2-isoquinolin-3-yl-chromen-4-one oxime;
2-isoquinolin-3-yl-7-(pyridin-2-yl-ethynyl)-chromen-4-one oxime;
2-isoquinolin-3-yl-7-(pyridin-2-yl-ethynyl)-chromen-4-one oxime;
2-isoquinolin-3-yl-7-(pyridin-4-yl)ethynyl-chromen-4-one oxime;
7-(4-dimethylaminophenyl)ethynyl-2-isoquinolin-3-yl-chromen-4-one oxime;
2-isoquinolin-3-yl-7-(3-methoxyphenyl)ethynyl-chromen-4-one oxime;
7-(3-aminophenyl)ethynyl-2-isoquinolin-3-yl-chromen-4-one oxime;
7-(3-hydroxyphenyl)ethynyl-2-isoquinolin-3-yl-chromen-4-one oxime;
2-isoquinolin-3-yl-7-(4-methoxyphenyl)ethynyl-chromen-4-one oxime;
7-(2-chlorophenyl)ethynyl-2-isoquinolin-3-yl-chromen-4-one oxime;
7-(3-dimethylamino-prop-1-ynyl)-2-isoquinolin-3-yl-chromen-4-one oxime;
6-cyclopropyl-2-isoquinolin-3-yl-chromen-4-one oxime;
2-isoquinolin-3-yl-6-(pyrrolidin-1-yl)-chromen-4-one oxime;
2-isoquinolin-3-yl-6-(vinyl)-chromen-4-one oxime;
6-ethyl-2-isoquinolin-3-yl-chromen-4-one oxime;
6-cyano-2-isoquinolin-3-yl-chromen-4-one oxime;
6-dimethylamino-2-isoquinolin-3-yl-chromen-4-one oxime;
2-isoquinolin-3-yl-6-(morpholin-4-yl-methyl)-chromen-4-one oxime;
6-hydroxy-2-isoquinolin-3-yl-chromen-4-one oxime;
2-isoquinolin-3-yl-6-methoxy-chromen-4-one oxime;
2-isoquinolin-3-yl-6-(2-methoxy-ethoxy)-chromen-4-one oxime;
6-(2-dimethylamino-ethoxy)-2-isoquinolin-3-yl-chromen-4-one oxime;
2-isoquinolin-3-yl-6-[3-(4-methyl-piperazin-1-yl)-propylamino]-chromen-4-one oxime;
2-isoquinolin-3-yl-6-[2-(4-methyl-piperazin-1-yl)-ethoxy]-chromen-4-one oxime;
2-isoquinolin-3-yl-7-phenyl-chromen-4-one oxime;
7-(4-biphenyl)-2-isoquinolin-3-yl-chromen-4-one oxime;
2-isoquinolin-3-yl-7-[3-(4-methyl-piperazin-1-yl)-propylamino]-chromen-4-one oxime;
2-Isoquinolin-3-yl-7-{3-[2-(4-methyl-piperazin-1-yl)-ethoxy]-phenylethynyl}-chromen-4-one oxime;
2-Isoquinolin-3-yl-7-{3-methylaminophenylethynyl}-chromen-4-one oxime;
7-(4-Hydroxy-but-1-ynyl)-2-isoquinolin-3-yl-chromen-4-one oxime;
2-Isoquinolin-3-yl-7-{3-(2-methoxy-ethoxy)-phenylethynyl}-chromen-4-one oxime;

2-Isoquinolin-3-yl-7-[3-(2-methoxy-ethoxy)-prop-1-ynyl]-chromen-4-one oxime;
7-but-3-en-1-ynyl-2-Isoquinolin-3-yl-chromen-4-one oxime;
2-isoquinolin-3-yl-7-methoxy-chromen-4-one oxime;
2-isoquinolin-3-yl-7-(2-methoxy-ethoxy)-chromen-4-one oxime;
7-cyano-2-isoquinolin-3-yl-chromen-4-one oxime;
2-Isoquinolin-3-yl-7-[3-(4-methyl-piperazin-1-yl)-prop-1-ynyl]-chromen-4-one oxime;
2-(7-hydroxy-isoquinolin-3-yl)-chromen-4-one oxime;
2-[2,6]Naphthyndin-3-yl-chromen-4-one oxime;
2-[1,6]Naphthyridin-3-yl-chromen-4-one oxime;
2-Pyrrolo[1,2-c]pyrimidin-3-yl-chromen-4-one oxime;
2-(5,7-dimethyl-Pyrrolo[1,2-c]pyrimidin-3-yl)-chromen-4-one oxime;
2-(6-bromo-Pyrrolo[1,2-o]pyrimidin-3-yl)-chromen-4-one oxime;
6-bromo-2-Pyrrolo[1,2-c]pyrimidin-3-yl-chromen-4-one oxime;
6-methoxyethoxy-2-Pyrrolo[1,2-c]pyrimidin-3-yl-chromen-4-one oxime;
2-(1-Benzyl-1H-imidazo[4,5-c]pyridin-6-yl)-chromen-4-one oxime;
2-Thieno[2,3-c]pyridin-5-yl-chromen-4-one oxime;
2-Thieno[3,2-c]pyridin-6-yl-chromen-4-one oxime;
2-Isoquinolin-3-yl-3-methyl-chromen-4-one oxime;
3-{4-[(E)-Hydroxyimino]-4H-1-chromen-2-yl}-2H-isoquinolin-1-one;
2-Imidazo[1,2-c]pyrimidin-7-yl-chromen-4-one oxime;
2-(1H-Pyrrolo[2,3-c]pyridin-5-yl)-chromen-4-one oxime;
2-(1-Hydroxy-1H-pyrrolo[2,3-c]pyridin-5-yl)-chromen-4-one oxime;
2-(1-Methyl-1H-pyrrolo[2,3-c]pyridin-5-yl)-chromen-4-one oxime;
2-(1-Methoxy-1H-pyrrolo[2,3-c]pyridin-5-yl)-chromen-4-one oxime;
6-Hydroxy-2-pyrrolo[1,2-c]pyrimidin-3-yl-chromen-4-one oxime;
2-Thiazolo[5,4-c]pyridin-6-yl-chromen-4-one oxime;
6-(3-Methoxy-propyl)-2-pyrrolo[1,2-c]pyrimidin-3-yl-chromen-4-one oxime;
6-(3-Dimethylamino-propoxy)-2-pyrrolo[1,2-c]pyrimidin-3-yl-chromen-4-one oxime;
6-(3-Morpholin-4-yl-ethoxy)-2-pyrrolo[1,2-c]pyrimidin-3-yl-chromen-4-one oxime;
6-(2,3-Dihydroxy-propoxy)-2-pyrrolo[1,2-c]pyrimidin-3-yl-chromen-4-one oxime;
6-(2-Pyrrolidin-1-yl-ethoxy)-2-pyrrolo[1,2-c]pyrimidin-3-yl-chromen-4-one oxime;
6-(2-Piperidin-1-yl-ethoxy)-2-pyrrolo[1,2-c]pyrimidin-3-yl-chromen-4-one oxime;
6-(2-dimethylamino-ethoxy)-2-pyrrolo[1,2-c]pyrimidin-3-yl-chromen-4-one oxime;
6-(2-diethylamino-ethoxy)-2-pyrrolo[1,2-c]pyrimidin-3-yl-chromen-4-one oxime;
2-Pyrrolo[1,2-a]pyrazin-3-yl-chromen-4-one oxime;
6-[2-(2-methyl-pyrrolidin-1-yl)-ethoxy]-2-pyrrolo[1,2-c]pyrimidin-3-yl-chromen-4-one oxime;
6-[2-(4-methyl-piperazin-1-yl)-ethoxy]-2-pyrrolo[1,2-c]pyrimidin-3-yl-chromen-4-one oxime;
6-[2-(4-methyl-[1,4]diazepan-1-yl)-ethoxy]-2-pyrrolo[1,2-c]pyrimidin-3-yl-chromen-4-one oxime;
6-[2-((S)-2-hydroxymethylpyrroridin-1-yl)-ethoxy]-2-pyrrolo[1,2-c]pyrimidin-3-yl-chromen-4-one oxime;
6-[2-((S)-2-methoxymethylpyrrolidin-1-yl)-ethoxy]-2-pyrrolo[1,2-c]pyrimidin-3-yl-chromen-4-one oxime;
6-[2-((R)-2-methoxymethylpyrrolidin-1-yl)-ethoxy]-2-pyrrolo[1,2-c]pyrimidin-3-yl-chromen-4-one oxime;
6-[2-(3-hydroxy-pyrrolidin-1-yl)-ethoxy]-2-pyrrolo[1,2-c]pyrimidin-3-yl-chromen-4-one oxime;
6-[2-(4-dimethylamino-piperidin-1-yl)-ethoxy]-2-pyrrolo[1,2-c]pyrimidin-3-yl-chromen-4-one oxime;
6-(2-cyclopentylamino-ethoxy)-2-pyrrolo[1,2-c]pyrimidin-3-yl-chromen-4-one oxime;
6-(3-morpholin-4-yl-propoxy)-2-pyrrolo[1,2-c]pyrimidin-3-yl-chromen-4-one oxime;
6-(4-morpholin-4-yl-butyl)-2-pyrrolo[1,2-c]pyrimidin-3-yl-chromen-4-one oxime;
6-(4,4-difluoro-piperidin-1-yl)-2-pyrrolo[1,2-c]pyrimidin-3-yl-chromen-4-one oxime;
6-{2-[bis-(2-methoxy-ethyl)-amino]-ethoxy}-2-pyrrolo[1,2-c]pyrimidin-3-yl-chromen-4-one oxime;
6-(2-Imidazol-1-yl-ethoxy)-2-pyrrolo[1,2-c]pyrimidin-3-yl-chromen-4-one oxime;
6-(3-morpholin-4-yl-propyl)-2-pyrrolo[1,2-c]pyrimidin-3-yl-chromen-4-one oxime;
6-((Z)-3-Morpholin-4-yl-propenyl))-2-pyrrolo[1,2-c]pyrimidin-3-yl-chromen-4-one oxime;
6-[2-(3-methoxy-piperidin-1-yl)-ethoxy]-2-pyrrolo[1,2-c]pyrimidin-3-yl-chromen-4-one oxime;
6-[2-(4-fluoro-phenyl)-ethoxy]-2-pyrrolo[1,2-c]pyrimidin-3-yl-chromen-4-one oxime;
2-quinazolin-2-yl-chromen-4-one oxime;
6-[(1S,4S)-2-(2-oxa-5-aza-bicyclo[2.2.1]hept-5-yl)-ethoxy]-2-pyrrolo[1,2-c]pyrimidin-3-yl-chromen-4-one oxime;
6-[2-(cis-2,6-dimethyl-morpholin-4-yl)-ethoxy]-2-pyrrolo[1,2-c]pyrimidin-3-yl-chromen-4-one oxime;
2-pyrrolo[1,2-c]pyrimidin-3-yl-6-[2-(4-trifluoromethyl-piperidin-1-yl)-ethoxy]-chromen-4-one oxime;
6-[2-(3,3-difluoro-piperidin-1-yl)-ethoxy]-2-pyrrolo[1,2-c]pyrimidin-3-yl-chromen-4-one oxime;
4-(hydroxyimino)-2-pyrrolo[1,2-c]pyrimidin-3-yl-4H-chromene-6-carboxylic acid (2-morpholin-4-yl-ethyl)-amide;
6-(2-[1,4']bipiperidinyl-1'-yl-ethoxy)-2-pyrrolo[1,2-c]pyrimidin-3-yl-chromen-4-one oxime;
6-(2-[1,4]oxazepan-4-yl-ethoxy)-2-pyrrolo[1,2-c]pyrimidin-3-yl-chromen-4-one oxime;
6-[2-(4-pyrrolidin-1-yl-piperidin-1-yl)-ethoxy]-2-pyrrolo[1,2-c]pyrimidin-3-yl-chromen-4-one oxime;
6-[2-(3,3-difluoro-pyrrolidin-1-yl)-ethoxy]-2-pyrrolo[1,2-c]pyrimidin-3-yl-chromen-4-one oxime;
7-[3-(3-dimethylamino-propoxy)-phenylethynyl]-2-pyrrolo[1,2-c]pyrimidin-3-yl-chromen-4-one oxime;
6-[2-(4-ethyl-piperazin-1-yl)-ethoxy]-2-pyrrolo[1,2-c]pyrimidin-3-yl-chromen-4-one oxime;
6-(2-amino-ethoxy)-2-pyrrolo[1,2-c]pyrimidin-3-yl-chromen-4-one oxime;
6-(2-Morpholin-4-yl-ethoxy)-2-(8aH-pyrrolo[1,2-a]pyrazin-3-yl)-chromen-4-one oxime;
6-[2-(4,4-Difluoro-piperidin-1-yl)-ethoxy]-2-pyrrolo[1,2-a]pyrazin-3-yl-chromen-4-one oxime;
6-(2-Imidazol-1-yl-ethoxy)-2-pyrrolo[1,2-a]pyrazin-3-yl-chromen-4-one oxime;
6-[2-(4-Fluoro-phenyl)-ethoxy]-2-pyrrolo[1,2-a]pyrazin-3-yl-chromen-4-one oxime;
6-(2-Morpholin-4-yl-ethoxy)-2-thieno[3,2-c]pyridin-6-yl-chromen-4-one oxime;
6-[2-(4,4-Difluoro-piperidin-1-yl)-ethoxy]-2-thieno[3,2-c]pyridin-6-yl-chromen-4-one oxime;
6-(2-imidazol-1-yl-ethoxy)2-thieno[3,2-c]pyridin-6-yl-chromen-4-one oxime;

6-[2-(4-Fluoro-phenyl)-ethoxy]-2-thieno[3,2-c]pyridin-6-yl-chromen-4-one oxime;
6-[2-(3,3-Difluoro-piperidin-1-yl)-ethoxy]-2-thieno[3,2-c]pyridin-6-yl-chromen-4-one oxime;
6-[2-(2,6-Dimethyl-morpholin-4-yl)-ethoxy]-2-thieno[3,2-c]pyridin-6-yl-chromen-4-one oxime;
6-[2-(3,3-Difluoro-pyrrolidin-1-yl)-ethoxy]-2-thieno[3,2-c]pyridin-6-yl-chromen-4-one oxime;
6-(3-Pyridin-4-yl-propoxy)-2-thieno[3,2-c]pyridin-6-yl-chromen-4-one oxime;
6-(3-Pyridin-3-yl-propoxy)-2-thieno[3,2-c]pyridin-6-yl-chromen-4-one oxime;
6-(2-Pyridin-4-yl-ethoxy)-2-pyrrolo[1,2-c]pyrimidin-3-yl-chromen-4-one oxime;
2-Pyrrolo[1,2-c]pyrimidin-3-yl-6-[2-(4-trifluoromethyl-phenyl)-ethoxy]-chromen-4-one, oxime;
6-[2-(3-Fluoro-phenyl)-ethoxy]-2-pyrrolo[1,2-c]pyrimidin-3-yl-chromen-4-one, oxime;
5-Methoxy-2-pyrrolo[1,2-c]pyrimidin-3-yl-chromen-4-one oxime;
6-[2-(4-Chloro-phenyl)-ethoxy]-2-pyrrolo[1,2-c]pyrimidin-3-yl-chromen-4-one oxime;
2-Pyrrolo[1,2-c]pyrimidin-3-yl-6-[2-(3-trifluoromethyl-phenyl)-ethoxy]-chromen-4-one oxime;
7-(2-Morpholin-4-yl-ethoxy)-2-pyrrolo[1,2-c]pyrimidin-3-yl-chromen-4-one oxime;
7-(3-Morpholin-4-yl-propoxy)-2-pyrrolo[1,2-c]pyrimidin-3-yl-chromen-4-one oxime;
6-[(4-Fluoro-benzylamino)-methyl]-2-pyrrolo[1,2-c]pyrimidin-3-yl-chromen-4-one oxime;
6-{[2-(4-Fluoro-phenyl)-ethylamino]-methyl}-2-pyrrolo[1,2-c]pyrimidin-3-yl-chromen-4-one oxime;
6-Phenethyloxy-2-pyrrolo[1,2-c]pyrimidin-3-yl-chromen-4-one oxime;
6-[2-(Pyridin-4-yloxy)-ethoxy]-2-pyrrolo[1,2-c]pyrimidin-3-yl-chromen-4-one oxime;
6-[2-(Pyridin-3-yloxy)-ethoxy]-2-pyrrolo[1,2-c]pyrimidin-3-yl-chromen-4-one oxime;
6-[3-(Pyridin-3-yloxy)-propoxy]-2-pyrrolo[1,2-c]pyrimidin-3-yl-chromen-4-one oxime;
N-(4-Fluoro-phenyl)-2-{4-hydroxyimino-2-pyrrolo[1,2-c]pyrimidin-3-yl-4H-chromen-6-yloxy}-acetamide;
N-(4-Fluoro-phenyl)-2-{4-hydroxyimino-2-pyrrolo[1,2-c]pyrimidin-3-yl-4H-chromen-6-yloxy}-N-methyl-acetamide;
N-(5-Fluoro-pyridin-2-yl)-2-{4-hydroxyimino-2-pyrrolo[1,2-c]pyrimidin-3-yl-4H-chromen-6-yloxy}-acetamide;
2-Pyrrolo[1,2-c]pyrimidin-3-yl-5-trifluoromethyl-chromen-4-one oxime;
2-(7-tert-Butyl-pyrrolo[1,2-c]pyrimidin-3-yl)-6-(2-morpholin-4-yl-ethoxy)-chromen-4-one oxime;
7-(2-Morpholin-4-yl-ethoxy)-2-thieno[2,3-c]pyridin-5-yl-chromen-4-one oxime;
5-(2-Morpholin-4-yl-ethoxy)-2-pyrrolo[1,2-c]pyrimidin-3-yl-chromen-4-one oxime;
5-(3-Morpholin-4-yl-propoxy)-2-pyrrolo[1,2-c]pyrimidin-3-yl-chromen-4-one oxime;
6-(2-Morpholin-4-yl-ethoxy)-2-thieno[2,3-c]pyridin-5-yl-chromen-4-one oxime;
6-(3-Pyridin-4-yl-propoxy)-2-pyrrolo[1,2-c]pyrimidin-3-yl-chromen-4-one oxime;
6-(2-Phenoxy-ethoxy)-2-pyrrolo[1,2-c]pyrimidin-3-yl-chromen-4-one oxime;
6-[3-(4-Fluoro-phenoxy)-propoxy]-2-pyrrolo[1,2-c]pyrimidin-3-yl-chromen-4-one oxime;
6-(3-Phenoxy-propoxy)-2-pyrrolo[1,2-c]pyrimidin-3-yl-chromen-4-one oxime;
6-[3-(3-Fluoro-phenoxy)-propoxy]-2-pyrrolo[1,2-c]pyrimidin-3-yl-chromen-4-one oxime;
6-[3-(3,4-Difluoro-phenoxy)-propoxy]-2-pyrrolo[1,2-c]pyrimidin-3-yl-chromen-4-one oxime;
6-(2-[1,4]Oxazepan-4-yl-ethoxy)-2-thieno[3,2-c]pyridin-6-yl-chromen-4-one oxime;
6-[2-(3,4-Dihydro-1H-isoquinolin-2-yl)-ethoxy]-2-thieno[3,2-c]pyridin-6-yl-chromen-4-one oxime;
6-[2-(4-fluoro-piperidin-1-yl)-ethoxy]-2-thieno[3,2-c]pyridin-6-yl-chromen-4-one oxime;
6-[2-(1,1-Dioxo-1-thiamorpholin-4-yl)-ethoxy]-2-thieno[3,2-c]pyridin-6-yl-chromen-4-one oxime;
6-(1-Pyrimidin-2-yl-piperidin-4-yloxy)-2-thieno[3,2-c]pyridin-6-yl-chromen-4-one oxime;
6-(3,4,5,6-Tetrahydro-2H-[1,2']bipyridinyl-4-yloxy)-2-thieno[3,2-c]pyridin-6-yl-chromen-4-one oxime; and pharmaceutically acceptable salts, solvates and prodrugs thereof.

Compounds of the present invention are characterized in that they provide mGluR4 activity due to two specific features: 1) the presence of a bicyclic ring on position 2 of the chromone ring (i.e. as group A in formula (I)), and 2) the presence of a nitrogen atom on the first ring of that bicyclic ring and at the position adjacent to the carbon linked to the chromone moiety but not adjacent to any of the two ring atoms which form part of both rings condensed to said bicyclic ring, as shown in the scheme below. It will be understood that this is a schematic representation, and that the N atom in the bicyclic system can be bound via a double bond in the ring structure or can carry a substituent as defined above:

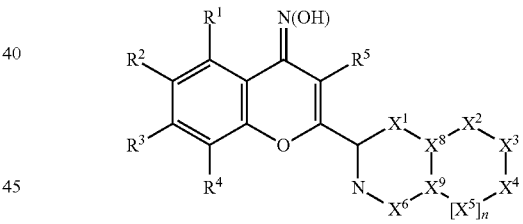

This can be demonstrated, e.g. from the comparison of activities of the compounds depicted in the following scheme:

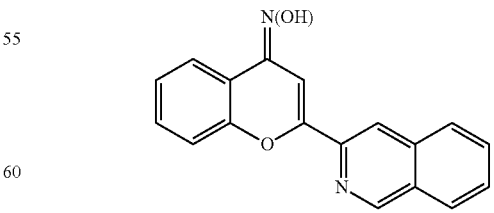

Example 1
mGluR4 PAM
$EC_{50} < 0.5$ μM

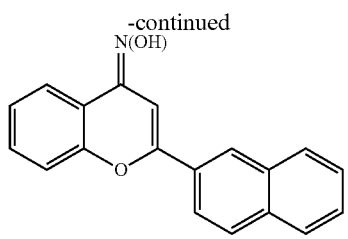

Example 74 (reference)
Inactive on mGluR4 up to 100 μM

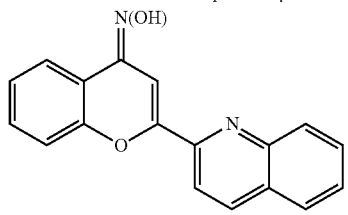

Example 79 (reference)
Inactive on mGluR4 up to 100 μM

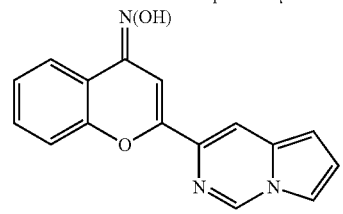

Example 63
mGluR4 PAM
$EC_{50} < 0.5$ μM

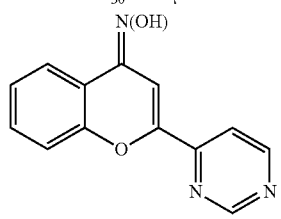

Example 80 (reference)
Inactive on mGluR4 up to 100 μM

Example 1 is a positive allosteric modulator (PAM) of mGluR4 having an $EC_{50}$ lower than 1 μM. Example 74 (reference), which has no PAM activity on mGluR4 up to 100 μM, is the isoster of example 1 without the nitrogen atom on the required position. Example 79 (reference), which has no PAM activity on mGluR4 up to 100 μM, is the isomer of example 1 with a nitrogen atom on the other position adjacent to the carbon linked to the chromone moiety. Comparison of activities of these three molecules demonstrates that a nitrogen atom on the position $X^7$ of Formula (II) is required for the mGluR4 PAM activity.

Similarly, example 63 is an mGluR4 PAM having an $EC_{50}$ lower than 1 μM. Example 80 (reference), that has no PAM activity on mGluR4 up to 100 μM, is an analog of example 63 with a monocyclic heteroaryl. Comparison of activities of these two molecules demonstrates that a bicyclic ring is required as moiety A in formula (I) for the mGluR4 PAM activity.

Experimental details of the syntheses and evaluations of examples 1, 63, 74 (reference), 79 (reference) and 80 (reference) are provided in the Examples section of this application.

All isomers, including configuration isomers and possible stereoisomers of the compounds according to the invention are contemplated as part of the present invention, either in admixture or in pure or substantially pure form. In particular, the compounds and compositions of the invention may have the E- and the Z-configuration of the oxime group (=N(OH)) shown in formula (I), and the invention comprises compounds and compositions only showing the E-configuration, those showing only the Z-configuration, and mixtures of the E- and the Z-configuration.

As for stereoisomers, it embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active counterpart followed by crystallization.

As used herein, "alkyl" represents a straight or branched chain saturated hydrocarbon residue which does not comprise any carbon-to-carbon double bonds or carbon-to-carbon triple bonds.

As used herein, "alkenyl" represents a straight or branched chain unsaturated hydrocarbon residue comprising at least one carbon-to-carbon double bond.

As used herein, "alkynyl" represents a straight or branched chain unsaturated hydrocarbon residue comprising at least one carbon-to-carbon triple bond.

As used herein, "alkylene" represents a straight or branched chain alkanediyl group which does not comprise any carbon-to-carbon double bonds or carbon-to-carbon triple bonds.

As used herein, "alkenylene" represents a straight or branched chain alkenediyl group comprising at least one carbon-to-carbon double bond.

As used herein, "alkynylene" represents a straight or branched chain alkynediyl group comprising at least one carbon-to-carbon triple bond.

As used herein, "aryl" represents a 6-10 membered aromatic hydrocarbon ring, including bridged ring or fused ring systems containing at least one aromatic ring. "Aryl" may, for example, refer to phenyl or naphthyl.

As used herein, "heteroaryl" represents a 5-14 membered aromatic ring, including bridged ring or fused ring systems containing at least one aromatic ring, comprising one or more (such as, e.g., one, two, or three) ring heteroatoms independently selected from O, S, or N, wherein one or more of said S ring atoms (if present) and/or one or more of said N ring atoms (if present) may optionally be oxidized. A "heteroaryl", as defined herein above, preferably represents a 5-14 membered aromatic ring, including bridged ring or fused ring systems containing at least one aromatic ring, comprising one or more (such as, e.g., one, two, or three) ring heteroatoms independently selected from O, S, or N. "Heteroaryl" may, for example, refer to thienyl (thiophenyl), benzo[b]thienyl, naphtho[2,3-b]thienyl, thianthrenyl, furyl (furanyl), isobenzofuranyl, chromenyl, xanthenyl, phenoxathiinyl, pyrrolyl (including, without limitation, 2H-pyrrolyl), imidazolyl, pyrazolyl, pyridyl (pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, perimidinyl, phenanthrolinyl (including, without limitation, [1,10]

phenanthrolinyl, [1,7]phenanthro-linyl, and [4,7]phenanthrolinyl), phenazinyl, isothiazolyl, phenothiazinyl, oxazolyl, isoxazolyl, furazanyl, phenoxazinyl, pyrazolo[1,5-a]pyrimidinyl (including, without limitation, pyrazolo[1,5-a]pyrimidin-3-yl), 1,2-benzoisoxazol-3-yl, or benzimidazolyl.

As used herein, "cycloalkyl" represents a 3-10 membered saturated hydrocarbon ring, including bridged ring or fused ring systems. "Cycloalkyl" may, for example, refer to cyclopropyl, cyclobutyl, cyclopentyl, cyclohexyl, or cycloheptyl.

As used herein, "heterocycloalkyl" represents a 3-10 membered saturated ring, including bridged ring, spiro ring or fused ring systems, containing one or more (such as, e.g., one, two, or three) ring heteroatoms independently selected from O, S, or N, wherein one or more of said S ring atoms (if present) and/or one or more of said N ring atoms (if present) may optionally be oxidized. A "heterocycloalkyl", as defined herein above, preferably represents a 3-10 membered saturated ring, including bridged ring or fused ring systems, containing one or more (such as, e.g., one, two, or three) ring heteroatoms independently selected from O, S, or N. "Heterocycloalkyl" may, for example, refer to tetrahydrofuranyl, piperidinyl, piperazinyl, aziridinyl, azetidinyl, pyrrolidinyl, imidazolidinyl, morpholinyl, pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl.

As used herein, "halogen" represents fluoro, chloro, bromo, or iodo, and in particular fluoro, chloro, or bromo.

Various groups are referred to as being "optionally substituted" in the context of this description. Generally, these groups may carry one or more, such as e.g. one, two, three or four substituents. Unless defined otherwise in the specific context, these groups carry preferably not more than two substituents.

The scope of the invention embraces all pharmaceutically acceptable salt forms of the compounds of the general formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of the general formula (I) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Pharmaceutically acceptable prodrugs of compounds that can be used in the present invention, in particular the compounds of the general formula (I), are derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention, in particular a compound of the general formula (I), has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamidoester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$. Accordingly, the oxime —OH group of the compounds of the general formula (I) may be in the form of an O-acyl-oxime (or acyloxy derivative), such as, e.g., —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. The oxime —OH group of the compounds of the general formula (I) may also be in the form of O-alkyl-oxime such as, e.g., —O—CH$_3$, —O—C$_2$H$_5$, —O—C$_3$H$_7$ or —O-(tert-butyl). The oxime —OH group of the compounds of the general formula (I) may also be in the form of O-dialkylphosphinyloxy such as —O—P(=O)—[O—(CH$_3$)$_2$], —O—P(=O)—[O—(C$_2$-C$_5$)$_2$], —O—P(=O)—[O—(C$_3$-C$_7$)$_2$] or —O—P(=O)—[O-(tert-butyl)$_2$] or in the form of O-phosphoric acid —O—P(=O)—(OH)$_2$ or in the form of —O-sulfuric acid —O—SO$_2$—OH.

The compounds described herein, in particular the compounds of general formula (I), may be administered as compounds per se or may be formulated as medicaments. Within the scope of the present invention are pharmaceutical compositions comprising as an active ingredient one or more compounds of the general formula (I), as defined herein above. The pharmaceutical compositions may optionally comprise one or more pharmaceutically acceptable excipients, such as carriers, diluents, fillers, disintegrants, lubricating agents, binders, colorants, pigments, stabilizers, preservatives, or antioxidants.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds according to the invention, in particular the compounds of the general formula (I), or the above described pharmaceutical compositions comprising one or more compounds of the general formula (I) may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water:

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the general formula (I) for administration to a human (of approximately 70 kg body weight) may be 0.05 to 2000 mg, preferably 0.1 mg to 1000 mg, of the active ingredient per unit dose.

The unit dose may be administered, for example, 1 to 4 times per day. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

The subject or patient, such as the subject in need of treatment or prophylaxis, may be a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melagonaster* and nematodes like *Caenorhabditis olegans*. Non-limiting examples of agronomically important animals are sheep, cattle and pig, while, for example, cats and dogs may be considered as economically important animals. Preferably, the subject/patient is a mammal; more preferably, the subject/patient is a human.

The term "treatment of a disorder or disease" as used herein is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e. diagnose a disorder or disease).

"Treatment of a disorder or disease" may, for example, lead to a halt in the progression of the disorder or disease (e.g. no deterioration of symptoms) or a delay in the progression of the disorder or disease (in case the halt in progression is of a transient nature only). "Treatment of a disorder or disease" may also lead to a partial response (e.g. amelioration of symptoms) or complete response (e.g. disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g. the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prophylaxis of a disorder or disease" as used herein is well known in the art. For example, a patient/subject suspected of being prone to suffer from a disorder or disease as defined herein may, in particular, benefit from a prophylaxis of the disorder or disease. Said subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in said patient/subject (for example, said patient/subject does not show any clinical or pathological symptoms). Thus, the term "prophylaxis" comprises the use of compounds of the present invention before any clinical and/or pathological symptoms are diagnosed or determined or can be diagnosed or determined by the attending physician. The terms "prophylaxis" and "prevention" are used herein interchangeably.

In the method for identifying an agent that binds to metabotropic glutamate receptor 4 (mGluR4) described herein above, the test agent may, for example, be selected from nucleic acids, DNA, RNA, PNA, oligonucleotides, aptamers (Gold, Ann. Rev. Biochem. 64 (1995), 763-797)), aptazymes, RNAzymes, ribozymes (see e.g., EP-B1 0 291 533, EP-A1 0 321 201, EP-B1 0 360 257), antisense DNA, antisense oligonucleotides, antisense RNA, siRNA, RNAi, shRNA, amino acids, peptides, polypeptides, proteins, glycoproteins, lipoproteins, nucleoproteins, antibodies (Harlow and Lane "Antibodies, A Laboratory Manual", CSH Press, Cold Spring Harbor, 1988), monocloncal antibodies, polyclonal antibodies, immunoglobulins, affibodies (Hansson, Immunotechnology 4 (1999), 237-252; Henning, Hum Gene Ther. 13 (2000), 1427-1439), immunoreactive fragments, immunoreactive derivatives, antigens, epitopes, haptens, cell-surface molecules, cofactors, ligands, small organic molecules, lectins or derivatives thereof, lectin fragments, trinectins (Phylos Inc., Lexington, Mass., USA; Xu, Chem. Biol. 9 (2002), 933), anticalins (EP-B-1 1 017 814), hormones, peptide and protein hormones, non-peptide hormones, steroids, interleukins, interferons, cytokines, neurotransmitters, toxins, enzymes, polysaccharides, carbohydrates, lipids, lipopolysaccharides, vitamins, crown ethers, cyclodextrins, cryptands, calixarenes, aldehydes, thiols, amines, drugs, drugs of abuse, therapeutic agents, medicaments, pharmaceuticals, substrates, fragments, portions, components or products of microorganisms, metabolites of or antibodies to any of the above substances and the like.

EXPERIMENTAL PROCEDURES

Method A

The 2-heterocyclic substituted chromones of the invention may be prepared using a common synthetic scheme illustrated in example 1A, differing only in the starting phenol and heteroaryl ester (or heterocycloalkyl ester) compounds. (J. Med. Chem., 1999, 42 (11), 1881-1893).

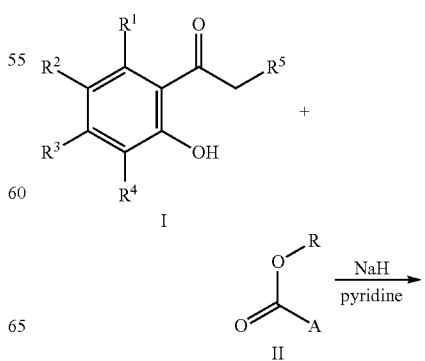

-continued

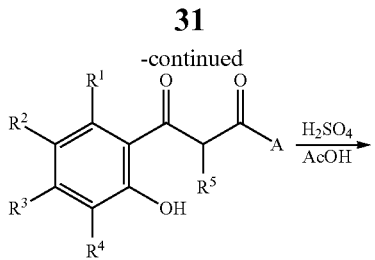

III

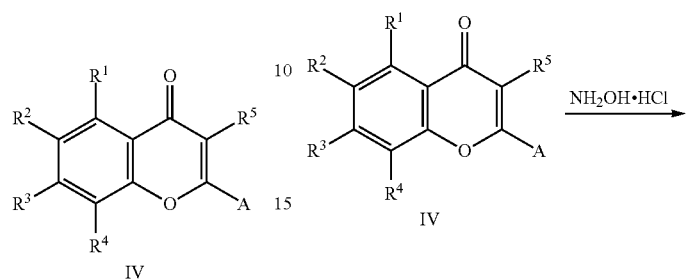

IV

Specifically, a substituted 2'-hydroxyphenyl ketone of Formula I, wherein $R^1$, $R^2$, $R^3$, $R^4$, and $R^5$ are as described and defined herein above, is reacted with an appropriate heteroaryl ester or heterocycloalkyl ester of Formula II, wherein R is methyl or ethyl and A is as described and defined herein above, in a solvent such as pyridine and in presence of a strong base, preferentially sodium hydride, to yield the corresponding diketone III. The diketone III is treated in strong acidic conditions especially with sulfuric acid ($H_2SO_4$) in acetic acid (AcOH) to give the desired chromone IV.

Method B 2-heterocyclic substituted chromones IV can also be prepared using a typical 3 steps procedure well known in the art for flavone derivatives synthesis (eg. *J. Med. Chem.*, 2004, 47, 6466-6475; *J. Org. Chem.* 1993, 68, 7903-7905; US04065467). Substituted 2'-hydroxyacetophenone I is reacted with a heteroaryl carboxylic acid or a heterocycloalkyl carboxylic acid of formula II, wherein R is hydrogen and A is as described and defined herein above, preferentially activated as acid chloride in pyridine to yield the corresponding ester of Formula V. The ester is treated with a strong base, preferentially potassium hydroxide, in a suitable solvent such as pyridine to perform the mixed Claisen rearrangement and to give the corresponding diketone of formula III. The diketone III is then treated in strong acidic conditions especially with sulfuric acid in acetic acid to give the desired chromone of formula IV.

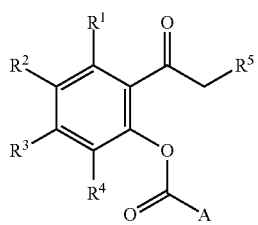

V

Method C

The chromone oximes of the invention of formula VI, in particular the compounds of the general formula (I), may be prepared by the following procedure illustrated in example 73. The chromone derivative of formula IV, which may be prepared according to method A or method B as described herein above, is treated with hydroxylamine hydrochloride in pyridine or methanol under microwave irradiation to yield directly the oxime compound of formula VI.

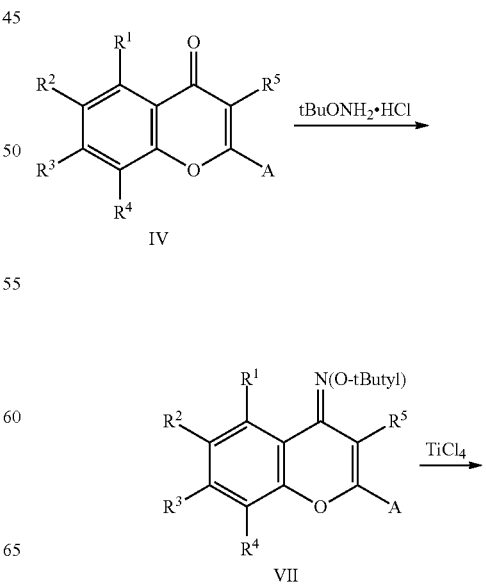

Method D

The chromone oximes of the invention of formula VI, in particular the compounds of the general formula (I), may also be obtained using the following two steps procedure illustrated in example 1B and 1C: The appropriate chromone of formula IV, which may be prepared according to method A or method B as described herein above, is reacted with tert-butyl hydroxylamine hydrochloride in a suitable solvent such as methanol and under microwave irradiation to yield the protected tert-butyloxime product of formula VII (step 1). The protected oxime VII is treated with a Lewis acid such as titanium tetrachloride in an inert solvent, preferentially dichloromethane, to give the desired free oxime of formula VI (WO2004/52869) (step 2).

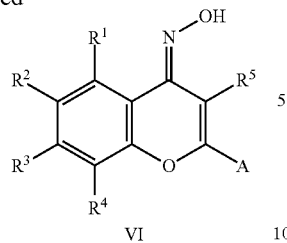

VI

The compounds of the present invention can be radiolabeled by carrying out their synthesis using precursors comprising at least one atom which is a radioisotope. Preferably, radioisotopes of carbon atoms, hydrogen atoms, sulfur atoms, or iodine atoms are employed, such as e.g., $^{14}C$, $^{3}H$, $^{35}S$, or $^{125}I$. Compounds labeled with $^{3}H$ (tritium) can also be prepared by subjecting a compound of the invention to a hydrogen exchange reaction such as, e.g., a platinum-catalyzed exchange reaction in tritiated acetic acid (i.e., acetic acid comprising $^{3}H$ instead of $^{1}H$), an acid-catalyzed exchange reaction in tritiated trifluoroacetic acid, or a heterogeneous-catalyzed exchange reaction with tritium gas. For a person skilled in the field of synthetic chemistry, various further ways for radio-labeling the compounds of the present invention or preparing radio-labeled derivatives of the compounds are readily apparent. Fluorescent labels can be bound to the compounds according to the invention following methods well established in the art.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BRIEF DESCRIPTION OF DRAWINGS

The invention is also illustrated by the following illustrative figures. The appended figures show.

Figure 1:
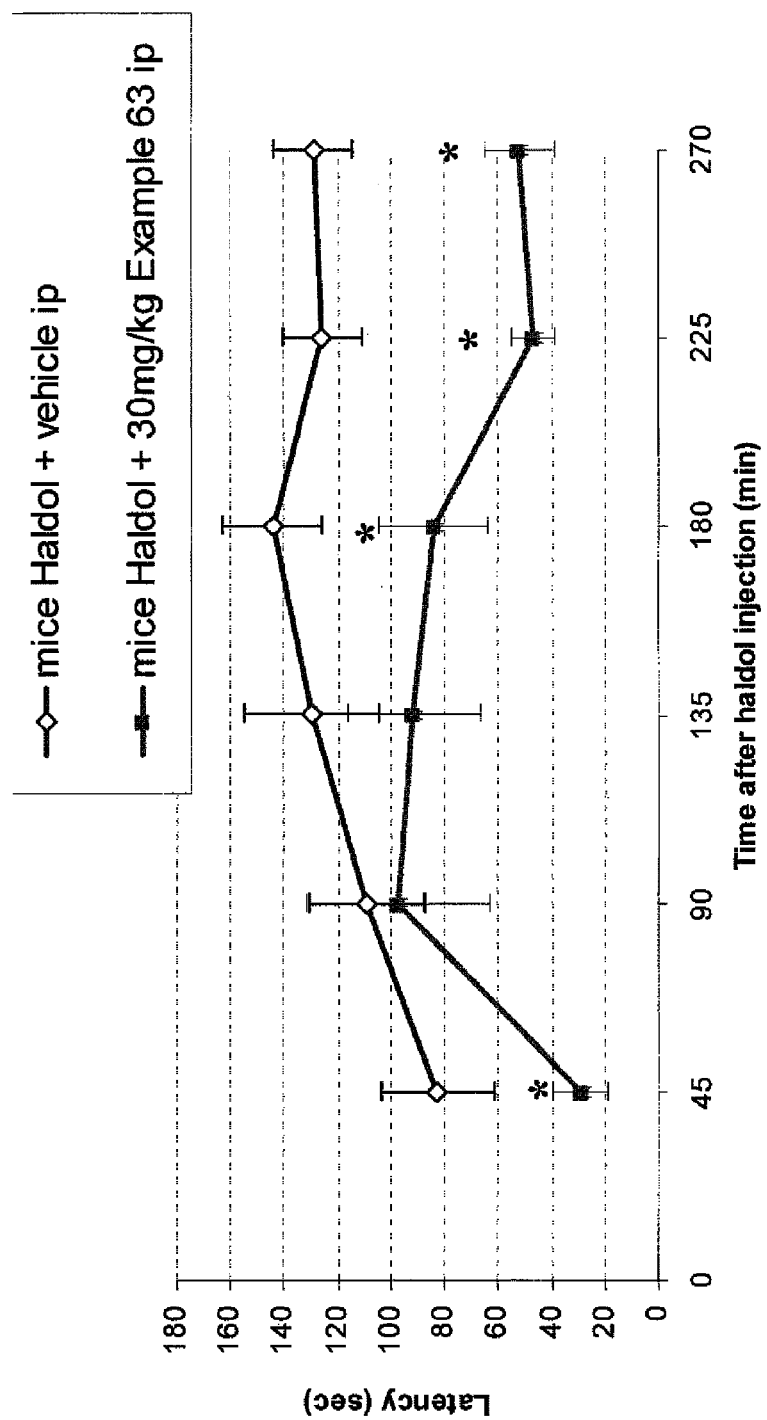
FIG. 1: Effect of the compound of Example 63 administered intraperitoneally in the haloperidol-induced catalepsy test in the mouse. As also explained in Example 172, the figure shows the mean time of latency spent on the bar in each group of animals. At each time-point, the anticataleptic effect of the compound of Example 63 was compared to the vehicle-treated group using ANOVA test followed by the Dunnett's test (*=p<0.05).

The invention will now be described by reference to the following examples, which are merely illustrative and are not to be construed as a limitation of the scope of the present invention. It will be understood that both possible configurations of the oxime group in the figures of the examples can be obtained.

Example 1

2-isoquinolin-3-yl-chromen-4-one oxime

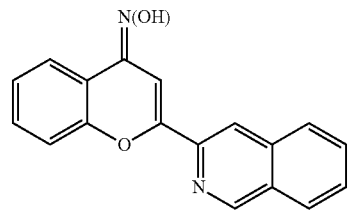

Example 1A 2-isoquinolin-3-yl-chromen-4-one

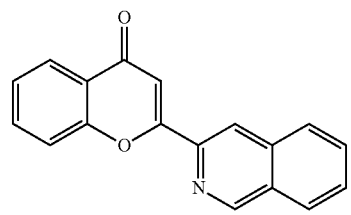

To a suspension of sodium hydride (60% in mineral oil, 227 mg, 5.7 mmol) in dry pyridine (4 ml) was added dropwise a solution of methyl isoquinoline-3-carboxylate (390 mg, 2.08 mmol) and 2'-hydroxy-acetophenone (257 mg, 1.89 mmol) in dry pyridine (4 ml). The mixture was heated at 90° C. for 15 min., cooled to room temperature and poured into an ice cooled 1N hydrochloric acid aqueous solution. The product was extracted in dichloromethane. The organic layers were washed with a 1N hydrochloric acid solution, brine, dried over sodium sulfate and concentrated to dryness. The residue was dissolved in acetic acid (10 ml) and treated with sulfuric acid (40 µl). The solution was heated to 100° C. for 30 min. and cooled to room temperature. The solvents were removed under vacuum distillation. The solid was triturated in water, filtered, washed with a saturated solution of sodium hydrogenocarbonate and water. The solid was dried under vacuum to yield 2-Isoquinolin-3-yl-chromen-4-one (459 mg, 89%) as beige solid.

1H NMR CDCl$_3$ δ (ppm): 9.32 (s, 1H), 8.49 (s, 1H), 8.27 (d, J=7.3 Hz, 1H), 8.06 (d, J=7.9 Hz, 1H), 8.01 (d, J=7.9 Hz, 1H), 7.85-7.63 (m, 4H), 7.59 (s, 1H), 7.44 (t, J=7.2 Hz, 1H).

Example 1B 2-isoquinolin-3-yl-chromen-4-one O-tert-butyl-oxime

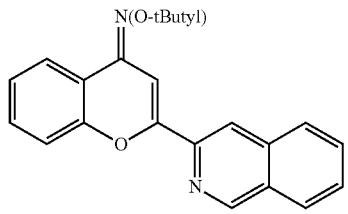

To a suspension of 2-isoquinolin-3-yl-chromen-4-one (459 mg, 1.67 mmol) in methanol (11 ml) was added O-tert-butyl hydroxylamine hydrochloride (421 mg, 3.35 mml). The mixture was heated to 130° C. under microwave irradiation for 30 min. The volatiles were removed by vacuum distillation and the residue was purified by flash chromatography (cyclohexane/ethyl acetate 95/5) to yield 2-isoquinolin-3-yl-chromen-4-one O-tert-butyl-oxime (387 mg, 67%) as a yellow solid.

1H NMR: CDCl$_3$ δ (ppm): 9.29 (s, 1H), 8.10 (dd, J=7.9 Hz, J=1.5 Hz, 1H), 8.01 (d, J=7.7 Hz, 1H), 7.95 (d, J=7.9 Hz, 1H), 7.80 (s, 1H), 7.75 (td, J=7.0 Hz, J=1.1 Hz, 1H), 7.65 (td, J=7.5 Hz, J=1.1 Hz, 1H), 7.42 (td, J=7.7 Hz, J=1.7 Hz, 1H), 7.34 (dd, J=8.3 Hz, J=1.3 Hz, 1H), 7.21 (td, J=7.4 Hz, J=1.3 Hz, 1H), 1.43 (s, 9H).

Example 1C 2-isoquinolin-3-yl-chromen-4-one oxime

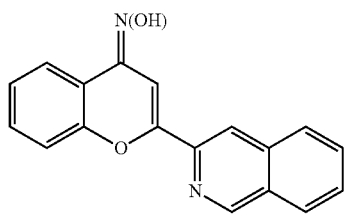

To an ice cooled solution of 2-isoquinolin-3-yl-chromen-4-one O-tert-butyl-oxime (136 mg, 0.39 mmol) in dichloromethane (10 ml) was cautiously added dropwise a 1M solution of titanium tetrachloride in dichloromethane (1.2 ml, 1.2 mmol). The mixture was stirred at 0° C. 2 hours, then at room temperature 2 more hours and poured onto ice cold water (100 ml). The mixture was basified using a 6N aqueous sodium hydroxide solution until pH 10 and the yellow precipitate was collected by filtration. The solid was washed with water, dried and purified by flash chromatography (cyclohexane/ethyl acetate/dichloromethane:80/10/10; 60/30/10 then 0/50/50) to yield 2-isoquinolin-3-yl-chromen-4-one oxime (71 mg, 62%) as a yellow solid. The product was isolated as a 95/5 mixture of Z/E oxime isomers.

Mp: 247-249° C.

HPLC (gradient 5% 95 ACN/H$_2$O+0.1% HCOOH): >95%; RT=4.94 min.

MS (ESI+): 289.3 [C$_{18}$H$_{12}$N$_2$O$_2$+H]$^+$ (m/z).

1H NMR of the major Z isomer: DMSO-d$_6$ δ (ppm): 11.08 (s, 1H), 9.42 (s, 1H), 8.50 (s, 1H), 8.22 (d, J=7.9 Hz, 1H), 8.15 (d, J=7.9 Hz, 1H), 7.93 (dd, J=8.1 Hz, J=1.2 Hz, 1H), 7.88 (td, J=7.5 Hz, J=1.1 Hz, 1H), 7.78 (td, J=7.4 Hz, J=1.1 Hz, 1H), 7.77 (s, 1H), 7.60-7.48 (m, 2H), 7.31 (td, J=7.4 Hz, J=1.3 Hz, 1H).

In a similar manner but utilizing the appropriate substituted 2'-hydroxy-acetophenones and/or heteroaryl esters were also prepared:

Example 2

7-bromo-2-isoquinolin-3-yl-chromen-4-one oxime

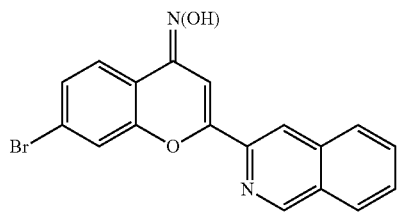

Example 2A 7-bromo-2-isoquinolin-3-yl-7-bromo-chromen-4-one was prepared using the method A illustrated in example 1A. 4'-Bromo-2'-hydroxyacetophenone (627 mg, 2.91 mmol) and methyl-2-isoquinoline-3-carboxylate (600 mg, 3.21 mmol), was treated first with sodium hydride (60% in mineral oil, 350 mg, 8.73 mmol) in dry pyridine (2×6 ml) at 90° C. for 15 min. and then with sulfuric acid (73 µl) in acetic acid (15 ml) at 100° C. for 45 min. to yield 7-bromo-2-isoquinolin-3-yl-chromen-4-one (684 mg, 67%) as pink solid after purification by flash chromatography over silica gel (cyclohexane/ethyl acetate: 80/20 then 50/50).

1H NMR: CDCl$_3$ δ (ppm): 9.32 (s, 1H), 8.46 (s, 1H), 8.13 (d, J=8.5 Hz, 1H), 8.07 (d, J=8.1 Hz, 1H), 8.01 (d, J=8.1 Hz, 1H), 7.89 (d, J=1.7 Hz, 1H), 7.82 (td, J=6.8 Hz, J=1.3 Hz, 1H), 7.75 (td, J=6.9 Hz, J=1.3 Hz, 1H), 7.59 (s, 1H), 7.56 (dd, J=8.5 Hz, J=1.7 Hz, 1H).

Example 2B 7-bromo-2-isoquinolin-3-yl-chromen-4-one O-tert-butyl oxime was prepared using the method D (step 1) illustrated in example 1B. 7-bromo-2-isoquinolin-3-yl-chromen-4-one (682 mg, 1.94 mmol) was treated with O-tert-butyl-hydroxylamine hydrochloride (486 mg, 3.87 mmol) in methanol (9 ml) under microwave irradiation to yield 7-bromo-2-isoquinolin-3-yl-chromen-4-one O-tert-butyl oxime (629 mg, 77%) as a yellow solid after purification by flash chromatography over silica gel (cyclohexane/ethyl acetate: 50/50).

1H NMR: CDCl$_3$ δ (ppm): 9.28 (s, 1H), 8.26 (s, 1H), 8.02 (d, J=8.1 Hz, 1H), 7.94 (d, J=8.6 Hz, 1H), 7.93 (d, J=8.1 Hz, 1H), 7.78 (s, 1H), 7.76 (td, J=7.6 Hz, J=1.3 Hz, 1H), 7.66 (td, J=7.5 Hz, J=1.3 Hz, 1H), 7.53 (d, J=1.9 Hz, 1H), 7.31 (dd, J=8.5 Hz, J=1.9 Hz, 1H), 1.42 (s, 9H).

Example 2C 7-bromo-2-isoquinolin-3-yl-chromen-4-one oxime was prepared using the method D, (step 2) illustrated in example 1C. 7-bromo-2-isoquinolin-3-yl-chromen-4-one O-tert-butyl oxime (150 mg, 0.35 mmol) was treated with a 1M solution of titanium tetrachloride (1.1 ml, 1.1 mmol) in dichloromethane (7.5 ml) to yield 7-bromo-2-isoquinolin-3-yl-chromen-4-one oxime (56 mg, 37%) as a beige solid after recrystallization in hot chloroform. The product was isolated as a 90/10 mixture of Z/E oxime isomers.

Mp: 279-283° C.

HPLC (gradient 5%-95% ACN/H$_2$O+0.1% HCOOH): >95%; RT=5.47 min.

MS (ESI+): 369.3 $[C_{18}H_{11}BrN_2O_2+H]^+$ (m/z).

1H NMR of the major Z isomer: DMSO-d$_6$ δ (ppm): 11.26 (s, 1H), 9.42 (s, 1H), 8.52 (s, 1H), 8.22 (d, J=8.1 Hz, 1H), 8.10 (d, J=7.9 Hz, 1H), 7.89 (td, J=7.6 Hz, J=1.3 Hz, 1H), 7.86-7.75 (m, 4H), 7.74 (s, 1H), 7.49 (dd, J=8.5 Hz, J=1.9 Hz, 1H).

1H NMR of the minor E isomer: DMSO-d$_6$ δ (ppm): 11.74 (s, 1H), 9.38 (s, 1H), 8.92 (d. J=8.8 Hz, 1H), 8.40 (s, 1H), 8.19 (d, J=8.1 Hz, 1H), 8.06 (d, J=7.9 Hz, 1H), 7.86 (t, J=7.1 Hz, 1H), 7.81 (s, 1H), 7.75 (t, J=8.1 Hz, 1H), 7.46 (dd, J=8.8 Hz, J=2.2 Hz, 1H), 7.10 (s, 1H).

Example 3

7-bromo-2-isoquinolin-3-yl-6-methyl-chromen-4-one oxime

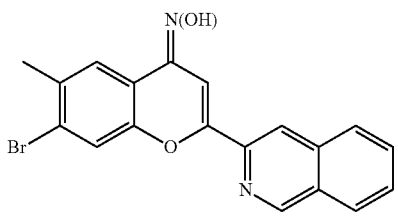

Example 3A 7-bromo-2-isoquinolin-3-yl-6-methyl-chromen-4-one was prepared using the method A illustrated in example 1A. 4'-Bromo-5'-methyl-2'-hydroxyacetophenone (556 mg, 2.42 mmol) and methyl-2-isoquinoline-3-carboxylate (500 mg, 2.67 mmol), was treated with sodium hydride (60% in mineral oil, 291 mg, 7.28 mmol) in dry pyridine (13 ml) at 90° C. for 15 min. and then with sulfuric acid (100 µl) in acetic acid (15 ml) at 100° C. for 30 min. to yield 7-bromo-2-isoquinolin-3-yl-6-methyl-chromen-4-one (738 mg, 83%) as beige solid.

1H NMR: CDCl$_3$ δ (ppm): 9.32 (s, 1H), 8.45 (s, 1H), 8.09 (s, 1H), 8.07 (d, J=8.1 Hz, 1H), 8.01 (d, J=8.1 Hz, 1H), 7.89 (d, J=1.7 Hz, 1H), 7.82 (td, J=6.8 Hz, J=1.3 Hz, 1H), 7.75 (td, J=6.9 Hz, J=1.3 Hz, 1H), 7.59 (s, 1H), 7.56 (dd, J=8.5 Hz, J=1.7 Hz, 1H), 2.52 (s, 3H).

Example 3B 7-bromo-2-isoquinolin-3-yl-6-methyl-chromen-4-one O-tert-butyl oxime was prepared using the method D (step 1) illustrated in example 1B. 7-bromo-2-isoquinolin-3-yl-6-methyl-chromen-4-one (730 mg, 1.98 mmol) was treated with O-tert-butyl-hydroxylamine hydrochloride (500 mg, 3.98 mmol) in methanol (13 ml) under microwave irradiation to yield 7-bromo-2-isoquinolin-3-yl-6-methyl-chromen-4-one O-tert-butyl oxime (383 mg, 44%) as a yellow solid after purification by flash chromatography over silica gel (cyclohexane/Chloroform/ethyl acetate: 96/4/0; 50/50/0; 0/100/0 0/50/50).

1H NMR: CDCl$_3$ δ (ppm): 9.27 (s, 1H), 8.25 (s, 1H), 8.00 (d, J=8.1 Hz, 1H), 7.92 (d, J=8.5 Hz, 1H), 7.90 (s, 1H), 7.77 (s, 1H), 7.75 (td, J=8.1 Hz, J=1.3 Hz, 1H), 7.65 (td, J=7.5 Hz, J=1.3 Hz, 1H), 7.57 (s, 1H), 2.44 (s, 3H), 1.42 (s, 9H).

Example 3C 7-bromo-2-isoquinolin-3-yl-6-methyl-chromen-4-one oxime was prepared using the method D, (step 2) illustrated in example 1C. 7-bromo-2-isoquinolin-3-yl-6-methyl-chromen-4-one O-tert-butyl oxime (100 mg, 0.22 mmol) was treated with a 1M solution of titanium tetrachloride (0.68 ml, 0.68 mmol) in dichloromethane (4 ml) to yield 7-bromo-2-isoquinolin-3-yl-6-methyl-chromen-4-one oxime (79 mg, 94%) as a yellow solid after recrystallization in hot chloroform. The compound was isolated as a 88/12 mixture of Z/E oxime isomers.

Mp: 267-270° C.

HPLC (gradient 5%-95% ACN/H$_2$O+0.1% HCOOH): >95%; RT=5.82 min.

MS (ESI+): 383.3 $[C_{19}H_{13}BrN_2O_2+H]^+$ (m/z).

1H NMR of the major Z isomer: DMSO-d$_6$ δ (ppm): 11.17 (s, 1H), 9.39 (s, 1H), 8.47 (s, 1H), 8.20 (d, J=7.9 Hz, 1H), 8.08 (d, J=7.9 Hz, 1H), 8.00-7.65 (m, 4H), 7.72 (s, 1H), 2.38 (s, 3H).

Example 4

6-bromo-2-isoquinolin-3-yl-chromen-4-one oxime

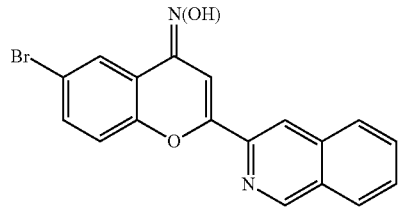

Example 4A 6-bromo-2-isoquinolin-3-yl-chromen-4-one was prepared using the method A illustrated in example 1A. 5'-Bromo-2'-hydroxyacetophenone (1.56 g, 7.28 mmol) and methyl-2-isoquinoline-3-carboxylate (1.50 g, 8.0 mmol), was first treated with sodium hydride (60% in mineral oil, 960 mg, 24.0 mmol) in dry pyridine (40 ml) at 90° C. for 15 min. and then with sulfuric acid (440 µl) in acetic acid (54 ml) at 100° C. for 5 hours to yield 6-bromo-2-isoquinolin-3-yl-chromen-4-one (2.6 g, 90%) as brown needles.

1H NMR: CDCl$_3$ δ (ppm): 9.31 (s, 1H), 8.46 (s, 1H), 8.38 (d, J=2.4 Hz, 1H), 8.06 (d, J=7.7 Hz, 1H), 8.01 (d, J=8.1 Hz, 1H), 7.81 (t, J=6.3 Hz, 1H), 7.80 (d, J=8.6 Hz, 1H), 7.74 (td, J=6.9 Hz, J=1.3 Hz, 1H), 7.59 (s, 1H), 7.56 (d, J=8.8 Hz, 1H).

Example 4B 6-bromo-2-isoquinolin-3-yl-chromen-4-one O-tert-butyl oxime was prepared using the method D (step 1) illustrated in example 1B. 6-bromo-2-isoquinolin-3-yl-chromen-4-one (600 mg, 1.7 mmol) was treated with O-tert-butyl-hydroxylamine hydrochloride (427 mg, 3.4 mmol) in methanol (10 ml) under microwave irradiation to yield 6-bromo-2-isoquinolin-3-yl-chromen-4-one O-tert-butyl oxime (546 mg, 76%) as a yellow solid.

1H NMR: CDCl$_3$ δ (ppm): 9.28 (s, 1H), 8.27 (s, 1H), 8.19 (d, J=2.4 Hz, 1H), 8.02 (d, J=8.3 Hz, 1H), 7.94 (d, J=8.3 Hz, 1H), 7.78 (s, 1H), 7.76 (td, J=8.1 Hz, J=1.3 Hz, 1H), 7.67 (td, J=7.5 Hz, J=1.3 Hz, 1H), 7.50 (dd, J=8.6 Hz, J=2.4 Hz, 1H), 7.22 (d, J=8.8 Hz, 1H), 1.43 (s, 9H).

Example 4C 6-bromo-2-isoquinolin-3-yl-chromen-4-one oxime was prepared using the method D, (step 2) illustrated in example 1C. 6-bromo-2-isoquinolin-3-yl-chromen-4-one O-tert-butyl oxime (50 mg, 0.12 mmol) was treated with a 1M solution of titanium tetrachloride (0.35 ml, 0.35 mmol) in dichloromethane (3 ml) to yield 6-bromo-2-isoquinolin-3-yl-chromen-4-one oxime (37 mg, 85%) as a yellow solid after recrystallization in hot chloroform. The compound was isolated as a 98/2 mixture of Z/E oxime isomers.

Mp: 266-269° C.

HPLC (gradient 5%-95% ACN/H$_2$O+0.1% HCOOH): >98%; RT=5.41 min.

MS (ESI+): 369.3 [C$_{18}$H$_{11}$BrN$_2$O$_2$+H]$^+$ (m/z).

1H NMR of the major Z isomer: DMSO-d$_6$ δ (ppm): 11.31 (s, 1H), 9.41 (s, 1H), 8.49 (s, 1H), 8.22 (d, J=7.9 Hz, 1H), 8.13 (d, J=7.9 Hz, 1H), 7.97 (d, J=2.4 Hz, 1H), 7.88 (td, J=7.5 Hz, J=1.3 Hz, 1H), 7.78 (td, J=7.9 Hz, J=1.3 Hz, 1H), 7.75 (s, 1H), 7.72 (dd, J=8.8 Hz, J=2.4 Hz, 1H), 7.50 (d, J=8.8 Hz, 1H).

Example 5

2-isoquinolin-3-yl-6-methyl-chromen-4-one oxime was isolated in 21% overall yield as a pale yellow solid and as a 98/2 mixture of Z/E oxime isomers.

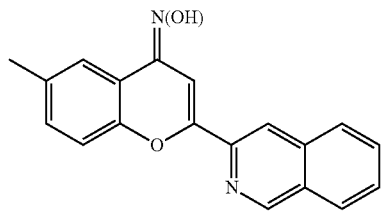

Mp: 260-264° C.

MS (ESI+): 303.4 [C$_{19}$H$_{14}$N$_2$O$_2$+H]$^+$ (m/z).

1H NMR of the major Z isomer: DMSO-d$_6$ δ (ppm): 11.04 (s, 1H), 9.42 (s, 1H), 8.48 (s, 1H), 8.22 (d, J=8.1 Hz, 1H), 8.15 (d, J=8.1 Hz, 1H), 7.88 (td, J=7.8 Hz, J=1.3 Hz, 1H), 7.78 (td, J=7.9 Hz, J=1.3 Hz, 1H), 7.75 (s, 1H), 7.71 (s, 1H), 7.42 (d, J=8.3 Hz, 1H), 7.36 (dd, J=8.8 Hz, J=1.7 Hz, 1H), 2.37 (s, 3H).

Example 6

6-fluoro-2-isoquinolin-3-yl-chromen-4-one oxime was isolated in 36% overall yield as a yellow solid and as a 95/5 mixture of Z/E oxime isomers.

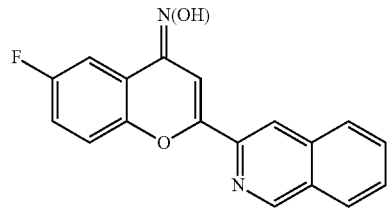

Mp: 278-280° C.

MS (ESI+): 307.3 [C$_{18}$H$_{11}$FN$_2$O$_2$+H]$^+$ (m/z).

1H NMR of the major Z isomer: DMSO-d$_6$ δ (ppm): 11.27 (s, 1H), 9.42 (s, 1H), 8.50 (s, 1H), 8.22 (d, J=7.7 Hz, 1H), 8.14 (d, J=8.1 Hz, 1H), 7.88 (t, J=6.8 Hz, 1H), 7.78 (td, J=7.1 Hz, J=1.3 Hz, 1H), 7.74 (s, 1H), 7.64-7.53 (m, 2H), 7.43 (td, J=8.6 Hz, J=3.2 Hz, 1H).

Example 7

6,8-difluoro-2-isoquinolin-3-yl-chromen-4-one oxime was isolated in 31% overall yield as a beige solid and as a 96/4 mixture of Z/E oxime isomers.

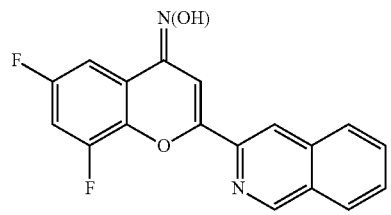

Mp: 253-256° C.

MS (ESI+): 325.1 [C$_{18}$H$_{10}$F$_2$N$_2$O$_2$+H]$^+$ (m/z).

1H NMR of the major Z isomer: DMSO-d$_6$ δ (ppm): 11.48 (s, 1H), 9.42 (s, 1H), 8.33 (s, 1H), 8.21 (d, J=7.5 Hz, 1H), 8.20 (d, J=7.7 Hz, 1H), 7.87 (td, J=7.5 Hz, J=1.2 Hz, 1H), 7.78 (t, J=7.2 Hz, 1H), 7.76 (s, 1H), 7.63 (ddd, 11.1 Hz, J=8.7 Hz, 2.8 Hz, 1H), 7.40 (dm, J=11.1 Hz, 1H).

Example 8

8-chloro-2-isoquinolin-3-yl-chromen-4-one oxime was isolated in 12% overall yield as a beige powder and as a 95/5 mixture of Z/E oxime isomers,

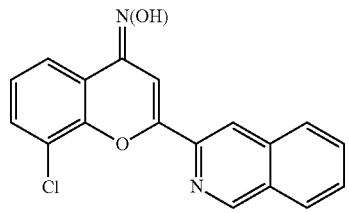

Mp: 270-272° C.

MS (ESI+): 323.1 [C$_{18}$H$_{11}$ClN$_2$O$_2$+H]$^+$ (m/z).

1H NMR of the major Z isomer: DMSO-d$_6$ δ (ppm): 11.34 (s, 1H), 9.44 (s, 1H), 8.38 (s, 1H), 8.23 (d, J=8.1 Hz, 1H), 8.17 (d, J=8.1 Hz, 1H), 7.89 (t, J=7.4 Hz, 1H), 7.87 (d, J=7.0 Hz, 1H), 7.79 (t, J=7.4 Hz, 1H), 7.79 (s, 1H), 7.71 (d, J=7.9 Hz, 1H), 7.31 (t, J=7.9 Hz, 1H).

Example 9

4-fluoro-2-isoquinolin-3-yl-chromen-4-one-(Z)-oxime was isolated in 54% overall yield as a yellow solid.

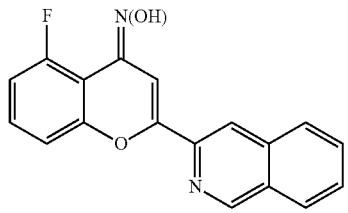

Mp: 275-278° C.
MS (ESI+): 307.1 [C$_{18}$H$_{11}$FN$_2$O$_2$+H]$^+$ (m/z).

1H NMR: DMSO-d$_6$ δ (ppm): 11.40 (s, 1H), 9.42 (s, 1H), 8.48 (s, 1H), 8.22 (d, J=7.9 Hz, 1H),), 8.15 (d, J=7.9 Hz, 1H), 7.88 (td, J=7.5 Hz, J=1.3 Hz, 1H), 7.83 (s, 1H), 7.78 (td, J=7.5 Hz, J=1.3 Hz, 1H), 7.54 (td, J=8.3 Hz, J=5.6 Hz, 1H), 7.37 (d, J=8.3 Hz, 1H), 7.16 (ddd, J=11.1 Hz, J=8.2 Hz, J=0.9 Hz, 1H).

Example 10

2-isoquinolin-3-yl-6-trifluoromethoxy-chromen-4-one oxime was isolated in 15% overall yield as a yellow powder and as a 95/5 mixture of Z/E oxime isomers.

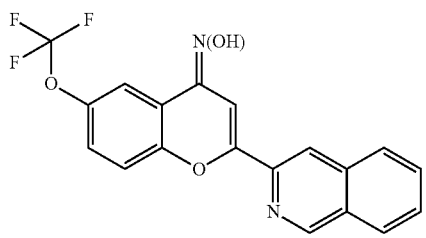

Mp: 250-254° C.
MS (ESI+): 373.1 [C$_{19}$H$_{11}$F$_3$N$_2$O$_3$+H]$^+$ (m/z).

1H NMR of the major Z isomer: DMSO-d$_6$ δ (ppm): 11.34 (s, 1H), 9.43 (s, 1H), 8.51 (s, 1H), 8.22 (d, J=7.9 Hz, 1H),), 8.15 (d, J=7.9 Hz, 1H), 7.89 (td, J=7.6 Hz, J=1.3 Hz, 1H), 7.79 (td, J=7.5 Hz, J=1.3 Hz, 1H), 7.76 (m, 1H), 7.75 (s, 1H), 7.66 (d, J=9.0 Hz, 1H), 7.57 (dd, J=9.0 Hz, J=2.5 Hz, 1H).

Example 11

2-isoquinolin-3-yl-6-trifluoromethyl-chromen-4-one oxime was isolated in 10% overall yield starting from 2'-hydroxy-5'-trifluoromethyl-acetophenone (example 11A) and methyl isoquinoline-3-carboxylate. The yellow solid product was a 95/5 mixture of Z/E oxime isomers.

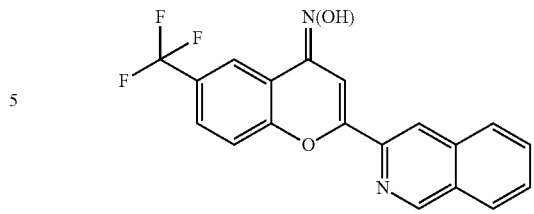

Mp: 245-247° C.
MS (ESI+): 357.1 [C$_{19}$H$_{11}$F$_3$N$_2$O$_2$+H]$^+$ (m/z).

1H NMR of the major Z isomer: DMSO-d$_6$ δ (ppm): 11.39 (s, 1H), 9.43 (s, 1H), 8.54 (s, 1H), 8.23 (d, J=7.9 Hz, 1H),), 8.15 (m, 2H), 7.94-7.85 (m, 2H), 7.79 (td, J=7.5 Hz, J=1.3 Hz, 1H), 7.78 (s, 1H), 7.73 (d, J=8.7 Hz, 1H).

Example 11A

2'-hydroxy-5'-trifluoromethyl-acetophenone was prepared using the following process (*JACS*, 2004, 126(3), 712-713). To a cooled solution of 2'-methoxy-5'-trifluoromethyl-acetophenone (650 mg, 2.98 mmol) at −78° C. in dry dichloromethane (40 ml) was slowly added a 1 M solution of boron trichloride in dichloromethane (7.5 ml, 7.5 mmol) keeping the internal temperature below −70° C. The brown-orange solution was slowly warmed up to room temperature within 2 hours.

The solution was ice cooled and cautiously hydrolyzed with a 1N aqueous hydrochloride solution (40 ml). The organic layer was treated with 1 N HCl, washed with water and dried over sodium sulfate. The filtrated solution was concentrated and the residue purified by flash chromatography over silica gel (gradient cyclohexane/ethyl acetate: 0-10%) to yield 2'-hydroxy-5'-trifluoromethyl-acetophenone (467 mg, 77%) as a light yellow oil.

1H NMR: CDCl$_3$ δ (ppm): 12.55 (s, 1H), 7.99 (d, J=2.0 Hz, 1H), 7.70 (dd, J=8.8 Hz, J=2.0 Hz, 1H), 7.08 (d, J=8.9 Hz, 1H), 2.69 (s, 3H).

Example 11B

2'-methoxy-5'-trifluoromethyl-acetophenone was prepared as follow (US2003/0109574): In a water bath at room temperature, to a solution of trifluoromethane sulfonic acid (5 ml, 56.7 mmol) under argon was slowly added a solution of 4-trifluoromethyl-anisol (2.0 g, 11.35 mmol) in acetic anhydride (2.15 ml, 22.7 mmol). The resulting dark mixture was stirred for 3 hours at room temperature then poured onto ice water (26 ml). The product was extracted several times with ether. The ethereal layer was washed with a 10% solution of sodium hydrogenocarbonate, water, dried over sodium sulfate and concentrated to dryness. The residue was purified by flash chromatography over silica gel (gradient cyclohexane/dichloromethane: 0-50%) to yield 2'-methoxy-5'-trifluoromethyl-acetophenone (1.7 g, 67%) as a white solid.

1H NMR: CDCl$_3$ δ (ppm): 8.00 (d, J=2.3 Hz, 1H), 7.71 (dd, J=8.8 Hz, J=2.3 Hz, 1H), 7.05 (d, J=8.7 Hz, 1H), 3.98 (s, 3H), 2.63 (s, 3H).

Example 12

2-(7-fluoro-isoquinolin-3-yl)-chromen-4-one oxime was isolated in 11% overall yield using method A and D, starting from 2'-hydroxy-acetophenone and methyl 7-fluoro-isoquinoline-3-carboxylate (example 12A) as a yellow solid and a 95/5 mixture of Z/E oxime isomers.

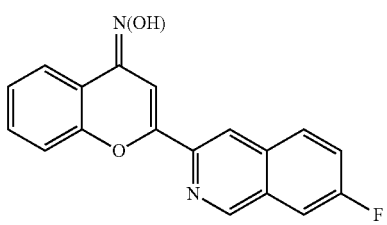

Mp: 233-235° C.

MS (ESI+): 307.0 $[C_{18}H_{11}FN_2O_2+H]^+$ (m/z).

1H NMR of the major Z isomer: DMSO-$d_6$ δ (ppm): 11.09 (s, 1H), 9.41 (s, 1H), 8.53 (s, 1H), 8.28 (d, J=9.0 Hz, 1H), 8.25 (d, J=9.0 Hz, 1H), 8.04 (dd, J=9.2 Hz, J=2.5 Hz, 1H), 7.92 (dd, J=7.9 Hz, J=1.3 Hz, 1H), 7.81 (td, J=9.0 Hz, J=2.6 Hz, 1H), 7.75 (s, 1H), 7.60-7.45 (m, 2H), 7.31 (td, J=8.0 Hz, J=1.3 Hz, 1H).

Example 12A methyl 7-fluoro-isoquinoline-3-carboxylate

A sealed tube was charged with 2-bromo-5-fluorobenzaldehyde (300 mg, 1.47 mmol), dry dimethylformamide (1.5 ml), triethylamine (0.7 ml, 5.02 mmol), methyl 2-acetamidoacrylate (273 mg, 1.91 mmol), tris-o-tolyl-phosphine (89 mg, 0.29 mmol) and palladium acetate (33 mg, 0.14 mmol). The solution was degassed with Argon for 10 min. and then warmed at 110° C. for 4.5 hours. The mixture was cooled to room temperature and poured onto an aqueous solution of ammonium chloride. The mixture was extracted with ethyl acetate, washed with brine, dried over sodium sulfate and concentrated. The residue was purified by flash chromatography over silica gel (gradient cyclohexane/dichloromethane: 0-80%) to yield methyl 7-fluoro-isoquinoline-3-carboxylate (120 mg, 39%) as beige solid.

1H NMR: CDCl$_3$ δ (ppm): 9.29 (s, 1H), 8.60 (s, 1H), 8.01 (dd, J=9.0 Hz, J=5.2 Hz, 1H), 7.68 (dd, J=8.4 Hz, J=2.4 Hz, 1H), 7.57 (td, J=8.4 Hz, J=2.4 Hz, 1H), 4.06 (s, 3H).

Example 13

2-(7-methoxy-isoquinolin-3-yl)-chromen-4-one oxime was isolated in 3% overall yield using method A and D, starting from 2'-hydroxy-acetophenone and methyl 7-fluoro-isoquinoline-3-carboxylate (example 12A). The brown solid product was a 80/20 mixture of Z/E oxime isomers.

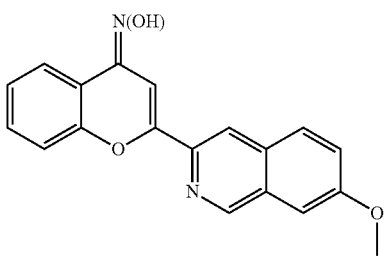

Mp: 239-241° C.

MS (ESI+): 319.1 $[C_{19}H_{14}N_2O_3+H]^+$ (m/z).

1H NMR of the major Z isomer: DMSO-$d_6$ δ (ppm): 11.02 (s, 1H), 9.31 (s, 1H), 8.42 (s, 1H), 8.08 (d, J=9.0 Hz, 1H) 7.92 (dd, J=7.9 Hz, J=1.3 Hz, 1H), 7.70 (s, 1H), 7.63 (d, J=2.5 Hz, 1H), 7.60-7.44 (m, 3H), 7.30 (td, J=7.3 Hz, J=1.5 Hz, 1H), 3.96 (s, 3H).

Example 14

2-(6,7-dimethoxy-isoquinolin-3-yl)-chromen-4-one oxime was isolated in 8% overall yield using method A and D, starting from 2'-hydroxy-acetophenone and methyl 6,7-dimethoxy-isoquinoline-3-carboxylate (US054777252) as a yellow solid and a 95/5 mixture of Z/E oxime isomers.

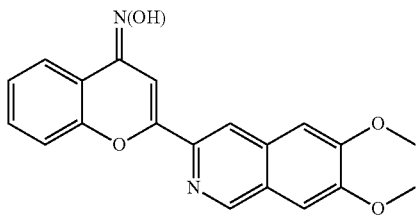

Mp: 266-269° C.

MS (ESI+): 349.0 $[C_{20}H_{16}N_2O_4+H]^+$ (m/z).

1H NMR of the major Z isomer: DMSO-$d_6$ δ (ppm): 10.99 (s, 1H), 9.16 (s, 1H), 8.33 (s, 1H), 7.92 (dd, J=7.9 Hz, J=1.3 Hz, 1H), 7.69 (s, 1H), 7.60 (s, 1H), 7.55 (s, 1H), 7.55 (td, J=7.7 Hz, J=1.5 Hz, 1H), 7.45 (d, J=7.4 Hz, 1H), 7.30 (t, J=7.4 Hz, 1H), 3.97 (s, 3H), 3.96 (s, 3H).

Example 15

2-(6-methyl-isoquinolin-3-yl)-chromen-4-one oxime was isolated in 35% overall yield using method A and D starting from 2'-hydroxy-acetophenone and methyl 6-methyl-isoquinoline-3-carboxylate (example 15A) as a yellow solid and a 95/5 mixture of Z/E oxime isomers.

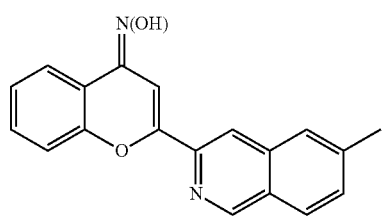

Mp: 245-247° C.

MS (ESI+): 349.0 $[C_{19}H_{14}N_2O_2+H]^+$ (m/z).

1H NMR of the major Z isomer: DMSO-$d_6$ δ (ppm): 11.06 (s, 1H), 9.33 (s, 1H), 8.37 (s, 1H), 8.10 (d, J=8.3 Hz, 1H), 7.92 (dd, J=7.9 Hz, J=1.3 Hz, 1H), 7.91 (s, 1H), 7.75 (s, 1H), 7.6-7.45 (m, 3H), 7.30 (td, J=7.4 Hz, J=1.3 Hz, 1H), 2.55 (s, 3H).

Example 15A methyl 6-methyl-isoquinoline-3-carboxylate was prepared using the procedure described in example 12A: 2-bromo-4-methylbenzaldehyde was reacted with methyl 2-acetamidoacrylate at 110° C. for 18 hours to yield methyl 6-methyl-isoquinoline-3-carboxylate (50%) as brown solid.

1H NMR: CDCl$_3$ δ (ppm): 9.25 (s, 1H), 8.51 (s, 1H), 7.94 (d, J=8.3 Hz, 1H), 7.73 (s, 1H), 7.57 (dd, J=8.4 Hz, J=1.5 Hz, 1H), 4.05 (s, 3H), 2.58 (s, 3H).

Example 16

2-(7-chloro-isoquinolin-3-yl)-chromen-4-one oxime was isolated in 20% overall yield using method A and D starting from 2'-hydroxy-acetophenone and methyl 7-chloro-iso-quinoline-3-carboxylate (example 16A) as pale a yellow solid and a 90/10 mixture of Z/E oxime isomers.

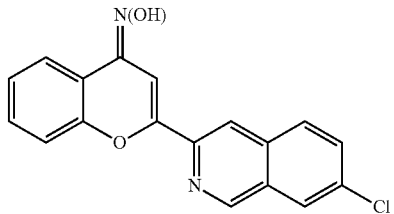

Mp: 260-261° C.
MS (ESI+): 323.1 $[C_{16}H_{11}ClN_2O_2+H]^+$ (m/z).
1H NMR of the major Z isomer: DMSO-$d_6$ δ (ppm): 11.13 (s, 1H), 9.39 (s, 1H), 8.51 (s, 1H), 8.34 (d, J=2.1 Hz, 1H), 8.19 (d, J=8.8 Hz, 1H), 7.90 (td, J=8.6 Hz, J=2.1 Hz, 1H), 7.90 (s, 1H), 7.75 (s, 1H), 7.60-7.45 (m, 2H), 7.30 (td, J=7.5 Hz, J=1.3 Hz, 1H).

Example 16A methyl 7-chloro-isoquinoline-3-carboxylate was prepared using the procedure described in example 12A: 2-bromo-5-chlorobenzaldehyde was reacted with methyl 2-acetamidoacrylate at 110° C. for 24 hours to yield methyl 7-chloro-isoquinoline-3-carboxylate (25%) as brown solid.

1H NMR: CDCl$_3$ δ (ppm): 9.27 (s, 1H), 8.58 (s, 1H), 8.05 (d, J=1.7 Hz, 1H), 7.93 (d, J=8.8 Hz, 1H), 7.73 (dd, J=8.7 Hz, J=1.9 Hz, 1H), 4.06 (s, 3H).

Example 17

2-(5-bromo-isoquinolin-3-yl)-chromen-4-one oxime was isolated in 15% overall yield using method A and D, starting from 2'-hydroxy-acetophenone and methyl 5-bromo-isoquinoline-3-carboxylate (example 17A) as a yellow solid and a 90/10 mixture of Z/E oxime isomers.

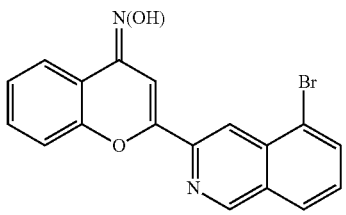

Mp: 268-270° C.
MS (ESI+): 366.9 $[C_{18}H_{11}BrN_2O_2+H]^+$ (m/z).
1H NMR of the major Z isomer: DMSO-$d_6$ δ (ppm): 11.17 (br. s, 1H), 9.47 (s, 1H), 8.48 (s, 1H), 8.28 (d, J=8.1 Hz, 1H), 8.24 (d, J=8.1 Hz, 1H), 7.93 (d, J=7.2 Hz, 1H), 7.82 (s, 1H), 7.71 (t, J=7.8 Hz, 1H), 7.60-7.48 (m, 2H), 7.32 (td, J=7.8 Hz, J=1.9 Hz, 1H).

Example 17A methyl-5-bromo-isoquinoline-3-carboxylate was prepared using the following procedure describe in US054777252 for methyl-6,7-dimethoxy-isoquinoline-3-carboxylate:

5-bromo-1,2,3,4-tetrahydroisoquinoline-3-carboxylic acid methyl ester (880 mg, 3.26 mmol) was treated with 2,3-Dichloro-5,6-dicyanobenzoquinone (1.62 mg, 7.19 mmol) in dry tetrahydrofuran (19 ml) at reflux temperature for 18 hours. The cooled dark mixture was filtered and the solid washed with dichloromethane. The filtrate was treated with a 1M aqueous sodium hydroxide solution and the aqueous layer was extracted twice with dichloromethane. The organic layer was washed with water, brine, dried over sodium sulfate and concentrated to dryness. The residue was purified by flash chromatography over silica gel (gradient cyclohexane/ethyl acetate: 0-100%) to yield methyl 5-bromo-isoquinoline-3-carboxylate (793 mg, 91%) as beige solid.

1H NMR: CDCl$_3$ δ (ppm): 9.31 (s, 1H), 8.90 (s, 1H), 8.05 (t, J=9.4 Hz, 2H), 7.61 (t, J=7.5 Hz, 1H), 4.09 (s, 3H).

Example 18

2-(5-hydroxy-isoquinolin-3-yl)-chromen-4-one oxime was isolated in 14% yield using method D (step 2), starting from 2-(5-hydroxy-isoquinolin-3-yl)-chromen-4-one O-tert-butyl oxime (example 18A) as orange solid and as a 80/20 mixture of Z/E oxime isomers.

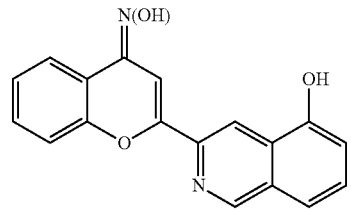

MS (ESI+): 305.1 $[C_{18}H_{12}N_2O_3+H]^+$ (m/z).
1H NMR of the major Z isomer: DMSO-$d_6$ δ (ppm): 11.04 (s⁻, 1H), 10.82 (br. s, 1H), 9.32 (s, 1H), 8.55 (s, 1H), 7.92 (d, J=77 Hz, 1H), 7.75 (s, 1H), 7.70-7.50 (m, 4H), 7.35-7.25 (m, 1H), 7.20 (d, J=7.0 Hz, 1H).

Example 18A 2-(5-hydroxy-isoquinolin-3-yl)-chromen-4-one O-tert-butyl oxime was prepared using a palladium coupling procedure describes by K. W. Anderson (*JACS*, 2006, 128, 10694-10695):

A solution of 2-(5-bromo-isoquinolin-3-yl)-chromen-4-one O-tert-butyl oxime (370 mg, 0.87 mmol), potassium hydroxide (300 mg, 5.24 mmol), tris(dibenzylideneacetone) dipalladium (40 mg, 0.043 mmol) and 2-di-tert-butylphosphino-2',4',6'-triisopropylbiphenyl (37 mg, 0.087 mmol) in dioxane (1.9 ml) and water (1.9 ml) was degassed with argon for 5 min. and then warmed to 100° C. for 18 hours.

The reaction mixture was diluted with water and extracted with ethyl acetate. The organic layers were washed with brine, dried over sodium sulfate, filtered and concentrated. The residue was purified by flash chromatography over silica gel (gradient cyclohexane/ethyl acetate: 0-40%) to yield 2-(5-hydroxy-isoquinolin-3-yl)-chromen-4-one O-tert-butyl oxime (230 mg, 73%) as a yellow solid.

MS (ESI+): 361.1.1 $[C_{22}H_{20}N_2O_3+H]^+$ (m/z).
1H NMR: acetone-$d_6$ δ (ppm): 9.30 (s, 1H), 8.69 (s, 1H), 8.08 (d, J=7.1 Hz, 1H), 7.86 (s, 1H), 7.67 (d, J=7.9 Hz, 1H), 7.63-7.48 (m, 3H), 7.35-7.20 (m, 2H), 1.43 (s, 9H).

Example 19

2-(5-methoxy-isoquinolin-3-yl)-chromen-4-one oxime was isolated in 94% yield using method D (step 2), starting from 2-(5-methoxy-isoquinolin-3-yl)-chromen-4-one O-tert-butyl oxime (example 19A) as a yellow solid and as a 90/10 mixture of Z/E oxime isomers.

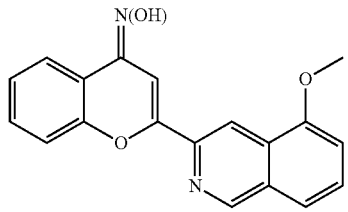

Mp: 245-247° C.
MS (ESI+): 319.1 $[C_{19}H_{14}N_2O_3+H]^+$ (m/z).
1H NMR of the major Z isomer: DMSO-$d_6$ δ (ppm): 11.07 (s, 1H), 9.37 (s, 1H), 8.52 (s, 1H), 7.92 (d, J=7.7 Hz, 1H), 7.76 (s, 1H), 7.75 (d, J=7.7 Hz, 1H), 7.70 (t, J=8.0 Hz, 1H), 7.55-7.50 (m, 2H), 7.36-7.26 (m, 2H), 4.07 (s, 3H).

Example 19A 2-(5-methoxy-isoquinolin-3-yl)-chromen-4-one O-tert-butyl oxime

To a ice-water bath cooled solution of 2-(5-hydroxy-isoquinolin-3-yl)-chromen-4-one O-tert-butyl oxime (80 mg, 0.22 mmol) in dimethylformamide (2.5 ml) was added sodium hydride (60% in mineral oil, 13 mg, 0.33 mmol) under argon and the mixture was stirred at room temperature for 1 hour. The solution was cooled to 0° C. and iodomethane (15 μl, 0.24 mmol) was added. The resulting solution was stirred at room temperature for 20 hours and then hydrolyzed with brine. The mixture was extracted with ethyl acetate, washed with brine, dried over sodium sulfate and then purified by flash chromatography over silica gel (cyclohexane/ethyl acetate: 80/20) to yield 2-(5-methoxy-isoquinolin-3-yl)-chromen-4-one O-tert-butyl oxime (65 mg, 79%) as a yellow solid.
MS (ESI+): 375.1 $[C_{23}H_{22}N_2O_3+H]^+$ (m/z).
1H NMR: CDCl$_3$ δ (ppm): 9.23 (d, J=0.9 Hz, 1H), 8.63 (s, 1H), 8.09 (d, J=8.5 Hz, 1H), 7.78 (s, 1H), 7.43-7.38 (m, 2H), 7.24-7.17 (m, 1H), 7.08-7.03 (m, 1H), 4.08 (s, 3H), 1.43 (s, 9H).

Example 20

2-isoquinolin-3-yl-7-phenylethynyl-chromen-4-one oxime

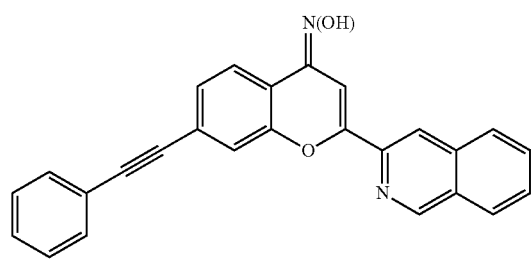

A solution of 7-bromo-2-isoquinolin-3-yl-chromen-4-one oxime (52 mg, 0.142 mmol), trans-dichlorobis(triphenylphosphine)palladium (10 mg, 0.014 mmol), copper iodide (5.3 mg, 0.028 mmol) in dimethylformamide (3 ml) was degassed with argon for 10 min and then treated with triethylamine (30 μl, 0.213 mmol) and phenyl acetylene (19 μl, 0.170 mmol). The solution was warmed to 90° C. for 18 hours and then poured onto a 0.5N aqueous solution of hydrogen chloride, extracted with ethyl acetate and purified by preparative HPLC (gradient 25-10% Water/acetonitrile+ 0.05% trifluoroacetic acid) to yield 2-isoquinolin-3-yl-7-phenylethynyl-chromen-4-one oxime (7.3 mg, 13%) as a yellow solid and a 80/20 mixture of Z/E oxime isomers.
MS (ESI+): 389.2 $[C_{26}H_{16}N_2O_2+H]^+$ (m/z).

Example 21

2-isoquinolin-3-yl-7-((E)-styryl)-chromen-4-one oxime was isolated in 55% yield using method D (step 2), starting from 2-Isoquinolin-3-yl-7-((E)-styryl)-chromen-4-one O-tert-butyl oxime (example 21A) as a pale yellow solid and as a 90/10 mixture of Z/E oxime isomers

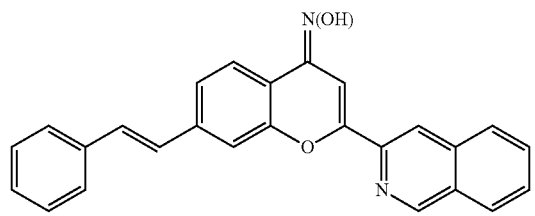

Mp: 273-276° C.
MS (ESI+): 391.5 $[C_{26}H_{16}N_2O_2+H]^+$ (m/z).
1H NMR of the major Z isomer: DMSO-$d_6$ δ (ppm): 11.15 (s, 1H), 9.44 (s, 1H), 8.51 (s, 1H), 8.24 (d, J=8.1 Hz, 1H), 8.15 (d, J=8.2 Hz, 1H), 7.90 (d, J=8.2 Hz, 1H), 7.90 (t, J=7.0 Hz, 1H), 7.79 (t, J=7.4 Hz, 2H), 7.76 (s, 1H), 7.67 (d, J=7.3 Hz, 2H), 7.56 (d, J=7.3 Hz, 1H), 7.5-7.28 (m, 5H).

Example 21A 2-isoquinolin-3-yl-7-((E)-styryl)-chromen-4-one O-tert-butyl oxime In a microwave vial, a solution of 7-bromo-2-isoquinolin-3-yl-chromen-4-one O-tert-butyl oxime (200 mg, 0.47 mmol), cesium fluoride (213 mg, 1.41 mmol) and trans-styryl boronic acid (160 mg, 1.07 mmol) in 1,2-dimethoxyethane (3.2 ml) and methanol (1.6 ml) was degassed with argon for 20 min and then tetrakis(triphenylphosphine)palladium (30 mg, 0.026 mmol) was added. The vial was sealed and the mixture was heated under microwave irradiation to 150° C. for 5 min. After cooling, the solution was diluted with dichloromethane and absorbed over silica gel for purification by flash chromatography (gradient cyclohexane/dichloromethane: 0-80%) to yield 2-Isoquinolin-3-yl-7-((E)-styryl)-chromen-4-one O-tert-butyl oxime (160 mg, 76%) as a yellow solid.
MS (ESI+): 447.6 $[C_{30}H_{26}N_2O_2+H]^+$ (m/z).
1H NMR: CDCl$_3$ δ (ppm): 9.29 (s, 1H), 8.33 (s, 1H), 8.06 (d, J=8.1 Hz, 1H), 8.02 (d, J=7.7 Hz, 1H), 7.96 (d, J=7.9 Hz, 1H), 7.80 (s, 2H), 7.76 (td, J=7.5 Hz, J=1.3 Hz, 1H), 7.66 (td, J=7.4 Hz, J=1.3 Hz, 1H), 7.56 (d, J=7.3 Hz, 2H), 7.49 (d, J=1.7 Hz, 1H), 7.44-7.26 (m, 4H), 7.23 (d, J=16 Hz, 1H), 7.23 (d, J=16 Hz, 1H),

Example 22

2-isoquinolin-3-yl-7-phenethyl-chromen-4-one oxime was isolated using method D (step 2), starting from 2-Isoquinolin-3-yl-7-phenethyl-chromen-4-one O-tert-butyl oxime (example 22A) as a yellow solid and as a 95/5 mixture of Z/E oxime isomers

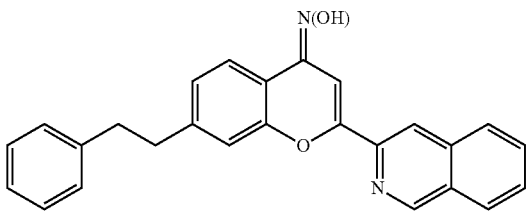

MS (ESI+): 393.1 $[C_{26}H_{20}N_2O_2+H]^+$ (m/z).

1H NMR of the major Z isomer: DMSO-$d_6$ δ (ppm): 11.04 (s, 1H), 9.50 (s, 1H), 8.56 (s, 1H), 8.30 (d, J=8.0 Hz, 1H), 8.21 (d, J=8.0 Hz, 1H), 7.97 (t, J=7.2 Hz, 1H), 7.90-7.80 (m, 3H), 7.49 (s, 1H), 7.40-7.35 (m, 4H), 7.35-7.20 (m, 2H), 3.06 (s, 4H).

Example 22A 2-isoquinolin-3-yl-7-phenethyl-chromen-4-one O-tert-butyl oxime

A solution of 2-isoquinolin-3-yl-7-phenylethynyl-chromen-4-one O-tert-butyl oxime (60 mg, 0.13 mmol) (prepared using the procedure described in example 20 starting from example 2B) and Lindlar's catalyst (22.5 mg) in tetrahydrofuran (9.2 ml) and methanol (1.8 ml) was stirred at room temperature under 1 atmosphere of hydrogen for 18 h. The catalyst was removed by filtration and the solvent evaporated under reduce pressure to yield the title compound in 60% yield.

Example 23

7-ethynyl-2-isoquinolin-3-yl-chromen-4-one oxime was isolated in 72% yield using method D (step 2), starting from 7-ethynyl-2-isoquinolin-3-yl-chromen-4-one O-tert-butyl oxime (example 23A) as a yellow solid and as a 90/10 mixture of Z/E oxime isomers. Example 23 was purified by preparative HPLC (gradient 35-20% Water/acetonitrile+0.05% trifluoroacetic acid)

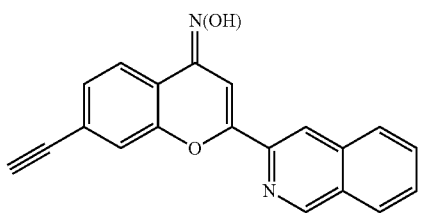

MS (ESI+): 313.4 $[C_{20}H_{12}N_2O_2+H]^+$ (m/z).

1H NMR of the major Z isomer: DMSO-$d_6$ δ (ppm): 11.29 (s, 1H), 9.42 (s, 1H), 8.52 (s, 1H), 8.22 (d, J=7.9 Hz, 1H), 8.11 (d, J=8.0 Hz, 1H), 7.90 (d, J=8.0 Hz, 1H), 7.89 (t, J=8.1 Hz, 1H), 7.79 (t, J=8.0 Hz, 1H), 7.74 (s, 1H), 7.64 (d, J=1.3 Hz, 1H), 7.38 (dd, J=8.3 Hz, J=1.5 Hz, 1H), 4.44 (s, 1H).

Example 23A 7-ethynyl-2-isoquinolin-3-yl-chromen-4-one O-tert-butyl oxime

A solution of 7-bromo-2-isoquinolin-3-yl-chromen-4-one O-tert-butyl oxime (120 mg, 0.28 mmol), trans-dichlorobis(triphenylphosphine)palladium (19 mg, 0.028 mmol), copper iodide (10 mg, 0.056 mmol), triphenylphosphine (14 mg, 0.056 mmol) in a mixture of dimethylformamide (3 ml) and acetonitrile (3 ml) was degassed with argon for 10 min and then treated with diethylamine (42 μl, 0.40 mmol) and trimethylsilylacetylene (46 μl, 0.326 mmol). The solution was warmed to 90° C. for 20 hours and then poured onto a 0.5N aqueous solution of hydrogen chloride, extracted with ethyl acetate and purified by flash chromatography over silica gel (gradient cyclohexane/ethyl acetate: 20-50%) to yield 2-isoquinolin-3-yl-7-trimethylsilylethynyl-chromen-4-one O-tert-butyl oxime (63 mg, 50%) as a yellow solid. The solid was dissolved in methanol (10 ml) and treated with potassium carbonate (39 mg, 0.28 mmol) and stirred at room temperature for 18 hours. Methanol was evaporated and the residue was extracted with ethyl acetate washed with water and brine, dried over sodium sulfate and the solution concentrated to dryness to yield 7-ethynyl-2-isoquinolin-3-yl-chromen-4-one O-tert-butyl oxime (49 mg, 89%) as beige solid.

MS (ESI+): 369.3 $[C_{24}H_{20}N_2O_2+H]^+$ (m/z).

Example 24

2-isoquinolin-3-yl-7-(pyridin-2-yl-ethynyl)-chromen-4-one oxime was isolated in 42% yield using method D (step 2), starting from 2-isoquinolin-3-yl-7-(pyridin-2-yl-ethynyl)-chromen-4-one O-tert-butyl oxime (example 24A) as a yellow solid after recrystallization in hot chloroform.

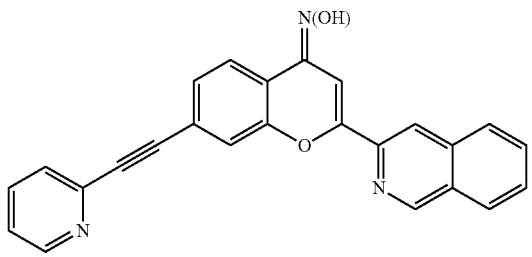

Mp: 248-251° C.

MS (ESI+): 390.5 $[C_{25}H_{15}N_3O_2+H]^+$ (m/z).

1H NMR: DMSO-$d_6$ δ (ppm): 11.33 (s, 1H), 9.43 (s, 1H), 8.65 (d, J=4.1 Hz, 1H), 8.54 (s, 1H), 8.23 (d, J=8.0 Hz, 1H), 8.12 (d, J=7.9 Hz, 1H), 7.96 (d, J=8.1 Hz, 1H), 7.90 (t, J=7.7 Hz, 2H), 7.83-7.75 (m, 3H), 7.71 (d, J=7.7 Hz, 1H), 7.51 (dd, J=8.1 Hz, J=1.5 Hz, 1H), 7.46 (ddd, J=8.1 Hz, J=5.0 Hz, J=1.1 Hz, 1H).

Example 24A 2-isoquinolin-3-yl-7-(pyridin-2-yl-ethynyl)-chromen-4-one O-tert-butyl oxime A solution of 7-bromo-2-isoquinolin-3-yl-chromen-4-one O-tert-butyl oxime (150 mg, 0.35 mmol), trans-dichlorobis(triphenylphosphine)palladium (22 mg, 0.035 mmol), copper iodide (13 mg, 0.071 mmol), triphenylphosphine (19 mg, 0.071 mmol) in dimethylformamide (3 ml) was degassed with argon for 10 min and then treated with triethylamine (74 μl, 0.53 mmol) and 2-ethynylpyridine (45 μl, 0.45 mmol). The solution was warmed to 120° C. under microwave irradiation (power max=80 W) for 1 hour and then poured onto a saturated aqueous solution of sodium hydrogenocarbonate, extracted with ethyl acetate, washed with water and brine, dried over sodium sulfate and purified by flash chromatography over silica gel (cyclohexane/ethyl acetate: 20-40%) to yield 2-isoquinolin-3-yl-7-(pyridin-2-yl-ethynyl)-chromen-4-one O-tert-butyl oxime (100 mg, 63%) as a yellow solid.

1H NMR: CDCl$_3$ δ (ppm): 9.29 (s, 1H), 8.66 (Br. s, 1H), 8.29 (s, 1H), 8.08 (d, J=8.0 Hz, 1H), 8.02 (d, J=7.9 Hz, 1H), 7.96 (d, J=8.1 Hz, 1H), 7.80 (s, 1H), 7.76 (t, J=8.3 Hz, 2H), 7.66 (t, J=7.6 Hz, 1H), 7.63-7.56 (m, 2H), 7.43 (dd, J=8.2 Hz, J=1.5 Hz, 1H), 7.31 (br. t, J=5.9 Hz 1H), 1.43 (s, 9H).

Example 25

2-isoquinolin-3-yl-7-(pyridin-2-yl-ethynyl)-chromen-4-one oxime was prepared in 18% overall yield using the method described in example 23, starting from 7-bromo-2-isoquinolin-3-yl-6-methyl-chromen-4-one O-led-butyl oxime (example 3B) and phenylacetylene. The title compound was isolated as a yellow solid and as a 95/5 mixture of Z/E oxime isomers.

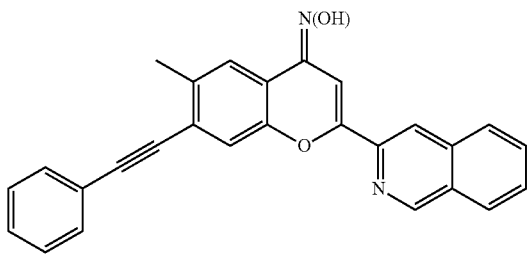

Mp: 248-250° C.
MS (ESI+): 403.5 [C$_{27}$H$_{18}$N$_2$O$_2$+H]$^+$ (m/z).
1H NMR of the major Z isomer: DMSO-d$_6$ δ (ppm): 11.23 (s, 1H), 9.42 (s, 1H), 8.52 (d, J=4.1 Hz, 1H), 8.23 (d, J=8.1 Hz, 1H), 8.11 (d, J=7.9 Hz, 1H), 7.89 (t, J=7.0 Hz, 1H), 7.85-7.75 (m, 1H), 7.81 (s, 1H), 7.75 (s, 1H), 7.68 (s, 1H), 7.66-7.59 (m, 2H), 7.52-7.45 (m, 3H), 2.50 (s, 3H).

Example 26

2-isoquinolin-3-yl-7-(pyridin-4-yl)ethynyl-chromen-4-one oxime was prepared in 6% overall yield using the method described in example 24, starting from 7-bromo-2-isoquinolin-3-yl-chromen-4-one O-tert-butyl oxime (example 2B) and 4-ethynylpyridine. The title compound was isolated as a yellow solid and as a 95/5 mixture of Z/E oxime isomers.

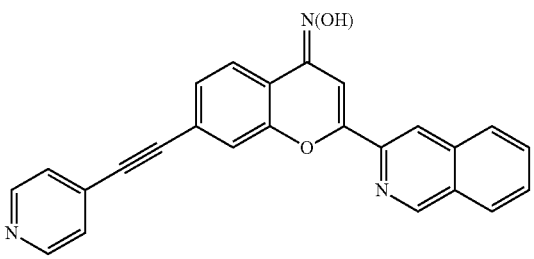

Mp: 265-270° C.
MS (ESI+): 390.4 [C$_{25}$H$_{15}$N$_3$O$_2$+H]$^+$ (m/z).
1H NMR of the major Z isomer: DMSO-d$_6$ δ (ppm): 11.34 (s, 1H), 9.43 (s, 1H), 8.68 (d, J=5.6 Hz, 2H), 8.52 (s, 1H), 8.23 (d, J=8.1 Hz, 1H), 8.12 (d, J=7.9 Hz, 1H), 7.96 (d, J=8.2 Hz, 1H), 7.89 (t, J=7.1 Hz, 1H), 7.84-7.74 (m, 3H), 7.58 (m, 2H), 7.52 (d, J=8.1 Hz, 1H).

Example 27

7-(4-dimethylaminophenyl)ethynyl-2-isoquinolin-3-yl-chromen-4-one oxime was prepared in 8% overall yield using the method described in example 24, starting from 7-bromo-2-isoquinolin-3-yl-chromen-4-one O-tert-butyl oxime (example 2B) and 4-dimethylaminophenylacetylene. The title compound was isolated as an orange solid and as a 95/5 mixture of Z/E oxime isomers.

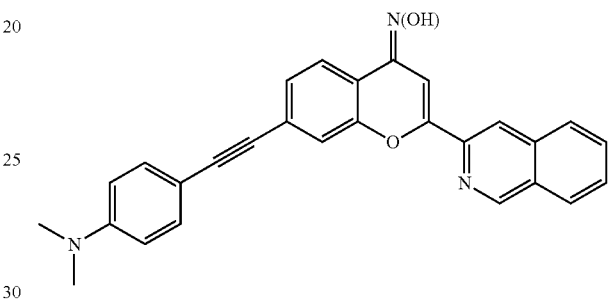

Mp: 235-240° C.
MS (ESI+): 432.5 [C$_{28}$H$_{21}$N$_3$O$_2$+H]$^+$ (m/z).
1H NMR of the major Z isomer: DMSO-d$_6$ δ (ppm): 11.21 (s, 1H), 9.43 (s, 1H), 8.53 (s, 1H), 8.23 (d, J=8.0 Hz, 1H), 8.12 (d, J=8.0 Hz, 1H), 7.89 (d, J=7.8 Hz, 2H), 7.79 (t, J=7.6 Hz, 1H), 7.75 (s, 1H), 7.63 (s, 1H), 7.45-7.25 (m, 3H), 6.74 (d, J=8.6 Hz, 2H), 2.97 (s, 6H).

Example 28

2-isoquinolin-3-yl-7-(3-methoxyphenyl)ethynyl-chromen-4-one oxime was prepared in 22% overall yield using the method described in example 24, starting from 7-bromo-2-isoquinolin-3-yl-chromen-4-one O-tert-butyl oxime (example 2B) and 3-methoxyphenylacetylene. The title compound was isolated as an orange solid and as a 93/7 mixture of Z/E oxime isomers.

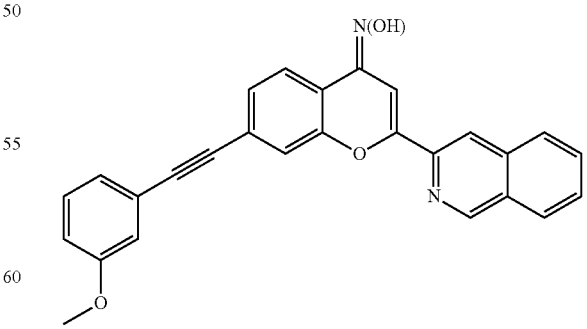

Mp: 248-251° C.
MS (ESI+): 419.5 [C$_{27}$H$_{18}$N$_2$O$_3$+H]$^+$ (m/z).
1H NMR of the major Z isomer: DMSO-d$_6$ δ (ppm): 11.28 (s, 1H), 9.43 (s, 1H), 8.53 (s, 1H), 8.22 (d, J=7.9 Hz, 1H), 8.12

(d, J=8.1 Hz, 1H), 7.93 (d, J=8.3 Hz, 2H), 7.89 (t, J=7.1 Hz, 1H), 7.79 (t, J=7.2 Hz, 1H), 7.76 (s, 1H), 7.72 (d, J=1.3 Hz, 1H), 7.46 (dd, J=8.1 Hz, J=1.3 Hz, 1H), 7.38 (t, J=7.9 Hz, 1H), 7.22-7.14 (m, 2H), 7.04 (dd, J=8.5 Hz, J=1.2 Hz, 1H), 3.82 (s, 3H).

Example 29

7-(3-aminophenyl)ethynyl-2-isoquinolin-3-yl-chromen-4-one oxime was prepared in 17% overall yield using the method described in example 24, starting from 7-bromo-2-isoquinolin-3-yl-chromen-4-one O-tert-butyl oxime (example 2B) and 3-aminophenylacetylene. The title compound was isolated as a yellow solid and as a 95/5 mixture of Z/E oxime isomers.

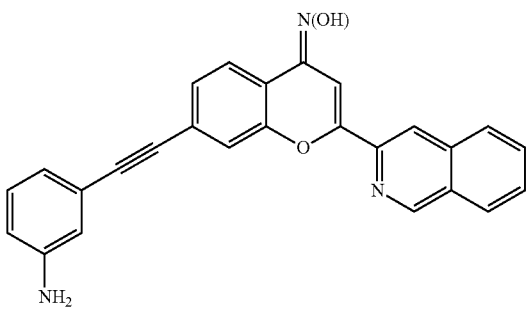

Mp: 272-275° C.
MS (ESI+): 404.4 [$C_{26}H_{17}N_3O_2$+H]$^+$ (m/z).
1H NMR of the major Z isomer: DMSO-$d_6$ δ (ppm): 11.26 (s, 1H), 9.43 (s, 1H), 8.54 (s, 1H), 8.23 (d, J=7.9 Hz, 1H), 8.12 (d, J=8.0 Hz, 1H), 7.95-7.86 (m, 2H), 7.79 (t, J=7.7 Hz, 1H), 7.76 (s, 1H), 7.68 (d, J=1.3 Hz, 1H), 7.42 (dd, J=8.1 Hz, J=1.3 Hz, 1H), 7.09 (t, J=7.7 Hz, 1H), 6.77 (s, 1H), 6.73 (d, J=7.5 Hz, 1H), 6.65 (d, J=8.1 Hz, 1H), 5.30 (s, 2H).

Example 30

7-(3-hydroxyphenyl)ethynyl-2-isoquinolin-3-yl-chromen-4-one oxime was prepared in 28% overall yield using the method described in example 24, starting from 7-bromo-2-isoquinolin-3-yl-chromen-4-one O-tert-butyl oxime (example 2B) and 3-hydroxyphenylacetylene. The title compound was isolated as a yellow solid and as a 80/20 mixture of Z/E oxime isomers.

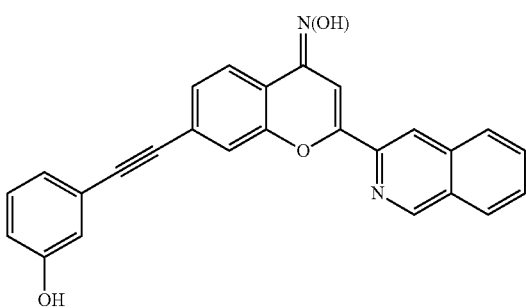

Mp: 255-259° C.
MS (ESI+): 405.4 [$C_{26}H_{16}N_2O_3$+H]$^+$ (m/z).
1H NMR of the major Z isomer: DMSO-$d_6$ δ (ppm): 11.30 (s, 1H), 9.79 (s, 1H), 9.43 (s, 1H), 8.54 (s, 1H), 8.23 (d, J=8.1 Hz, 1H), 8.12 (d, J=8.2 Hz, 1H), 7.92 (d, J=8.3 Hz, 1H), 7.90 (t, J=7.1 Hz, 1H, 1H), 7.79 (t, J=8.1 Hz, 1H), 7.75 (s, 1H), 7.72 (d, J=1.4 Hz, 1H), 7.45 (dd, J=8.1 Hz, J=1.3 Hz, 1H), 7.26 (t, J=7.9 Hz, 1H), 6.03 (d, J=7.5 Hz, 1H), 6.96 (s, 1H), 6.85 (dd, J=7.3 Hz, J=2.5 Hz, 1H).

Example 31

2-isoquinolin-3-yl-7-(4-methoxyphenyl)ethynyl-chromen-4-one oxime was prepared in 9% overall yield using the method described in example 24, starting from 7-bromo-2-isoquinolin-3-yl-chromen-4-one O-tert-butyl oxime (example 2B) and 4-methoxyphenylacetylene. The title compound was purified by preparative HPLC (gradient 35-20% Water/acetonitrile+0.05% trifluoroacetic acid) and isolated as a yellow solid and as a 95/05 mixture of Z/E oxime isomers.

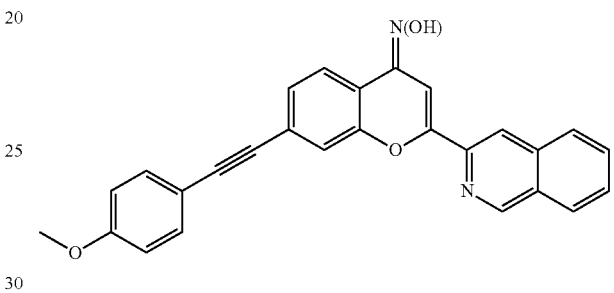

MS (ESI+): 419.1 [$C_{27}H_{18}N_2O_3$+H]$^+$ (m/z).
1H NMR of the major Z isomer: DMSO-$d_6$ δ (ppm): 11.31 (s, 1H), 9.49 (s, 1H), 8.60 (s, 1H), 8.29 (d, J=8.1 Hz, 1H), 8.18 (d, J=8.0 Hz, 1H), 8.00-7.90 (m, 2H), 7.90-7.80 (m, 1H), 7.81 (s, 1H), 7.75 (s, 1H), 7.61 (d, J=8.6 Hz, 2H), 7.48 (d, J=7.5 Hz, 1H), 7.09 (d, J=8.6 Hz, 2H), 3.88 (s, 3H).

Example 32

7-(2-chlorophenyl)ethynyl-2-isoquinolin-3-yl-chromen-4-one oxime was prepared in 10% overall yield using the method described in example 24, starting from 7-bromo-2-isoquinolin-3-yl-chromen-4-one O-tert-butyl oxime (example 2B) and 2-chlorophenylacetylene. The title compound was isolated as an orange solid and as a 80/20 mixture of Z/E oxime isomers.

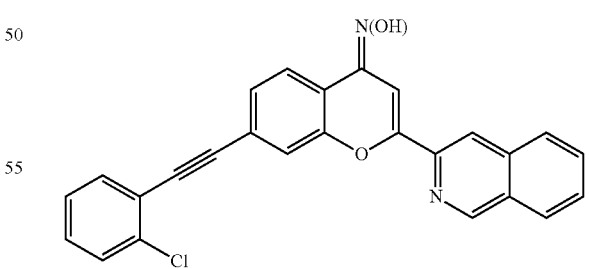

Mp: 292-297° C.
MS (ESI+): 423.4 [$C_{26}H_{15}ClN_2O_2$+H]$^+$ (m/z).
1H NMR of the major. Z isomer: DMSO-$d_6$ δ (ppm): 11.31 (s, 1H), 9.43 (s, 1H), 8.56 (s, 1H), 8.22 (d, J=7.8 Hz, 1H), 8.12 (d, J=7.8 Hz, 1H), 7.95 (d, J=8.1 Hz, 1H), 7.89 (t, J=7.7 Hz, 1H), 7.80-7.65 (m, 4H), 7.64 (d, J=7.5 Hz, 1H), 7.55-7.30 (m, 3H).

Example 33

7-(3-dimethylamino-prop-1-ynyl)-2-isoquinolin-3-yl-chromen-4-one oxime was prepared in 20% overall yield using the method described in example 24, starting from 7-bromo-2-isoquinolin-3-yl-chromen-4-one O-tert-butyl oxime (example 2B) and N,N-dimethylamino-2-propyne. The title compound was purified by preparative HPLC (gradient 70-55% Water/acetonitrile+0.05% trifluoroacetic acid) and isolated as an orange solid and as a 85/15 mixture of Z/E oxime isomers.

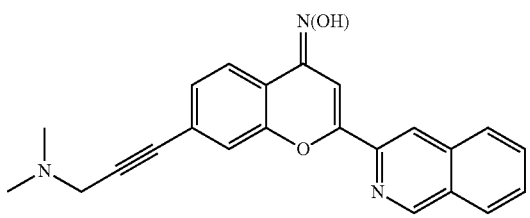

MS (ESI+): 370.1 $[C_{23}H_{19}N_3O_2+H]^+$ (m/z).

Example 34

6-cyclopropyl-2-isoquinolin-3-yl-chromen-4-one oxime was isolated in 60% yield using method D (step 2), starting from 6-cyclopropyl-2-isoquinolin-3-yl-chromen-4-one O-tert-butyl oxime (example 34A) as a yellow solid after purification by preparative HPLC (gradient 50-35% Water/acetonitrile+0.05% trifluoroacetic acid). The title compound was isolated as a 85/15 mixture of Z/E oxime isomers.

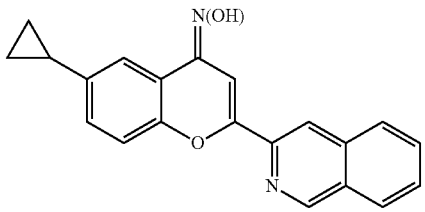

MS (ESI+): 329.2 $[C_{21}H_{16}N_2O_2+H]^+$ (m/z).
1H NMR of the major Z isomer: DMSO-$d_6$ δ (ppm): 11.48 (s, 1H), 9.38 (s, 1H), 8.36 (s, 1H), 8.19 (d, J=8.1 Hz, 1H), 8.12 (d, J=8.0 Hz, 1H), 7.90-7.65 (m, 2H), 7.41 (d, J=8.4 Hz, 2H), 7.29 (d, J=7.7 Hz, 1H), 7.08 (s, 1H), 2.00 (m, 1H), 0.98 (m, 2H), 0.67 (m, 2H).

Example 34A 6-cyclopropyl-2-isoquinolin-3-yl-chromen-4-one O-tert-butyl oxime A solution of 6-bromo-2-isoquinolin-3-yl-chromen-4-one O-tert-butyl oxime (100 mg, 0.236 mmol), palladium acetate (3 mg, 0.014 mmol), potassium phosphate (175 mg, 0.826 mmol), dicyclohexylbiphenylphosphine (8 mg, 0.024 mmol), Cyclopropylboronic acid pinacol ester (99 mg, 0.59 mmol) in toluene (3 ml) was degassed with argon for 10 min. The reactor was sealed and heated at 120° C. for 18 hours. The mixture was poured onto a saturated aqueous solution of ammonium chloride, extracted with ethyl acetate, washed with water and brine, dried over sodium sulfate and purified by flash chromatography over silica gel (cyclohexane/dichloromethane: 0-80%) to yield 2-isoquinolin-3-yl-7-(pyridin-2-yl-ethynyl)-chromen-4-one O-tert-butyl oxime (18 mg, 20%).

MS (ESI+): 385.1 $[C_{25}H_{24}N_2O_2+H]^+$ (m/z).

Example 35

2-isoquinolin-3-yl-6-(pyrrolidin-1-yl)-chromen-4-one oxime was isolated in 63% yield using method D (step 2), starting from 2-isoquinolin-3-yl-6-(pyrrolidin-1-yl)-chromen-4-one O-tert-butyl oxime (example 35A) as an orange solid after triturating in hot chloroform. The title compound was isolated as a 97/3 mixture of Z/E oxime isomers.

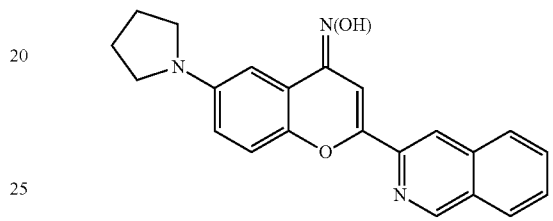

MS (ESI+): 358.1 $[C_{22}H_{19}N_3O_2+H]^+$ (m/z).
1H NMR of the major Z isomer: DMSO-$d_6$ δ (ppm): 10.85 (s, 1H), 9.41 (s, 1H), 8.45 (s, 1H), 8.21 (d, J=8.1 Hz, 1H), 8.14 (d, J=7.9 Hz, 1H), 7.86 (t, J=7.0 Hz, 1H), 7.76 (t, J=7.1 Hz, 1H), 7.71 (s, 1H), 7.38 (d, J=9.0 Hz, 1H), 6.90 (d, J=2.6 Hz, 1H), 6.82 (dd, J=9.0 Hz, J=2.6 Hz, 1H), 3.27 (br. s, 4H), 1.98 (br. s, 4H).

Example 35A 2-isoquinolin-3-yl-6-(pyrrolidin-1-yl)-chromen-4-one O-tert-butyl oxime A vial was charged with 6-bromo-2-isoquinolin-3-yl-chromen-4-one O-tert-butyl oxime (100 mg, 0.236 mmol), Pd-PEPPSI® (3 mg, 0.005 mmol), potassium tert-butoxide (40 mg, 0.354 mmol) and purged with argon for 15 min. Pyrrolidine (24 μl, 0.283 mmol) and dry 1,2-dimethoxyethane (1 ml) were added and the solution was heated at 80° C. for 18 hours. The mixture was diluted with ethyl acetate washed with a saturated aqueous solution of ammonium chloride, water and brine, dried over sodium sulfate and purified by flash chromatography over silica gel (cyclohexane/dichloromethane: 0-80%) to yield 2-isoquinolin-3-yl-6-(pyrrolidin-1-yl)-chromen-4-one O-tert-butyl oxime (64 mg, 65%).

MS (ESI+): 414.5 $[C_{25}H_{27}N_3O_2+H]^+$ (m/z).

Example 36

2-isoquinolin-3-yl-6-(vinyl)-chromen-4-one oxime was isolated in 40% yield using method D (step 2), starting from 2-isoquinolin-3-yl-6-(vinyl)-chromen-4-one O-tert-butyl oxime (example 36A) as a yellow solid after purification by flash chromatography over silica gel (cyclohexane/ethyl acetate: 0-40%)

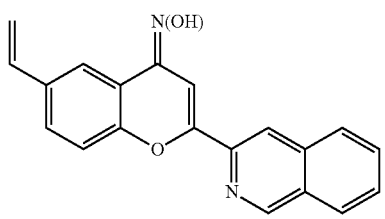

Mp: 198-200° C.

MS (ESI+): 315.3 $[C_{20}H_{14}N_2O_2+H]^+$ (m/z).

1H NMR of the major Z isomer: DMSO-$d_6$ δ (ppm): 11.10 (s, 1H), 9.42 (s, 1H), 8.50 (s, 1H), 8.23 (d, J=7.9 Hz, 1H), 8.15 (d, J=7.9 Hz, 1H), 7.92 (d, J=2.0 Hz, 1H), 7.88 (t, J=7.0 Hz, 1H), 7.78 (t, J=7.1 Hz, 1H), 7.77 (s, 1H), 7.72 (dd, J=8.9 Hz, J=2.2 Hz, 1H), 7.51 (dd, J=8.6 Hz, J=9.0 Hz, 1H), 6.82 (dd, J=17.7 Hz, J=11.1 Hz, 1H), 5.85 (d, J=17.7 Hz, 1H), 5.32 (d, J=11.1 Hz, 1H).

Example 36A 2-isoquinolin-3-yl-6-(vinyl)-chromen-4-one O-tert-butyl oxime

In a sealed tube was degassed with argon for 15 min. a solution of 6-bromo-2-isoquinolin-3-yl-chromen-4-one O-tert-butyl oxime (100 mg, 0.236 mmol) in toluene. Tributyl (vinyl)tin (76 μl, 0.26 mmol) and tetrakis(triphenylphosphine)palladium (13 mg, 0.012 mmol) were added degassing was continued for 5 min. The tube was sealed and heated at 120° C. for 8 hours. The mixture was filtered, concentrated and purified by flash chromatography over silica gel (cyclohexane/ethyl acetate: 0-10%) to yield 2-isoquinolin-3-yl-6-(vinyl)-chromen-4-one O-tert-butyl oxime (84 mg, 96%).

MS (ESI+): 371.0 $[C_{24}H_{22}N_2O_2+H]^+$ (m/z).

Example 37

6-ethyl-2-isoquinolin-3-yl-chromen-4-one oxime was isolated in 50% yield using method D (step 2), starting from 6-ethyl-2-isoquinolin-3-yl-chromen-4-one O-tert-butyl oxime (example 37A) as a yellow solid after purification by flash chromatography over silica gel (cyclohexane/ethyl acetate: 0-20%)

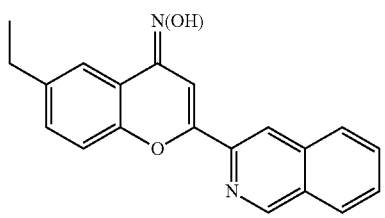

Mp: 210-212° C.

MS (ESI+): 317.0 $[C_{20}H_{16}N_2O_2+H]^+$ (m/z).

1H NMR of the major Z isomer: DMSO-$d_6$ δ (ppm): 11.00 (s, 1H), 9.42 (s, 1H), 8.48 (s, 1H), 8.22 (d, J=8.0 Hz, 1H), 8.15 (d, J=7.9 Hz, 1H), 7.88 (t, J=7.0 Hz, 1H), 7.82-7.72 (m, 2H), 7.77 (s, 1H), 7.46-7.35 (m, 2H), 2.68 (q, J=7.5 Hz, 2H), 1.22 (t, J=7.5 Hz, 3H).

Example 37A 6-ethyl-2-isoquinolin-3-yl-chromen-4-one O-tert-butyl oxime

A solution of 2-isoquinolin-3-yl-6-(vinyl)-chromen-4-one O-tea-butyl oxime (50 mg, 0.135 mmol) in mixture of tetrahydrofuran (4 ml) and methanol (1 ml) was hydrogenated over 10% palladium Pd/C (10 mg) under 1 atmosphere at room temperature for 6 to 8 hours. The catalyst was removed by filtration and the filtrate was concentrated to dryness to yield 6-ethyl-2-isoquinolin-3-yl-chromen-4-one O-tert-butyl oxime (46 mg, 90%) that was used without further purification.

1H NMR: CDCl$_3$ δ (ppm): 9.28 (s, 1H), 8.30 (s, 1H), 8.01 (d, J=7.7 Hz, 1H), 7.94 (d, J=7.5 Hz, 1H), 7.89 (m, 1H), 7.79 (s, 1H), 7.75 (td, J=8.2 Hz, J=1.5 Hz, 1H), 7.65 (td, J=7.5 Hz, J=1.5 Hz, 1H), 2.71 (q, J=7.5 Hz, 2H), 1.29 (t, J=7.5 Hz, 3H).

Example 38

6-cyano-2-isoquinolin-3-yl-chromen-4-one oxime was prepared in 63% yield using method D (step 2), starting from 6-cyano-2-isoquinolin-3-yl-chromen-4-one O-tert-butyl oxime (example 38A) as a pale yellow solid after recrystallization in hot chloroform. The title compound was isolated as a 90/10 mixture of Z/E oxime isomers.

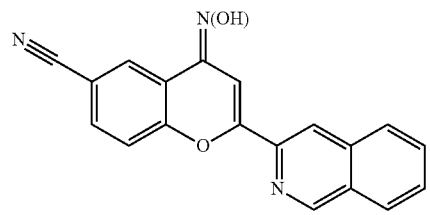

Mp: 280° C. dec.

MS (ESI-): 314.3 $[C_{19}H_{11}N_3O_2+H]^+$ (m/z).

1H NMR of the major Z isomer: DMSO-$d_6$ δ (ppm): 11.47 (s, 1H), 9.41 (s, 1H), 8.49 (s, 1H), 8.25-8.18 (m, 2H), 8.12 (d, J=8.1 Hz, 1H), 7.98 (dd, J=8.6 Hz, J=2.0 Hz, 1H), 7.88 (t, J=7.0 Hz, 1H), 7.78 (t, J=7.0 Hz, 1H), 7.76 (s, 1H), 7.68 (d, J=8.6 Hz, 1H).

Example 38A 6-cyano-2-isoquinolin-3-yl-chromen-4-one O-tert-butyl oxime

In a microwave vial was degassed with argon for 15 min. a mixture of 6-bromo-2-isoquinolin-3-yl-chromen-4-one O-tert-butyl oxime (50 mg, 0.118 mmol), zinc cyanide (14 mg, 0.118 mmol) in dimethylformamide (1.5 ml). Tetrakis (triphenylphosphine)palladium (4 ma, 0.003 mmol) was added and the vial was sealed and heated at 120° C. under microwave irradiation for 10 min. The mixture was diluted with ethyl acetate, washed with a 5% aqueous solution of ammonia, brine and dried over sodium sulfate. The solution was concentrated and purified by flash chromatography over silica gel (cyclohexane/ethyl acetate: 0-20%) to yield 6-cyano-2-isoquinolin-3-yl-chromen-4-one O-tert-butyl oxime (33 mg, 76%).

MS (ESI+): 370.4 $[C_{23}H_{19}N_3O_2+H]^+$ (m/z).

Example 39

6-dimethylamino-2-isoquinolin-3-yl-chromen-4-one oxime was prepared in 51% overall yield following the method described in example 35, starting from 6-bromo-2-isoquinolin-3-yl-chromen-4-one O-tert-butyl oxime and dimethylamine (2.0 M in tetrahydrofuran). The title compound was isolated as a pale yellow solid after purification by flash chromatography over silica gel (cyclohexane/ethyl acetate: 0-60%).

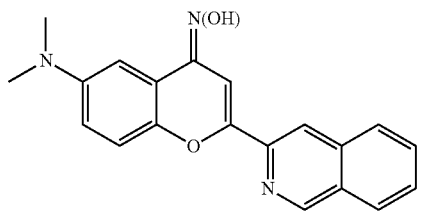

Mp: 223-225° C.
MS (ESI+): 332.1 $[C_{20}H_{17}N_3O_2+H]^+$ (m/z).
1H NMR: DMSO-$d_6$ δ (ppm): 10.91 (s, 1H), 9.41 (s, 1H), 8.46 (s, 1H), 8.21 (d, J=8.1 Hz, 1H), 8.14 (d, J=8.1 Hz, 1H), 7.87 (t, J=8.3 Hz, 1H), 7.76 (t, J=7.0 Hz, 1H), 7.71 (s, 1H), 7.39 (d, J=9.0 Hz, 1H), 7.10-7.00 (m, 2H), 2.94 (s, 6H).

Example 40

2-isoquinolin-3-yl-6-(morpholin-4-yl-methyl)-chromen-4-one oxime was prepared in 30% yield using method D (step 2), starting from 2-isoquinolin-3-yl-6-(morpholin-4-yl-methyl)-chromen-4-one O-tad-butyl oxime (example 40A) as a yellow solid after purification by flash chromatography over silica gel (cyclohexane/ethyl acetate: 0-100%). The title compound was isolated as a 70/30 mixture of Z/E oxime isomers.

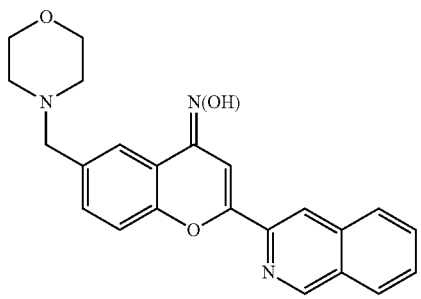

MS (ESI+): 388.5 $[C_{23}H_{21}N_3O_3+H]^+$ (m/z).
1H NMR of the major Z isomer: DMSO-$d_6$ δ (ppm): 11.04 (s, 1H), 9.42 (s, 1H), 8.49 (s, 1H), 8.22 (d, J=8.1 Hz, 1H), 8.19 (d, J=8.1 Hz, 1H), 7.90-7.85 (m, 2H), 7.85-7.72 (m, 1H), 7.76 (s, 1H), 7.55-7.42 (m, 2H), 3.59 (br. s, 4H), 3.52 (s, 2H), 2.39 (br. S, 4H).

Example 40A 2-isoquinolin-3-yl-6-(morpholin-4-yl-methyl)-chromen-4-one O-tert-butyl oxime In a sealed tube was degassed with argon for 15 min. a mixture of 6-bromo-2-isoquinolin-3-yl-chromen-4-one O-tert-butyl oxime (100 mg, 0.236 mmol), cesium carbonate (230 mg, 0.708 mmol), dichloro[1,1-bis(diphenylphosphino)ferrocene]palladium(II) dichloromethane adduct (10 mg, 0.012 mmol) and potassium trifluoroboratomethylmorpholine in toluene (7.5 ml) and water (2.5 ml). The tube was sealed and heated at 100° C. for 72 hours. The mixture was diluted with ethyl acetate, washed with water, a saturated aqueous solution of ammonium chloride, and extracted three times with a 1N solution of hydrochloric acid. The aqueous layers were neutralized with a 6N solution of sodium hydroxide and extracted with ethyl acetate. The organic layers were dried over sodium sulfate and concentrated to dryness to yield 2-isoquinolin-3-yl-6-(morpholin-4-yl-methyl)-chromen-4-one O-tert-butyl oxime (10 mg, 10%) as a brown residue that was used without further purification.
MS (ESI+): 444.2 $[C_{27}H_{29}N_3O_3+H]^+$ (m/z).

Example 41

6-hydroxy-2-isoquinolin-3-yl-chromen-4-one oxime was prepared in 56% yield using method D (step 2), starting from 6-hydroxy-2-isoquinolin-3-yl-chromen-4-one O-tert-butyl oxime (example 41A) as a yellow solid after purification by flash chromatography over silica gel (cyclohexane/ethyl acetate: 0-80%). The title compound was isolated as a 95/5 mixture of Z/E oxime isomers.

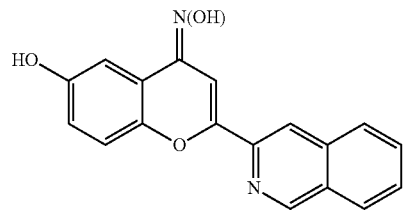

Mp: 255-260° C.
MS (ESI+): 305.0 $[C_{18}H_{12}N_2O_3+H]^+$ (m/z).
1H NMR of the major Z isomer: DMSO-$d_6$ δ (ppm): 10.96 (s, 1H), 9.66 (s, 1H), 9.41 (s, 1H), 8.45 (s, 1H), 8.21 (d, J=7.9 Hz, 1H), 8.14 (d, J=8.2 Hz, 1H), 7.87 (t, J=6.9 Hz, 1H), 7.79 (t, J=7.9 Hz, 1H), 7.70 (s, 1H), 7.36 (d, J=8.8 Hz, 1H), 7.27 (s, 1H), 6.96 (d, J=8.5 Hz, 1H).

Example 41A 6-hydroxy-2-isoquinolin-3-yl-chromen-4-one O-tert-butyl oxime was prepared in 89% yield following the method describe in example 18A, starting from 6-bromo-2-isoquinolin-3-yl-chromen-4-one O-tert-butyl oxime after purification by flash chromatography over silica gel (cyclohexane/ethyl acetate: 0-20%). The title compound was isolated as a yellow solid.
1H NMR: CDCl$_3$ δ (ppm): 9.28 (s, 1H), 8.29 (s, 1H), 8.01 (d, J=7.7 Hz, 1H), 7.94 (d, J=, 7.9 Hz, 1H), 7.75 (t, J=7.4 Hz, 1H), 7.75 (s, 1H), 7.65 (t, J=7.5 Hz, 1H), 7.50 (d, J=3.0 Hz, 1H), 7.28-7.22 (m, 1H), 6.90 (dd, J=8.8 Hz, J=2.5 Hz, 1H), 5.08 (s, 1H), 1.42 (s, 9H).

Example 42

2-isoquinolin-3-yl-6-methoxy-chromen-4-one oxime was prepared in 62% yield using method D (step 2), starting from 2-isoquinolin-3-yl-6-methoxy-chromen-4-one O-tert-butyl oxime (example 42A) as a yellow solid after purification by flash chromatography over silica gel (cyclohexane/ethyl acetate: 0-80%, then dichloromethane/methanol: 0-10%). The title compound was isolated as a 90/10 mixture of Z/E oxime isomers.

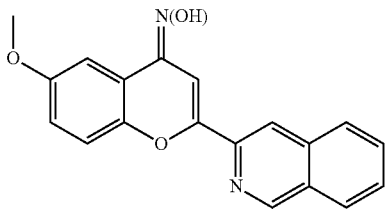

Mp: 250-255° C.

MS (ESI+): 319.0 $[C_{19}H_{14}N_2O_3+H]^+$ (m/z).

1H NMR of the major Z isomer: DMSO-$d_6$ δ (ppm): 11.04 (s, 1H), 9.41 (s, 1H), 8.47 (s, 1H), 8.21 (d, J=8.1 Hz, 1H), 8.14 (d, J=8.0 Hz, 1H), 7.87 (t, J=7.5 Hz, 1H), 7.77 (t, J=7.9 Hz, 1H), 7.75 (s, 1H), 7.47 (d, J=9.0 Hz, 1H), 7.34 (d, J=3.0 Hz, 1H), 7.15 (dd, J=9.0 Hz, J=3.0 Hz, 1H), 3.81 (s, 3H).

Example 42A 2-isoquinolin-3-yl-6-methoxy-chromen-4-one O-tert-butyl oxime was prepared in 67% yield following the method described in example 19A, starting from 6-hydroxy-2-isoquinolin-3-yl-chromen-4-one O-tert-butyl oxime (example 41A). The title compound was isolated as a yellow solid after purification by flash chromatography over silica gel (cyclohexane/ethyl acetate: 0-20%).

1H NMR: CDCl$_3$ δ (ppm): 9.28 (s, 1H), 8.29 (s, 1H), 8.01 (d, J=7.9 Hz, 1H), 7.94 (d, J=7.9 Hz, 1H), 7.77 (s, 1H), 7.74 (t, J=7.5 Hz, 1H), 7.65 (t, J=7.5 Hz, 1H), 7.54 (d, J=3.0 Hz, 1H), 7.29 (d, J=9.4 Hz, 1H), 7.10 (dd, J=9.0 Hz, J=3.0 Hz, 1H), 3.88 (s, 3H), 1.43 (s, 9H).

Example 43

2-isoquinolin-3-yl-6-(2-methoxy-ethoxy)-chromen-4-one oxime was prepared in 67% overall yield using the method described in example 42 and 42A, starting from 6-hydroxy-2-isoquinolin-3-yl-chromen-4-one O-tert-butyl oxime (example 41A) and bromoethylmethylether instead of iodomethane. The title compound was isolated as a yellow solid after purification by flash chromatography over silica gel (cyclohexane/ethyl acetate: 0-80%), and as a 85/15 mixture of Z/E oxime isomers.

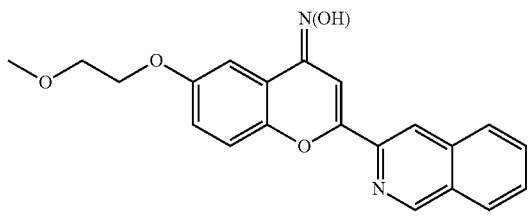

Mp: 198-204° C.

MS (ESI+): 363.2 $[C_{21}H_{18}N_2O_4+H]^+$ (m/z).

1H NMR of the major Z isomer: DMSO-$d_6$ δ (ppm): 11.04 (s, 1H), 9.41 (s, 1H), 8.47 (s, 1H), 8.21 (d, J=8.1 Hz, 1H), 8.14 (d, J=8.0 Hz, 1H), 7.87 (t, J=7.7 Hz, 1H), 7.77 (t, J=7.9 Hz, 1H), 7.73 (s, 1H), 7.46 (d, J=8.9 Hz, 1H), 7.34 (d, J=3.0 Hz, 1H), 7.16 (dd, J=9.0 Hz, J=3.0 Hz, 1H), 4.14 (m, 2H), 3.39 (m, 2H) 3.32 (s, 3H).

Example 44

6-(2-dimethylamino-ethoxy)-2-isoquinolin-3-yl-chromen-4-one oxime was prepared in 66% yield using method D (step 2), starting from 6-(2-dimethylamino-ethoxy)-2-isoquinolin-3-yl-chromen-4-one O-tert-butyl oxime (example 44A) as an orange solid and as a 90/10 mixture of Z/E oxime isomers.

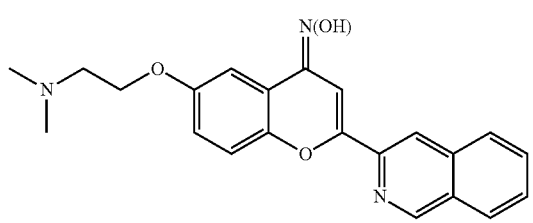

Mp: 203-205° C.

MS (ESI+): 376.5 $[C_{22}H_{21}N_3O_3+H]^+$ (m/z).

1H NMR of the major Z isomer: DMSO-$d_6$ δ (ppm): 11.04 (s, 1H), 9.41 (s, 1H), 8.47 (s, 1H), 8.21 (d, J=8.1 Hz, 1H), 8.14 (d, J=8.0 Hz, 1H), 7.87 (t, J=7.0 Hz, 1H), 7.77 (t, J=7.7 Hz, 1H), 7.73 (s, 1H), 7.46 (d, J=9.0 Hz, 1H), 7.33 (d, J=3.0 Hz, 1H), 7.15 (dd, J=9.0 Hz, J=3.0 Hz, 1H), 4.09 (m, 2H), 2.64 (m, 2H) 2.23 (s, 6H).

Example 44A 6-(2-dimethylamino-ethoxy)-2-isoquinolin-3-yl-chromen-4-one O-tert-butyl oxime To a cold solution of triphenylphosphine (110 mg, 0.41 mmol) in tetrahydrofuran (3 ml) under argon were successively added 2-dimethylamino-ethanol (30 μl, 0.27 mmol), a solution of diethylazodicarboxylate (40% in toluene, 190 μl, 0.41 mmol) and 6-hydroxy-2-isoquinolin-3-yl-chromen-4-one O-tert-butyl oxime (100 mg, 0.27 mmol). The solution was stirred at room temperature for 18 hours. The mixture was poured onto a saturated solution of sodium hydrogenocarbonate and extracted three times with dichloromethane. The organic layers were washed with brine, dried over sodium sulfate and concentrated to dryness to yield 2-isoquinolin-3-yl-6-(morpholin-4-yl-methyl)-chromen-4-one O-tert-butyl oxime (30 mg, 22%) as a yellow solid after purification by flash chromatography over silica gel (dichloromethane/methanol: 0-20%)

MS (ESI+): 432.3 $[C_{20}H_{29}N_3O_3+H]^+$ (m/z).

Example 45

2-isoquinolin-3-yl-6-[3-(4-methyl-piperazin-1-yl)-propylamino]-chromen-4-one oxime was prepared in 85% overall yield using the method described in examples 35 and 35A, starting from 6-bromo-2-isoquinolin-3-yl-chromen-4-one O-tert-butyl oxime (example 4B) and 3-(4-methyl-piperazin-1-yl)-propylamine. The title compound was isolated as a yellow solid and as a 95/5 mixture of Z/E oxime isomers.

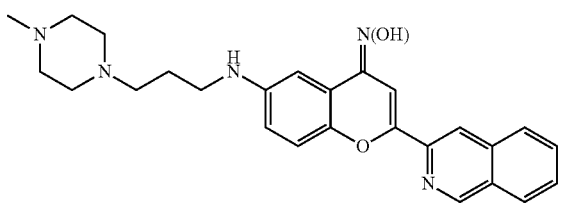

Mp: 208-211° C.
MS (ESI+): 444.5 $[C_{26}H_{29}N_5O_2+H]^+$ (m/z).
1H NMR of the major Z isomer: DMSO-$d_6$ δ (ppm): 10.83 (s, 1H), 9.40 (s, 1H), 8.43 (s, 1H), 8.20 (d, J=8.1 Hz, 1H), 8.13 (d, J=8.1 Hz, 1H), 7.85 (t, J=7.2 Hz, 1H), 7.76 (t, J=7.5 Hz, 1H), 7.69 (s, 1H), 7.28 (d, J=8.8 Hz, 1H), 6.94 (d, J=3.0 Hz, 1H), 6.82 (dd, J=8.9 Hz, J=3.0 Hz, 1H), 5.88 (m, 1H), 3.04 (m, 2H) 2.45-2.20 (m, 10H), 2.14 (s, 3H), 1.70 (m, 2H).

Example 46

2-isoquinolin-3-yl-6-[2-(4-methyl-piperazin-1-yl)-ethoxy]-chromen-4-one oxime was prepared in 49% overall yield using the method described in examples 44 and 44A, starting from 6-hydroxy-2-isoquinolin-3-yl-chromen-4-one O-tert-butyl oxime (example 41A) and 2-(4-methyl-piperazin-1-yl)-ethanol. The title compound was isolated as a yellow solid and as a 90/10 mixture of Z/E oxime isomers.

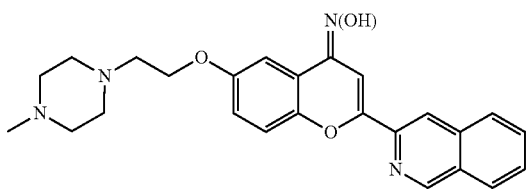

Mp: 233-236° C.
MS (ESI+): 431.3 $[C_{26}H_{26}N_4O_3+H]^+$ (m/z).
1H NMR of the major Z isomer: DMSO-$d_6$ δ (ppm): 11.03 (s, 1H), 9.41 (s, 1H), 8.47 (s, 1H), 8.21 (d, J=8.1 Hz, 1H), 8.14 (d, J=8.1 Hz, 1H), 7.87 (t, J=7.4 Hz, 1H), 7.77 (t, J=7.5 Hz, 1H), 7.73 (s, 1H), 7.46 (d, J=9.2 Hz, 1H), 7.33 (d, J=2.5 Hz, 1H), 7.15 (dd, J=9.0 Hz, J=2.5 Hz, 1H), 4.11 (t, J=5.6 Hz, 2H), 2.70 (t, J=5.6 Hz, 2H) 2.60-2.40 (m, 4H), 2.40-2.20 (m, 4H), 2.14 (s, 3H).

Example 47

2-isoquinolin-3-yl-7-phenyl-chromen-4-one oxime was isolated in 30% yield using method D (step 2), starting from 2-Isoquinolin-3-yl-7-phenyl-chromen-4-one O-tert-butyl oxime (example 47A) as a pale yellow solid after recrystallization in hot chloroform.

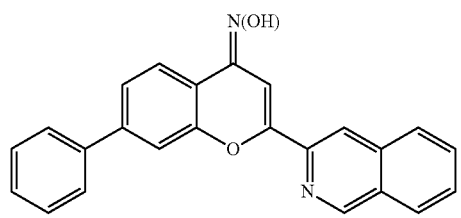

Mp: 275-278° C.
MS (ESI-9: 365.4 $[C_{24}H_{16}N_2O_2+H]^+$ (m/z).

1H NMR: DMSO-$d_6$ δ (ppm): 11.13 (s, 1H), 9.44 (s, 1H), 8.57 (s, 1H), 8.23 (d, J=7.9 Hz, 1H), 8.13 (d, J=8.1 Hz, 1H), 7.99 (d, J=8.2 Hz, 1H), 7.90 (t, J=7.0 Hz, 1H), 7.86-7.75 (m, 4H), 7.79 (s, 1H), 7.65 (dd, J=8.3 Hz, J=1.9 Hz, 1H), 7.54 (t, J=7.7 Hz, 2H), 7.44 (t, J=7.3 Hz, 1H).

Example 47A 2-isoquinolin-3-yl-7-phenyl-chromen-4-one O-tert-butyl oxime

In a sealed tube, a solution of 7-bromo-2-isoquinolin-3-yl-chromen-4-one O-tert-butyl oxime (150 mg, 0.35 mmol) phenylboronic acid (60 mg, 0.49 mmol) a 2M aqueous solution of sodium carbonate (350 µl, 0.70 mmol) in toluene (2.4 ml) and ethanol (0.5 ml) was degassed with argon for 10 min and then tetrakis(triphenylphosphine)palladium (20 mg, 0.018 mmol) was added. The tube was sealed and the mixture was heated under argon at 120° C. for 4 hours. After cooling, the reaction mixture was poured onto a saturated solution of ammonium chloride and extracted with ethyl acetate. The extracts were washed with brine, dried over sodium sulfate and absorbed over silica gel for purification by flash chromatography (gradient cyclohexane/dichloromethane: 0-80%) to yield 2-Isoquinolin-3-yl-7-phenyl-chromen-4-one O-tert-butyl oxime (135 mg, 91%) as a yellow solid.

MS (ESI+): 447.6 $[C_{30}H_{26}N_2O_2+H]^+$ (m/z).
1H NMR: CDCl$_3$ δ (ppm): 9.30 (s, 1H), 8.34 (s, 1H), 8.15 (d, J=8.3 Hz, 1H), 8.02 (d, J=7.7 Hz, 1H), 7.96 (d, J=7.9 Hz, 1H), 7.82 (s, 1H), 7.76 (td, J=6.8 Hz, J=1.3 Hz, 1H), 7.72-7.63 (m, 3H), 7.59 (d, J=1.7 Hz, 1H), 7.53-7.44 (m, 3H), 7.44-7.36 (m, 1H), 1.45 (s, 9H).

Example 48

7-(4-biphenyl)-2-isoquinolin-3-yl-chromen-4-one oxime was isolated in 26% overall yield using the method described in examples 47 and 47A, starting from 7-bromo-2-Isoquinolin-3-yl-chromen-4-one O-tert-butyl oxime and 4-biphenyl-boronic acid. The title compound was isolated as a beige solid after triturating in hot chloroform and as a 80/20 mixture of Z/E oxime isomers.

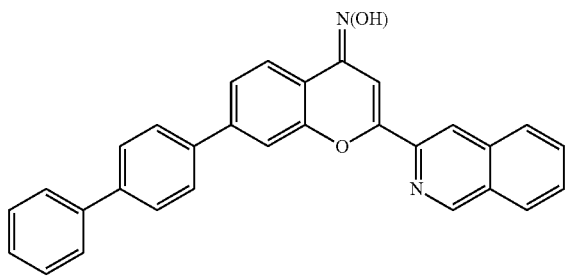

Mp: 283-285° C.
MS (ESI+): 441.0 $[C_{30}H_{20}N_2O_2+H]^+$ (m/z).
1H NMR: DMSO-$d_6$ δ (ppm): 11.20 (s, 1H), 9.45 (s, 1H), 8.59 (s, 1H), 8.24 (d, J=8.3 Hz, 1H), 8.15 (d, J=8.1 Hz, 1H), 8.01 (d, J=8.3 Hz, 1H), 7.96-7.68 (m, 11H), 7.51 (t, J=7.7 Hz, 2H), 7.41 (t, J=7.3 Hz, 1H).

Example 49

2-isoquinolin-3-yl-7-[3-(4-methyl-piperazin-1-yl)-propylamino]-chromen-4-one oxime was prepared in 19% overall yield using the method described in examples 45, starting from 7-bromo-2-isoquinolin-3-yl-chromen-4-one O-tert-butyl oxime (example 2B) and 3-(4-methyl-piperazin-1-yl)-propylamine. The title compound was isolated as a yellow solid.

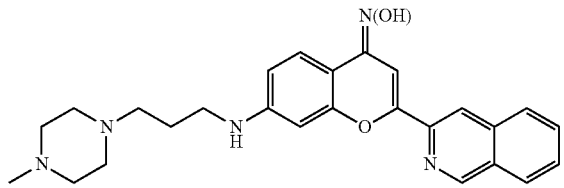

Mp: 228-233° C.
MS (ESI+): 444.4 $[C_{26}H_{29}N_5O_2+H]^+$ (m/z).
1H NMR: DMSO-$d_6$ δ (ppm): 10.45 (s, 1H), 9.40 (s, 1H), 8.45 (s, 1H), 8.20 (d, J=8.1 Hz, 1H), 8.15 (d, J=8.1 Hz, 1H), 7.87 (t, J=7.0 Hz, 1H), 7.76 (t, J=7.0 Hz, 1H), 7.70 (s, 1H), 7.58 (d, J=8.7 Hz, 1H), 6.57 (d, J=8.7 Hz, 1H), 6.52 (s, 1H), 6.31 (m, 1H), 3.13 (m, 2H) 2.45-2.20 (m, 10H), 2.18 (s, 3H), 1.75 (m, 2H).

Example 50

2-Isoquinolin-3-yl-7-{3-[2-(4-methyl-piperazin-1-yl)-ethoxy]-phenylethynyl}-chromen-4-one oxime was prepared in 9% overall yield using the method described in examples 44 and 44A, starting from 7-(3-hydroxyphenyl)ethynyl-2-isoquinolin-3-yl-chromen-4-one O-tert-butyl oxime (tert-butyl protected oxime of example 30) and 2-(4-methyl-piperazin-1-yl)-ethanol. The title compound was isolated as a yellow solid and as a 90/10 mixture of Z/E oxime isomers after Preparative HPLC purification (gradient 65-50% Water/acetonitrile+0.05% trifluoroacetic acid).

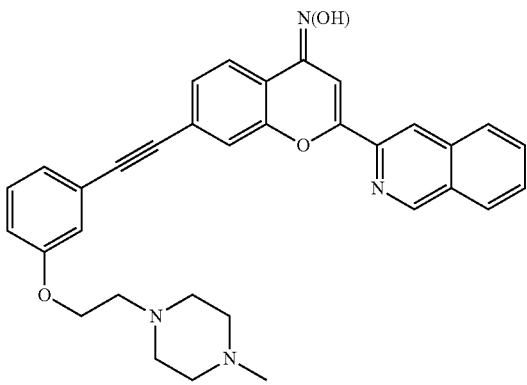

HPLC (gradient 5%-95% ACN/$H_2O$+0.1% HCOOH): >95%; RT=4.94 min.
MS (ESI+): 531.2 $[C_{33}H_{30}N_4O_3+H]^+$ (m/z).
1H NMR of the major Z isomer: DMSO-$d_6$ δ (ppm): 11.30 (s, 1H), 9.44 (s, 1H), 8.54 (s, 1H), 8.30 (d, J=8.1 Hz, 1H), 8.18 (d, J=8.1 Hz, 1H), 8.01 (d, J=8.1 Hz, 1H), 7.96 (t, J=7.4 Hz, 1H), 7.86 (t, J=7.5 Hz, 1H), 7.82 (s, 1H), 7.79 (s, 1H), 7.45-7.55 (m, 2H), 7.32 (s, 1H), 7.21-7.18 (m, 1H), 4.11 (t, J=5.6 Hz, 2H), 2.70 (t, J=5.6 Hz, 2H) 2.60-2.40 (m, 4H), 2.40-2.20 (m, 4H), 2.14 (s, 3H).

Example 51

2-Isoquinolin-3-yl-7-{3-methylaminophenylethynyl}-chromen-4-one oxime was prepared using method D (step 2) starting from 2-isoquinolin-3-yl-7-{3-methylaminophenylethynyl}-chromen-4-one O-tert-butyl oxime (example 51A). The title compound was isolated as a yellow solid and as a 90/10 mixture of Z/E oxime isomers after Preparative HPLC purification (gradient 50-35% Water/acetonitrile+0.05% trifluoroacetic acid).

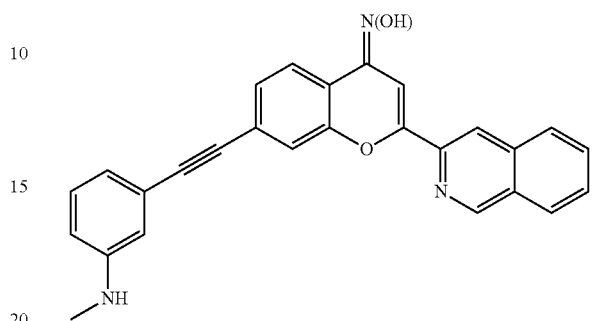

HPLC (gradient 95%-40% $H_2O$/ACN+0.05% TFA (in 12 min.): >90%; RT=12.25 min.
MS (ESI+): 418.1 $[C_{27}H_{19}N_3O_2+H]^+$ (m/z).
1H NMR of the major Z isomer: (400 MHz) DMSO-$d_6$ δ (ppm): 11.26 (s, 1H), 9.43 (s, 1H), 8.54 (s, 1H), 8.23 (d, J=8.0 Hz, 1H), 8.12 (d, J=8.1 Hz, 1H), 7.95-7.85 (m, 2H), 7.82-7.75 (m, 1H), 7.76 (s, 1H), 7.70 (s, 1H), 7.43 (d, J=8.0 Hz, 1H), 7.15 (t, J=8.0 Hz, 1H), 6.77 (d, J=7.6 Hz, 1H), 6.72 (s, 1H), 6.63 (d, J=8.0 Hz, 1H), 5.88 (m, 1H), 2.71 (d, J=5.2 Hz, 3H).

Example 51A

2-Isoquinolin-3-yl-7-{3-methylaminophenylethynyl}-chromen-4-one O-tert-butyl oxime. A solution of 7-(3-aminophenylethynyl)-2-(Isoquinolin-3-yl)-chromen-4-one O-tert-butyl oxime (tert-butyl protected oxime of example 29) (127 mg, 0.286 mmol) in dimethylformamide (3 ml) was added to a cold suspension of sodium hydride (60% in mineral oil, 24 mg, 0.608 mmol) in DMF (1 ml). The reaction mixture was stirred for 1 hour at room temperature and cooled to 0° C. Iodomethane (43 μl, 0.690 mmol) was added and the solution was stirred at room temperature for 18 hours. The mixture was poured onto water and extracted with ethyl acetate. The organic extracts were washed with water, brine, dried over sodium sulfate and absorbed over silica gel for purification by flash chromatography (gradient cyclohexane/dichloromethane: 0-45%) to yield 2-Isoquinolin-3-yl-7-{3-methylaminophenylethynyl}-chromen-4-one O-tert-butyl oxime (65 mg, 50%) as a beige solid.
1H NMR: (300 MHz) CDCl$_3$ δ (ppm): 9.29 (s, 1H), 8.29 (s, 1H), 8.05 (d, J=8.3 Hz, 1H), 8.02 (d, J=7.9 Hz, 1H), 7.94 (d, J=7.9 Hz, 1H), 7.79 (s, 1H), 7.76 (td, J=7.4 Hz, J=1.2 Hz, 1H), 7.66 (td, J=7.5 Hz, J=1.2 Hz, 1H), 7.52 (d, J=1.5 Hz, 1H), 7.35 (dd, J=8.3 Hz, J=1.5 Hz, 1H), 7.18 (t, J=7.9 Hz, 1H), 6.93 (d, J=8.4 Hz, 1H), 6.80 (m, 1H), 6.62 (dd, J=8.3 Hz, J=1.7 Hz, 1H), 3.78 (br. s, 1H), 2.87 (s, 3H), 1.43 (s, 9H).

Example 52

7-(4-Hydroxy-but-1-ynyl)-2-isoquinolin-3-yl-chromen-4-one oxime was prepared in 10% overall yield using the method described in example 24, starting from 7-bromo-2-isoquinolin-3-yl-chromen-4-one O-tert-butyl oxime (example 2B) and 3-butyn-1-ol. The title compound was isolated as a yellow solid and as a 70/30 mixture of Z/E oxime isomers.

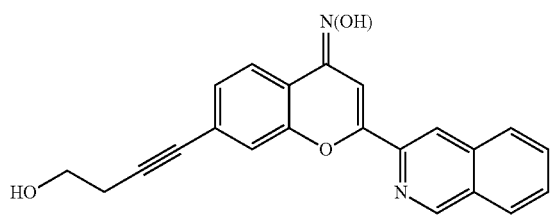

Mp: 238-240° C.
MS (ESI+): 357.1 $[C_{22}H_{16}N_2O_3+H]^+$ (m/z).
1H NMR of the major Z isomer: (300 MHz) DMSO-$d_6$ δ (ppm): 11.20 (s, 1H), 9.42 (s, 1H), 8.51 (s, 1H), 8.22 (d, J=7.9 Hz, 1H), 8.11 (d, J=8.0 Hz, 1H), 7.92-7.72 (m, 3H), 7.73 (s, 1H), 7.55 (s, 1H), 7.29 (dd, J=8.1 Hz, J=1.5 Hz, 1H), 4.95 (t, J=6.7 Hz, 1H), 3.63 (d, J=6.7 Hz, 2H), 2.61 (d, J=6.7 Hz, 2H).

Example 53

2-Isoquinolin-3-yl-7-[3-(2-methoxy-ethoxy)-phenylethynyl]-chromen-4-one oxime was prepared in 48% overall yield using the methods described in examples 42 and 42A, starting from 7-(3-hydroxyphenyl)ethynyl-2-isoquinolin-3-yl-chromen-4-one O-tea-butyl oxime (tert-butyl protected oxime of example 30) and bromoethylmethylether instead of iodomethane. The title compound was isolated as a yellow solid and as a 90/10 mixture of Z/E oxime isomers after purification by flash chromatography over silica gel (gradient cyclohexane/ethyl acetate: 0-50%).

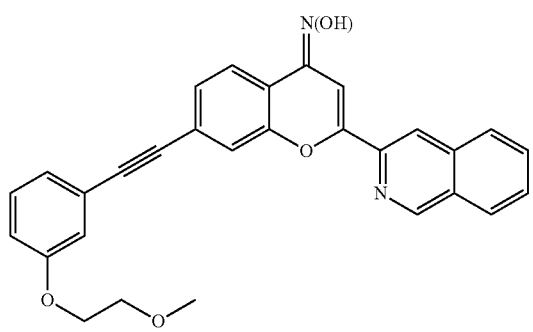

Mp: 155-160° C.
MS (ESI+): 463.1 $[C_{29}H_{22}N_2O_4+H]^+$ (m/z).
1H NMR of the major Z isomer: (300 MHz) DMSO-$d_6$ δ (ppm): 11.28 (s, 1H), 9.43 (s, 1H), 8.53 (s, 1H), 8.23 (d, J=8.1 Hz, 1H), 8.11 (d, J=8.1 Hz, 1H), 7.96-7.86 (m, 2H), 7.82-7.70 (m, 3H), 7.46 (dd, J=8.2 Hz, J=1.5 Hz, 1H), 7.37 (t, J=8.2 Hz, 1H), 7.21-7.16 (m, 2H), 7.05 (d, J=9.2 Hz, 1H), 4.16 (m, 2H), 3.68 (m, 2H), 3.32 (s, 3H).

Example 54

2-Isoquinolin-3-yl-7-[3-(2-methoxy-ethoxy)-prop-1-ynyl]-chromen-4-one oxime was prepared in 7% overall yield using the methods described in examples 42 and 42A, starting from 7-(3-hydroxy-prop-1-ynyl)-2-Isoquinolin-3-yl-chromen-4-one O-tert-butyl oxime (example 54A) and bromoethylmethylether. The title compound was isolated as a beige solid and as a 90/10 mixture of Z/E oxime isomers after triturating in diethyl ether.

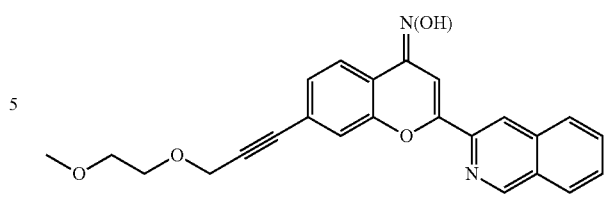

Mp: 158-160° C.
MS (ESI+): 401.1 $[C_{24}H_{20}N_2O_4+H]^+$ (m/z).
1H NMR of the major Z isomer: (300 MHz) DMSO-$d_6$ δ (ppm): 11.26 (s, 1H), 9.43 (s, 1H), 8.52 (s, 1H), 8.22 (d, J=8.3 Hz, 1H), 8.11 (d, J=7.9 Hz, 1H), 7.94-7.86 (m, 2H), 7.79 (m, 2H), 7.74 (s, 1H), 7.63 (s, 1H), 7.36 (d, J=8.2 Hz, 1H), 4.45 (s, 1H), 3.68 (m, 2H), 3.52 (m, 2H), 3.31 (s, 3H).

Example 54A 7-(3-hydroxy-prop-1-ynyl)-2-isoquinolin-3-yl-chromen-4-one O-tert-butyl-oxime was prepared in 58% overall yield using the method described in example 23A, starting from 7-bromo-2-isoquinolin-3-yl-chromen-4-one O-tert-butyl oxime (example 2B) and 2-propyn-1-ol.

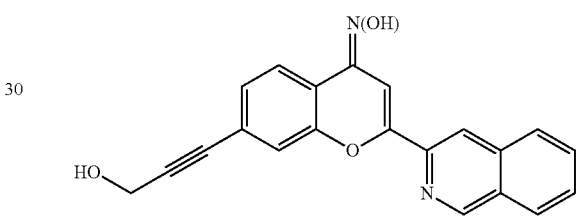

1H NMR: (300 MHz) CDCl$_3$ δ (ppm): 9.28 (s, 1H), 8.26 (s, 1H), 8.02 (2d, J=7.9 Hz, 2H), 7.94 (d, J=7.9 Hz, 1H), 7.78 (s, 1H), 7.76 (td, J=7.4 Hz, J=1.2 Hz, 1H), 7.66 (td, J=7.5 Hz, J=1.2 Hz, 1H), 7.42 (d, J=1.5 Hz, 1H), 7.30-7.23 (m, 1H), 4.54 (d, J=6.2 Hz, 2H), 1.76 (t, J=6.2 Hz, 1H), 1.42 (s, 9H).

Example 55

7-but-3-en-1-ynyl-2-Isoquinolin-3-yl-chromen-4-one oxime was prepared using method D (step 2) starting from 7-(but-3-en-1-ynyl)-2-Isoquinolin-3-yl-chromen-4-one O-tert-butyl oxime (example 55A). The title compound was isolated in 93% yield as a yellow solid and as a 90/10 mixture of Z/E oxime isomers.

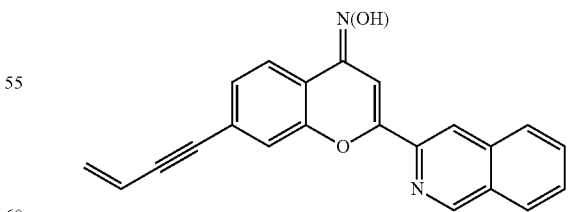

Mp: >210° C. dec.
MS (ESI+): 339.1 $[C_{22}H_{14}N_2O_2+H]^+$ (m/z).
1H NMR of the major Z isomer: (300 MHz) DMSO-$d_6$ δ (ppm): 11.27 (s, 1H), 9.42 (s, 1H), 8.51 (s, 1H), 8.22 (d, J=8.0 Hz, 1H), 8.11 (d, J=8.0 Hz, 1H), 7.92-7.86 (m, 2H), 7.76 (t, J=7.0 Hz, 1H), 7.74 (s, 1H), 7.62 (s, 1H), 7.36 (dd, J=8.2 Hz, J=1.5 Hz, 1H), 6.2 (dd, J=17.5 Hz, J=11.2 Hz, 1H), 5.82 (d, J=17.5 Hz, 1H), 5.73 (d, J=11.2 Hz, 1H).

Example 55A 7-(but-3-en-1-ynyl)-2-Isoquinolin-3-yl-chromen-4-one O-tort-butyl oxime To a cold solution of 7-(4-Hydroxy-but-1-ynyl)-2-isoquinolin-3-yl-chromen-4-one O-tert-butyl oxime (tert-butyl protected oxime of example 52) (200 mg, 0.485 mmol) and triethylamine (0.15 ml, 1.067 mmol) in dichloromethane (3 ml) was added dropwise methanesulfonyl chloride (75 µl, 0.970 mmol). The reaction mixture was stirred for 1.5 hours at 0° C. and poured onto a saturated solution of sodium hydrogenocarbonate. The product was extracted with dichloromethane, washed with brine, dried over sodium sulfate and concentrated to dryness to yield methanesulfonic acid 4-{4-[(E)-tert-butoxyimino]-2-isoquinolin-3-yl-4H-chromen-7-yl}-but-3-ynyl ester. The methansulfonic ester was dissolved in dimethylformamide (4 ml) and treated with potassium carbonate (201 mg, 1.46 mmol) and methyl piperazine (73 mg, 0.728 mmol) and the mixture was stirred at 40° C. for 20 hours. The mixture was poured onto a saturated solution of sodium hydrogenocarbonate. The reaction mixture was extracted with dichloromethane, washed with water, brine, dried over sodium sulfate and absorbed over silica gel for purification by flash chromatography (gradient cyclohexane/dichloromethane: 0-45%) to yield 7-(but-3-en-1-ynyl)-2-Isoquinolin-3-yl-chromen-4-one O-tert-butyl oxime (156 mg, 82%) as a yellow solid.

1H NMR: (300 MHz) CDCl$_3$ δ (ppm): 9.29 (s, 1H), 8.27 (s, 1H), 8.03 (d, J=8.3 Hz, 1H), 8.02 (d, J=7.9 Hz, 1H), 7.94 (d, J=7.9 Hz, 1H), 7.79 (s, 1H), 7.76 (td, J=7.5 Hz, J=1.3 Hz, 1H), 7.66 (td, J=7.5 Hz, J=1.3 Hz, 1H), 7.44 (d, J=1.5 Hz, 1H), 7.27 (m, 1H), 6.05 (dd, J=17.5 Hz, J=11.1 Hz, 1H), 5.79 (dd, J=17.5 Hz, J=2.1 Hz, 1H), 5.60 (d, J=11.2 Hz, J=2.1 Hz, 1H), 1.43 (s, 9H).

Example 56

2-isoquinolin-3-yl-7-methoxy-chromen-4-one oxime was prepared in 18% overall yield using the methods described in examples 41 and 42, starting from 7-bromo-2-isoquinolin-3-yl-chromen-4-one O-tert-butyl oxime (example 2B). The title compound was isolated as a yellow solid and as a 80/20 mixture of Z/E oxime isomers.

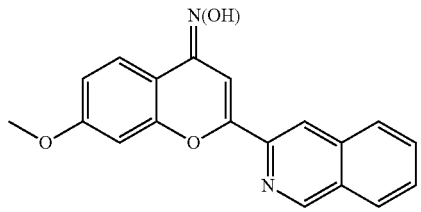

Mp: 246-248° C.
MS (ESI+): 319.0 [C$_{19}$H$_{14}$N$_2$O$_3$+H]$^+$ (m/z).
1H NMR of the major Z isomer: (300 MHz) DMSO-d$_6$ δ (ppm): 10.85 (s, 1H), 9.42 (s, 1H), 8.48 (s, 1H), 8.22 (d, J=8.0 Hz, 1H), 8.12 (d, J=8.0 Hz, 1H), 7.88 (t, J=6.9 Hz, 1H), 7.85-7.75 (m, 2H), 7.75 (s, 1H), 7.09 (d, J=2.5 Hz, 1H), 6.91 (dd, J=8.8 Hz, J=2.9 Hz, 1H), 3.87 (s, 3H).

Example 57

2-isoquinolin-3-yl-7-(2-methoxy-ethoxy)-chromes-4-one oxime was prepared in 22% overall yield using the methods described in examples 41 and 43, starting from 7-bromo-2-isoquinolin-3-yl-chromen-4-one O-tert-butyl oxime (example 2B). The title compound was isolated as a yellow solid and as a 80/20 mixture of Z/E oxime isomers after purification by flash chromatography over silica gel (gradient cyclohexane/ethyl acetate: 20-50%).

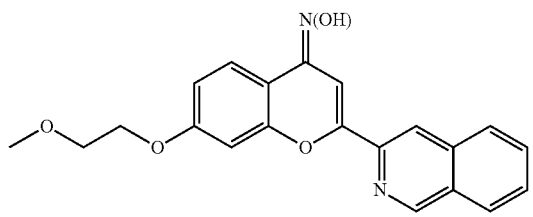

Mp: 223-225° C.
MS (ESI+): 363.2 [C$_{21}$H$_{18}$N$_2$O$_4$+H]$^+$ (m/z).
1H NMR of the major Z isomer: (300 MHz) DMSO-d$_6$ δ (ppm): 10.84 (s, 1H), 9.42 (s, 1H), 8.50 (s, 1H), 8.22 (d, J=8.0 Hz, 1H), 8.13 (d, J=8.0 Hz, 1H), 7.89 (t, J=7.0 Hz, 1H), 7.85-7.75 (m, 2H), 7.75 (s, 1H), 7.11 (d, J=2.5 Hz, 1H), 6.91 (dd, J=8.8 Hz, J=2.9 Hz, 1H), 4.22 (m, 2H), 3.72 (m, 2H), 3.34 (s, 3H).

Example 58

7-cyano-2-isoquinolin-3-yl-chromen-4-one oxime was Prepared in 8% overall yield using the methods described in examples 38 and 38A, starting from 7-bromo-2-isoquinolin-3-yl-chromen-4-one O-tert-butyl oxime (example 2B). The title compound was isolated as a beige solid after purification by flash chromatography over silica gel (gradient cyclohexane/ethyl acetate: 0-60%).

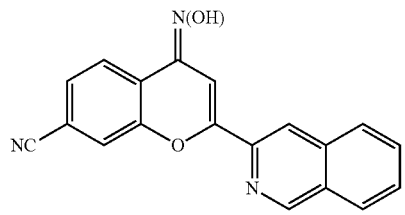

Mp: 279-281° C.
MS (ESI+): 314.3 [C$_{19}$H$_{11}$N$_3$O$_2$+H]$^+$ (m/z).
1H NMR: (300 MHz) DMSO-d$_6$ δ (ppm): 11.57 (s, 1H), 9.43 (s, 1H), 8.49 (s, 1H), 8.23 (d, J=8.1 Hz, 1H), 8.12-8.00 (m, 3H), 7.90 (t, J=7.6 Hz, 1H), 7.80-7.68 (m, 2H), 7.75 (s, 1H).

Example 59

2-Isoquinolin-3-yl-7-[3-(4-methyl-piperazin-1-yl)-prop-1-ynyl]-chromen-4-one oxime was prepared in 67% yield using method D (step 2) starting from 2-Isoquinolin-3-yl-7-[3-(4-methyl-piperazin-1-yl)-prop-1-ynyl]-chromen-4-one O-tert-butyl oxime (example 59A). The title compound was isolated as a yellow solid and as a 95/5 mixture of Z/E oxime isomers after Preparative HPLC purification (gradient 75-60% Water/acetonitrile+0.05% trifluoroacetic acid),

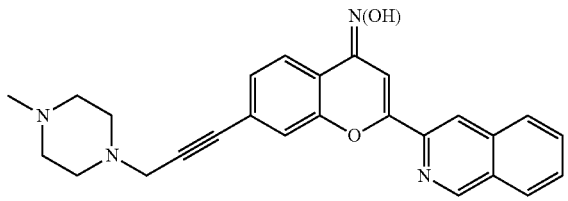

HPLC (gradient 95%-40% H$_2$O/ACN+0.05% TFA (in 12 min.): >95%; RT=8.45 min.

MS (ESI+): 425.2 [C$_{26}$H$_{24}$N$_4$O$_2$+H]$^+$ (m/z).

1H NMR of the major Z isomer: (400 MHz) DMSO-d$_6$ δ (ppm): 9.48 (s, 1H), 8.58 (s, 1H), 8.29 (d, J=8.0 Hz, 1H), 8.18 (d, J=8.0 Hz, 1H), 8.00-7.90 (m, 2H), 7.86 (t, J=7.2 Hz, 1H), 7.81 (s, 1H), 7.80 (s, 1H), 7.50 (d, J=8.4 Hz, 1H), 4.26 (5, 2H), 3.80-3.20 (br multiplets, 8H), 2.92 (s, 3H).

Example 59A

2-Isoquinolin-3-yl-7-[3-(4-methyl-piperazin-1-yl)-prop-1-ynyl]-chromen-4-one O-tert-butyl oxime To a cold solution of 7-(3-Hydroxy-prop-1-ynyl)-2-isoquinolin-3-yl-chromen-4-one O-tert-butyl oxime (example 54A) (230 mg, 0.577 mmol) and triethylamine (0.18 ml, 1.27 mmol) in dichloromethane (3 ml) was added dropwise methanesulfonyl chloride (90 μl, 1.15 mmol). The reaction mixture was stirred for 4 hours at 0° C. and poured onto a saturated solution of ammonium chloride. The product was extracted with dichloromethane, washed with brine, dried over sodium sulfate and concentrated to dryness. The residue methansulfonic ester was dissolved in acetone (3 ml) and treated with potassium carbonate (239 mg, 1.73 mmol) and methyl piperazine (87 mg, 0.866 mmol) and the mixture was stirred at 25° C. for 20 hours. The mixture was poured onto water and extracted with ethyl acetate, washed with water, brine, dried over sodium sulfate and absorbed over silica gel for purification by flash chromatography (ethyl acetate/methanol 90/10 then ethyl acetate/7N ammoniac in methanol: 90/10) to yield 2-isoquinolin-3-yl-7-[3-(4-methyl-piperazin-1-yl)-prop-1-ynyl]-chromen-4-one O-tert-butyl oxime (49 mg, 18%) as a brown solid.

Example 60

2-(7-hydroxy-isoquinolin-3-yl)-chromen-4-one oxime was prepared in 51% yield using the method described in example 18, starting from 2-(7-chloro-isoquinolin-3-yl)-chromen-4-one oxime (example 16) instead of 2-(5-bromo-isoquinolin-3-yl)-chromen-4-one O-tert-butyl oxime. The title compound was isolated as a yellow solid after purification by flash chromatography over silica gel (gradient cyclohexane/ethyl acetate: 0-80%).

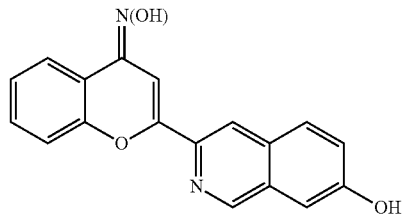

MP: 248-250° C.

MS (ESI+): 305.1 [C$_{18}$H$_{12}$N$_2$O$_3$+H]$^+$ (m/z).

1H NMR: (300 MHz) DMSO-d$_6$ δ (ppm): 10.98 (s, 1H), 10.43 (br. s, 1H), 9.20 (s, 1H), 8.36 (s, 1H), 8.02 (d, J=8.8 Hz, 1H), 7.91 (dd, J=8.1 Hz, J=2.6 Hz, 1H), 7.67 (s, 1H), 7.60-7.45 (m, 2H), 7.44-7.36 (m, 2H), 7.29 (dd, J=7.3 Hz, J=1.5 Hz, 1H).

Example 61

2-[2,6]Naphthyridin-3-yl-chromen-4-one oxime was isolated using methods A and D starting from 2'-hydroxy-acetophenone and [2,6]Naphthyridine-3-carboxylic acid methyl ester (example 61A) as a yellow solid after preparative HPLC purification (gradient 75-60% Water/acetonitrile+0.05% trifluoroacetic acid).

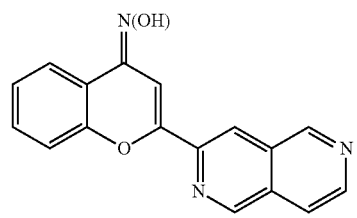

HPLC (gradient 95%-40% H$_2$O/ACN+0.05% TFA (in 12 min.): >95%; RT=9.04 min.

MS (ESI+): 290.1 [C$_{17}$H$_{11}$N$_3$O$_2$+H]$^+$ (m/z).

1H NMR: (400 MHz) DMSO-d$_6$ δ (ppm): 11.17 (s, 1H), 9.61 (s, 1H), 9.57 (s, 1H), 8.81 (d, J=5.6 Hz, 1H), 8.67 (s, 1H), 8.13 (d, J=5.6 Hz, 1H), 7.93 (dd, J=8.0 Hz, J=1.2 Hz, 1H), 7.79 (s, 1H), 7.57 (td, J=8.4 Hz, J=1.2 Hz, 1H), 7.52 (d, J=7.6 Hz, 1H), 7.32 (td, J=8.0 Hz, J=1.2 Hz, 1H).

Example 61A methyl 6-methyl-isoquinoline-3-carboxylate

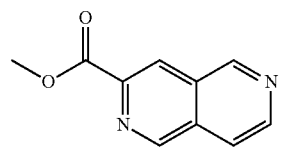

To a cold solution of 4-Dimethoxymethyl-pyridine-3-carbaldehyde (tetrahedron letters 2004 (45), 553-556) (400 mg, 1.91 mmol) in dichloromethane (10 ml) was slowly added a solution of Acetylamino-(dimethoxy-phosphoryl)-acetic acid methyl ester (synthesis 1984, 53-60) (503 mg, 2.1 mmol) and 1,8-diazabicyclo[5.4.0]undec-7-ene (0.31 ml, 2.1 mmol). The solution was stirred at 0° C. for 1 hour then at room temperature for 18 hours. The mixture was poured onto a cold saturated solution of sodium hydrogenocarbonate, extracted with dichloromethane, dried over sodium sulfate and concentrated to dryness. The residue was dissolved in toluene (49 ml) and treated with p-toleunesulfonic acid (315 mg, 1.66 mmol). The mixture was heated at reflux temperature for 18 hours and then concentrated under vacuum. The brown residue was dissolved in ethyl acetate, washed with a saturated solution of sodium hydrogenocarbonate, brine, dried over sodium sulfate and concentrated to yield methyl 6-methyl-isoquinoline-3-carboxylate (241 mg, 62%) as a brown solid.

1H NMR: (300 MHz) CDCl$_3$ δ (ppm): 9.49 (s, 1H), 9.43 (s, 1H), 8.87 (d, J=5.6 Hz, 1H), 8.72 (s, 1H), 7.88 (d, J=5.6 Hz, 1H), 4.09 (s, 3H).

Example 62

2-[1,6]Naphthyridin-3-yl-chromen-4-one oxime was isolated in 7% overall yield using methods A and D starting from 2'-hydroxy-acetophenone and [1,6]Naphthyridine-3-carboxylic acid methyl ester (example 62A) as a yellow solid and a 80/20 mixture of Z/E oxime isomers after Preparative HPLC purification (gradient 45-30% Water/Methanol+0.05% trifluoroacetic acid).

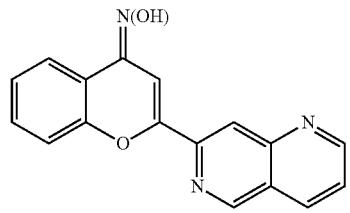

HPLC (gradient 85-25% H$_2$O/MeOH+0.05% TFA (in 12 min.): >95%; RT=11.72 min. (Z isomer); 12.09 min. (E isomer).

MS (ESI+): 290.1 [C$_{17}$H$_{11}$N$_3$O$_2$+H]$^+$ (m/z).

1H NMR of the major Z isomer: (400 MHz) DMSO-d$_6$ δ (ppm): 11.16 (s, 1H), 9.52 (s, 1H), 9.25-9.15 (m, 1H), 8.70-8.60 (m, 1H), 8.50 (s, 1H), 7.93 (dd, J=7.6 Hz, J=1.2 Hz, 1H), 7.83 (s, 1H), 7.82-7.72 (m, 1H), 7.65-7.50 (m, 2H), 7.35-7.25 (m, 1H).

Example 62A methyl 6-methyl-isoquinoline-3-carboxylate was prepared in 43% yield according to the method described in example 61A, starting from 3-Dimethoxymethyl-pyridine-2-carbaldehyde instead of 4-Dimethoxymethyl-pyridine-3-carbaldehyde.

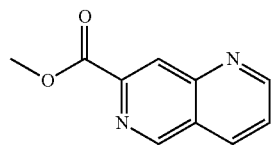

1H NMR: (300 MHz) CDCl$_3$ δ (ppm): 9.39 (dd, J=2.4 Hz, J=0.75 Hz, 1H), 9.21 (dd, J=4.3 Hz, J=1.9 Hz, 1H), 8.81 (s, 1H), 8.39 (dm, J=8.4 Hz, 1H), 7.67 (ddd, J=8.3 Hz, J=4.1 Hz, J=2.0 Hz, 1H), 4.09 (s, 3H).

Example 63

2-Pyrrolo[1,2-c]pyrimidin-3-yl-chromen-4-one oxime was isolated in 43% overall yield using methods A and D, starting from 2'-hydroxy-acetophenone and Pyrrolo[1,2-c]pyrimidine-3-carboxylic acid methyl ester as a green-yellow solid after recrystallization in 1-butanol.

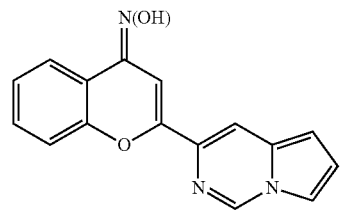

MP: 260-263° C.

HPLC (gradient 5%-95 ACN/H$_2$O+0.1% HCOOH): >95%; RT=5.38 min.

MS (ESI+): 278.1 [C$_{16}$H$_{11}$N$_3$O$_2$+H]$^+$ (m/z).

1H NMR: (300 MHz) DMSO-d$_6$ δ (ppm): 10.97 (s, 1H). 9.22 (s, 1H), 8.05 (s, 1H), 7.88 (dd, J=7.9 Hz, J=1.4 Hz, 1H), 7.82 (d, J=2.4 Hz, 1H), 7.54-7.42 (m, 2H), 7.46 (s, 1H), 7.27 (t, J=6.8 Hz, 1H), 6.97 (t, J=2.9 Hz, 1H), 6.74 (d, J=3.7 Hz, 1H).

Example 64

2-(5,7-dimethyl-Pyrrolo[1,2-c]pyrimidin-3-yl)-chromen-4-one oxime was isolated as a yellow solid in 19% overall yield using method A and D starting from 2'-hydroxy-acetophenone and 5,7-dimethyl-Pyrrolo[1,2-c]pyrimidine-3-carboxylic acid methyl ester.

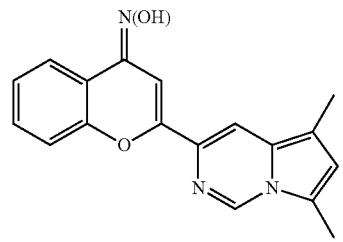

MP: >250° C. dec.

HPLC (gradient 5%-95% ACN/H$_2$O+0.1% HCOOH): >95%; RT=5.63 min.

MS (ESI+): 306.1 [C$_{18}$H$_{15}$N$_3$O$_2$+H]$^+$ (m/z).

1H NMR: (300 MHz) DMSO-d$_6$ δ (ppm): 10.89 (s, 1H), 8.89 (s, 1H), 7.94 (d, J=1.3 Hz, 1H), 7.88 (d, J=7.9 Hz, 1H), 7.54-7.45 (m, 2H), 7.41 (s, 1H), 7.26 (m, 1H), 6.61 (s, 1H), 2.54 (s, 3H), 2.35 (s, 3H).

Example 65

2-(6-bromo-Pyrrolo[1,2-c]pyrimidin-3-yl)-chromen-4-one oxime was isolated as a yellow solid using method A and D starting from 2'-hydroxy-acetophenone and 6-bromo-Pyrrolo[1,2-c]pyrimidine-3-carboxylic acid methyl ester.

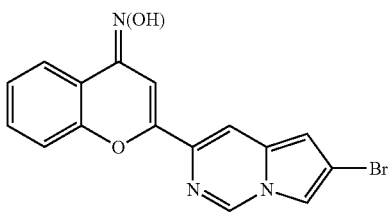

MP: 244-245° C.

HPLC (gradient 5%-95% ACN/H₂O+0.1% HCOOH): >95%; RT=5.69 min.

MS (ESI+): 356.1 [C$_{16}$H$_{10}$BrN$_3$O$_2$+H]$^+$ (m/z).

1H NMR: (300 Mhz) DMSO-d$_6$ δ (ppm): 11.03 (s, 1H), 9.15 (s, 1H), 8.01 (s, 1H), 7.98 (d, J=0.75 Hz, 1H), 7.88 (dd, J=8.0 Hz, J=1.3 Hz, 1H), 7.52 (td, J=7.7 Hz, J=1.5 Hz, 1H), 7.48 (s, 1H), 7.43 (dd, J=8.4 Hz, J=1.1 Hz, 1H), 7.27 (td, J=7.5 Hz, J=1.3 Hz, 1H), 6.86 (s, 1H).

Example 66

6-bromo-2-Pyrrolo[1,2-c]pyrimidin-3-yl-chromen-4-one oxime was prepared in 34% overall yield using methods A and D, starting from 5'-bromo-2'-hydroxy-acetophenone and pyrrolo[1,2-c]pyrimidine-3-carboxylic acid methyl ester. The title compound was isolated as a yellow solid and a 80/20 mixture of Z/E oxime isomers after Preparative HPLC purification (gradient 45-30% Water/acetonitrile+0.05% trifluoroacetic acid).

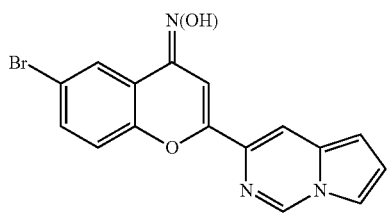

HPLC (gradient 5%-60% ACN/H₂O+0.1% TEA): >95%; RT=4.52 min. (Z isomer); 3.95 min. (E isomer).

MS (ESI+): 357.9 [C$_{16}$H$_{10}$BrN$_3$O$_2$+H]$^+$ (m/z).

1H NMR of the major Z isomer: (400 Mz) DMSO-d$_6$ δ (ppm): 11.23 (s, 1H), 9.27 (s, 1H), 8.12 (s, 1H), 8.00 (d, J=2.4 Hz, 1H), 7.88 (d, J=2.4 Hz, 1H), 7.75 (dd, J=9.2 Hz, J=2.4 Hz, 1H), 7.54-7.48 (m, 2H), 7.07-7.00 (m, 1H), 6.80 (d, J=3.6 Hz, 1H).

Example 67

6-methoxyethoxy-2-Pyrrolo[1,2-c]pyrimidin-3-yl-chromen-4-one oxime was prepared in 23% overall yield using the methods described in examples 41 and 43, starting from 6-bromo-2-pyrrolo[1,2-c]pyrimidin-3-yl-chromen-4-one O-tert-butyl oxime (tert-butyl protected oxime of example 66). The title compound was isolated as an orange solid.

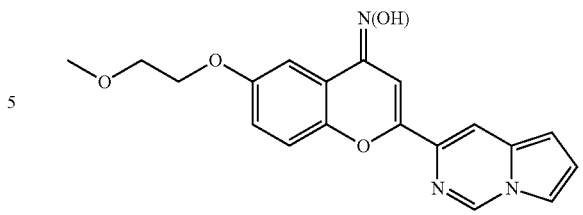

Mp: 212-215° C.

MS (ESI+): 352.1 [C$_{19}$H$_{17}$N$_3$O$_4$+H]$^+$ (m/z).

1H NMR: (300 MHz) DMSO-d$_6$ δ (ppm): 10.93 (s, 1H), 9.21 (s, 1H), 8.03 (s, 1H), 7.81 (d, J=2.5 Hz, 1H), 7.43 (s, 1H), 7.40 (d, J=9.0 Hz, 1H), 7.30 (d, J=3.0 Hz, 1H), 7.13 (dd, J=9.2 Hz, J=3.2 Hz, 1H), 6.98 (dd, J=3.8 Hz, J=2.8 Hz, 1H), 6.73 (d, J=3.8 Hz, 1H), 4.13 (m, 2H), 3.67 (m, 2H), 3.39 (s, 3H).

Example 68

2-(1-Benzyl-1H-imidazo[4,5-c]pyridin-6-yl)-chromen-4-one oxime was prepared in 20% overall yield using methods A and D, starting from 2'-hydroxy-acetophenone and 1-Benzyl-1H-imidazo[4,5-c]pyridine-6-carboxylic acid methyl ester (example 68A). The title compound was isolated as a yellow solid and a 90/10 mixture of Z/E oxime isomers.

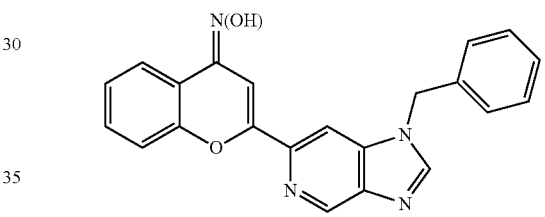

Mp: 148-150° C.

MS (ESI+): 369.2 [C$_{22}$H$_{16}$N$_4$O$_2$+H]$^+$ (m/z).

1H NMR of the major Z isomer: (300 MHz) DMSO-d$_6$ δ (ppm): 10.94 (s, 1H), 9.03 (s, 1H), 8.74 (s, 1H), 8.34 (s, 1H), 7.89 (d, J=7.4 Hz, 1H), 7.59 (s, 1H), 7.55-7.50 (m, 2H), 7.45-7.27 (m, 6H), 5.66 (s, 2H).

Example 68A

1-Benzyl-1H-imidazo[4,5-c]pyridin-6-carboxylic acid methyl ester

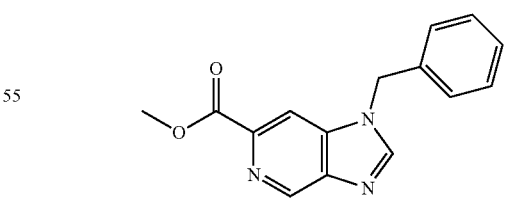

A solution of H-His-(Bzl)-OH (2.0 g, 8.16 mmol) and formaldehyde (37% in water, 0.92 ml, 12.24 mmol) in water (16 ml) was heated to reflux for 4 hours and concentrated to dryness. The residue was dissolved in methanol (4.6 ml) cooled to 0° C. and treated with thionyl chloride (0.6 ml, 8.12 mmol). The reaction mixture was reflux for 2.5 hours and concentrated. The solid was dissolved in dichloromethane, washed with a saturated solution of sodium hydrogenocarbonate, brine, dried over sodium sulfate and concentrated to dryness to yield 1-Benzyl-4,5,6,7-tetrahydro-1H-imidazo[4,5-c]pyridine-6-carboxylic acid methyl ester (1.58 g, 71%). The ester was dissolved in tetrahydrofuran (26 ml), cooled to 0° C. and treated with 2,3-Dichloro-5,6-dicyanobenzoquinone (2.9 g, 12.81 mmol) in tetrahydrofuran (26 ml) and the reaction mixture was reflux for 4 hours. The solvent was removed and the black residue was dissolved in dichloromethane and treated with a 1M aqueous solution of sodium hydroxide. The aqueous solution was extracted several times with dichloromethane. The combined organic extracts were washed with brine, dried over sodium sulfate, concentrated and purified by flash chromatography over silica gel (gradient ethyl acetate/methanol: 0-10%) to yield 1-Benzyl-1H-imidazo[4,5-c]pyridin-6-carboxylic acid methyl ester (525 mg, 34%) as a beige solid.

1H NMR: (300 MHz) CHCl$_3$-d$_1$ δ (ppm): 8.77 (s, 1H), 8.62 (s, 1H), 8.15 (s, 1H), 7.42-7.35 (m, 3H), 7.28-7.21 (m, 2H), 5.48 (s, 2H), 4.02 (s, 3H).

Example 69

2-Thieno[2,3-c]pyridin-5-yl-chromen-4-one oxime was prepared in 21% overall yield using methods A and D, starting from 2'-hydroxy-acetophenone and Thieno[2,3-c]pyridin-5-carboxylic acid methyl ester (*J. Med. Chem.* 2006, 49, 4425-4436). The title compound was isolated as a beige solid and a 95/5 mixture of Z/E oxime isomers.

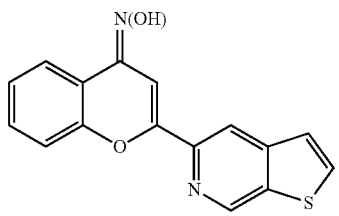

Mp: 243-245° C.
MS (ESI+): 295.0 [C$_{16}$H$_{10}$N$_2$O$_2$S+H]$^+$ (m/z).
1H NMR of the major Z isomer: (300 MHz) DMSO-d$_6$ δ (ppm): 11.04 (s, 1H), 9.38 (s, 1H), 8.52 (s, 1H), 8.24 (d, J=5.3 Hz, 1H), 7.92 (dd, J=7.9 Hz, J=1.4 Hz, 1H), 7.72 (d, J=4.9 Hz, 1H), 7.71 (s, 1H), 7.58-7.45 (m, 2H), 7.30 (t, J=7.4 Hz, 1H).

Example 70

2-Thieno[3,2-c]pyridin-6-yl-chromen-4-one oxime was prepared in 43% overall yield using methods A and D, starting from 2'-hydroxy-acetophenone and Thieno[3,2-c]pyridin-6-carboxylic acid methyl ester (*J. Med. Chem.* 2006, 49, 4425-4436). The title compound was isolated as a yellow solid.

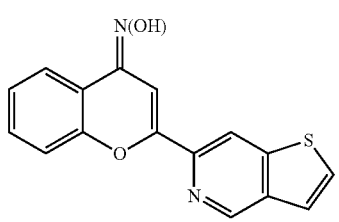

Mp: 272-275° C.
MS (ESI+): 295.0 [C$_{16}$H$_{10}$N$_2$O$_2$S+H]$^+$ (m/z).

1H NMR: (300 MHz) DMSO-d$_6$ δ (ppm); 11.05 (s, 1H), 9.25 (s, 1H), 8.76 (s, 1H) 8.03 (d, J=5.3 Hz, 1H), 7.91 (dd, J=7.9 Hz, J=1.3 Hz, 1H), 7.72 (d, J=4.8 Hz, 1H), 7.71 (s, 1H), 7.58-7.46 (m, 2H), 7.30 (t, J=7.5 Hz, 1H).

Example 71

2-Isoquinolin-3-yl-3-methyl-chromen-4-one oxime

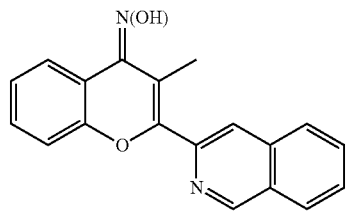

To a suspension of 2-Isoquinolin-3-yl-3-methyl-chromen-4-one (example 71A) (200 mg, 0.69 mmol) in anhydrous pyridine (5 ml) was added hydroxylamine hydrochloride (96 mg, 1.39 mmol). The mixture was heated to 130° C. under microwave irradiation for 30 min. The reaction mixture was poured into a 1N aqueous solution of hydrochloric acid and extracted with ethyl acetate. The organic layer was washed successively with a 1N aqueous solution of hydrochloric acid, brine and dried over sodium sulfate and concentrated. The title compound was isolated as a white solid after Preparative HPLC purification (gradient 45-30% Water/Methanol+ 0.05% trifluoroacetic acid) (9 mg, 4%).

HPLC (gradient 85%-25% H2O/MeOH+0.05% TFA (in 12 min.): >95%; RT=12.00 min.
MS (ESI+): 303.1 [C$_{19}$H$_{14}$N$_2$O$_2$+H]$^+$ (m/z).
1H NMR: (400 MHz) DMSO-d$_6$ δ (ppm): 10.13 (s, 1H), 9.49 (s, 1H), 8.44 (s, 1H), 8.22 (d, J=8.4 Hz, 1H), 8.16 (d, J=8.4 Hz, 1H), 7.88 (t, J=7.2 Hz, 1H), 7.79 (t, J=7.2 Hz, 1H), 7.42 (d, J=7.6 Hz, 1H), 7.38 (d, J=7.6 Hz, 1H), 7.05 (d, J=8.0 Hz, 1H), 6.98 (t, J=7.6 Hz, 1H), 2.27 (s, 3H).

Example 71A

2-Isoquinolin-3-yl-3-methyl-chromen-4-one was prepared in 76% yield using method A, starting from 2'-hydroxy-propiophenone and methyl isoquinoline-3-carboxylate.

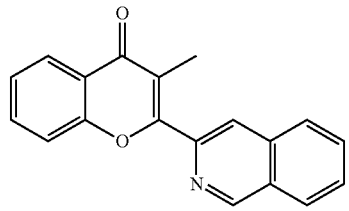 [SMILES: Cc1c(-c2cc3ccccc3cn2)oc2ccccc2c1=O]

1H NMR: (300 MHz) CHCl$_3$-d$_1$ δ (ppm): 9.40 (s, 1H), 8.29 (dd, J=7.9 Hz, J=1.3 Hz, 1H), 8.18 (s, 1H), 8.09 (d, J=8.3 Hz, 1H), 7.98 (d, J=8.2 Hz, 1H), 7.84-7.65 (multiplets, 3H), 7.55 (dd, J=8.5 Hz, J=0.6 Hz, 1H), 7.42 (td, J=7.6 Hz, J=1.1 Hz, 1H), 2.37 (s, 3H).

Example 72

3-{4-[(E)-Hydroxyimino]-4H-chromen-2-yl}-2H-isoquinolin-1-one was prepared in 9% overall yield using methods A and D, starting from 2′-hydroxy-acetophenone and 1-oxo-1,2-dihydro-isoquinoline-3-carboxylic acid methyl ester. The title compound was isolated as a pale yellow solid and a 90/10 mixture of Z/E oxime isomers.

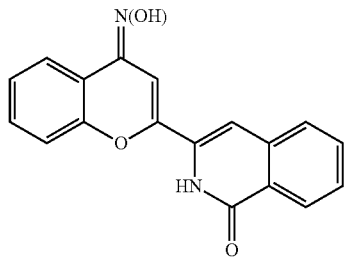

Mp: 310-315° C. dec.

MS (ESI+): 305.3 $[C_{18}H_{12}N_2O_3+H]^+$ (m/z).

1H NMR of the major Z isomer: (300 MHz) DMSO-$d_6$ δ (ppm): 11.66 (br. s, 1H), 11.84 (s, 1H), 2.23 (d, J=7.9 Hz, 1H), 7.90-7.74 (m, 3H), 7.60-7.45 (m, 3H), 7.46 (s, 1H), 7.39 (s, 1H), 7.29 (t, J=7.3 Hz, 1H).

Example 73

2-Imidazo[1,2-c]pyrimidin-7-yl-chromen-4-one oxime was prepared in 0.3% overall yield using methods A and C, starting from 2′-hydroxy-acetophenone and Imidazo[1,2-c]pyrimidine-7-carboxylic acid ethyl ester (US2003/236264). The title compound was isolated as a yellow solid and a 60/40 mixture of Z/E oxime isomers after purification by silica gel thin layer chromatography (dichloromethane/methanol:96/4).

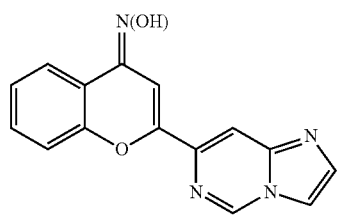

MS (ESI+): 279.1 $[C_{15}H_{10}N_4O_2+H]^+$ (m/z).

HPLC (gradient 5%-95% ACN/H$_2$O+0.1% HCOOH): >95%; RT=4.44 min. (E isomer) and 4.59 min. (Z isomer).

Example 74

Reference

2-Naphthalen-2-yl-chromen-4-one oxime was isolated in 69% yield using method D starting from 2-Naphthalen-2-yl-chromen-4-one (compound 74A) as a yellow solid and a 95/5 mixture of Z/E oxime isomers.

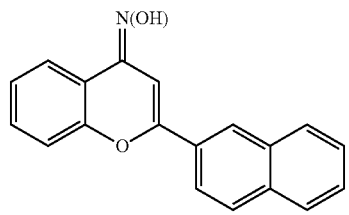

Mp: 224-226° C.

MS (ESI+): 288.0 $[C_{19}H_{13}NO_2+H]^+$ (m/z).

1H NMR: (300 MHz) DMSO-$d_6$ δ (ppm): 11.06 (s, 1H), 8.56 (s, 1H), 8.14-8.06 (m, 8.04-7.95 (m, 3H), 7.92 (dd, J=8.1 Hz, J=1.3 Hz, 1H), 7.64-7.56 (m, 2H), 7.55-7.47 (m, 2H), 7.34-7.26 (m, 1H), 7.28 (s, 1H).

Compound 74A: 2-Naphthalen-2-yl-chromen-4-one

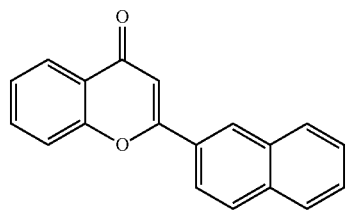 [SMILES: O=c1cc(-c2ccc3ccccc3c2)oc2ccccc12]

Method B: To a cold suspension of 2-naphtoic acid (2.0 g, 11.6 mmol) in dichloromethane (60 ml) were added oxalyl chloride (1.12 ml, 12.7 mmol) and then dimethylformamide (10 drops). The mixture was stirred at room temperature for 2 hours and concentrated to dryness to give the crude 2-naphtoic acid chloride (2.5 g). The crude product was dissolved in dry pyridine (50 ml) under argon, cooled to 0° C. and treated with 2′-hydroxy-acetophenone (1.43 g, 10.5 mmol). The reaction mixture was heated to 60° C. for 2 hours and poured into ice-cold water (150 ml). The solution was acidified to pH 1 with concentrated hydrochloric acid and the precipitate isolated by filtration, washed with water to yield Naphthalene-2-carboxylic acid 2′-acetyl-phenyl ester (2.7 g, 80%). The ester was dissolved in dimethylsulfoxide (30 ml) under argon and treated with freshly crushed potassium hydroxide (1.4 g, 25.8 mmol) and stirred at room temperature for 14 hours. The mixture was poured into ice-cold water and acidified to pH 3-4 with a 6N aqueous hydrochloric acid solution. The solid was filtered, washed with water, dried under vacuum to yield 1-(2-Hydroxy-phenyl)-3-naphthalen-2-yl-propane-1,3-dione (1.44 g, 86%). The diketone was dissolved in dimethylsulfoxide (25 ml), treated with para-toluene-sulfonic acid monohydrate (660 mg, 3.47 mmol) and heated to 90° C. for 4 hours. The reaction mixture was poured into ice-cold water and filtrated. The solid was dissolved in dichloromethane, dried over sodium sulfate and concentrated. The residue was purified by silica gel flash chromatography (cyclohexane/ethyl acetate: 80/20) to yield 2-Naphthalen-2-yl-chromen-4-one (956 mg, 70%) as a brown solid.

1H NMR: (300 MHz) DMSO-$d_6$ δ (ppm): 8.50 (s, 1H), 8.26 (dd, J=8.1 Hz, J=1.3 Hz, 1H), 8.02-7.87 (m, 4H), 7.74

(td, J=7.8 Hz, J=1.7 Hz, 1H), 7.65 (dd, J=8.2 Hz, J=1.0 Hz, 1H), 7.62-7.55 (m, 2H), 7.45 (td, J=8.1 Hz, J=1.1 Hz, 1H), 6.99 (s, 1H).

Example 75

2-(1H-Pyrrolo[2,3-c]pyridin-5-yl)-chromen-4-one oxime

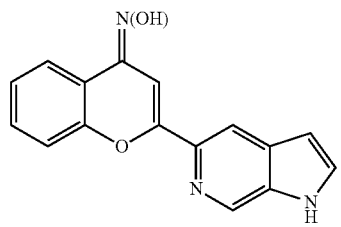

Mp: 270-275° C. dec.
MS (ESI+): 278.1 [C$_{16}$H$_{11}$N$_3$O$_2$+H]$^+$ (m/z).
1H NMR: (300 MHz) DMSO-d$_6$ δ (ppm): 11.89 (br. S, 1H), 10.83 (s, 1H), 8.85 (s, 1H), 8.26 (s, 1H), 7.90 (d, J=7.9 Hz, 1H), 7.70 (s, 1H), 7.60 (s, 1H), 7.52-7.46 (m, 2H), 7.28 (t, J=7.1 Hz, 1H), 6.67 (s, 1H).

Example 76

2-(1-Hydroxy-7H-pyrrolo[2,3-c]pyridin-5-yl)-chromen-4-one oxime

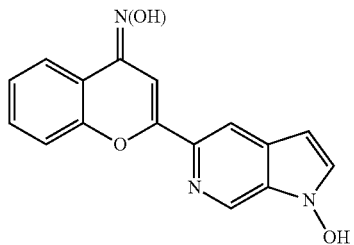

MS (ESI+): 294.0 [C$_{16}$H$_{11}$N$_3$O$_3$+H]$^+$ (m/z).
1H NMR: (400 MHz) DMSO-d$_6$ δ (ppm): 11.99 (br. S, 1H), 10.88 (s, 1H), 8.89 (s, 1H), 8.28 (s, 1H), 7.91 (d, J=7.9 Hz, 1H), 7.83 (s, 1H), 7.60 (s, 1H), 7.56-7.46 (m, 2H), 7.29 (t, J=7.4 Hz, 1H), 6.58 (t, J=2.4 Hz, 1H).

Examples 75 and 76 were prepared simultaneously by the following procedure:

To a suspension of 2-(4-Methyl-5-nitro-pyridin-2-yl)-chromen-4-one O-tert-butyl-oxime (example 75A) (250 mg, 0.70 mmol) in dimethylformamide (6 ml) under argon was added dimethylformamide-dimethylacetal (127 µl, 0.95 mmol) and the mixture was stirred at 90° C. for 2.5 hours. The solvents were removed under vacuum and the residue was dissolved in absolute ethanol. 10% palladium black was added (50 mg) and the mixture was stirred under 1 atmosphere of hydrogen at room temperature for 16 hours. The catalyst was removed by filtration ant the filtrate purified by silica gel chromatography (cyclohexane/ethyl acetate 0-20%) to give a 70/30 mixture of 2-(1H-Pyrrolo[2,3-c]pyridin-5-yl)-chromen-4-one O-tert-butyl-oxime and 2-(1-Hydroxy-1H-pyrrolo[2,3-c]pyridin-5-yl)-chromen-4-one O-tert-butyl-oxime (165 mg, 70%). The former mixture tert-butyl protected oximes (70 mg) was treated with titanium tetrachloride (0.63 mmol) in dichloromethane (6 ml) (method D, step 2) to yield separately after purification by flash chromatography (dichloromethane/ethyl acetate: gradient 50-100%) and preparative HPLC (gradient 70-55% Water/Methanol+ 0.05% trifluoroacetic acid) 2-(1H-Pyrrolo[2,3-c]pyridin-5-yl)-chromen-4-one oxime (example 75; 39 mg, 70%) and 2-(1-Hydroxy-1H-Pyrrolo[2,3-c]pyridin-5-yl)-chromen-4-one oxime (example 77; 5 mg, 8%).

Example 75A 2-(4-Methyl-5-nitro-pyridin-2-yl)-chromen-4-one O-tert-butyl-oxime

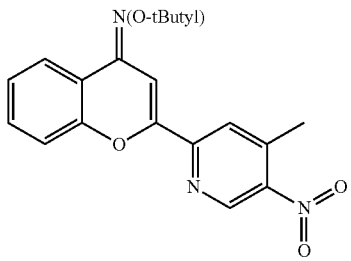

A solution of 2'-hydroxyacetophenone (1.68 g, 12.39 mmol) in tetrahydrofuran (120 ml) under argon was cooled to −78° C. and treated dropwise with lithium hexamethyldisilazane (1M in tetrahydrofuran, 2.25 ml, 2.25 mmol). The solution was stirred at −78° C. for 1 hour and at −10° C. for 2 hours then cooled down to −78° C. and treated dropwise with a solution of 4-Methyl-5-nitro-pyridine-2-carboxylic acid methyl ester (WO2005/103003) (2.42 g, 12.39 mmol) in tetrahydrofuran (60 ml). The dark red solution was stirred at −78° C. for 1 hour then at room temperature for 18 hours. The mixture was poured into a ice-cold 1 N solution of hydrochloric acid (200 ml) and extracted several times with ethyl acetate. The combined extracts were dried over sodium sulfate and concentrated to dryness. The residue was dissolved in acetic acid (60 ml), treated with sulfuric acid (0.33 ml) and heated to 100° C. for 30 minutes. After cooling to room temperature, the solution was concentrated and the residue added with water and neutralized with a saturated solution of sodium hydrogenocarbonate. The precipitate was filtrated, washed with water and dried under vacuum to yield 2-(4-Methyl-5-nitro-pyridin-2-yl)-chromen-4-one (2.33 g, 66%) as a brown solid. The previous chromen-4-none (770 mg, 2.72 mmol) was treated with tert-butyl-hydroxylamine hydrochloride (685 mg, 5.45 mmol) in methanol (20 ml) at 130° C. for 30 minutes under microwave irradiation (method D, step 1) to yield the title compound (394 mg, 41%) after purification by silica gel flash chromatography (gradient cyclohexane/dichloromethane 0-80%) as a gold solid.

1H NMR: (300 MHz) DMSO-d$_6$ δ (ppm): 9.23 (s, 1H), 8.08 (dd, J=7.9 Hz, J=1.7 Hz, 1H), 7.89 (s, 1H), 7.78 (s, 1H), 7.42 (td, J=7.6 Hz, J=1.7 Hz, 1H), 7.32-7.19 (m, 2H), 2.76 (s, 3H), 1.42 (s, 9H).

Example 77

2-(1-Methyl-1H-pyrrolo[2,3-c]pyridin-5-yl)-chromen-4-one oxime

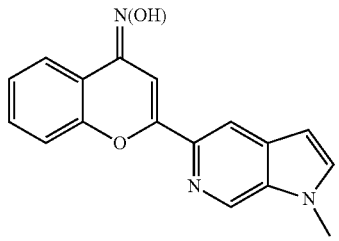

Mp: 270-275° C. dec.
MS (ESI+): 292.1 [C$_{17}$H$_{13}$N$_3$O$_2$+H]$^+$ (m/z).
1H NMR: (400 MHz) DMSO-d$_6$ δ (ppm): 11.00 (br. s, 1H), 9.05 (s, 1H), 8.39 (s, 1H), 7.90 (d, J=8.0 Hz, 1H), 7.83 (s, 1H), 7.61 (s, 1H), 7.57-7.47 (m, 2H), 7.30 (t, J=7.4 Hz, 1H), 6.76 (t, J=2.8 Hz, 1H), 4.02 (s, 3H).

Example 78

2-(1-Methoxy-1H-pyrrolo[2,3-c]pyridin-5-yl)-chromen-4-one oxime

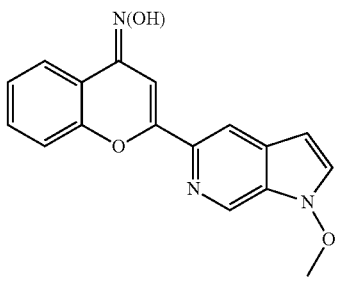

MS (ESI+): 308.0 [C$_{17}$H$_{13}$N$_3$O+H]$^+$ (m/z).
1H NMR: (400 MHz) DMSO-d$_6$ δ (ppm): 10.92 (s, 1H), 9.00 (s, 1H), 8.30 (s, 1H), 8.05 (s, 1H), 7.91 (d, J=7.9 Hz, 1H), 7.62 (s, 1H), 7.56-7.46 (m, 2H), 7.29 (td, J=7.4 Hz, J=1.2 Hz, 1H), 6.58 (d, J=3.2 Hz, 1H), 4.21 (s, 3H).

Examples 77 and 78 were prepared simultaneously by the following procedure:

A 70/30 mixture of 2-(1H-Pyrrolo[2,3-c]pyridin-5-yl)-chromen-4-one O-tert-butyl-oxime and 2-(1-Hydroxy-1H-pyrrolo[2,3-c]pyridin-5-yl)-chromen-4-one O-tert-butyl-oxime (77 mg) in dimethylformamide (5 ml) was cooled to 0° C. and treated with sodium hydride (60% in mineral oil, 10 mg, 0.25 mmol) and stirred at room temperature for 1 hour. The solution was cooled down to 0° C. and treated with iodomethane (16 μl, 0.25 mmol). The solution was slowly warmed up to room temperature during 1 hour and poured into brine, extracted with ethyl acetate, washed with brine, dried over sodium sulfate and concentrated to dryness. The crude mixture of 2-(1-methyl-1H-pyrrolo[2,3-c]pyridin-5-yl)-chromen-4-one O-tert-butyl-oxime and 2-(1-methoxy-1H-pyrrolo[2,3-c]pyridin-5-yl)-chromen-4-one O-tert-butyl-oxime was treated with titanium tetrachloride (0.70 mmol) in dichloromethane (7.5 ml) (method D) to yield separately after purification by preparative HPLC (gradient 65-50% Water/Methanol+0.05% trifluoroacetic acid), 2-(1-methyl-1H-pyrrolo[2,3-c]pyridin-5-yl)-chromen-4-one oxime (example 77, 17 mg) and 2-(1-methoxy-1H-pyrrolo[2,3-c]pyridin-5-yl)-chromen-4-one oxime (example 78, 12 mg) as yellow solids.

Example 79

Reference

2-Quinolin-2-yl-chromen-4-one oxime was prepared in 24% overall yield using method B and D as described in compound A, starting from quinaldyl chloride. The title compound was isolated as a yellow solid.

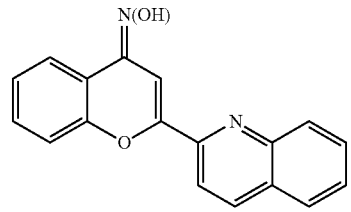

Mp: 232-235° C.
MS (ESI+): 289.0 [C$_{18}$H$_{12}$N$_2$O$_2$+H]$^+$ (m/z).
1H NMR: (300 MHz) DMSO-d$_6$ δ (ppm): 11.20 (s, 1H), 8.59 (d, J=8.5, 1H), 8.19 (d, J=8.7, 1H), 8.14 (d, J=8.5, 1H), 8.07 (d, J=8.5, 1H), 7.93 (d, J=8.3, 1H), 7.85 (td, J=7.6 Hz, J=1.3 Hz, 1H), 7.80 (s, 1H), 7.68 (td, J=7.9 Hz, J=1.2 Hz, 1H), 7.60-7.49 (m, 2H), 7.31 (td, J=7.1 Hz, J=1.4 Hz, 1H).

Example 80

Reference

2-Pyrimidin-4-yl-chromen-4-one oxime was prepared in 61% overall yield using method A and D, starting from 2'-hydroxyacetophenone and pyrimidine-4-carboxylic acid methyl ester. The title compound was isolated as a yellow solid.

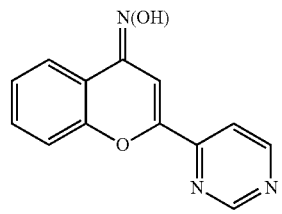

Mp: 208-211° C.
MS (ESI+): 240.1 [C$_{13}$H$_9$N$_3$O$_2$+H]$^+$ (m/z).
1H NMR: (300 MHz) DMSO-d$_6$ δ (ppm): 11.37 (br. s, 1H), 9.31 (d, J=1.3, 1H), 9.04 (d, J=5.3, 1H), 8.05 (dd, J=5.3, J=8.7, 1H), 7.90 (dd, J=8.1, J=1.5, 1H), 7.75 (s, 1H), 7.54 (td, J=7.7 Hz, J=1.3 Hz, 1H), 7.47 (dd, J=8.3 Hz, J=1.2 Hz, 1H), 7.31 (td, J=7.4 Hz, J=1.3 Hz, 1H).

Example 81

6-Hydroxy-2-pyrrolo[1,2-c]pyrimidin-3-yl-chromen-4-one oxime was prepared using method D (step 2) starting from 6-Hydroxy-2-pyrrolo[1,2-c]pyrimidin-3-yl-chromen-4-one O-tert-butyl-oxime (example 81A) and isolated as a yellow powder.

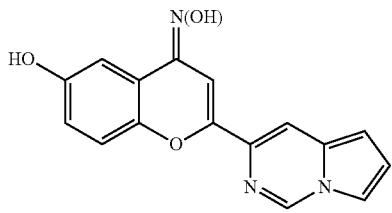

Mp: 263-235° C.
MS (ESI+): 294.1 $[C_{16}H_{11}N_3O_3+H]^+$ (m/z).
1H NMR: (300 MHz) DMSO-$d_6$ δ (ppm): 9.61 (s, 1H), 9.20 (s, 1H), 8.00 (s, 1H), 7.80 (d, J=2.5 Hz, 1H), 7.40 (s, 1H), 7.29 (d, J=8.9 Hz, 1H), 7.23 (d, J=2.9 Hz, 1H), 6.97 (dd, J=3.7 Hz, J=2.8 Hz, 1H), 6.90 (dd, 8.9 Hz, J=3.0 Hz, 1H), 6.72 (d, J=3.8 Hz, 1H).

Example 81A

6-Hydroxy-2-pyrrolo[1,2-c]pyrimidin-3-yl-chromen-4-one O-tert-butyl-oxime was prepared in 59% yield using the procedure described in example 18A, starting from 6-bromo-2-pyrrolo[1,2-c]pyrimidin-3-yl-chromen-4-one O-tert-butyl oxime (tert-butyl protected oxime of example 66). The title compound was isolated as a yellow solid.

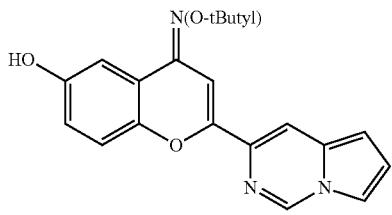

1H NMR: (300 MHz) CHCl$_3$-$d_1$ δ (ppm): 8.79 (s, 1H), 7.90 (s, 1H), 7.52 (d, J=3.0 Hz, 1H), 7.49 (s, 1H), 7.44 (d, J=2.9 Hz, 1H), 7.17 (d, J=8.8 Hz, 1H), 6.95-6.88 (m, 2H), 6.63 (d, J=3.8 Hz, 1H), 5.56 (br s., 1H), 1.41 (s, 9H).

Example 82

2-Thiazolo[5,4-c]pyridin-6-yl-chromen-4-one oxime was prepared in 0.2% overall yield using the method described in example 75A, starting from Thiazolo[5,4-c]pyridine-6-carboxylic acid ethyl ester (U.S. Pat. No. 6,342,606).

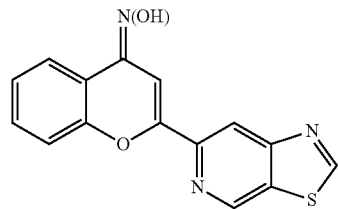

HPLC (gradient 5% 95% ACN/H$_2$O+0.1% HCOOH): >95%; RT=5.11 min.
MS (ESI+): 296.1 $[C_{15}H_9N_3O_2S+H]^+$ (m/z).

Example 83

6-(3-Methoxy-propyl)-2-pyrrolo[1,2-c]pyrimidin-3-yl-chromen-4-one oxime was prepared in 32% yield using method D (step 2) starting from 6-(3-Methoxy-propyl)-2-pyrrolo[1,2-c]pyrimidin-3-yl-chromen-4-one O-tert-butyl-oxime (example 83A) and isolated as a yellow solid and a 95/5 mixture of Z/E isomers.

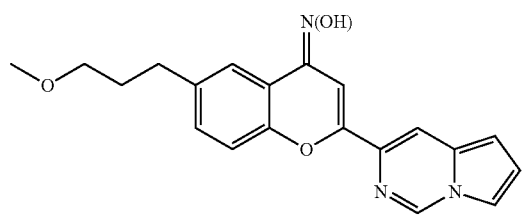

Mp: 172-173° C.
MS (ESI+): 350.2 $[C_{20}H_{19}N_3O_3+H]^+$ (m/z).
1H NMR of the major Z isomer: (300 MHz) DMSO-$d_6$ δ (ppm): 10.93 (s, 1H), 9.22 (s, 1H), 8.03 (s, 1H), 7.81 (d, J=2.4 Hz, 1H), 7.68 (s, 1H), 7.45 (s, 1H), 7.36 (s, 2H), 6.98 (m, 1H), 6.74 (d, J=3.8 Hz, 1H), 3.35-3.25 (m, 2H), 3.23 (s, 3H), 2.66 (m, 2H), 1.80 (m, 2H).

Example 83A 6-(3-Methoxy-propyl)-2-pyrrolo[1,2-c]pyrimidin-3-yl-chromen-4-one O-tert-butyl-oxime

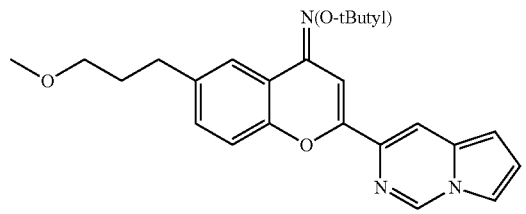

A solution of 6-(3-Methoxy-prop-1-ynyl)-2-pyrrolo[1,2-c]pyrimidin-3-yl-chromen-4-one O-tert-butyl-oxime (example 83B) (30 mg, 0.075 mmol) and 10% platinum black (10 mg) in ethyl acetate (10 ml) was hydrogenated at room temperature under 1 atmosphere of hydrogen during 48 hours. The catalyst was removed by filtration over Celite® and the filtrates concentrated to dryness to yield the title compound (18 mg, 60%) as a yellow solid that was used for the next step without further purification.

HPLC (gradient 5%-95% ACN/H₂O+0.1% HCOOH): >80%; RT=6.47 min.
MS (ESI+): 405.5 [C$_{24}$H$_{27}$N$_{3}$O$_{3}$+H]$^{+}$ (m/z).

Example 83B 6-(3-Methoxy-prop-1-ynyl)-2-pyrrolo[1,2-c]pyrimidin-3-yl-chromen-4-one O-tert-butyl-oxime was prepared in 39% yield using the procedure described in example 23A, starting from 6-bromo-2-pyrrolo[1,2-c]pyrimidin-3-yl-chromen-4-one O-tert-butyl oxime (tert-butyl protected oxime of example 66) and 3-Methoxy-propyne. The title compound was isolated as a yellow solid.

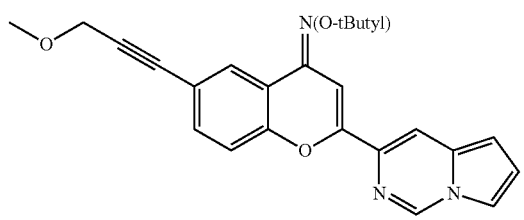

1H NMR: (300 MHz) CHCl₃-d₁ δ (ppm): 8.84 (s, 1H), 8.30 (d, J=1.9 Hz, 1H), 7.93 (s, 1H), 7.55 (s, 1H), 7.56-7.46 (m, 2H), 7.24 (m, 1H), 6.96 (t, J=3.3 Hz, 1H), 6.68 (d, J=3.8 Hz, 1H), 4.35 (s, 2H), 3.48 (s, 3H), 1.43 (s, 9H).

Example 84

6-(3-Dimethylamino-propoxy)-2-pyrrolo[1,2-c]pyrimidin-3-yl-chromen-4-one oxime hydrochloride 6-(3-Dimethylamino-propoxy)-2-pyrrolo[1,2-c]pyrimidin-3-yl-chromen-4-one oxime was prepared in 22% overall yield using the procedure described in example 42A, starting from 6-hydroxy-2-pyrrolo[1,2-c]pyrimidin-3-yl-chromen-4-one O-tert-butyl oxime (example 81A) and (3-Chloro-propyl)-dimethyl-amine hydrochloride. The compound was treated with a 1.25 N solution of hydrogen chloride in isopropanol to yield 6-(3-Dimethylamino-propoxy)-2-pyrrolo[1,2-c]pyrimidin-3-yl-chromen-4-one oxime hydrochloride as an orange solid.

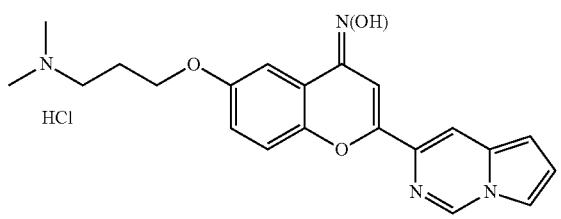

Mp: >270° C. dec.
MS (ESI+): 793.2 [C$_{21}$H$_{22}$N$_{4}$O$_{3}$+H]$^{+}$ (m/z).
1H NMR: (300 MHz) DMSO-d₆ δ (ppm): 10.93 (br. s, 1H), 10.38 (br. s, 1H), 9.22 (s, 1H), 8.03 (s, 1H), 7.82 (s, 1H), 7.43 (s, 1H), 7.42 (d, J=8.3 Hz, 1H), 7.33 (d, J=3.0 Hz, 1H), 7.14 (d, J=3.0 Hz, 1H), 7.11 (d, J=3.0 Hz, 1H), 6.98 (d, J=3.7 Hz, 1H), 4.10 (t, J=5.9 Hz, 2H), 3.18 (m, 2H), 2.79, 2.77 (2s, 6H), 2.27 (m, 2H).

Example 85

6-(3-Morpholin-4-yl-ethoxy)-2-pyrrolo[1,2-c]pyrimidin-3-yl-chromen-4-one oxime hydrochloride was prepared in 65% overall yield using method D (step 2), starting from 6-(3-Morpholin-4-yl-ethoxy)-2-pyrrolo[1,2-c]pyrimidin-3-yl-chromen-4-one O-tert-butyl oxime (example 85A). The hydrochloride salt of the title compound was isolated as an orange solid after treatment with a 1.25 M solution of hydrogen chloride in isopropanol,

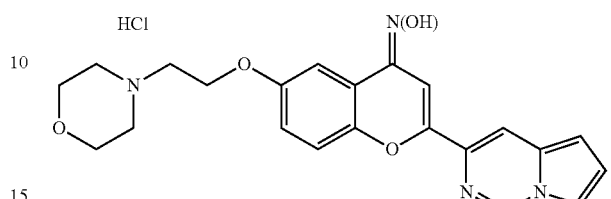

Mp: >270° C. dec.
MS (ESI+): 407.3 [C$_{22}$H$_{22}$N$_{4}$O$_{4}$+H]$^{+}$ (m/z).
1H NMR: (300 MHz) DMSO-d₆ δ (ppm): 10.99 (br. s, 1H), 10.67 (br. s, 1H), 9.22 (s, 1H), 8.05 (s, 1H), 7.82 (d, J=2.6 Hz, 1H), 7.46 (d, J=9.2 Hz, 1H), 7.44 (s, 1H), 7.39 (d, J=3.0 Hz, 1H), 7.20 (dd, J=9.0 Hz, J=3.0 Hz, 1H), 6.98 (dd, J=3.6 Hz, J=2.8 Hz, 1H), 6.74 (d, J=3.7 Hz, 1H), 4.45 (m, 2H), 3.98 (br. d, J=11:1 Hz, 2H), 3.90-3.70 (m, 2H), 3.65-345 (m, 4H), 3.30-3.12 (m, 2H).

Example 85A

6-(3-Morpholin-4-yl-ethoxy)-2-pyrrolo[1,2-c]pyrimidin-3-yl-chromen-4-one O-tert-butyl oxime

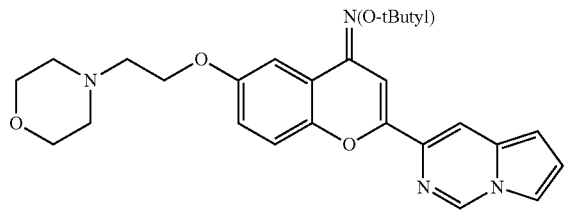

A mixture of 6-Hydroxy-2-pyrrolo[1,2-c]pyrimidin-3-yl-chromen-4-one O-tert-butyl-oxime (example 81A) (100 mg, 0.286 mmol), 4-(2-chloroethyl)morpholine hydrochloride (80 mg, 0.430 mmol) and potassium carbonate (119 mg, 0.858 mmol) in dry acetone (2.5 ml) was stirred at 60° C. for 20 hours. The solvent was removed under vacuum. The residue was treated with water and extracted with ethyl acetate. The combined organic layers was washed with brine, dried over sodium sulfate and concentrated to dryness. The residue was purified by silica gel flash chromatography (gradient cyclohexane/ethyl acetate: 20-100%) to yield the title compound (89 mg, 67%) as a yellow solid.
1H NMR: (300 MHz) CHCl₃-d₁ δ (ppm): 8.79 (m, 1H), 7.90 (s, 1H), 7.51 (d, J=3.0 Hz, 1H), 7.49 (s, 1H), 7.45 (d, J=2.5 Hz, 1H), 7.20 (d, J=9.1 Hz, 1H), 6.99 (dd, J=9.0 Hz, J=3.0 Hz, 1H), 6.92 (dd, J=3.8 Hz, J=2.8 Hz, 1H), 6.63 (d, J=3.8 Hz, 1H), 4.21 (br. m, 2H), 3.79 (br. m, 4H), 2.89 (br. m, 2H), 2.63 (br. m, 4H), 1.41 (s, 9H).

Example 86

6-(2,3-Dihydroxy-propoxy)-2-pyrrolo[1,2-c]pyrimidin-3-yl-chromen-4-one oxime A solution of 6-(2,3-Dihydroxy-propoxy)-2-pyrrolo[1,2-c]pyrimidin-3-yl-chromen-4-one O-tert-butyl oxime (example 86A) (100 mg, 0.236 mmol) in toluene (8 ml) was treated at 0° C. with trifluoro acetic acid (2 ml) and heated at 60° C. for 5.5 hours. The solution was concentrated under vacuum, the residue dissolved in ethyl acetate and washed successively with a saturated solution of sodium hydrogenocarbonate, brine, dried over sodium sulfate and concentrated. The residue was purified by silica gel flash chromatography (gradient cyclohexane/ethyl acetate: 0-100% then ethyl acetate/methanol:90/10) to yield the title compound (38 mg, 44%) as a brown-yellow solid.

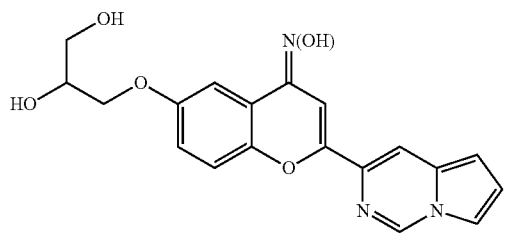

MS (ESI+): 368.1 $[C_{19}H_{17}N_3O_5+H]^+$ (m/z).

1H NMR of the major Z isomer: (300 MHz) DMSO-$d_6$ δ (ppm): 10.92 (br. s, 1H), 9.22 (s, 1H), 8.05 (s, 1H), 7.82 (d, J=2.4 Hz, 1H), 7.44 (s, 1H), 7.41 (d, J=9.2 Hz, 1H), 7.34 (s, 1H), 7.13 (dd, J=9.2 Hz, J=2.3 Hz, 1H), 6.99 (dd, J=3.6 Hz, J=2.8 Hz, 1H), 6.74 (d, J=4.4 Hz, 1H), 4.05 (m, 2H), 3.89 (m, 2H), 3.81 (m, 1H).

Example 86A 6-(2,3-Dihydroxy-propoxy)-2-pyrrolo[1,2-c]pyrimidin-3-yl-chromen-4-one O-tert-butyl oxime was prepared in 74% yield using the method described in example 85A, starting from 6-Hydroxy-2-pyrrolo[1,2-c]pyrimidin-3-yl-chromen-4-one O-tert-butyl-oxime (example 81A) and 3-chloro-1,2-propandiol. The title compound was isolated as a yellow solid.

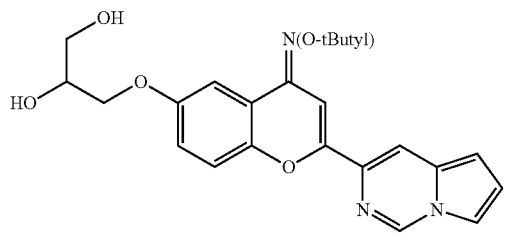

1H NMR: (300 MHz) CHCl$_3$-d$_1$ δ (ppm): 8.81 (s, 1H), 7.96 (s, 1H), 7.57 (m, 1H), 7.47 (s, 1H), 7.29-7.15 (m, 2H), 7.06 (m, 1H), 6.94 (m, 1H), 6.67 (d, J=3.6 Hz, 1H), 4.30-4.00 (m, 3H), 3.95-3.60 (m, 2H), 1.45 (s, 9H).

Example 87

6-(2-Pyrrolidin-1-yl-ethoxy)-2-pyrrolo[1,2-c]pyrimidin-3-yl-chromen-4-one oxime, hydrochloride was prepared in 37% yield using method D (step 2), starting from 6-(2-Pyrrolidin-1-yl-ethoxy)-2-pyrrolo[1,2-c]pyrimidin-3-yl-chromen-4-one O-tert-butyl oxime (example 87A). The hydrochloride salt of the title compound was isolated as an orange solid after treatment with a 1.25 M solution of hydrogen chloride in isopropanol.

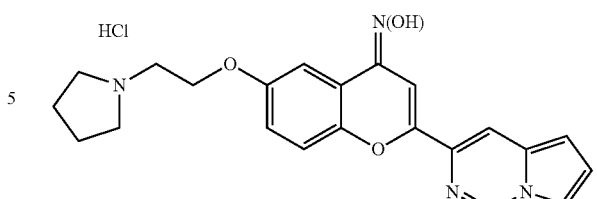

Mp: >260° C. dec.

MS (ESI+): 391.2 $[C_{22}H_{22}N_4O_3+H]^+$ (m/z).

1H NMR: (300 MHz) DMSO-$d_6$ δ (ppm): 10.94 (br. s, 1H), 10.16 (br. s, 1H), 9.22 (s, 1H), 8.04 (s, 1H), 7.82 (s, 1H), 7.46 (d, J=9.2 Hz, 1H), 7.44 (s, 1H), 7.38 (d, J=3.0 Hz, 1H), 7.20 (dd, J=9.0 Hz, J=3.0 Hz, 1H), 6.99 (dd, J=3.6 Hz, J=2.8 Hz, 1H), 6.74 (d, J=3.6 Hz, 1H), 4.37 (m, 2H), 3.50 (m, 4H), 3.15 (m, 2H), 2.03 (m, 2H), 1.90 (m, 2H).

Example 87A 6-(2-Pyrrolidin-1-yl-ethoxy)-2-pyrrolo[1,2-c]pyrimidin-3-yl-chromen-4-one O-tert-butyl oxime

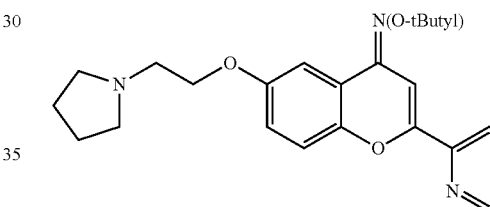

A mixture of 6-(2-chloro-ethoxy)-2-pyrrolo[1,2-c]pyrimidin-3-yl-chromen-4-one O-tert-butyl oxime (example 87B) (64 mg, 0.16 mmol), potassium carbonate (64 mg, 0.46 mmol) and pyrrolidine (19 μl, 0.24 mmol), in acetonitrile (1.5 ml) was heated in a sealed tube at 100° C. for 18 hours. The yellow suspension was filtered, the solid washed with ethyl acetate and the combined filtrates concentrated to dryness. The residue was purified by silica gel flash chromatography (gradient ethyl acetate/methanol 0-2%) to yield the title compound (49 mg, 71%) as a yellow solid.

1H NMR: (300 MHz) CHCl$_3$-d$_1$ δ (ppm): 8.79 (s, 1H), 7.90 (s, 1H), 7.51 (d, J=3.0 Hz, 1H), 7.49 (s, 1H), 7.45 (d, J=2.8 Hz, 1H), 7.21 (d, J=9.0 Hz, 1H), 7.00 (d, J=9.0 Hz, J=3.0 Hz, 1H), 6.92 (d, J=3.7 Hz, J=2.8 Hz, 1H), 6.63 (d, J=3.7 Hz, 1H), 4.40-4.25 (br. m, 2H), 3.24-3.09 (m, 2H), 3.08-2.60 (m, 4H), 2.03-1.90 (m, 4H), 1.41 (s, 9H).

Example 87B 6-(2-chloro-ethoxy)-2-pyrrolo[1,2-c]pyrimidin-3-yl-chromen-4-one O-tert-butyl oxime was prepared in 60% yield using the method described in example 85A, starting from 6-hydroxy-2-pyrrolo[1,2-c]pyrimidin-3-yl-chromen-4-one O-tert-butyl-oxime (example 81A) and 1,2-dichloroethane in dimethylformamide. The title compound was isolated as a yellow solid.

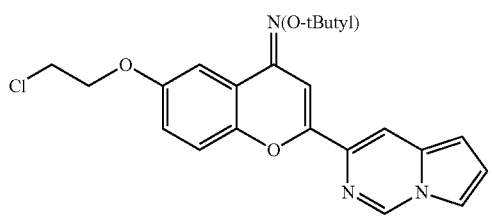

1H NMR: (300 MHz) CHCl₃-d₁ δ (ppm): 8.79 (s, 1H), 7.89 (s, 1H), 7.54 (d, J=3.0 Hz, 1H), 7.50 (s, 1H), 7.44 (s, 1H), 7.22 (d, J=9.0 Hz, 1H), 7.01 (dd, J=9.0 Hz, J=3.0 Hz, 1H), 6.92 (dd, J=3.7 Hz, J=2.8 Hz, 1H), 6.62 (d, J=3.7 Hz, 1H), 4.30 (t, J=5.7 Hz, 2H), 3.85 (t, J=5.7 Hz, 2H), 1.42 (s, 9H).

Example 88

6-(2-Piperidin-1-yl-ethoxy)-2-pyrrolo[1,2-c]pyrimidin-3-yl-chromen-4-one oxime, hydrochloride was prepared in 27% overall yield using the method described in example 85, starting from 6-hydroxy-2-pyrrolo[1,2-c]pyrimidin-3-yl-chromen-4-one O-tert-butyl oxime (example 81A) and 1-(2-chloroethyl)-piperidine hydrochloride.

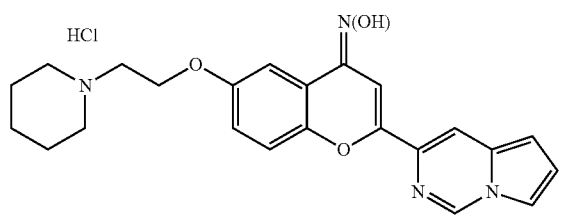

Mp: >255° C. dec.
MS (ESI+): 405.2 [C₂₃H₂₄N₄O₃+H]⁺ (m/z).
1H NMR: (300 MHz) DMSO-d₆ δ (ppm): 11.00 (br. s, 1H), 10.26 (br. s, 1H), 9.22 (s, 1H), 8.05 (s, 1H), 7.82 (s, 1H), 7.47 (d, J=9.0 Hz, 1H), 7.45 (s, 1H), 7.39 (d, J=3.0 Hz, 1H), 7.20 (dd, J=9.0 Hz, J=3.0 Hz, 1H), 6.99 (dd, J=3.7 Hz, J=2.8 Hz, 1H), 6.74 (d, J=3.7 Hz, 1H), 4.45 (m, 2H), 3.49 (m, 4H), 3.02 (m, 2H), 1.79 (m, 4H), 1.72 (m, 1H), 1.41 (m, 1H).

Example 89

6-(2-dimethylamino-ethoxy)-2-pyrrolo[1,2-c]pyrimidin-3-yl-chromen-4-one oxime, hydrochloride was prepared in 39% overall yield using the method described in example 85, starting from 6-hydroxy-2-pyrrolo[1,2-c]pyrimidin-3-yl-chromen-4-one O-tert-butyl oxime (example 81A) and 1-(2-chloroethyl)-dimethylamine hydrochloride.

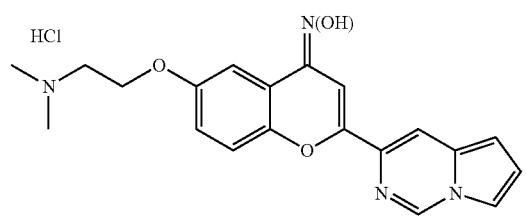

Mp: >275° C. dec.
MS (ESI+): 365.2 [C₂₀H₂₀N₄O₃+H]⁺ (m/z).
1H NMR: (300 MHz) DMSO-d₆ δ (ppm): 11.00 (br. s, 1H), 10.40 (br. s, 1H), 9.23 (s, 1H), 8.05 (s, 1H), 7.82 (s, 1H), 7.48 (d, J=9.0 Hz, 1H), 7.45 (s, 1H), 7.42 (d, J=3.0 Hz, 1H), 7.21 (dd, J=9.0 Hz, J=3.0 Hz, 1H), 6.99 (dd, J=3.7 Hz, J=2.9 Hz, 1H), 6.74 (d, J=3.7 Hz, 1H), 4.40 (m, 2H), 3.52 (m, 2H), 2.86 (s, 3H), 2.84 (s, 3H).

Example 90

6-(2-diethylamino-ethoxy)-2-pyrrolo[1,2-c]pyrimidin-3-yl-chromen-4-one oxime, hydrochloride was prepared using the method described in example 87, starting from 6-(2-chloro-ethoxy)-2-pyrrolo[1,2-c]pyrimidin-3-yl-chromen-4-one O-tert-butyl oxime (example 87B) and 1-(2-chloroethyl)-diethylamine hydrochloride.

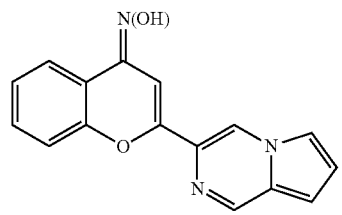

MS (ESI+): 393.2 [C₂₂H₂₄N₄O₃+H]⁺ (m/z).
1H NMR: (300 MHz) DMSO-d₆ δ (ppm): 10.94 (br. s, 1H), 8.80 (br. s, 1H), 9.22 (s, 1H), 8.05 (s, 1H), 7.83 (s, 1H), 7.47 (d, J=9.0 Hz, 1H), 7.45 (s, 1H), 7.39 (d, J=3.0 Hz, 1H), 7.20 (dd, J=9.0 Hz, J=3.0 Hz, 1H), 6.99 (dd, J=3.7 Hz, J=2.9 Hz, 1H), 6.74 (d, J=3.7 Hz, 1H), 4.40 (m, 2H), 3.50 (m, 2H), 3.23 (m, 4H), 1.26 (m, 6H).

Example 91

2-Pyrrolo[1,2-a]pyrazin-3-yl-chromen-4-one oxime was prepared in 41% yield using methods A and D, starting from 2'-hydroxyacetophenone and Pyrrolo[1,2-a]pyrazine-3-carboxylic acid methyl ester (example 91A). The title compound was isolated as a pale yellow solid.

Mp: >276-277° C.
MS (ESI+): 278.0 [C₁₆H₁₁N₃O₂+H]⁺ (m/z).
1H NMR: (300 MHz) DMSO-d₆ δ (ppm): 10.96 (s, 1H), 8.97 (s, 1H), 8.93 (s, 1H), 7.92 (s, 1H), 7.90 (dd, J=7.9 Hz, J=1.5 Hz, 1H), 7.53 (td, J=7.8 Hz, J=1.3 Hz, 1H), 7.48 (s, 1H), 7.40 (d, J=8.3 Hz, 1H), 7.28 (t, J=7.5 Hz, 1H), 7.00 (dd, J=3.9 Hz, J=2.4 Hz, 1H), 6.96 (d, J=3.9 Hz, 1H).

Example 91A

Pyrrolo[1,2-a]pyrazine-3-carboxylic acid methyl ester

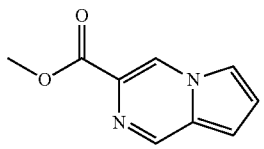

A solution of di-(2-tert-Butoxycarbonyl)-amino-3-(2-formyl-pyrrol-1-yl)-propionic acid methyl ester (J. Chem. Soc., Perkin Trans 1, 2000, 3317-3324) (500 mg, 1.26 mmol) in trifluoroacetic acid (4 ml) was stirred at room temperature for 1 hour. The reaction mixture was cautiously poured into a cold saturated aqueous solution of sodium hydrogenocarbonate and extracted with ethyl acetate. The extracts were washed with brine, dried over sodium sulfate and concentrated to dryness. The residue was purified by silica gel flash chromatography (gradient cyclohexane/ethyl acetate: 0-100%) to yield 3,4-Dihydro-pyrrolo[1,2-a]pyrazine-3-carboxylic acid methyl ester (169 mg, 75%) as an orange oil. This oil was dissolved in dichloromethane and treated with manganese dioxide (800 mg, 9.2 mmol) at 40° C. for 1 hour. The black solids were removed by filtration over Celite® and washed abundantly with dichloromethane. The filtrate was concentrated to dryness to yield Pyrrolo[1,2-a]pyrazine-3-carboxylic acid methyl ester (130 mg, 80%) as a yellow solid.

1H NMR: (300 MHz) CHCl$_3$-d$_1$ δ (ppm): 8.85 (s, 1H), 8.78 (s, 1H), 7.56 (d, J=2.5 Hz, 1H), 7.02 (dd, J=4.1 Hz, J=2.6 Hz, 1H), 6.91 (d, J=3.9 Hz, 1H), 4.00 (s, 3H).

Example 92

6-[2-(2-methyl-pyrrolidin-1-yl)-ethoxy]-2-pyrrolo[1,2-c]pyrimidin-3-yl-chromen-4-one oxime, hydrochloride was prepared in 22% overall yield using the method described in example 87, starting from 6-(2-chloro-ethoxy)-2-pyrrolo[1,2-c]pyrimidin-3-yl-chromen-4-one O-tert-butyl oxime (example 87B) and 2-methylpyrrolidine.

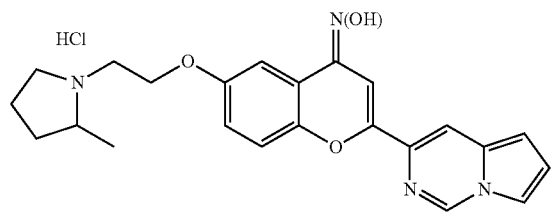

MS (ESI+): 405.3 [C$_{23}$H$_{24}$N$_4$O$_3$+H]$^+$ (m/z).
1H NMR: (300 MHz) DMSO-d$_6$ δ (ppm): 10.98 (br. s, 1H), 10.19 (br. s, 1H), 9.22 (s, 1H), 8.05 (s, 1H), 7.82 (s, 1H), 7.47 (d, J=9.0 Hz, 1H), 7.45 (s, 1H), 7.40 (d, J=3.0 Hz, 1H), 7.21 (dd, J=9.0 Hz, J=3.0 Hz, 1H), 6.99 (dd, J=3.7 Hz, J=2.9 Hz, 1H), 6.74 (d, J=3.7 Hz, 1H), 4.40 (m, 2H), 3.80-3.60 (m, 2H), 3.60-3.30 (m, 2H), 3.30-3.10 (m, 2H), 2.30-2.15 (m, 1H), 2.10-1.85 (m, 2H), 1.70-1.55 (m, 1H), 1.43 (d, J=8.9 Hz, 3H).

Example 93

6-[2-(4-methyl-piperazin-1-yl)-ethoxy]-2-pyrrolo[1,2-c]pyrimidin-3-yl-chromen-4-one oxime, dihydrochloride was prepared in 26% overall yield using the method described in example 87, starting from 6-(2-chloro-ethoxy)-2-pyrrolo[1,2-c]pyrimidin-3-yl-chromen-4-one O-tert-butyl oxime (example 87B) and 4-methyl-piperazine.

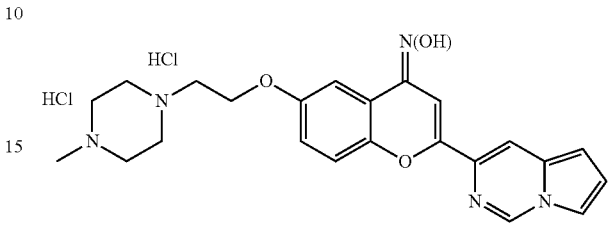

Mp: >230° C. dec.
MS (ESI+): 420.2 [C$_{23}$H$_{25}$N$_5$O$_3$+H]$^+$ (m/z).
1H NMR: (300 MHz) DMSO-d$_6$ δ (ppm): 11.56 (br. s, 1H), 10.98 (br. s, 1H), 9.22 (s, 1H), 8.05 (s, 1H), 7.82 (s, 1H), 7.46 (d, J=9.0 Hz, 1H), 7.45 (s, 1H), 7.39 (d, J=3.0 Hz, 1H), 7.21 (dd, J=9.0 Hz, J=3.0 Hz, 1H), 6.99 (dd, J=3.7 Hz, J=2.9 Hz, 1H), 6.74 (d, J=3.7 Hz, 1H), 4.44 (m, 2H), 4.00-3.20 (multiplets, 10H), 2.84 (s, 3H).

Example 94

6-[2-(4-methyl-[1,4]diazepan-1-yl)-ethoxy]-2-pyrrolo[1,2-c]pyrimidin-3-yl-chromen-4-one oxime, dihydrochloride was prepared in 13% overall yield using the method described in example 87, starting from 6-(2-chloro-ethoxy)-2-pyrrolo[1,2-c]pyrimidin-3-yl-chromen-4-one O-tert-butyl oxime (example 87B) and 1-methyl-[1,4]diazepane.

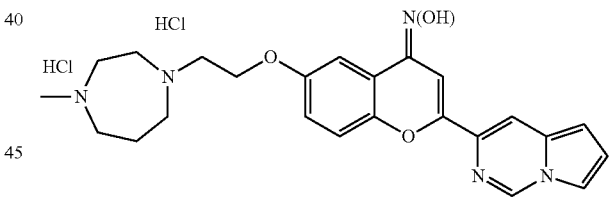

Mp: >210° C. dec.
MS (ESI+): 434.3 [C$_{24}$H$_{27}$N$_5$O$_3$+H]$^+$ (m/z).
1H NMR: (300 MHz) DMSO-d$_6$ δ (ppm): 10.90 (br. s, 1H), 9.20 (s, 1H), 8.03 (s, 1H), 7.81 (s, 1H), 7.43 (s, 1H), 7.40 (d, J=9.1 Hz, 1H), 7.31 (d, J=3.0 Hz, 1H), 7.12 (dd, J=9.0 Hz, J=3.0 Hz, 1H), 6.98 (dd, J=3.7 Hz, J=2.8 Hz, 1H), 6.73 (d, J=2.9 Hz, 1H), 4.10 (m, 2H), 3.33-3.27 (m, 2H), 3.10-2.70 (multiplets, 11H), 1.84 (m, 2H).

Example 95

6-[2-((S)-2-hydroxymethylpyrrolidin-1-yl)-ethoxy]-2-pyrrolo[1,2-c]pyrimidin-3-yl-chromen-4-one oxime, hydrochloride was prepared in 8% overall yield using the method described in example 87, starting from 6-(2-chloro-ethoxy)-2-pyrrolo[1,2-c]pyrimidin-3-yl-chromen-4-one O-tert-butyl oxime (example 87B) and 2-((S)-2-hydroxymethylpyrrolidine.

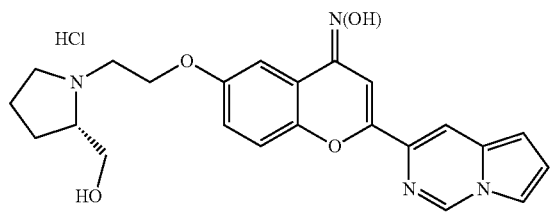

Mp: >220° C. dec.

MS (ESI+): 421.3 [$C_{23}H_{24}N_4O_4$+H]$^+$ (m/z).

1H NMR: (300 MHz) DMSO-$d_6$ δ (ppm): 10.94 (br. s, 1H), 9.61 (br. s, 1H), 9.22 (s, 1H), 8.04 (s, 1H), 7.82 (s, 1H), 7.46 (d, J=9.1 Hz, 1H), 7.44 (s, 1H), 7.38 (d, J=3.0 Hz, 1H), 7.19 (dd, J=9.0 Hz, J=3.0 Hz, 1H), 6.99 (dd, J=3.7 Hz, J=2.8 Hz, 1H), 6.74 (d, J=2.9 Hz, 1H), 4.40 (m, 2H), 3.85-3.60 (multiplets, 3H), 3.60-3.40 (multiplets, 3H), 3.34-3.19 (m, 1H), 2.17-1.95 (m, 2H), 1.95-1.82 (m, 1H), 1.72-1.67 (m, 1H).

Example 96

6-[2-((S)-2-methoxymethylpyrrolidin-1-yl)-ethoxy]-2-pyrrolo[1,2-c]pyrimidin-3-yl-chromen-4-one oxime, hydrochloride was prepared in 40% overall yield using the method described in example 87, starting from 6-(2-chloro-ethoxy)-2-pyrrolo[1,2-d]pyrimidin-3-yl-chromen-4-one O-tert-butyl oxime (example 87B) and 2-((S)-2-methoxymethylpyrrolidine.

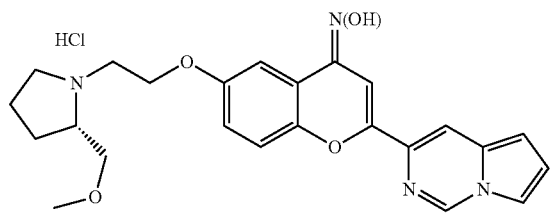

Mp: >225° C. dec.

MS (ESI+): 435.3 [$C_{24}H_{26}N_4O_4$+H]$^+$ (m/z).

1H NMR: (300 MHz) DMSO-$d_6$ δ (ppm): 10.99 (br. s, 1H), 10.39 (br. s, 1H), 9.22 (s, 1H), 8.05 (s, 1H), 7.83 (s, 1H), 7.46 (d, J=9.0 Hz, 1H), 7.45 (s, 1H), 7.38 (d, J=3.0 Hz, 1H), 7.20 (dd, J=9.0 Hz, J=3.0 Hz, 1H), 6.99 (dd, J=3.8 Hz, J=2.9 Hz, 1H), 6.74 (d, J=2.9 Hz, 1H), 4.41 (m, 2H), 3.85-3.45 (multiplets, 6H), 3.35-3.15 (m, 1H), 3.30 (s, 3H), 2.20-1.80 (multiplets, 3H), 1.75-1.55 (m, 1H).

Example 97

6-[2-((R)-2-methoxymethylpyrrolidin-1-yl)-ethoxy]-2-pyrrolo[1,2-c]pyrimidin-3-yl-chromen-4-one oxime, hydrochloride was prepared in 33% overall yield using the method described in example 87, starting from 6-(2-chloro-ethoxy)-2-pyrrolo[1,2-c]pyrimidin-3-yl-chromen-4-one O-tert-butyl oxime (example 87B) and 2-((R)-2-methoxymethylpyrrolidine.

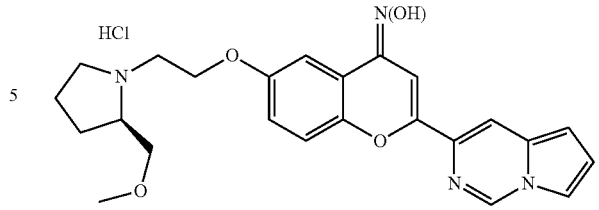

Mp: 210° C. dec.

MS (ESI+): 435.3 [$C_{24}H_{26}N_4O_4$+H]$^+$ (m/z).

1H NMR: (300 MHz) DMSO-$d_6$ δ (ppm): 11.00 (br. s, 1H), 10.39 (br. s, 1H), 9.23 (s, 1H), 8.06 (s, 1H), 7.83 (s, 1H), 7.46 (d, J=9.0 Hz, 1H), 7.45 (s, 1H), 7.40 (d, J=3.0 Hz, 1H), 7.21 (dd, J=9.0 Hz, J=3.0 Hz, 1H), 6.99 (dd, J=3.8 Hz, J=2.9 Hz, 1H), 6.74 (d, J=2.9 Hz, 1H), 4.41 (m, 2H), 3.85-3.45 (multiplets, 6H), 3.35-3.15 (m, 1H), 3.30 (s, 3H), 2.22-1.80 (multiplets, 3H), 1.78-1.55 (m, 1H).

Example 98

6-[2-(3-hydroxy-pyrrolidin-1-yl)-ethoxy]-2-pyrrolo[1,2-c]pyrimidin-3-yl-chromen-4-one oxime, hydrochloride was prepared in 23% overall yield using the method described in example 87, starting from 6-(2-chloro-ethoxy)-2-pyrrolo[1,2-c]pyrimidin-3-yl-chromen-4-one O-tert-butyl oxime (example 87B) and 3-pyrrolidinol.

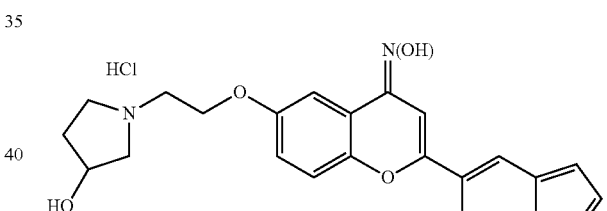

Mp: >230° C. dec.

MS (ESI+): 407.2 [$C_{22}H_{22}N_4O_4$+H]$^+$ (m/z).

1H NMR: (300 MHz) DMSO-$d_6$ δ (ppm): 10.96 (br. s, 1H), 10.62 (br. s, 1H), 10.39 (br. s, 1H), 9.22 (s, 1H), 8.04 (s, 1H), 7.82 (s, 1H), 7.46 (d, J=9.1 Hz, 1H), 7.45 (s, 1H), 7.38 (d, J=3.0 Hz, 1H), 7.21 (dd, J=9.0 Hz, J=3.0 Hz, 1H), 6.99 (dd, J=3.7 Hz, J=2.8 Hz, 1H), 6.74 (d, J=2.9 Hz, 1H), 4.46 (m, 1H), 4.38 (m, 1H), 3.80-3.05 (multiplets, 6H), 3.35-3.15 (m, 1H), 2.40-2.15 (m, 0.5H), 2.10-1.75 (multiplets, 1.5H).

Example 99

6-[2-(4-dimethylamino-piperidin-1-yl)-ethoxy]-2-pyrrolo[1,2-c]pyrimidin-3-yl-chromen-4-one oxime, dihydrochloride was prepared in 30% overall yield using the method described in example 87, starting from 6-(2-chloro-ethoxy)-2-pyrrolo[1,2-c]pyrimidin-3-yl-chromen-4-one O-tert-butyl oxime (example 87B) and 4-dimethylaminopiperidine.

97

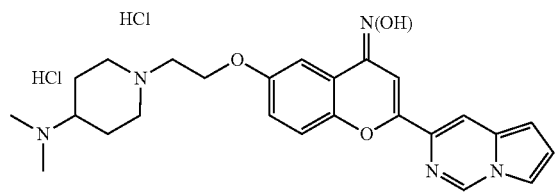

Mp: >255° C. dec.

MS (ESI+): 448.3 [C$_{26}$H$_{29}$N$_5$O$_3$+H]$^+$ (m/z).

1H NMR: (300 MHz) DMSO-d$_6$ δ (ppm): 11.30-10.80 (br. s, 3H), 9.23 (s, 1H), 8.05 (s, 1H), 7.82 (s, 1H), 7.46 (d, J=9.0 Hz, 1H), 7.45 (s, 1H), 7.39 (d, J=3.0 Hz, 1H), 7.21 (dd, J=9.0 Hz, J=3.0 Hz, 1H), 6.99 (dd, J=3.7 Hz, J=2.8 Hz, 1H), 6.74 (d, J=2.9 Hz, 1H), 4.46 (m, 1H), 3.73 (br. d, J=11.4 Hz, 2H), 3.54 (br. s, 2H), 3.38 (br. m, 1H), 3.22-3.05 (m, 2H), 2.80-2.60 (m, 1H), 2.73, 2.72 (2s, 6H), 2.35-2.00 (multiplets, 4H).

Example 100

6-(2-cyclopentylamino-ethoxy)-2-pyrrolo[1,2-c]pyrimidin-3-yl-chromen-4-one oxime, hydrochloride was prepared in 17% overall yield using the method described in example 87, starting from 6-(2-chloro-ethoxy)-2-pyrrolo[1,2-c]pyrimidin-3-yl-chromen-4-one O-tert-butyl oxime (example 87B) and cyclopentylamine.

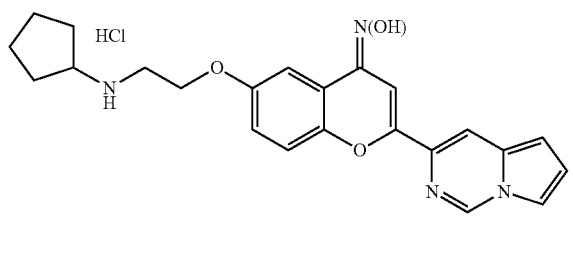

Mp: >230° C. dec.

MS (ESI+): 405.3 [C$_{23}$H$_{24}$N$_4$O$_3$+H]$^+$ (m/z).

1H NMR: (300 MHz) DMSO-d$_6$ δ (ppm): 10.98 (br. s, 1H), 9.22 (s, 1H), 9.01 (br. s, 2H), 8.05 (s, 1H), 7.82 (s, 1H), 7.48 (d, J=9.4 Hz, 1H), 7.45 (s, 1H), 7.40 (d, J=3.0 Hz, 1H), 7.20 (dd, J=9.2 Hz, J=3.0 Hz, 1H), 6.99 (dd, J=3.4 Hz, J=3.0 Hz, 1H), 674 (d, J=3.0 Hz, 1H), 4.30 (m, 2H), 3.56 (m, 1H), 3.36 (m, 2H), 1.99 (m, 2H), 1.80-1.45 (multiplets, 6H).

Example 101

6-(3-morpholin-4-yl-propoxy)-2-pyrrolo[1,2-c]pyrimidin-3-yl-chromen-4-one oxime, hydrochloride was prepared in 29% overall yield using the method described in example 87, starting from 6-(3-chloro-propoxy)-2-pyrrolo[1,2-c]pyrimidin-3-yl-chromen-4-one O-tert-butyl oxime (example 101A) and morpholine.

98

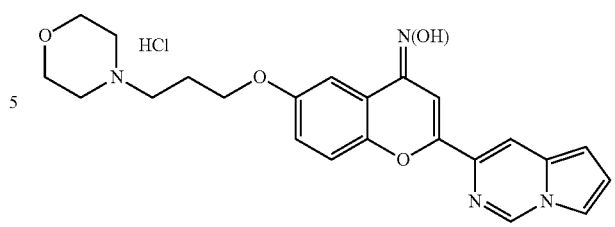

Mp: >220° C. dec.

MS (ESI+): 421.3 [C$_{23}$H$_{24}$N$_4$O$_4$+H]$^+$ (m/z).

1H NMR: (300 MHz) DMSO-d$_6$ δ (ppm): 11.05 (br. s, 2H), 9.22 (s, 1H), 8.06 (s, 1H), 7.82 (s, 1H), 7.46 (d, J=8.9 Hz, 1H), 7.45 (s, 1H), 7.39 (d, J=2.8 Hz, 1H), 7.15 (dd, J=9.0 Hz, J=3.0 Hz, 1H), 6.99 (dd, J=3.4 Hz, J=3.0 Hz, 1H), 6.74 (d, J=3.0 Hz, 1H), 4.12 (m, 2H), 3.97 (d, J=11.9 Hz, 2H), 3.82 (t, J=11.8 Hz, 2H), 3.46 (d, J=11.8 Hz, 2H), 3.27 (m, 2H), 3.20-3.00 (m, 2H), 2.22 (m, 2H).

Example 101A 6-(3-Chloro-propoxy)-2-pyrrolo[1,2-c]pyrimidin-3-yl-chromen-4-one O-tert-butyl oxime was prepared in 27% yield using the method described in example 85A, starting from 6-hydroxy-2-pyrrolo[1,2-c]pyrimidin-3-yl-chromen-4-one O-tert-butyl-oxime (example 81A) and 1-bromo-3-chloropropane in dimethylformamide. The title compound was isolated as a yellow solid.

1H NMR: (300 MHz) CHCl$_3$-d$_1$ δ (ppm): 8.79 (s, 1H), 7.81 (s, 1H), 7.56 (d, J=2.6 Hz, 1H), 7.50 (s, 1H), 7.45 (d, J=2.2 Hz, 1H), 7.21 (d, J=9.0 Hz, 1H), 6.98 (dd, J=9.0 Hz, J=3.0 Hz, 1H), 6.92 (dd, J=3.8 Hz, J=3.0 Hz, 1H), 6.63 (d, J=3.8 Hz, 1H), 4.19 (t, J=5.6 Hz, 2H), 3.38 (t, J=6.4 Hz, 2H), 2.27 (quint., J=6.0 Hz, 2H), 1.43 (s, 9H).

Example 102

6-(4-morpholin-4-yl-butyl)-2-pyrrolo[1,2-c]pyrimidin-3-yl-chromen-4-one oxime, hydrochloride was prepared in 45% overall yield using the method described in example 87, starting from methanesulfonic acid 4-{4-[(E)-tert-butoxyimino]-2-pyrrolo[1,2-c]pyrimidin-3-yl-4H-chromen-6-yl}-butyl ester (example 102A) and morpholine.

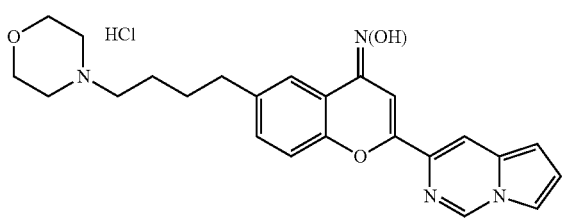

Mp: 180-185° C.
MS (ESI+): 419.3 [C$_{24}$H$_{26}$N$_4$O$_3$+H]$^+$ (m/z).
1H NMR: (300 MHz) DMSO-d$_6$ δ (ppm): 10.97 (br. s, 1H), 10.70 (br. s, 1H), 9.22 (s, 1H), 8.05 (s, 1H), 7.82 (s, 1H), 7.73 (s, 1H), 7.47 (s, 1H), 7.39 (s, 2H), 6.99 (dd, J=3.2 Hz, J=3.0 Hz, 1H), 6.74 (d, J=3.0 Hz, 1H), 3.92 (d, J=11.7 Hz, 2H), 3.76 (t, J=11.5 Hz, 2H), 3.37 (d, J=11.8 Hz, 2H), 3.20-2.90 (m, 4H), 2.75-2.60 (m, 2H), 1.80-1.55 (m, Example 102A methanesulfonic acid 4-{4-[(E)-tert-butoxyimino]-2-pyrrolo[1,2-c]pyrimidin-3-yl-4H-chromen-6-yl}-butyl ester A ice-cooled solution of 6-(4-Hydroxy-butyl)-2-pyrrolo[1,2-c]pyrimidin-3-yl-chromen-4-one O-tert-butyl-oxime (115 mg, 0.28 mmol) (example 102B) in dichloromethane (5 ml) was treated with triethylamine (100 µl, 0.7 mmol) and dropwise with methanesulfonyl chloride (26 µl, 0.34 mmol). The mixture was stirred at room temperature for 3 hours and treated with a saturated solution of ammonium chloride, extracted with dichloromethane, washed with brine, dried over sodium sulfate and concentrated to dryness. The crude mesylate was used for the next step without further purification.

Example 102B 6-(4-hydroxy-butyl)-2-pyrrolo[1,2-c]pyrimidin-3-yl-chromen-4-one O-tert-butyl-oxime was prepared in 17% overall yield using the methods described in examples 83A and 83B, starting from 6-bromo-2-pyrrolo[1,2-c]pyrimidin-3-yl-chromen-4-one O-tert-butyl-oxime (tert-butyl protected oxime of example 66) and But-3-yn-1-ol. The title compound was isolated as a yellow solid.

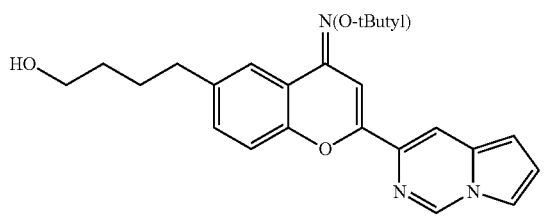

1H NMR: (300 MHz) CHCl$_3$-d$_1$ δ (ppm): 8.80 (s, 1H), 8.20 (d, J=1.9 Hz, 1H), 7.90 (s, 1H), 7.52 (s, 1H), 7.45 (d, J=3.7 Hz, 1H), 7.43 (dd, J=8.7 Hz, J=2.1 Hz, 1H), 7.20 (d, J=8.5 Hz, 1H), 6.93 (dd, J=3.8 Hz, J=3.3 Hz, 1H), 6.63 (d, J=3.8 Hz, 1H), 3.85 (1, J=6.2 Hz, 2H), 2.72 (1, J=6.2 Hz, 2H), 1.43 (s, 9H).

Example 103

6-(4,4-difluoro-piperidin-1-y)-2-pyrrolo[1,2-c]pyrimidin-3-yl-chromen-4-one oxime, hydrochloride was prepared in 48% overall yield using the method described in example 87, starting from 6-(2-chloro-ethoxy)-2-pyrrolo[1,2-c]pyrimidin-3-yl-chromen-4-one O-tert-butyl oxime (example 87B) and 4,4-difluoropiperidine.

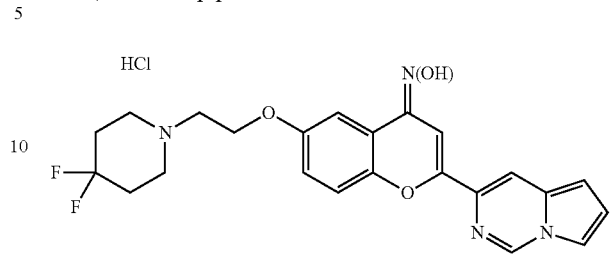

MS (ESI+): 441.1 [C$_{23}$H$_{22}$F$_2$N$_4$O$_3$+H]$^+$ (m/z).
1H NMR: (300 MHz) DMSO-d$_6$ δ (ppm): 11.27 (br. s, 1H), 10.99 (br. s, 1H), 9.23 (s, 1H), 8.06 (s, 1H), 7.82 (s, 1H), 7.47 (d, J=9.0 Hz, 1H), 7.45 (s, 1H), 7.41 (d, J=3.0 Hz, 1H), 7.22 (dd, J=9.0 Hz, J=3.0 Hz, 1H), 6.99 (dd, J=3.7 Hz, J=2.8 Hz, 1H), 6.74 (d, J=2.9 Hz, 1H), 4.49 (m, 2H), 3.90-3.70 (m, 2H), 3.64 (m, 2H), 3.31 (m, 2H), 2.60-2.30 (m, 4H).

Example 104

6-(2-[bis-(2-methoxy-ethyl)-amino]-ethoxy)-2-pyrrolo[1,2-c]pyrimidin-3-yl-chromen-4-one oxime, hydrochloride was prepared in 40% overall yield using the method described in example 87, starting from 6-(2-chloro-ethoxy)-2-pyrrolo[1,2-c]pyrimidin-3-yl-chromen-4-one O-tert-butyl oxime (example 87B) and bis-(2-methoxy-ethyl)-amine.

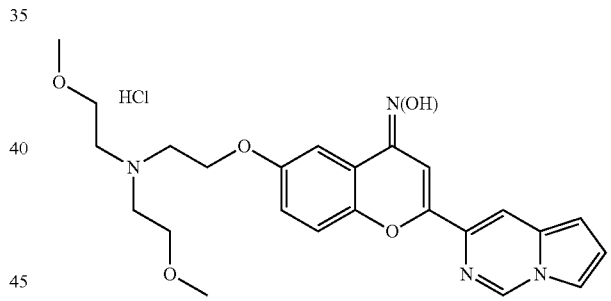

Mp: 155-160° C.
MS (ESI+): 453.3 [C$_{24}$H$_{28}$N$_4$O$_5$+H]$^+$ (m/z).
1H NMR: (300 MHz) DMSO-d$_6$ δ (ppm): 11.00 (br. s, 1H), 10.23 (br. s, 1H), 9.23 (s, 1H), 8.06 (s, 1H), 7.82 (s, 1H), 7.47 (d, J=9.0 Hz, 1H), 7.45 (s, 1H), 7.40 (d, J=3.0 Hz, 1H), 7.19 (dd, J=9.0 Hz, J=3.0 Hz, 1H), 6.99 (dd, J=3.3 Hz, J=3.0 Hz, 1H), 6.74 (d, J=3.0 Hz, 1H), 4.43 (m, 2H), 3.75 (m, 4H), 3.65 (m, 2H), 3.48 (m, 4H), 3.31 (s, 6H).

Example 105

6-(2-imidazol-1-O-ethoxy)-2-pyrrolo[1,2-c]pyrimidin-3-yl-chromen-4-one oxime was prepared in 57% overall yield using the method described in example 87, starting from 6-(2-chloro-ethoxy)-2-pyrrolo[1,2-c]pyrimidin-3-yl-chromen-4-one O-tert-butyl oxime (example 87B) and sodium imidazolate (prepared in situ from imidazole and sodium hydride in dimethylformamide).

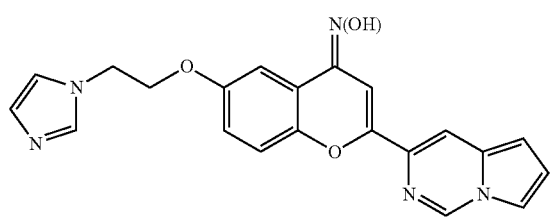

Mp: >250° C. dec.

MS (ESI+): 388.2 [$C_{21}H_{17}N_5O_3$+H]$^+$ (m/z).

1H NMR: (300 MHz) DMSO-$d_6$ δ (ppm): 10.86 (br. s, 1H), 9.21 (s, 1H), 8.02 (s, 1H), 7.80 (s, 1H), 7.69 (s, 1H), 7.42 (s, 1H), 7.39 (d, J=9.0 Hz, 1H), 7.29 (d, J=3.0 Hz, 1H), 7.26 (s, 1H), 7.11 (dd, J=9.0 Hz, J=3.0 Hz, 1H), 6.97 (dd, J=3.3 Hz, J=3.0 Hz, 1H), 6.89 (s, 1H), 6.73 (d, J=3.0 Hz, 1H), 4.36 (m, 2H), 4.30 (m, 2H).

Example 106

6-(3-morpholin-4-yl-propyl)-2-pyrrolo[1,2-c]pyrimidin-3-yl-chromen-4-one oxime, hydrochloride was prepared in 4% overall yield using the methods described in examples 102, 102A and 102B, starting from 6-bromo-2-pyrrolo[1,2-c]pyrimidin-3-yl-chromen-4-one O-tert-butyl-oxime (tert-butyl protected oxime of example 66) and prop-2-yn-1-ol.

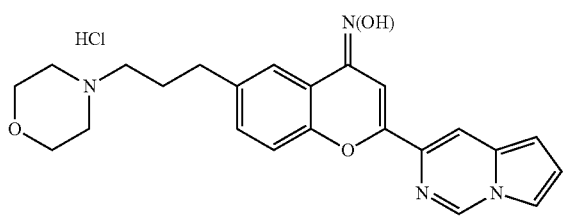

MS (ESI+): 405.2 [$C_{23}H_{24}N_4O_3$H]$^+$ (m/z).

1H NMR: (400 MHz) DMSO-$d_6$ δ (ppm): 10.91 (br. s, 1H), 10.20 (br. s, 1H), 9.22 (s, 1H), 8.05 (s, 1H), 7.82 (s, 1H), 7.75 (s, 1H), 7.47 (s, 1H), 7.41 (s, 2H), 6.99 (dd, J=3.2 Hz, J=3.0 Hz, 1H), 6.74 (d, J=3.0 Hz, 1H), 3.95 (d, J=12.0 Hz, 2H), 3.71 (t, J=12.0 Hz, 2H), 3.20-2.95 (m, 4H), 2.75-2.65 (m, 2H), 2.60-2.45 (m, 2H), 2.10-1.95 (m, 2H).

Example 107

6-((Z)-3-Morpholin-4-yl-propenyl))-2-pyrrolo[1,2-c]pyrimidin-3-yl-chromen-4-one oxime was isolated as byproduct during the synthesis of example 106.

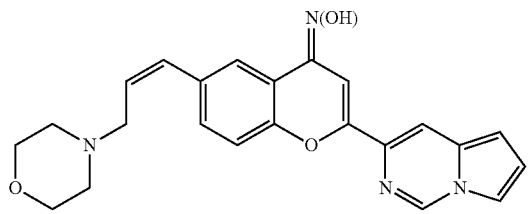

MS (ESI+): 403.2 [$C_{23}H_{22}N_4O_3$+H]$^+$ (m/z).

Example 108

6-[2-(3-methoxy-piperidin-1-yl)-ethoxy]-2-pyrrolo[1,2-c]pyrimidin-3-yl-chromen-4-one oxime, hydrochloride was prepared in 37% overall yield using the method described in example 87, starting from 6-(2-chloro-ethoxy)-2-pyrrolo[1,2-c]pyrimidin-3-yl-chromen-4-one O-tert-butyl oxime (example 87B) and 3-methoxy-piperidine.

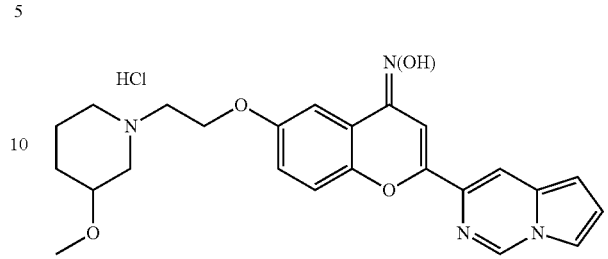

Mp: 178-184° C.

MS (ESI+): 435.3 [$C_{24}H_{26}N_4O_4$+H]$^+$ (m/z).

1H NMR: (300 MHz) DMSO-$d_6$ δ (ppm): 11.07 (br. s, 1H), 9.55 (br. s, 1H), 9.24 (s, 1H), 8.07 (s, 1H), 7.84 (s, 1H), 7.50 (d, J=9.2 Hz, 1H), 7.47 (s, 1H), 7.42 (t, J=2.8 Hz, 1H), 7.21 (dt, J=9.0 Hz, J=3.0 Hz, 1H), 6.99 (t, J=3.2 Hz, 1H), 6.75 (d, J=3.0 Hz, 1H), 4.55-4.35 (m, 2H), 3.80-2.75 (multiplets, 7H), 3.31 (s, 3H), 2.20-1.15 (multiplets, 4H).

Example 109

6-[2-(4-fluoro-phenyl)-ethoxy]-2-pyrrolo[1,2-c]pyrimidin-3-yl-chromen-4-one oxime, hydrochloride was prepared in 9% overall yield using the method described in example 85, starting from 6-hydroxy-2-pyrrolo[1,2-c]pyrimidin-3-yl-chromen-4-one O-tert-butyl oxime (example 81A) and 1-(2-Chloroethyl)-4-fluoro-benzene.

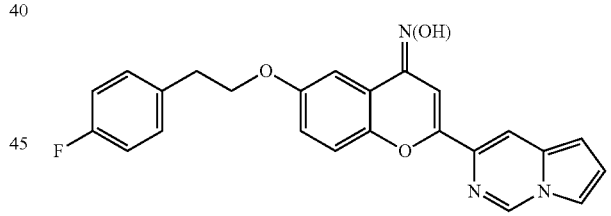

Mp: 234-236° C.

MS (ESI+): 416.3 [$C_{24}H_{18}N_3O_3$+H]$^+$ (m/z).

1H NMR: (300 MHz) DMSO-$d_6$ δ (ppm): 10.91 (s, 1H), 9.21 (s, 1H), 8.03 (s, 1H), 7.81 (s, 1H), 7.45-7.30 (m, 5H), 7.20-7.05 (m, 3H), 6.98 (m, 1H), 6.73 (d, J=3.0 Hz, 1H), 4.22 (t, J=6.4 Hz, 2H), 3.05 (t, J=6.4 Hz, 21-1).

Example 110

2-quinazolin-2-yl-chromen-4-one oxime was prepared in 23% overall yield using methods A and D, starting from 2'-hydroxyacetophenone and ethyl quinazoline-2-carboxylate.

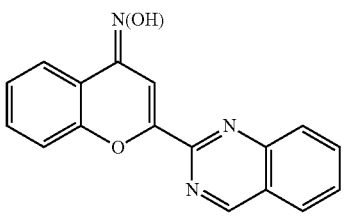

Mp: 239-241° C.

MS (ESI+): 290.1 $[C_{17}H_{11}N_3O_2+H]^+$ (m/z).

1H NMR: (300 MHz) DMSO-$d_6$ δ (ppm): 11.28 (s, 1H), 9.74 (s, 1H), 8.25 (d, J=8.3 Hz, 1H), 8.17 (d, J=7.9 Hz, 1H), 8.11 (td, J=7.6 Hz, J=1.3 Hz, 1H), 7.99 (s, 1H), 7.93 (td, J=7.9 Hz, J=1.5 Hz, 1H), 7.84 (td, J=7.4 Hz, J=1.3 Hz, 1H), 7.55 (td, J=8.4 Hz, J=1.5 Hz, 1H), 7.50 (td, J=8.3 Hz, J=1.5 Hz, 1H), 7.32 (td, J=7.3 Hz, J=1.3 Hz, 1H).

Example 111

6-[(1S,4S)-2-(2-oxa-5-aza-bicyclo[2.2.1]hept-5-yl)-ethoxy]-2-pyrrolo[1,2-c]pyrimidin-3-yl-chromen-4-one oxime, hydrochloride was prepared in 37% overall yield using the method described in example 87, starting from 6-(2-chloro-ethoxy)-2-pyrrolo[1,2-c]pyrimidin-3-yl-chromen-4-one O-tert-butyl oxime (example 87B) and (1S,4S)-2-oxa-5-aza-bicyclo[2.2.1]heptane.

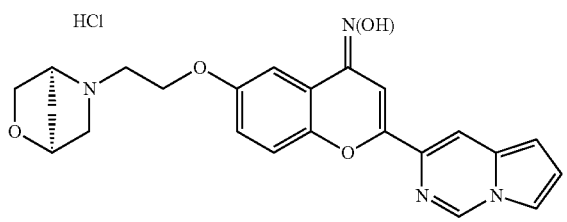

MS (ESI+): 419.1 $[C_{23}H_{22}N_4O_4+H]^+$ (m/z).

1H NMR: (400 MHz) DMSO-$d_6$ δ (ppm): 10.94 (br. s, 1H), 10.41 (br. s, 1H), 9.23 (s, 1H), 8.05 (s, 1H), 7.82 (d, J=2.4 Hz, 1H),), 7.47 (d, J=9.2 Hz, 1H), 7.45 (s, 1H), 7.39 (d, J=3.8 Hz, 1H), 7.21 (dd, J=9.2 Hz, J=4.0 Hz, 1H), 6.99 (dd, J=4.0 Hz, J=3.2 Hz, 1H), 6.74 (d, J=4.0 Hz, 1H), 4.70-4.50 (m, 2H), 4.50-4.30 (m, 2H), 4.30-4.10 (m, 1H), 3.80-3.50 (m, 4H), 3.35-3.05 (m, 1H), 2.10-1.95 (m, 2H).

Example 112

6-[2-(cis-2,6-dimethyl-morpholin-4-yl)-ethoxy]-2-pyrrolo[1,2-c]pyrimidin-3-yl-chromen-4-one oxime, hydrochloride was prepared in 17% overall yield using the method described in example 87, starting from 6-(2-chloro-ethoxy)-2-pyrrolo[1,2-c]pyrimidin-3-yl-chromen-4-one O-tert-butyl oxime (example 87B) and (cis)-2,6-dimethylmorpholine.

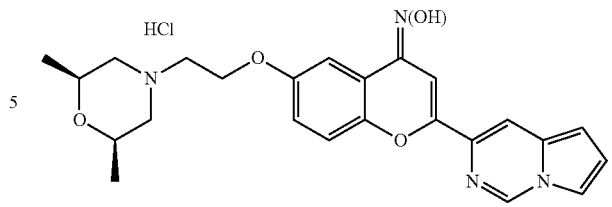

MS (ESI+): 435.1 $[C_{24}H_{26}N_4O_4+H]^+$ (m/z).

1H NMR: (400 MHz) DMSO-$d_6$ δ (ppm): 11.01 (br. s, 2H), 9.23 (s, 1H), 8.06 (s, 1H), 7.83 (s, 1H), 7.47 (d, J=10.0 Hz, 1H), 7.45 (s, 1H), 7.40 (d, J=3.2 Hz, 1H), 7.22 (dd, J=9.2 Hz, J=3.2 Hz, 1H), 6.99 (dd, J=3.4 Hz, J=2.8 Hz, 1H), 6.74 (d, J=3.6 Hz, 1H), 4.47 (m, 2H), 3.98 (m, 2H), 3.54 (m, 4H), 2.78 (m, 2H), 1.16 (s, 3H), 1.14 (s, 3H).

Example 113

2-pyrrolo[1,2-c]pyrimidin-3-yl-6-[2-(4-trifluoromethyl-piperidin-1-yl)-ethoxy]chromen-4-one oxime, hydrochloride was prepared in 34% overall yield using the method described in example 87, starting from 6-(2-chloro-ethoxy)-2-pyrrolo[1,2-c]pyrimidin-3-yl-chromen-4-one O-tert-butyl oxime (example 87B) and 4-trifluoromethyl-piperidine.

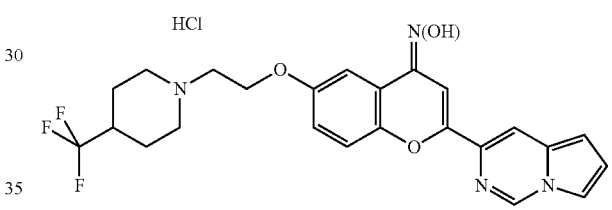

MS (ESI+): 473.1 $[C_{24}H_{23}F_3N_4O_3+H]^+$ (m/z).

1H NMR: (400 MHz) DMSO-$d_6$ δ (ppm): 10.96 (br. s, 1H), 10.19 (br. 5, 1H), 9.23 (s, 1H), 8.05 (s, 1H), 7.83 (s, 1H), 7.46 (d, J=9.2 Hz, 1H), 7.45 (s, 1H), 7.40 (d, J=3.2 Hz, 1H), 7.21 (dd, J=9.2 Hz, J=3.2 Hz, 1H), 6.99 (dd, J=3.4 Hz, J=2.8 Hz, 1H), 6.74 (d, J=3.2 Hz, 1H), 4.44 (m, 2H), 3.70 (d, J=11.2 Hz, 2H), 3.20-3.00 (m, 3H), 2.75-2.50 (m, 2H), 2.10-2.00 (m, 2H), 2.00-1.90 (m, 2H)

Example 114

6-[2-(3,3-difluoro-piperidin-1-yl)-ethoxy]-2-pyrrolo[1,2-c]pyrimidin-3-yl-chromen-4-one oxime, hydrochloride was prepared in 72% overall yield using the method described in example 87, starting from 6-(2-chloro-ethoxy)-2-pyrrolo[1,2-c]pyrimidin-3-yl-chromen-4-one O-tert-butyl oxime (example 87B) and 3,3-difluoro-piperidine.

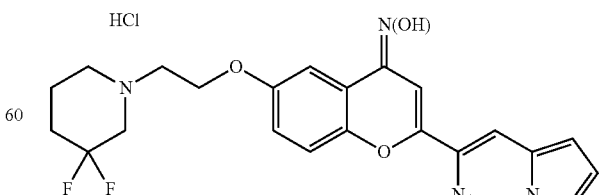

Mp: 190-195° C.

MS (ESI+): 441.3 $[C_{23}H_{22}F_2N_4O_34+H]^+$ (m/z).

1H NMR: (300 MHz) DMSO-d$_6$ δ (ppm): 11.27 (br. s, 2H), 9.23 (s, 1H), 8.07 (s, 1H), 7.82 (s, 1H), 7.47 (d, J=9.0 Hz, 1H), 7.46 (s, 1H), 7.43 (d, J=3.0 Hz, 1H), 7.23 (dd, J=9.0 Hz, J=3.0 Hz, 1H), 6.99 (dd, J=3.2 Hz, J=2.8 Hz, 1H), 6.74 (d, J=3.2 Hz, 1H), 4.52 (m, 2H), 4.15-3.10 (br, multiplets, 4H), 3.62 (m, 2H), 2.35-1.80 (br. multiplets, 4H).

Example 115

4-(hydroxyimino)-2-pyrrolo[1,2-c]pyrimidin-3-yl-4H-chromene-6-carboxylic acid (2-morpholin-4-yl-ethyl)-amide, hydrochloride was prepared in 54% yield using method D (step 2) starting from 4-(tert-Butoxyimino)-2-pyrrolo[1,2-c]pyrimidin-3-yl-4H-chromene-6-carboxylic acid (2-morpholin-4-yl-ethyl)-amide (example 115A). The hydrochloride salt of the title compound was isolated as an orange solid after treatment with a 1.25 M solution of hydrogen chloride in isopropanol.

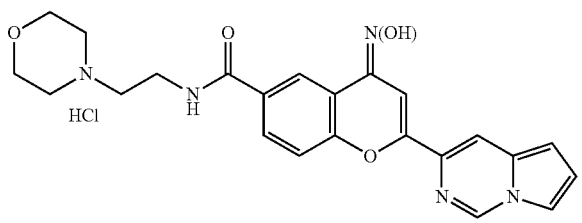

Mp: 230-235° C.
MS (ESI+): 434.3 [C$_{23}$H$_{23}$N$_5$O$_4$+H]$^+$ (m/z).
1H NMR: (300 MHz) DMSO-d$_6$ δ (ppm): 11.11 (br. s, 1H), 10.75 (br. s, 1H), 9.23 (s, 1H), 9.01 (m, 1H), 8.42 (s, 1H), 8.10-8.04 (m, 2H), 7.83 (s, 1H), 7.53 (d, J=8.7 Hz, 1H), 7.49 (s, 1H), 6.99 (dd, J=3.5 Hz, J=3.0 Hz, 1H), 6.76 (d, J=3.8 Hz, 1H), 4.99 (d, J=13.5 Hz, 2H), 3.80 (t, J=12.0 Hz, 2H), 3.69 (m, 2H), 3.55 (d, J=11.8 Hz, 2H), 3.32 (m, 2H), 3.13 (m, 2H).

Example 115A 4-(tert-Butoxyimino)-2-pyrrolo[1,2-c]pyrimidin-3-yl-4H-chromene-6-carboxylic acid (2-morpholin-4-yl-ethyl)-amide

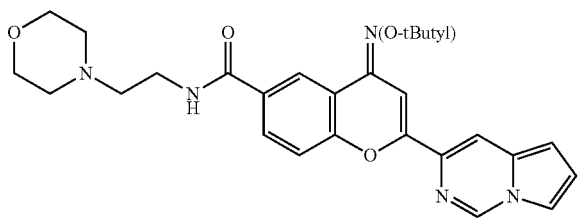

A suspension of 4-(tert-Butoxyimino)-2-pyrrolo[1,2-c]pyrimidin-3-yl-4H-chromene-6-carboxylic acid methyl ester (example 115B) (170 mg, 0.43 mmol) in a mixture of tetrahydrofuran/methanol/water (2.0 ml/0.5 ml/0.5 ml) was treated with lithium hydroxide monohydrate (55 mg, 1.29 mmol) and heated at 60° C. for 2 hours. The solvents were removed and the residue was diluted with water, neutralized to pH 5-6 with a 1N solution of hydrochloric acid and extracted with ethyl acetate. The combined organic extracts were washed with brine, dried over sodium sulfate and concentrated to dryness to give 4-(tert-Butoxyimino)-2-pyrrolo[1,2-c]pyrimidin-3-yl-4H-chromene-6-carboxylic acid (135 mg, 84%) as a green solid. A solution of the previous carboxylic acid, (3-Dimethylamino-propyl)-ethyl-carbodiimide, hydrochloride (90 mg, 0.47 mmol), 1-Hydroxybenzotriazole hydrate (68 mg, 0.50 mmol) and triethylamine (250 µl, 1.80 mmol) in dimethylformamide (6.0 ml) was stirred at 0° C. for 1 hour then 4-(2-aminoethyl)-morpholine (52 µl, 0.40 mmol) was added. The mixture was stirred at room temperature for 18 hours. The volatiles were removed under vacuum and the residue taken into ethyl acetate, washed several times with a saturated solution of sodium hydrogenocarbonate, brine, dried over sodium sulfate and concentrated to dryness. The residue was purified by silica gel flash chromatography (gradient ethyl acetate/methanol 0-8%) to yield the title compound as a yellow solid (137 mg, 78%).
1H NMR: (300 MHz) CHCl$_3$-d$_1$ δ (ppm): 8.79 (s, 1H), 8.41 (s, 1H), 7.97 (dd, J=8.7 Hz, J=2.0 Hz, 1H), 7.92 (s, 1H), 7.53 (s, 1H), 7.46 (d, J=2.6 Hz, 1H), 7.32 (d, J=8.6 Hz, 1H), 6.94 (dd, J=4.0 Hz, J=3.0 Hz, 1H), 6.65 (d, J=3.8 Hz, 1H), 3.82 (m, 4H), 3.63 (m, 2.73 (m, 2H), 2.64 (m, 4H), 1.43 (s, 9H).

Example 115B 4-(tert-Butoxyimino)-2-pyrrolo[1,2-c]pyrimidin-3-yl-4H-chromene-6-carboxylic acid methyl ester

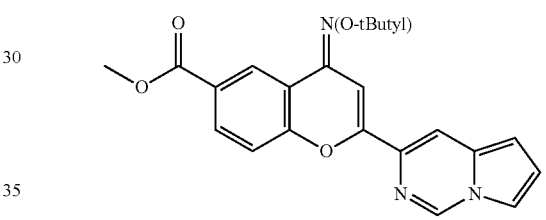

In a 75 ml sealed tube were charged 6-bromo-2-pyrrolo[1,2-c]pyrimidin-3-yl-chromen-4-one O-tert-butyl-oxime (tert-butyl protected oxime of example 66) (250 mg, 0.60 mmol), palladium acetate (14 mg, 0.06 mmol), 1,1'-bis(diphenylphosphino)ferrocene (68 mg, 0.12 mmol), triethylamine (170 µl, 1.22 mmol), methanol (125 µl, 3.03 mmol) and dimethylformamide (5 ml). The suspension was degazed with carbone monoxide for 15 minutes. The tube was sealed and heated to 100° C. for 18 hours. The mixture was degazed with argon to remove the excess of carbone monoxide and then diluted with ethyl acetate, washed with a saturated solution of ammonium chloride, water, brine, dried over sodium sulfate and concentrated to dryness. The residue was purified by silica gel flash chromatography (gradient cyclohexane/ethyl acetate 0-80%) to yield the title compound as a yellow solid (172 mg, 72%).
1H NMR: (300 MHz) CHCl$_3$-d$_1$ δ (ppm): 8.80 (s, 1H), 8.71 (d, J=2.1 Hz, 1H), 8.05 (dd, J=8.7 Hz, J=2.0 Hz, 1H), 7.90 (s, 1H), 7.54 (s, 1H), 7.45 (d, J=2.1 Hz, 1H), 7.28 (d, J=8.7 Hz, 1H), 6.93 (dd, J=4.0 Hz, J=3.0 Hz, 1H), 6.65 (d, J=3.8 Hz, 1H), 3.95 (s, 3H), 1.43 (s, 9H).

Example 116

6-(2-[1,4']bipiperidinyl-1'-yl-ethoxy)-2-pyrrolo[1,2-c]pyrimidin-3-yl-chromen-4-one oxime, dihydrochloride was prepared in 34% overall yield using the method described in example 87, starting from 6-(2-chloro-ethoxy)-2-pyrrolo[1,2-c]pyrimidin-3-yl-chromen-4-one O-tert-butyl oxime (example 87B) and N-(4-piperidino)piperidine.

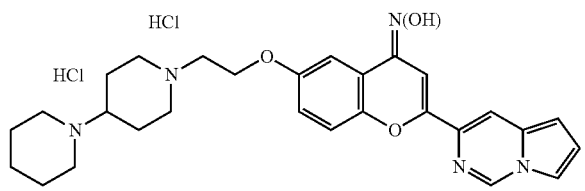

Mp: >235° C. dec.

MS (ESI+): 488.4 [$C_{28}H_{33}N_5O_3$+H]$^+$ (m/z).

1H NMR: (300 MHz) DMSO-$d_6$ δ (ppm): 10.99 (br. s, 1H), 10.74 (br. s, 1H), 9.23 (s, 1H), 8.05 (s, 1H), 7.82 (d, J=2.4 Hz, 1H), 7.46 (d, J=9.0 Hz, 1H), 7.45 (s, 1H), 7.39 (d, J=3.0 Hz, 1H), 7.21 (dd, J=9.0 Hz, J=3.0 Hz, 1H), 6.99 (dd, J=3.2 Hz, J=2.8 Hz, 1H), 6.74 (d, J=3.7 Hz, 1H), 4.46 (m, 2H), 3.8-3.45 (multiplets, 4H), 3.45-3.25 (m, 3.14 (m, 2H), 2.92 (m, 2H), 2.45-2.10 (multiplets, 4H), 2.00-1.60 (multiplets, 5H), 1.50-1.30 (m, 1H).

Example 117

6-(2-[1,4]oxazepan-4-yl-ethoxy)-2-pyrrolo[1,2-c]pyrimidin-3-yl-chromen-4-one oxime, hydrochloride was prepared in 45% overall yield using the method described in example 87, starting from 6-(2-chloro-ethoxy)-2-pyrrolo[1,2-c]pyrimidin-3-yl-chromen-4-one O-tert-butyl oxime (example 87B) and [1,4]oxazepane.

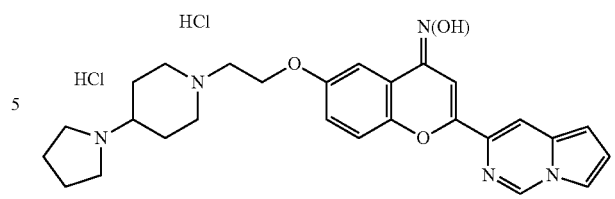

Mp: >210° C. dec.

MS (ESI+): 474.3 [$C_{27}H_{31}N_5O_3$+H]$^+$ (m/z).

1H NMR: (300 MHz) DMSO-$d_6$ δ (ppm): 11.25-10.75 (br. multiplets, 2H), 9.23 (s, 1H), 8.05 (s, 1H), 7.82 (d, J=2.3 Hz, 1H), 7.47 (d, J=9.0 Hz, 1H), 7.45 (s, 1H), 7.40 (d, J=3.0 Hz, 1H), 7.21 (dd, J=9.0 Hz, J=3.0 Hz, 1H), 6.99 (dd, J=3.3 Hz, J=2.8 Hz, 1H), 6.74 (d, J=3.7 Hz, 1H), 4.46 (m, 2H), 3.72 (m, 2H), 3.65-3.42 (multiplets, 4H), 3.40-3.22 (m, 1H), 3.20-2.95 (m, 4H), 2.40-2.05 (multiplets, 4H), 2.05-1.80 (multiplets, 4H).

Example 119

6-[2-(3,3-difluoro-pyrrolidin-1-yl)-ethoxy]-2-pyrrolo[1,2-c]pyrimidin-3-yl-chromen-4-one oxime, hydrochloride was prepared in 42% overall yield using the method described in example 87, starting from 6-(2-chloro-ethoxy)-2-pyrrolo[1,2-c]pyrimidin-3-yl-chromen-4-one O-tert-butyl oxime (example 87B) and 3,3-difluoro-pyrrolidine.

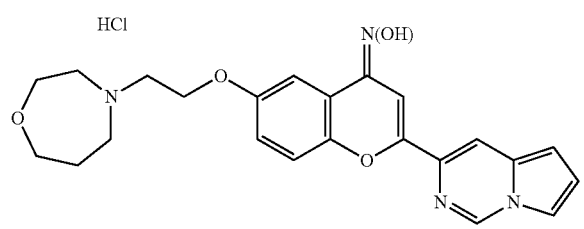

Mp: 240° C. dec.

MS (ESI+): 421.3 [$C_{23}H_{24}N_4O_4$+H]$^+$ (m/z).

1H NMR: (300 MHz) DMSO-$d_6$ δ (ppm): 10.87 (br. s, 2H), 9.23 (s, 1H), 8.06 (s, 1H), 7.82 (d, J=2.0 Hz, 1H), 7.46 (d, J=9.0 Hz, 1H), 7.45 (s, 1H), 7.40 (d, J=3.0 Hz, 1H), 7.21 (dd, J=9.0 Hz, J=3.0 Hz, 1H), 6.99 (dd, J=3.2 Hz, J=2.8 Hz, 1H), 6.74 (d, J=3.8 Hz, 1H), 4.47 (m, 2H), 3.88 (m, 2H), 3.85-3.68 (m, 2H), 3.65-3.47 (m, 4H), 3.45-3.25 (m, 2H), 2.37-2.17 (m, 1H), 2.12-1.95 (m, 1H).

Example 118

6-[2-(4-pyrrolidin-1-yl-piperidin-1-yl)-ethoxy]-2-pyrrolo[1,2-c]pyrimidin-3-yl-chromen-4-one oxime, dihydrochloride was prepared in 90% overall yield using the method described in example 87, starting from 6-(2-chloro-ethoxy)-2-pyrrolo[1,2-c]pyrimidin-3-yl-chromen-4-one O-tert-butyl oxime (example 87B) and 4-(1-pyrrolidinyl)piperidine.

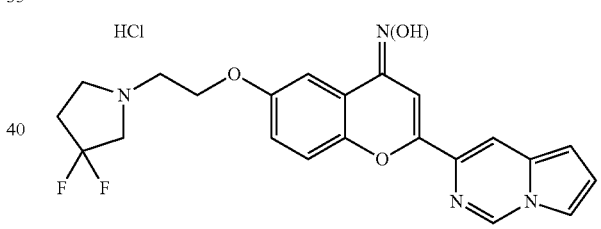

Mp: >230° C. dec.

MS (ESI+): 427.3 [$C_{22}H_{20}F_2N_4O_3$+H]$^+$ (m/z).

1H NMR: (300 MHz) DMSO-$d_6$ δ (ppm): 11.96 (br. s, 1H), 11.02 (br. s, 1H), 9.23 (s, 1H), 8.06 (s, 1H), 7.82 (s, 1H), 7.47 (d, J=9.0 Hz, 1H), 7.45 (s, 1H), 7.40 (d, J=3.0 Hz, 1H), 7.24 (dd, J=9.0 Hz, J=2.8 Hz, 1H), 6.99 (dd, J=3.2 Hz, J=3.0 Hz, 1H), 6.74 (d, J=3.4 Hz, 1H), 4.43 (m, 2H), 4.30-3.40 (m, 4H), 3.72 (m, 2H), 2.80-2.40 (m, 2H).

Example 120

7-[3-(3-dimethylamino-propoxy)-phenylethynyl]-2-pyrrolo[1,2-c]pyrimidin-3-yl-chromen-4-one oxime was prepared in 12% overall yield using the methods described in method D (step 1) and in example 86, starting from 7-[3-(3-dimethylamino-propoxy)-phenylethynyl]-2-pyrrolo[1,2-c]pyrimidin-3-yl-chromen-4-one (example 120A). The title compound was isolated as a yellow.

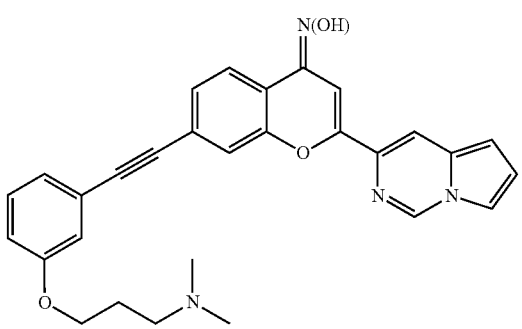

MS (ESI+): 479.1 [$C_{29}H_{26}N_4O_3$+H]$^+$ (m/z).

1H NMR: (400 MHz) DMSO-$d_6$ δ (ppm): 9.23 (s, 1H), 8.08 (s, 1H), 7.90 (d, J=8.0 Hz, 1H), 7.84 (s, 1H), 7.66 (d, J=1.6 Hz, 1H), 7.47 (s, 1H), 7.43 (dd, J=10.4 Hz, J=1.6 Hz, 1H), 7.36 (t, J=7.6 Hz, 1H), 7.18-7.12 (m, 2H), 7.05-7.00 (m, 2H), 6.75 (d, J=4 Hz, 1H), 4.06 (t, J=6.4 Hz, 2H), 2.36 (t, J=6.4 Hz, 2H), 2.17 (s, 6H), 1.88 (m, 2H).

Example 120A

7-[3-(3-dimethylamino-propoxy)-phenylethynyl]-2-pyrrolo[1,2-c]pyrimidin-3-yl-chromen-4-one was prepared in 52% yield using the method described in example 42, starting from 7-(3-hydroxy-phenylethynyl)-2-pyrrolo[1,2-c]pyrimidin-3-yl-chromen-4-one (example 120B) and (3-Chloro-propyl)-dimethyl-amine hydrochloride.

1H NMR: (300 MHz) CHCl$_3$-$d_1$ δ (ppm): 8.84 (t, J=1.3 Hz, 1H), 8.20 (d, J=8.5 Hz, 1H), 8.13 (d, J=1.2 Hz, 1H), 7.73 (d, J=0.9 Hz, 1H), 7.55-7.50 (m, 2H), 7.33 (s, 1H), 7.28 (d, J=12.2 Hz, 1H), 7.17 (td, J=7.7 Hz, J=1.1 Hz, 1H), 7.10 (dd, J=2.4 Hz, J=1.3 Hz, 1H), 6.99 (dd, J=3.7 Hz, J=2.6 Hz, 1H), 6.94 (ddd, J=8.3 Hz, J=2.6 Hz, J=1.0 Hz, 1H), 6.77 (d, J=3.8 Hz, 1H), 4.09 (t, J=6.2 Hz, 2H), 2.72 (t, J=6.9 Hz, 2H), 2.46 (s, 6H), 2.13 (quint, J=6.6 Hz, 2H).

Example 120B 7-(3-hydroxy-phenylethynyl)-2-pyrrolo[1,2-c]pyrimidin-3-yl-chromen-4-one was prepared in 71% yield using the method described in example 23A, starting from 7-bromo-2-pyrrolo[1,2-c]pyrimidin-3-yl-chromen-4-one (example 120C) and 3-hydroxyphenylacetylene. The title compound was isolated as a brown powder.

1H NMR: (300 MHz) DMSO-$d_6$ δ (ppm): 9.87 (s, 1H), 9.28 (s, 1H), 8.40 (s, 1H), 8.04 (d, J=8.3 Hz, 1H), 8.00 (d, J=1.3 Hz, 1H), 7.90 (d, J=2.5 Hz, 1H), 7.60 (dd, J=8.3 Hz, J=1.5 Hz, 1H), 7.27 (t, J=7.9 Hz, 1H), 7.10-6.98 (m, 4H), 6.93-6.85 (m, 2H).

Example 120C 7-bromo-2-pyrrolo[1,2-c]pyrimidin-3-yl-chromen-4-one was prepared in 89% yield using method A, starting from 4'-bromo-2'-hydroxyacetophenone and pyrrolo[1,2-c]pyrimidin-2-carboxylic acid ethyl ester. The title compound was isolated as a green powder.

1H NMR: (300 MHz) DMSO-$d_6$ δ (ppm): 9.28 (s, 1H), 8.40 (s, 1H), 8.16 (d, J=1.9 Hz, 1H), 7.96 (d, J=8.5 Hz, 1H), 7.91 (d, J=2.4 Hz, 1H), 7.68 (dd, J=8.4 Hz, J=1.7 Hz, 1H), 7.08-7.02 (m, 2H), 6.88 (d, J=3.8 Hz, 1H).

Example 121

6-[2-(4-ethyl-piperazin-1-yl-ethoxy]-2-pyrrolo[1,2-c]pyrimidin-3-yl-chromen-4-one oxime, dihydrochloride was prepared in 12% overall yield using the method described in example 87, starting from 6-(2-chloro-ethoxy)-2-pyrrolo[1,2-c]pyrimidin-3-yl-chromen-4-one O-tertbutyl oxime (example 87B) and 4-ethyl-piperazine.

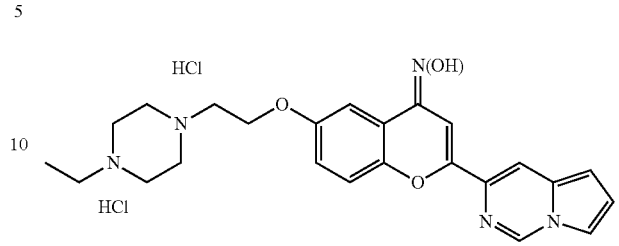

Mp: >240° C. dec.

MS (ESI+): 434.2 [$C_{24}H_{27}N_6O_3$+H]$^+$ (m/z).

1H NMR: (300 MHz) DMSO-$d_6$ δ (ppm): 10.95 (br. s, 1H), 9.22 (s, 1H), 8.04 (s, 1H), 7.81 (s, 1H), 7.46 (d, J=8.7 Hz, 1H), 7.44 (s, 1H), 7.38 (d, J=2.8 Hz, 1H), 7.20 (d, J=9.0 Hz, 1H), 6.99 (dd, J=3.2 Hz, J=3.0 Hz, 1H), 6.74 (d, J=3.7 Hz, 1H), 4.41 (m, 2H), 4.00-3.00 (multiplets, 12H), 1.26 (t, J=6.9 Hz, 3H).

Example 122

6-(2-amino-ethoxy)-2-pyrrolo[1,2-c]pyrimidin-3-yl-chromen-4-one oxime, hydrochloride was prepared in 26% yield using the method described in example 85, starting from 6-hydroxy-2-pyrrolo[1,2-c]pyrimidin-3-yl-chromen-4-one O-tert-butyl oxime (example 81A) and 2-(Boc-amino)ethyl bromide.

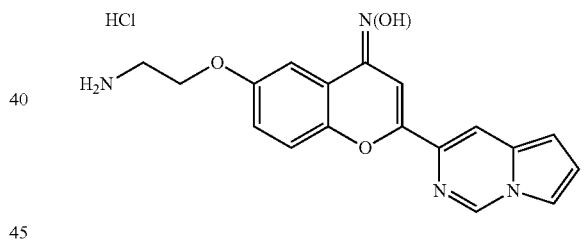

Mp: >270° C. dec.

MS (ESI+): 337.2 [$C_{18}H_{16}N_4O_3$+H]$^+$ (m/z).

1H NMR: (300 MHz) DMSO-$d_6$ δ (ppm): 10.99 (br. s, 1H), 9.22 (s, 1H), 8.15 (br. s, 3H), 8.05 (s, 1H), 7.82 (d, J=2.6 Hz, 1H), 7.46 (d, J=8.7 Hz, 1H), 7.45 (s, 1H), 7.39 (d, J=3.0 Hz, 1H), 7.18 (dd, J=9.0 Hz, d, J=3.0 Hz, 1H), 6.99 (dd, J=3.7 Hz, J=2.9 Hz, 1H), 6.74 (d, J=3.7 Hz, 1H), 4.22 (m, 2H), 3.24 (m, 2H).

Example 123

6-(2-Morpholin-4-yl-ethoxy)-2-(8aH-pyrrolo[1,2-a]pyrazin-3-yl)-chromen-4-one oxime, hydrochloride was prepared in 66% yield using method D (step 2), starting from 6-(2-Morpholin-4-yl-ethoxy)-2-pyrrolo[1,2-a]pyrazin-3-yl-chromen-4-one O-tert-butyl-oxime (example 123A). The hydrochloride salt of the title compound was isolated as a yellow solid after treatment with a 1.25 M solution of hydrogen chloride in isopropanol.

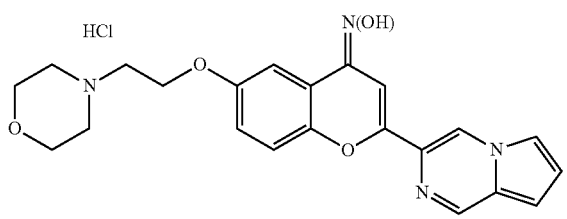

Mp: >250° C. dec.

MS (ESI+): 407.2 $[C_{22}H_{22}N_4O_4+H]^+$ (m/z).

1H NMR: (300 MHz) DMSO-$d_6$ δ (ppm): 11.33 (br. s, 1H), 10.95 (s, 1H), 8.95 (d, J=7.1 Hz, 2H), 7.92 (s, 1H), 7.41 (m, 3H), 7.21 (dd, J=9.0 Hz, J=3.0, 1H), 6.97 (m, 2H), 4.48 (br. s, 2H), 3.89 (m, 4H), 3.52 (m, 4H), 3.19 (br. s, 2H).

Example 123A 6-(2-Morpholin-4-yl-ethoxy)-2-pyrrolo[1,2-a]pyrazin-3-yl-chromen-4-one O-tert-butyl-oxime was prepared in 68% yield using the procedure described in example 85A, starting from 6-Hydroxy-2-pyrrolo[1,2-a]pyrazin-3-yl-chromen-4-one O-tert-butyl-oxime (example 123B) and 4-(2-chloroethyl) morpholine hydrochloride. The title compound was isolated as a beige solid.

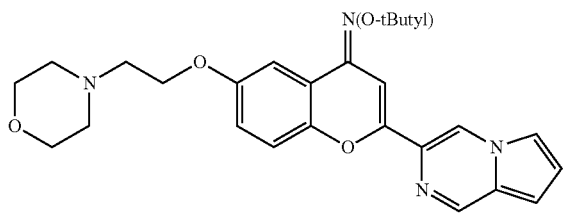

1H NMR: (300 MHz) CHCl$_3$-$d_1$ δ (ppm): 8.82 (s, 1H), 8.45 (s, 1H), 7.51 (m, 3H), 7.16 (d, J=9.0 Hz, 1H), 6.98 (dd, J=9.0 Hz, J=3.0 Hz, 1H), 6.91 (dd, J=4.1 Hz, J=2.6 Hz, 1H), 6.83 (d, J=4.1 Hz, 1H), 4.17 (t, J=5.6 Hz, 2H), 3.75 (t, J=4.7 Hz, 4H), 2.83 (t, J=5.6 Hz, 2H), 2.60 (t, J=4.7 Hz, 4H), 1.41 (s, 9H).

Example 123B

6-Hydroxy-2-pyrrolo[1,2-a]pyrazin-3-yl-chromen-4-one O-tert-butyl-oxime was prepared in 85% yield using the procedure described in example 18A, starting from 6-Bromo-2-pyrrolo[1,2-a]pyrazin-3-yl-chromen-4-one O-tert-butyl-oxime (example 123C). The title compound was isolated as a brown solid.

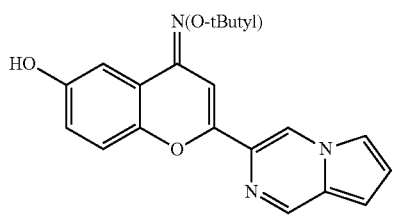

1H NMR: (300 MHz) DMSO-$d_6$ δ (ppm): 8.99 (d, J=2.2 Hz, 1H), 7.97 (s, 1H), 7.33 (s, 1H), 7.32 (d, J=3.0 Hz, 1H), 7.26 (d, J=8.8 Hz, 1H), 7.03 (m, 2H), 6.96 (dd, J=9.0 Hz, J=3.0, 1H), 5.03 (br s, 1H), 1.36 (s, 9H).

Example 123C

6-Bromo-2-pyrrolo[1,2-a]pyrazin-3-yl-chromen-4-one O-tert-butyl-oxime was prepared in 65% overall yield using methods A and D (step 1), starting from 5'-bromo-2'-hydroxy-acetophenone and Pyrrolo[1,2-a]pyrazine-3-carboxylic acid methyl ester (example 91A).

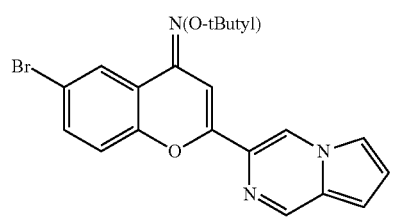

1H NMR: (300 MHz) CHCl$_3$-$d_1$ δ (ppm): 8.83 (s, 1H), 8.44 (s, 1H), 8.16 (d, J=2.4 Hz, 1H), 7.53-7.52 (m, 2H), 7.47 (dd, J=8.8 Hz, J=2.4, 1H), 7.21 (dd, J=9.0 Hz, J=3.0, 1H), 7.12 (d, J=8.6 Hz, 1H), 6.93 (dd, J=4.1 Hz, J=2.6, 1H), 6.85 (dt, J=3.9 Hz, J=1.1 Hz, 1H), 1.41 (s, 9H).

Example 124

6-[2-(4,4-Difluoro-piperidin-1-yl)-ethoxy]-2-pyrrolo[1,2-a]pyrazin-3-yl-chromen-4-one oxime, hydrochloride was prepared in 50% overall yield using the method described in example 123, starting from 6-Hydroxy-2-pyrrolo[1,2-a]pyrazin-3-yl-chromen-4-one O-tert-butyl-oxime (example 123B) and 1-(2-Chloro-ethyl)-4,4-difluoro-piperidine hydrochloride.

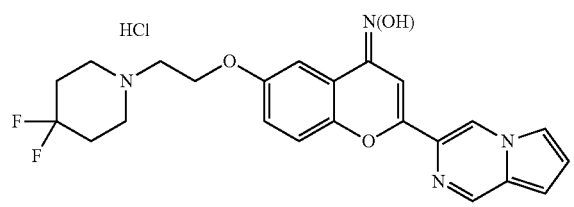

Mp: 225° C.-230° C.

MS (ESI+): 441.3 $[C_{23}H_{22}F_2N_4O_3+H]^+$ (m/z).

1H NMR: (300 MHz) DMSO-$d_6$ δ (ppm): 11.21 (br. s, 1H), 10.98 (br. s, 1H), 8.97 (d, J=7.1 Hz, 2H), 7.94 (s, 1H), 7.46 (s, 1H), 7.41 (m, 2H), 7.23 (dd, J=9.0 Hz, J=3.0, 1H), 7.00 (m, 2H), 4.48 (t, J=4.35 Hz, 2H), 3.67 (m, 4H), 3.31 (br. s, 2H), 2.39 (m, 4H).

Example 125

6-(2-Imidazol-1-yl-ethoxy)-2-pyrrolo[1,2-a]pyrazin-3-yl-chromen-4-one oxime, hydrochloride was prepared in 13% overall yield using the method described in example 123, starting from 6-Hydroxy-2-pyrrolo[1,2-a]pyrazin-3-yl-chromen-4-one O-tert-butyl-oxime (example 123B) and 1-(2-Chloro-ethyl)-1H-imidazole hydrochloride.

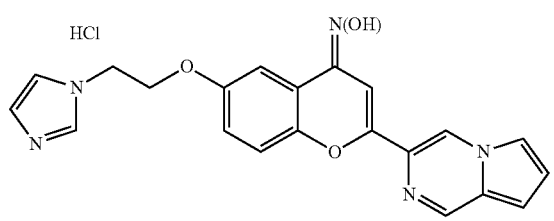

Mp: 238° C.-240° C.
MS (ESI+): 388.2 $[C_{21}H_{17}N_6O_3+H]^+$ (m/z).
1H NMR: (300 MHz) DMSO-$d_6$ δ (ppm): 14.68 (br. s, 1H), 10.94 (br. s, 1H), 9.25 (s, 1H), 8.95 (d, J=7.1 Hz, 2H), 7.93 (s, 1H), 7.87 (s, 1H), 7.71 (s, 1H), 7.44 (s, 1H), 7.36 (m, 2H), 7.14 (dd, J=9.0 Hz, J=3.0, 1H), 7.00 (m, 2H), 4.65 (br. s, 2H), 4.45 (s, 2H).

Example 126

6-[2-(4-Fluoro-phenyl)-ethoxy]-2-pyrrolo[1,2-a]pyrazin-3-yl-chromen-4-one oxime was prepared in 27% overall yield using the method described in example 123, starting from 6-Hydroxy-2-pyrrolo[1,2-a]pyrazin-3-yl-chromen-4-one O-tert-butyl-oxime (example 123B) and 1-(2-Chloro-ethyl)-4-fluorophenyl.

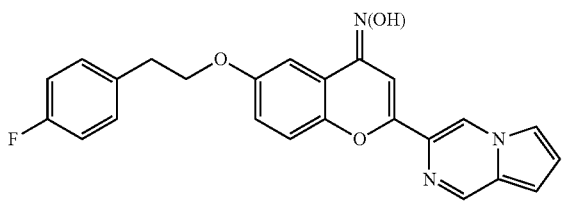

Mp: 248° C.-250° C.
MS (ESI+): 416.3 $[C_{24}H_{18}FN_3O_3+H]^+$ (m/z).
1H NMR: (300 MHz) DMSO-$d_6$ δ (ppm): 10.94 (br. s, 1H), 8.97 (d, J=7.1 Hz, 2H), 7.94 (s, 1H), 7.44 (s, 1H), 7.36 (m, 4H), 7.14 (m, 3H), 7.00 (m, 2H), 4.22 (t, J=6.7 Hz, 2H), 3.05 (t, J=6.7 Hz, 2H).

Example 127

6-(2-Morpholin-4-yl-ethoxy)-2-thieno[3,2-c]pyridin-6-yl-chromen-4-one oxime, hydrochloride was prepared in 39% yield using method D (step 2), staffing from 6-(2-Morpholin-4-yl-ethoxy)-2-thieno[3,2-c]pyridin-6-yl-chromen-4-one O-tert-butyl-oxime (example 127A). The hydrochloride salt of the title compound was isolated as a yellow solid after treatment with a 1.25 M solution of hydrogen chloride in isopropanol.

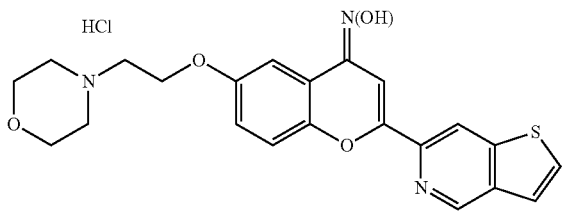

Mp: >230° C. dec.
MS (ESI+): 424.3 $[C_{22}H_{21}N_3O_4S+H]^+$ (m/z).

1H NMR: (300 MHz) DMSO-$d_6$ δ (ppm): 11.50 (br. s, 1H), 11.13 (br. s, 1H), 9.27 (s, 1H), 8.79 (s, 1H), 8.06 (d, J=5.3 Hz, 1H), 7.74-7.69 (m, 2H), 7.51 (d, J=9.0 Hz, 1H), 7.43 (s, 1H), 7.23 (d, J=9.0 Hz, 1H), 4.52-4.49 (m, 2H), 3.99-3.86 (m, 4H), 3.58-3.49 (m, 4H), 3.23-3.20 (m, 2H).

Example 127A 6-(2-Morpholin-4-yl-ethoxy)-2-thieno[3,2-c]pyridin-6-yl-chromen-4-one O-tert-butyl-oxime was prepared in 62% yield using the procedure described in example 85A, starting from 6-Hydroxy-2-thieno[3,2-c]pyridin-6-yl-chromen-4-one O-tert-butyl-oxime (example 127B) and 4-(2-chloroethyl)morpholine hydrochloride. The title compound was isolated as a yellow solid.

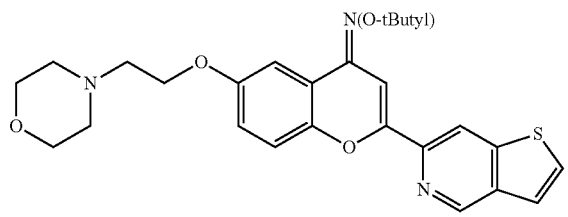

1H NMR: (300 MHz) CHCl$_3$-$d_1$ δ (ppm): 9.15 (s, 1H), 8.45 (s, 1H), 7.71 (s, 1H), 7.58 (d, J=5.4 Hz, 1H), 7.54-7.48 (m, 2H), 7.23 (m, 1H), 7.01 (dd, J=9.0 Hz, J=3.0 Hz, 1H), 4.18 (t, J=5.6 Hz, 2H), 3.76 (t, J=4.5 Hz, 4H), 2.84 (t, J=5.6 Hz, 2H), 2.61 (t, J=4.7 Hz, 4H), 1.42 (s, 9H).

Example 127B

6-Hydroxy-2-thieno[3,2-c]pyridin-6-yl-chromen-4-one O-tert-butyl-oxime was prepared in 99% yield using the procedure described in example 18A, starting from 6-Bromo-2-thieno[3,2-c]pyridin-6-yl-chromen-4-one O-tert-butyl-oxime (example 127C). The title compound was isolated as a yellow solid.

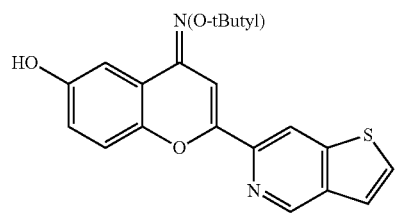

1H NMR: (300 MHz) CHCl$_3$-$d_1$ δ (ppm): 9.15 (s, 1H), 8.45 (s, 1H), 7.69 (s, 1H), 7.58 (d, J=5.4 Hz, 1H), 7.50-7.48 (m, 2H), 7.20 (d, J=9.0 Hz, 1H), 6.92 (dd, J=9.0 Hz, J=3.2 Hz, 1H), 5.42 (s, 1H), 1.40 (s, 9H).

Example 127C

6-Bromo-2-thieno[3,2-c]pyridin-6-yl-chromen-4-one O-tert-butyl-oxime was prepared in 64% overall yield using methods A and D (step 1), starting from 5'-bromo-2'-hydroxy-acetophenone and Thieno[3,2-c]pyridin-6-carboxylic acid methyl ester.

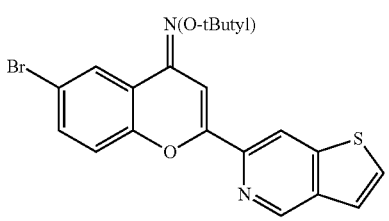

1H NMR: (300 MHz) CHCl₃-d₁ δ (ppm): 9.16 (s, 1H), 8.43 (s, 1H), 8.17 (d, J=2.4 Hz, 1H), 7.73 (s, 1H), 7.60 (d, J=5.4 Hz, 1H), 7.51-7.46 (m, 2H), 7.18 (d, J=8.6 Hz, 1H), 1.42 (s, 9H).

Example 128

6-[2-(4,4-Difluoro-piperidin-1-yl)-ethoxy]-2-thieno[3,2-c]pyridin-6-yl-chromen-4-one oxime, hydrochloride was prepared in 28% overall yield using the method described in example 127, starting from 6-Hydroxy-2-thieno[3,2-c]pyridin-6-yl-chromen-4-one O-tert-butyl-oxime (example 127B) and 1-(2-Chloro-ethyl)-4,4-difluoro-piperidine hydrochloride.

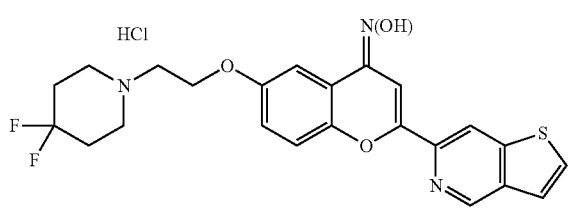

Mp: 225° C.-230° C.
MS (ESI+): 458.3 [C₂₃H₂₁F₂N₃O₃S+H]⁺ (m/z).
1H NMR: (300 MHz) DMSO-d₆ δ (ppm): 11.34 (br, s, 1H), 11.06 (br, s, 1H), 9.26 (s, 1H), 8.77 (s, 1H), 8.04 (d, J=5.3 Hz, 1H), 7.72 (d, J=5.4, 1H), 7.69 (s, 1H), 7.51 (d, J=9.0 Hz, 1H), 7.42 (d, J=2.9 Hz, 1H), 7.23 (dd, J=9.0 Hz, J=2.9 Hz, 1H), 4.50 (s, 2H), 3.70-3.64 (m, 4H), 3.31 (s, 2H), 2.43 (m, 4H).

Example 129

6-(2-imidazol-1-yl-ethoxy)2-thieno[3,2-c]pyridin-6-yl-chromen-4-one oxime, hydrochloride was prepared in 25% overall yield using the method described in example 127, starting from 6-Hydroxy-2-thieno[3,2-c]pyridin-6-yl-chromen-4-one O-tert-butyl-oxime (example 127B) and 1-(2-Chloro-ethyl)-1H-imidazole hydrochloride.

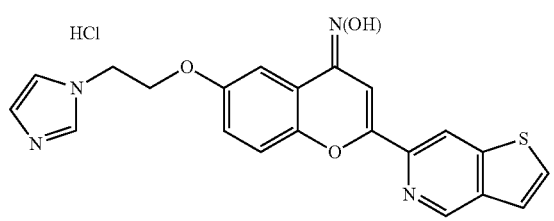

Mp: 218° C.-220° C.
MS (ESI+): 405.2 [C₂₁H₁₆N₄O₃S+H]⁺ (m/z).
1H NMR: (300 MHz) DMSO-d₆ δ (ppm): 11.10 (br. s, 1H), 9.26 (s, 2H), 8.78 (s, 1H), 8.06 (d, J=5.3 Hz, 1H), 7.87 (s, 1H), 7.74-7.68 (m, 3H), 7.48 (d, J=9.0 Hz, 1H), 7.38 (d, J=2.9 Hz, 1H), 7.18 (dd, J=9.0 Hz, J=2.9 Hz, 1H), 4.65 (t, J=4.6 Hz, 2H), 4.46 (t, J=4.6 Hz, 2H).

Example 130

6-[2-(4-Fluoro-phenyl)-ethoxy]-2-thieno[3,2-c]pyridin-6-yl-chromen-4-one oxime was prepared in 18% overall yield using the method described in example 127, starting from 6-Hydroxy-2-thieno[3,2-c]pyridin-6-yl-chromen-4-one O-tert-butyl-oxime (example 127B) and 1-(2-Chloro-ethyl)-4-fluorophenyl hydrochloride.

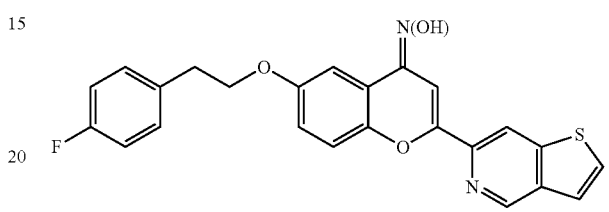

Mp: 228° C.-234° C.
MS (ESI+): 433.3 [C₂₄H₁₇FN₂O₃S+H]⁺ (m/z).
1H NMR: (300 MHz) DMSO-d₆ δ (ppm): 11.10 (br. s, 1H), 9.28 (s, 1H), 8.78 (s, 1H), 8.05 (d, J=5.3 Hz, 1H), 7.72 (d, J=5.4 Hz, 1H), 7.68 (s, 1H), 7.46-7.34 (m, 4H), 7.17-7.11 (m, 3H), 4.23 (t, J=6.6 Hz, 2H), 3.05 (t, J=6.6 Hz, 2H).

Example 131

6-[2-(3,3-Difluoro-piperidin-1-yl)-ethoxy]-2-thieno[3,2-c]pyridin-6-yl-chromen-4-one oxime, hydrochloride was prepared in 67% overall yield using the method described in example 127, starting from 6-Hydroxy-2-thieno[3,2-c]pyridin-6-yl-chromen-4-one O-tert-butyl-oxime (example 127B) and 1-(2-Chloro-ethyl)-3,3-difluoro-piperidine hydrochloride.

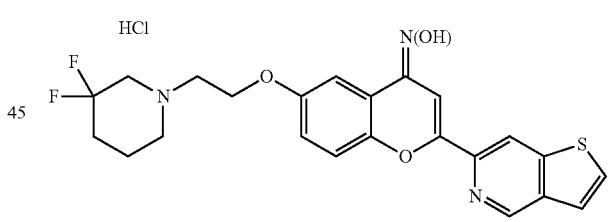

Mp: >250° C. dec.
MS (ESI+): 548.2 [C₂₃H₂₁F₂N₃O₃S+H]⁺ (m/z).
1H NMR: (300 MHz) DMSO-d₆ δ (ppm): 11.04 (br. s, 1H), 9.25 (s, 1H), 8.76 (s, 1H), 8.03 (d, J=5.4 Hz, 1H), 7.72 (d, J=5.4 Hz, 1H), 7.68 (s, 1H), 7.50 (d, J=9.1 Hz, 1H), 7.40 (d, J=3.0 Hz, 1H), 7.22 (dd, J=9.1 Hz, J=3.1 Hz, 1H), 4.49 (br. s, 2H), 3.61 (m, 6H), 2.16-1.99 (m, 4H).

Example 132

6-[2-(2,6-Dimethyl-morpholin-4-yl)-ethoxy]-2-thieno[3,2-c]pyridin-6-yl-chromen-4-one oxime, hydrochloride was prepared in 48% overall yield using the method described in example 127, starting from 6-Hydroxy-2-thieno[3,2-c]pyridin-6-yl-chromen-4-one O-tert-butyl-oxime (example 127B) and 4-(2-Chloro-ethyl)-2,6-dimethyl-morpholine hydrochloride (JACS 1949, 500-505; US2006/14948).

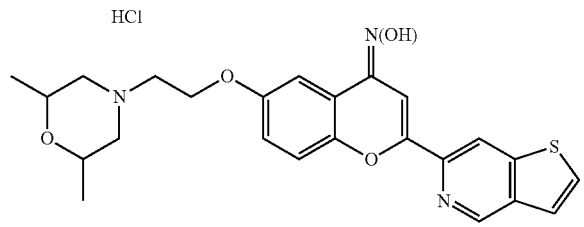

Mp: 222° C.-225° C.

MS (ESI+): 452.2 [C$_{24}$H$_{25}$N$_3$O$_4$S+H]$^+$ (m/z).

1H NMR: (300 MHz) DMSO-d$_6$ δ (ppm): 11.33 (br. s, 1H), 11.08 (br. s, 1H), 9.27 (s, 1H), 8.78 (s, 1H), 8.06 (d, J=5.4 Hz, 1H), 7.73 (d, J=5.4 Hz, 1H), 7.70 (s, 1H), 7.51 (d, J=9.1 Hz, 1H), 7.42 (d, J=3.0 Hz, 1H), 7.24 (dd, J=9.1 Hz, J=3.1 Hz, 1H), 4.02 (t, 6.4 Hz, 2H), 3.56-3.52 (m, 4H), 2.82-2.73 (m, 2H).

Example 133

6-[2-(3,3-Difluoro-pyrrolidin-1-yl)-ethoxy]-2-thieno[3,2-c]pyridin-6-yl-chromen-4-one oxime, hydrochloride was prepared in 62% overall yield using the method described in example 127, starting from 6-Hydroxy-2-thieno[3,2-c]pyridin-6-yl-chromen-4-one O-tert-butyl-oxime (example 127B) and 1-(2-Chloro-ethyl)-3,3-difluoro-pyrrolidine hydrochloride (WO2008/86404).

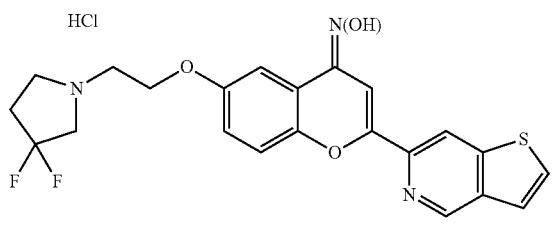

Mp: 226° C.-229° C.

MS (ESI+): 444.2 [C$_{22}$H$_{19}$F$_2$N$_3$O$_3$S+H]$^+$ (m/z).

1H NMR: (300 MHz) DMSO-d$_6$ δ (ppm): 11.06 (br. s, 1H), 9.27 (s, 1H), 8.78 (s, 1H), 8.06 (d, J=5.4 Hz, 1H), 7.73 (d, J=5.4 Hz, 1H), 7.70 (s, 1H), 7.51 (d, J=9.1 Hz, 1H), 7.42 (d, J=3.0 Hz, 1H), 7.26 (dd, J=9.1 Hz, J=3.1 Hz, 1H), 4.45-3.73 (m, 10H).

Example 134

6-(3-Pyridin-4-yl-propoxy)-2-thieno[3,2-c]pyridin-6-yl-chromen-4-one oxime, hydrochloride was prepared in 7% overall yield using the method described in example 127, starting from 6-hydroxy-2-thieno[3,2-c]pyridin-6-yl-chromen-4-one O-tert-butyl oxime (example 127A) and 4-(3-Chloro-propyl)-pyridine hydrochloride, prepared from 4-pyridine propanol (U.S. Pat. No. 6,362,336).

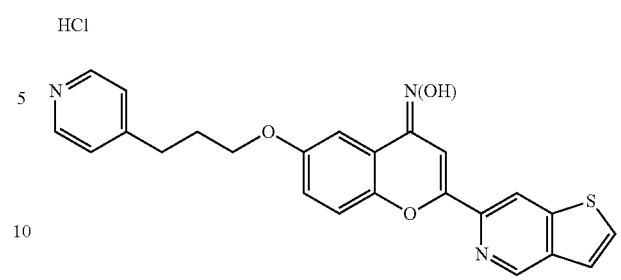

Mp: 236° C.-238° C.

MS (ESI+): 430.2 [C$_{24}$H$_{19}$N$_3$O$_3$S+H]$^+$ (m/z).

1H NMR: (300 MHz) DMSO-d$_6$ δ (ppm): 11.02 (br. s, 1H), 9.25 (s, 1H), 8.84 (d, J=6.6 Hz, 2H), 8.76 (s, 1H), 8.03 (dd, J=8.8 Hz, J=5.3 Hz, 3H), 7.72 (d, J=5.4 Hz, 1H), 7.67 (s, 1H), 7.45 (d, J=9.0 Hz, 1H), 7.30 (d, J=3.0 Hz, 1H), 7.11 (dd, J=9.2 Hz, J=3.0 Hz, 1H), 4.07 (t, J=6.0 Hz, 2H), 3.09 (t, J=7.3 Hz, 2H), 2.18 (q, J=7.7 Hz, 2H).

Example 135

6-(3-Pyridin-3-yl-propoxy)-2-thieno[3,2-c]pyridin-6-yl-chromen-4-one oxime, hydrochloride was prepared in 10% overall yield using the method described in example 127, starting from 6-hydroxy-2-thieno[3,2-c]pyridin-6-yl-chromen-4-one O-tert-butyl oxime (example 127A) and 3-(3-Chloro-propyl)-pyridine hydrochloride, prepared from 3-pyridine propanol (U.S. Pat. No. 6,362,336).

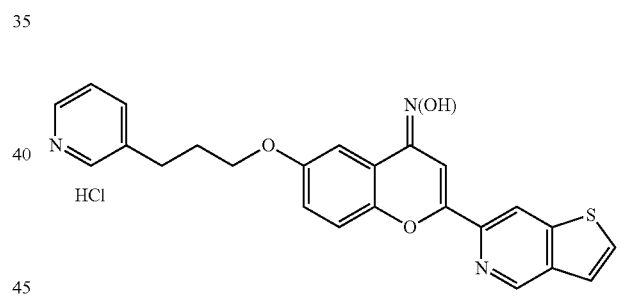

Mp: 252° C.-254° C.

MS (ESI+): 430.2 [C$_{24}$H$_{19}$N$_3$O$_3$S+H]$^+$ (m/z).

1H NMR: (300 MHz) DMSO-d$_6$ δ (ppm): 11.04 (br. s, 1H), 9.25 (s, 1H), 8.89 (s, 1H), 8.80 (d, J=5.4 Hz, 1H), 8.77 (s, 1H), 8.54 (d, J=7.9 Hz, 1H), 8.06-8.00 (m, 2H), 7.73 (d, J=5.0 Hz, 1H), 7.68 (s, 1H), 7.45 (d, J=9.0 Hz, 1H), 7.31 (d, J=3.0 Hz, 1H), 7.11 (dd, J=9.0 Hz, J=3.0 Hz, 1H), 4.07 (t, J=6.0 Hz, 2H), 3.01 (t, J=7.3 Hz, 2H), 2.16 (q, J=7.3 Hz, 2H).

Example 136

6-(2-Pyridin-4-yl-ethoxy)-2-pyrrolo[1,2-c]pyrimidin-3-yl-chromen-4-one oxime, hydrochloride was prepared in 30% overall yield using the method described in example 85, starting from 6-hydroxy-2-pyrrolo[1,2-c]pyrimidin-3-yl-chromen-4-one O-tert-butyl oxime (example 81A) and 4-(2-Chloro-ethyl)-pyridine.

Mp: >270° C. dec.
MS (ESI+): 399.2 [$C_{24}H_{18}N_4O_3$+H]$^+$ (m/z).
1H NMR: (300 MHz) DMSO-$d_6$ δ (ppm): 10.86 (br. s, 1H), 9.60 (br.s, 1H), 9.19 (s, 1H), 8.84 (d, J=6.57, 2H), 8.00 (m, 3H), 7.41 (s, 1H), 7.27 (m, 2H), 6.93 (dd, J=8.9 Hz, J=3.0 Hz, 1H), 6.76 (d, J=3.8 Hz, 1H), 6.67 (d, J=3.8 Hz, 1H), 3.46 (m, 2H), 3.39 (m, 2H).

Example 137

2-Pyrrolo[1,2-c]pyrimidin-3-yl-6-[2-(4-trifluoromethyl-phenyl)-ethoxy]-chromen-4-one, oxime was prepared in 7% overall yield using the method described in example 85, starting from 6-hydroxy-2-pyrrolo[1,2-c]pyrimidin-3-yl-chromen-4-one O-tert-butyl oxime (example 81A) and 1-(2-Bromo-ethyl)-4-trifluoromethyl-benzene.

Mp: 214° C.-215° C.
MS (ESI+): 466.2 [$C_{25}H_{18}F_3N_3O_3$+H]$^+$ (m/z).
1H NMR: (300 MHz) DMSO-$d_6$ δ (ppm): 10.90 (s, 1H), 9.20 (s, 1H), 8.02 (s, 1H), 7.81 (s, 1H), 7.68 (d, J=8.1 Hz, 2H), 7.57 (d, J=8.1 Hz, 2H), 7.42 (s, 1H), 7.38 (d, J=9.1 Hz, 1H), 7.31 (d, J=3.0 Hz, 1H), 7.10 (dd, J=9.1 Hz, J=3.0 Hz, 1H), 6.97 (dd, J=8.9 Hz, J=3.0 Hz, 1H), 6.73 (d, J=3.8 Hz, 1H), 4.29 (t, J=6.5 Hz, 2H), 3.16 (t, J=6.4 Hz, 2H).

Example 138

6-[2-(3-Fluoro-phenyl)-ethoxy]-2-pyrrolo[1,2-c]pyrimidin-3-yl-chromen-4-one, oxime was prepared in 44% overall yield using the method described in example 85, starting from 6-hydroxy-2-pyrrolo[1,2-c]pyrimidin-3-yl-chromen-4-one O-tert-butyl oxime (example 81A) and 1-(2-Bromo-ethyl)-3-fluoro-benzene.

Mp: 205° C.-207° C.
MS (ESI+): 416.2 [$C_{24}H_{18}FN_3O_3$+H]$^+$ (m/z).
1H NMR: (300 MHz) DMSO-$d_6$ δ (ppm): 10.90 (s, 1H), 9.20 (s, 1H), 8.02 (s, 1H), 7.81 (s, 1H), 7.42-7.30 (m, 4H), 7.21-6.97 (m, 5H), 6.73 (d, J=3.8 Hz, 1H), 4.25 (t, J=6.6 Hz, 2H), 3.08 (t, J=6.5 Hz, 2H).

Example 139

5-Methoxy-2-pyrrolo[1,2-c]pyrimidin-3-yl-chromen-4-one oxime was prepared in 8% overall yield using methods A and C, starting from 6'-methoxy-2'-hydroxy-acetophenone and pyrrolo[1,2-c]pyrimidine-3-carboxylic acid methyl ester.

Mp: 240° C.-243° C.
MS (ESI+): 308.1 [$C_{17}H_{13}N_3O_3$+H]$^+$ (m/z).
1H NMR: (300 MHz) DMSO-$d_6$ δ (ppm): 11.11 (s, 1H), 9.19 (s, 1H), 7.99 (5, 1H), 7.79 (s, 1H), 7.54 (s, 1H), 7.41 (t, J=8.3 Hz, 1H), 7.21-6.97 (m, 5H), 7.01 (d, J=8.1 Hz, 1H), 6.96 (t, J=3 Hz, 1H), 6.90 (d, J=8.3 Hz, 1H), 6.70 (d, J=3.4 Hz, 1H), 3.80 (s, 3H).

Example 140

6-[2-(4-Chloro-phenyl)-ethoxy]-2-pyrrolo[1,2-c]pyrimidin-3-yl-chromen-4-one oxime was prepared in 28% overall yield using the method described in example 85, starting from 6-hydroxy-2-pyrrolo[1,2-c]pyrimidin-3-yl-chromen-4-one O-tert-butyl oxime (example 81A) and 1-(2-Bromo-ethyl)-4-chloro-benzene.

Mp: 247° C.-249° C.
MS (ESI+): 432.2 [$C_{24}H_{18}ClN_3O_3$+H]$^+$ (m/z).
1H NMR: (300 MHz) DMSO-$d_6$ δ (ppm): 10.90 (s, 1H), 9.20 (s, 1H), 8.02 (s, 1H), 7.81 (s, 1H), 7.42 (s, 1H), 7.38 (m, 5H), 7.30 (d, J=3.0 Hz, 1H), 7.10 (dd, J=9.1 Hz, J=3.0 Hz, 1H), 6.97 (dd, J=8.9 Hz, J=3.0 Hz, 1H), 6.73 (d, J=3.8 Hz, 1H), 4.23 (t, J=6.6 Hz, 2H), 3.05 (t, J=6.5 Hz, 2H).

Example 141

2-Pyrrolo[1,2-c]pyrimidin-3-yl-6-[2-(3-trifluoromethyl-phenyl)-ethoxy]-chromen-4-one oxime was prepared in 22% overall yield using the method described in example 85, starting from 6-hydroxy-2-pyrrolo[1,2-c]pyrimidin-3-yl-chromen-4-one O-tert-butyl oxime (example 81A) and 1-(2-Bromo-ethyl)-3-trifluoromethyl-benzene.

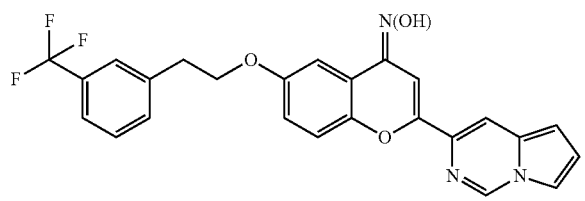

Mp: 217° C.-218° C.

MS (ESI+): 466.2 [C$_{25}$H$_{18}$F$_3$N$_3$O$_3$+H]$^+$ (m/z).

1H NMR: (300 MHz) DMSO-d$_6$ δ (ppm): 10.90 (s, 1H), 9.20 (s, 1H), 8.02 (s, 1H), 7.81 (s, 1H), 7.72 (s, 1H), 7.67 (d, J=7.0 Hz, 1H), 7.61-7.55 (m, 2H), 7.42 (s, 1H), 7.39 (d, J=9.1 Hz, 1H), 7.31 (d, J=3.0 Hz, 1H), 7.10 (dd, J=9.0 Hz, J=3.0 Hz, 1H), 6.97 (dd, J=3.8 Hz, J=2.9 Hz, 1H), 6.73 (d, J=3.8 Hz, 1H), 4.28 (t, J=6.6 Hz, 2H), 3.16 (t, J=6.5 Hz, 2H).

Example 142

7-(2-Morpholin-4-yl-ethoxy)-2-pyrrolo[1,2-c]pyrimidin-3-yl-chromen-4-one oxime, hydrochloride was prepared in 75% yield using method D (step 2), starting from 7-(2-Morpholin-4-yl-ethoxy)-2-pyrrolo[1,2-c]pyrimidin-3-yl-chromen-4-one O-tert-butyl-oxime (example 142A). The hydrochloride salt of the title compound was isolated as a yellow solid after treatment with a 1.25 M solution of hydrogen chloride in isopropanol.

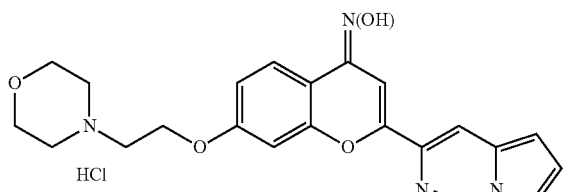

MS (ESI+): 407.0 [C$_{22}$H$_{22}$N$_4$O$_4$+H]$^+$ (m/z).

1H NMR: (400 MHz) DMSO-d$_6$ δ (ppm): 11.37 (br. s, 1H), 10.94 (br. s, 1H), 9.24 (s, 1H), 8.08 (s, 1H), 7.87 (d, J=8.8 Hz, 2H), 7.84 (s, 1H), 7.47 (s, 1H), 7.18 (s, 1H), 7.01-6.96 (m, 2H), 6.75 (d, J=1.6 Hz, 1H), 4.56 (t, J=4.8 Hz, 1H), 3.99 (m, 2H), 3.87 (m, 2H), 3.60 (m, 2H), 3.53 (m, 2H), 3.25 (m, 2H).

Example 142A 7-(2-Morpholin-4-yl-ethoxy)-2-pyrrolo[1,2-c]pyrimidin-3-yl-chromen-4-one O-tert-butyl-oxime was prepared in 57% yield using the procedure described in example 85A, starting from 7-Hydroxy-pyrrolo[1,2-c]pyrimidin-3-yl-chromen-4-one O-tert-butyl-oxime O-tert-butyl-oxime (example 142B) and 4-(2-chloroethyl) morpholine hydrochloride. The title compound was isolated as a yellow solid.

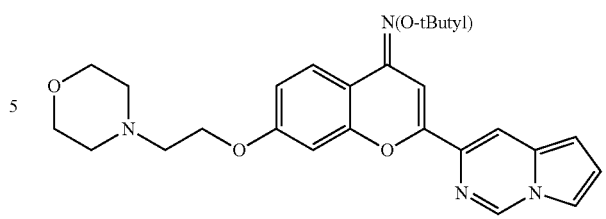

1H NMR: (300 MHz) CHCl$_3$-d$_1$ δ (ppm): 8.79 (s, 1H), 7.96 (d, J=8.9 Hz, 1H), 7.88 (s, 1H), 7.50 (s, 1H), 7.44 (d, J=2.6 Hz, 1H), 6.92 (dd, J=3.7 Hz, J=2.8 Hz, 1H), 6.80-6.75 (m, 2H), 6.62 (d, J=3.9 Hz, 1H), 4.17 (t, J=5.6 Hz, 2H), 3.75 (t, J=4.7 Hz, 4H), 2.84 (t, J=5.6 Hz, 2H), 2.60 (t, J=4.5 Hz, 4H), 1.40 (s, 9H).

Example 142B

7-Hydroxy-2-pyrrolo[1,2-c]pyrimidin-3-yl-chromen-4-one O-tert-butyl-oxime was prepared in 78% yield using the procedure described in example 18A, starting from 7-Bromo-2-pyrrolo[1,2-c]pyrimidin-3-yl-chromen-4-one O-tert-butyl-oxime (example 142C). The title compound was isolated as an orange solid.

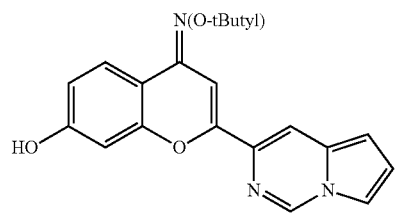

1H NMR: (300 MHz) CHCl$_3$-d$_1$ δ (ppm): 8.78 (s, 1H), 7.92 (d, J=8.4 Hz, 1H), 7.49 (s, 1H), 7.44 (s, 1H), 7.43 (s, 1H), 6.92 (dd, J=3.7 Hz, J=2.8 Hz, 1H), 6.71-6.61 (m, 3H), 5.53 (br s, 1H), 1.39 (s, 9H).

Example 142C

7-Bromo-2-pyrrolo[1,2-c]pyrimidin-3-yl-chromen-4-one O-tert-butyl-oxime was prepared in 64% overall yield using methods A and D (step 1), starting from 4'-bromo-2'-hydroxy-acetophenone and pyrrolo[1,2-c]pyrimidine-3-carboxylic acid methyl ester.

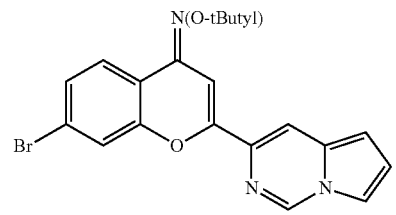

1H NMR: (300 MHz) CHCl$_3$-d$_1$ δ (ppm): 8.79 (s, 1H), 7.91 (d, J=6.4 Hz, 1H), 7.50 (s, 1H), 7.45 (dd, J=3.9 Hz, J=2.8 Hz, 2H), 7.29 (dd, J=6.4 Hz, J=1.3 Hz, 1H), 6.94-6.92 (m, 2H), 6.64 (d, J=3.0 Hz, 1H), 1.40 (s, 9H).

Example 143

7-(3-Morpholin-4-yl-propoxy)-2-pyrrolo[1,2-c]pyrimidin-3-yl-chromen-4-one oxime hydrochloride was prepared in 71% yield using method D (step 2), starting from 7-(3-Morpholin-4-yl-propoxy)-2-pyrrolo[1,2-c]pyrimidin-3-yl-chromen-4-one O-tert-butyl-oxime (example 143A). The hydrochloride salt of the title compound was isolated as a yellow solid after treatment with a 1.25 M solution of hydrogen chloride in isopropanol.

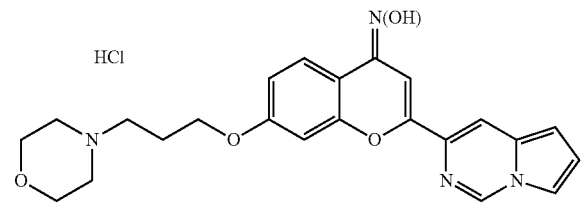

MS (ESI+): 421.0 [$C_{23}H_{24}N_4O_4$+H]$^+$ (m/z).
1H NMR: (400 MHz) DMSO-$d_6$ δ (ppm): 10.99 (br. s, 1H), 10.85 (br. s, 1H), 9.24 (s, 1H), 8.06 (s, 1H), 7.85-7.83 (m, 2H), 7.46 (s, 1H), 7.10 (s, 1H), 7.01-6.99 (m, 1H), 6.91 (dd, J=8.8 Hz, J=2.8 Hz, 1H), 6.75 (s, 1H), 3.99 (d, J=12.8 Hz, 2H), 3.82 (t, J=11.2 Hz, 2H), 3.48 (d, J=12.0 Hz, 2H), 3.30-3.25 (m, 2H), 3.14-3.06 (m, 2H), 2.29-2.22 (m, 2H).

Example 143A 7-(3-Morpholin-4-yl-propoxy)-2-pyrrolo[1,2-c]pyrimidin-3-yl-chromen-4-one O-tert-butyl-oxime was prepared in 55% yield using the method described in example 87A, starting from 7-(3-Chloro-propoxy)-2-pyrrolo[1,2-c]pyrimidin-3-yl-chromen-4-one O-tert-butyl oxime (example 143B) and morpholine.

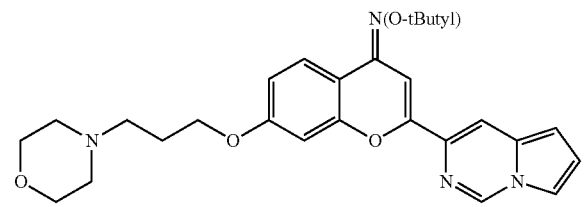

1H NMR: (300 MHz) CHCl$_3$-$d_1$ δ (ppm): 8.79 (s, 1H), 7.95 (d, J=9.2 Hz, 1H), 7.88 (s, 1H), 7.50 (s, 1H), 7.44 (d, J=2.6 Hz, 1H), 6.92 (dd, J=3.7 Hz, J=2.8 Hz, 1H), 6.79-6.76 (m, 2H), 6.61 (d, J=3.7 Hz, 1H), 4.08 (t, J=6.4 Hz, 2H), 3.74 (t, J=4.7 Hz, 4H), 2.54 (t, J=6.9 Hz, 2H), 2.48 (t, J=4.5 Hz, 4H), 2.00 (quint, J=6.4 Hz, 2H), 1.40 (s, 9H).

Example 143B 7-(3-Chloro-propoxy)-2-pyrrolo[1,2-c]pyrimidin-3-yl-chromen-4-one O-tert-butyl-oxime was prepared in 100% yield using the method described in example 85A, starting from 7-Hydroxy-pyrrolo[1,2-c]pyrimidin-3-yl-chromen-4-one O-tert-butyl-oxime (example 142B) and 1-bromo-3-chloropropane in dimethylformamide. The title compound was isolated as a brown solid.

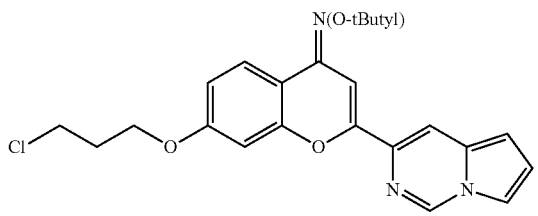

1H NMR: (300 MHz) CHCl$_3$-$d_1$ δ (ppm): 8.79 (s, 1H), 7.96 (d, J=9.4 Hz, 1H), 7.89 (s, 1H), 7.50 (s, 1H), 7.44 (d, J=2.4 Hz, 1H), 7.46 (s, 1H), 7.10 (s, 1H), 7.01-6.99 (m, 1H), 6.91 (dd, J=8.8 Hz, J=2.8 Hz, 1H), 4.18 (t, J=5.8 Hz, 2H), 3.77 (t, J=6.4 Hz, 2H), 2.28 (quint, J=6.0 Hz, 2H), 1.40 (s, 9H).

Example 144

6-[(4-Fluoro-benzylamino)-methyl]-2-pyrrolo[1,2-c]pyrimidin-3-yl-chromen-4-one oxime hydrochloride was prepared in 54% yield using method D (step 2), starting from 6-[(4-Fluoro-benzylamino)-methyl]-2-pyrrolo[1,2-c]pyrimidin-3-yl-chromen-4-one O-tert-butyl-oxime (example 144B). The hydrochloride salt of the title compound was isolated as a red solid after treatment with a 1.25 M solution of hydrogen chloride in isopropanol.

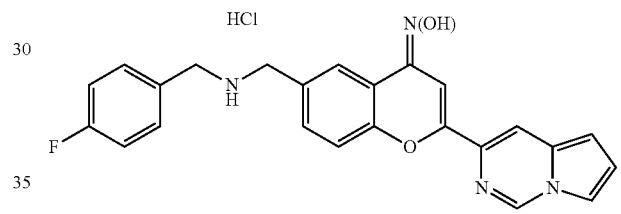

Mp: >210° C. dec.
MS (ESI+): 415.2 [$C_{24}H_{19}FN_4O_2$+H]$^+$ (m/z).
1H NMR: (300 MHz) DMSO-$d_6$ δ (ppm): 11.04 (br. s, 1H), 9.58 (br. s, 2H), 9.22 (s, 1H), 8.04 (s, 2H), 7.83 (s, 1H), 7.66-7.60 (m, 3H), 7.50 (d, J=9.6 Hz, 1H), 7.48 (s, 1H), 7.28 (t, J=8.8 Hz, 2H), 6.99 (t, J=3.6 Hz, 1H), 6.74 (d, J=3.8 Hz, 1H), 4.20 (s, 4H).

Example 144A

6-[(4-Fluoro-benzylamino)-methyl]-2-pyrrolo[1,2-c]pyrimidin-3-yl-chromen-4-one O-tert-butyl-oxime

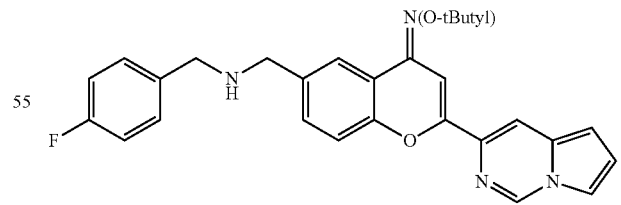

To a solution of 4-tert-Butoxyimino-2-pyrrolo[1,2-c]pyrimidin-3-yl-4H-chromene-6-carbaldehyde (example 144B) (50 mg; 0.14 mmol) in dichloromethane (5 ml), was added molecular sieves and 4-Fluoro-benzylamine (19 mg; 0.15 mmol). After 2 hours at room temperature, sodium triacetoxyborohydride (29 mg; 0.14 mmol) and acetique acid (2 ml), were added. After stirring at room temperature for 18 hours, the reaction mixture was quenched with a saturated solution of sodium hydrogenocarbonate and extracted with ethyl acetate. The organic layers were washed with water, brine, dried over sodium sulfate, filtered and concentrated. The residue was purified by flash chromatography over silica gel (gradient cyclohexane/ethyl acetate: 0-100%) to afford the title compound (20 mg, 30%) as a green solid.

1H NMR: (300 MHz) DMSO-$d_6$ δ (ppm): 8.79 (s, 7.96 (s, 1H), 7.90 (s, 1H), 7.50 (s, 1H), 7.45-7.33 (m, 4H), 7.23 (d, J=8.4 Hz, 1H), 7.05-7.00 (m, 2H), 6.92 (dd, J=3.7 Hz, J=2.8 Hz, 1H), 6.63 (d, J=3.7 Hz, 1H), 3.83 (s, 2H), 3.81 (s, 2H), 2.30 (br s, 1H), 1.42 (s, 9H).

Example 144B 4-tert-Butoxyimino-2-pyrrolo[1,2-c]pyrimidin-3-yl-4H-chromene-6-carbaldehyde

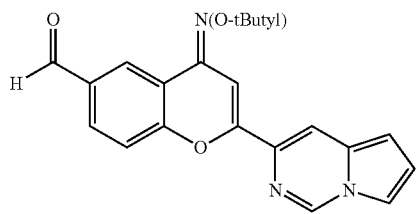

To a solution of 6-Hydroxymethyl-2-pyrrolo[1,2-c]pyrimidin-3-yl-chromen-4-one O-tert-butyl-oxime (example 144C) (575 mg, 1.58 mmol) in dichloromethane (60 ml), was added a Dess Martin solution (15 wt. % in DCM) (6.7 ml; 2.37 mmol). After 1 hour stirring at room temperature, an additional amount of Dess Martin solution (6 ml) was added to complete the reaction. The reaction mixture was quenched with water and added to a 1:1 solution of saturated sodium hydrogenocarbonate and 5% aq solution of $Na_2S_2O_3$. After extraction with ethyl acetate, the organic layers were washed with water, brine, dried over sodium sulfate and concentrated. The residue was purified by flash chromatography over silica gel (gradient cyclohexane/ethyl acetate: 0-40%) to afford the title compound (355 mg, 62%) as a yellow solid.

1H NMR: (300 MHz) CHCl$_3$-$d_1$ δ (ppm): 10.03 (s, 1H), 8.81 (s, 1H), 8.56 (d, J=2.0 Hz, 1H), 8.04 (s, 1H), 7.94 (dd, J=8.6 Hz, J=1.9 Hz, 1H), 7.55 (s, 1H), 7.47 (dd, J=2.4 Hz, 1H), 7.37 (d, J=8.4 Hz, 1H), 6.95 (dd, J=3.7 Hz, J=2.8 Hz, 1H), 6.67 (d, J=3.7 Hz, 1H), 1.43 (s, 9H).

Example 144C

6-Hydroxymethyl-2-pyrrolo[1,2-c]pyrimidin-3-yl-chromen-4-one O-tert-butyl-oxime

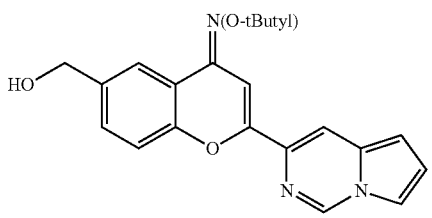

To a solution of 4-(tert-Butoxyimino)-2-pyrrolo[1,2-c]pyrimidin-3-yl-4H-chromene-6-carboxylic acid methyl ester (example 115B) (574 mg, 1.46 mmol) in dichloromethane (9 ml) at 0° C. was added a 1M solution of DIBAL-H in THF (12.8 ml). After 2 hours at 0° C. an additional amount of 1M solution of DIBAL-H in THF (6 ml) was added to complete the reaction. After hydrolysis with a 1M aqueous solution of hydrogen chloride, the reaction mixture was extracted with ethyl acetate. The organic layers were washed with water, brine, dried over sodium sulfate, filtered and concentrated. The product was used without further purification.

1H NMR: (300 MHz) CHCl$_3$-$d_1$ δ (ppm): 8.79 (s, 1H), 8.05 (d, J=1.9 Hz, 1H), 7.91 (s, 1H), 7.52 (s, 1H), 7.45-7.41 (m, 2H), 7.27-7.24 (m, 2H), 6.92 (dd, J=3.7 Hz, J=2.8 Hz, 1H), 6.64 (d, J=3.7 Hz, 1H), 4.73 (s, 2H), 1.42 (s, 9H).

Example 145

6-{[2-(4-Fluoro-phenyl)-ethylamino]-methyl}-2-pyrrolo[1,2-c]pyrimidin-3-yl-chromen-4-one oxime hydrochloride was prepared in 24% overall yield using the method described in example 144, starting from 4-tert-Butoxyimino-2-pyrrolo[1,2-c]pyrimidin-3-yl-4H-chromene-6-carbaldehyde (example 144B) and 4-fluorophenethylamine.

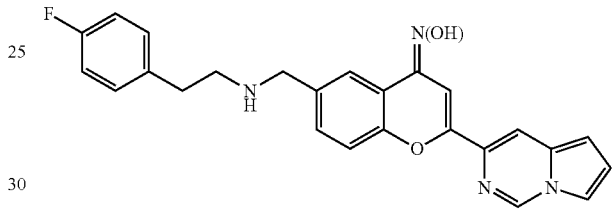

HPLC (gradient 15% 75% MeOH/H$_2$O+0.05% TFA): >95%; RT=10.51 min.
MS (ESI+): 429.0 [$C_{26}H_{21}FN_4O_2$+H]$^+$ (m/z).

Example 146

6-Phenethyloxy-2-pyrrolo[1,2-c]pyrimidin-3-yl-chromen-4-one oxime was prepared in 21% overall yield using the method described in example 85, starting from 6-hydroxy-2-pyrrolo[1,2-c]pyrimidin-3-yl-chromen-4-one O-tert-butyl oxime (example 81A) and (2-Bromo-ethyl)-benzene.

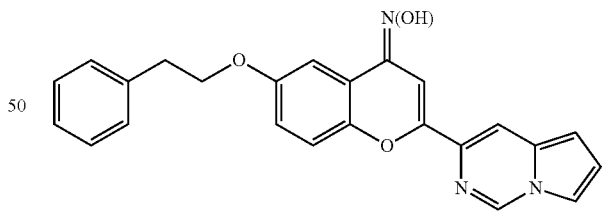

Mp: 210° C. 212° C.
MS (ESI+): 398.2 [$C_{24}H_{19}N_3O_3$+H]$^+$ (m/z).
1H NMR: (300 MHz) DMSO-$d_6$ δ (ppm): 10.90 (s, 1H), 9.21 (s, 1H), 8.02 (s, 1H), 7.81 (s, 1H), 7.42-7.23 (m, 8H), 7.10 (dd, J=9.0 Hz, J=3.0 Hz, 1H), 6.98 (s, 1H), 6.74 (d, J=3.8 Hz, 1H), 4.23 (t, J=6.7 Hz, 2H) 3.05 (t, J=6.5 Hz, 2H).

Example 147

6-[2-(Pyridin-4-yloxy)-ethoxy]-2-pyrrolo[1,2-c]pyrimidin-3-yl-chromen-4-one oxime was prepared in 17% yield using method D (step 2), starting from 6-[2-(Pyridin-4- yloxy)-ethoxy]-2-pyrrolo[1,2-c]pyrimidin-3-yl-chromen-4-one O-tertbutyl oxime (example 147A).

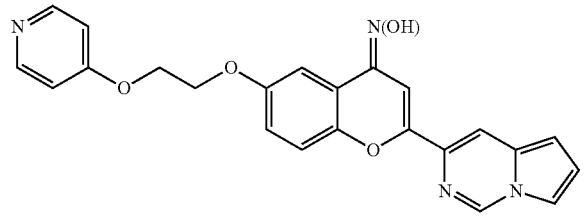

Mp: 198° C.-200° C.
MS (ESI+): 415.2 $[C_{23}H_{18}N_4O_4+H]^+$ (m/z).
1H NMR: (300 MHz) DMSO-$d_6$ δ (ppm): 10.97 (br. s, 1H), 9.22 (s, 1H), 8.79 (d, J=7.32 Hz, 2H), 8.05 (s, 1H), 7.82 (d, J=2.5 Hz, 1H), 7.67 (d, J=7.4 Hz, 2H), 7.45-7.42 (m, 2H), 7.36 (d, J=3.0 Hz, 1H), 7.16 (dd, J=9.0 Hz, J=3.0 Hz, 1H), 6.98 (dd, J=3.8 Hz, J=2.9 Hz, 1H), 6.73 (d, J=3.8 Hz, 1H), 4.74 (s, 2H), 4.46 (s, 2H).

Example 147A

6-[2-(Pyridin-4-yloxy)-ethoxy]-2-pyrrolo[1,2-c]pyrimidin-3-yl-chromen-4-one O-tert-butyl oxime

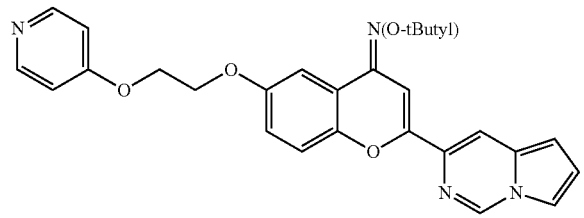

To a mixture of sodium hydride 60% in oil (11.5 mg, 0.28 mmol) in NMP (0.5 ml) was added at 0° C. a solution of 6-hydroxy-2-pyrrolo[1,2-c]pyrimidin-3-yl-chromen-4-one O-tert-butyl-oxime (example 81A) (100 mg, 0.28 mmol) in NMP (0.5 ml). After 1 hour at room temperature, a solution of 4-(2-Chloro-ethoxy)-pyridine (103 mg, 042 mmol), tetrabutyl ammonium iodide (53 mg, 0.14 mmol), 15-crown-5 (63 mg, 0.28 mmol) in NMP (0.5 ml) was added at 0° C. After stirring at room temperature for 24 hours, the reaction mixture was diluted with a saturated solution of ammonium chloride and extracted with ethyl acetate. The organic layers were washed with a saturated solution of ammonium chloride, water, brine, dried over sodium sulfate, filtered and concentrated. The residue was purified by flash chromatography over silica gel (gradient cyclohexane/ethyl acetate: 0-70%) to yield the title compound (54 mg, 42%) as a yellow solid.
1H NMR: (300 MHz) CHCl$_3$-d$_1$ δ (ppm): 8.79 (s, 1H), 8.41 (d, J=2.8 Hz, 1H), 8.27 (dd, J=4.5 Hz, J=1.3 Hz, 1H), 7.90 (s, 1H), 7.57 (d, J=3.0 Hz, 1H), 7.50 (s, 1H), 7.44 (d, J=2.4 Hz, 1H), 7.36-7.28 (m, 2H), 7.22 (d, J=9.0 Hz, 1H), 7.02 (dd, J=9.0 Hz, J=3.0 Hz, 1H), 6.92 (dd, J=3.8 Hz, J=2.8 Hz, 1H), 6.63 (d, J=3.8 Hz, 1H), 4.42 (s, 4H), 1.41 (s, 9H).

Example 148

6-[2-(Pyridin-3-yloxy)-ethoxy]-2-pyrrolo[1,2-c]pyrimidin-3-yl-chromen-4-one oxime was prepared in 16% overall yield using the method described in example 147, starting from 6-hydroxy-2-pyrrolo[1,2-c]pyrimidin-3-yl-chromen-4-one O-tert-butyl-oxime (example 81A) and 3-(2-Chloro-ethoxy)-pyridine.

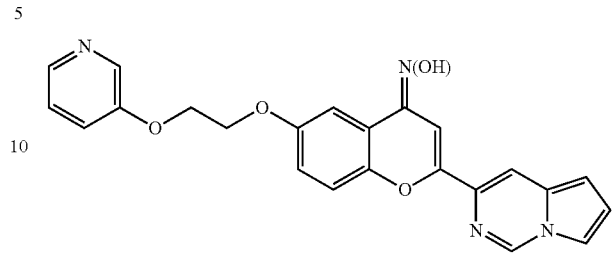

Mp: 170° C.-175° C.
MS (ESI+): 415.2 $[C_{23}H_{18}N_4O_4+H]^+$ (m/z).
1H NMR: (300 MHz) DMSO-$d_6$ δ (ppm): 10.97 (br. s, 1H), 9.22 (s, 1H), 8.64 (s, 1H), 8.42 (d, J=5.13 Hz, 1H), 8.05 (s, 1H), 7.99 (d, J=6.63 Hz, 1H), 7.82-7.74 (m, 2H), 7.45-7.42 (m, 2H), 7.36 (d, J=3.0 Hz, 1H), 7.16 (dd, J=9.0 Hz, J=3.0 Hz, 1H), 6.98 (m, 1H), 6.73 (d, J=3.8 Hz, 1H), 4.54 (m, 2H), 4.74 (m, 2H).

Example 149

6-[3-(Pyridin-3-yloxy)-propoxy]-2-pyrrolo[1,2-c]pyrimidin-3-yl-chromen-4-one oxime was prepared in 9% overall yield using the method described in example 147, starting from 6-hydroxy-2-pyrrolo[1,2-c]pyrimidin-3-yl-chromen-4-one O-tert-butyl-oxime (example 81A) and 3-(3-Chloro-propoxy)-pyridine.

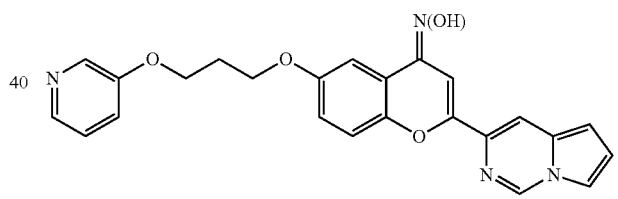

Mp: 202° C.-205° C.
MS (ESI+): 429.2 $[C_{24}H_{20}N_4O_4+H]^+$ (m/z).
1H NMR: (300 MHz) DMSO-$d_6$ δ (ppm): 10.91 (s, 1H), 9.21 (s, 1H), 8.32 (d, J=2.8 Hz, 1H), 8.17 (dd, J=4.6 Hz, J=1.2 Hz, 1H), 8.03 (s, 1H), 7.89 (s, 1H), 7.43-7.18 (m, 5H), 7.20 (dd, J=9.1 Hz, J=3.0 Hz, 1H), 6.97 (t, J=3.0 Hz, 1H), 6.73 (d, J=3.8 Hz, 1H), 4.25-4.18 (m, 4H), 2.21 (t, J=6.3 Hz, 2H).

Example 150

N-(4-Fluoro-phenyl)-2-{4-hydroxyimino-2-pyrrolo[1,2-c]pyrimidin-3-yl-4H-chromen-6-yloxy}-acetamide was prepared in 41% overall yield using the method described in example 147, starting from 6-hydroxy-2-pyrrolo[1,2-c]pyrimidin-3-yl-chromen-4-one O-tert-butyl-oxime (example 81A) and 2-Bromo-N-(4-fluoro-phenyl)-acetamide (Bioorg. Med. Chem. 11 (2003) 2769-2782).

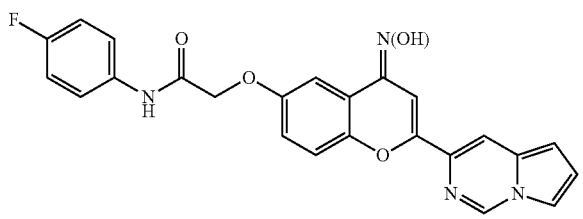

Mp: 278° C.-270° C.

MS (ESI+): 445.2 [C$_{24}$H$_{17}$FN$_4$O$_4$+H]$^+$ (m/z).

1H NMR: (300 MHz) DMSO-d$_6$ δ (ppm): 10.97 (s, 1H), 10.19 (s, 1H), 9.22 (s, 1H), 8.03 (s, 1H), 7.81 (d, J=2.6 Hz, 1H), 7.69-7.64 (m, 2H), 7.46-7.38 (m, 3H), 7.23-7.14 (m, 3H), 6.98 (dd, J=3.8 Hz, J=2.9 Hz, 1H), 6.73 (d, J=3.8 Hz, 1H), 4.75 (s, 2H).

Example 151

N-(4-Fluoro-phenyl)-2-{4-hydroxyimino-2-pyrrolo[1,2-c]pyrimidin-3-yl-4H-chromen-6-yloxy}-N-methyl-acetamide. was prepared in 90% yield using method D (step 2), starting from 2-{4-tert-Butoxyimino-2-pyrrolo[1,2-c]pyrimidin-3-yl-4H-chromen-6-yloxy}-N-(4-fluoro-phenyl)-N-methyl-acetamide (example 151A).

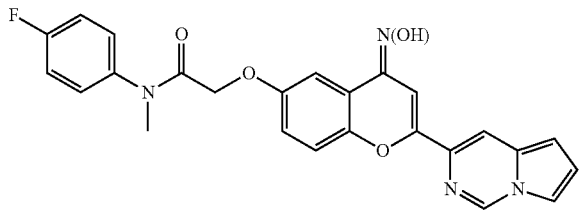

Mp: 268° C.-272° C.

MS (ESI+): 459.2 [C$_{26}$H$_{19}$FN$_4$O$_4$+H]$^+$ (m/z).

1H NMR: (400 MHz) DMSO-d$_6$ δ (ppm): 10.95 (s, 1H), 9.21 (s, 1H), 8.02 (s, 1H), 7.81 (d, 2.6 Hz, 1H), 7.54 (br. s, 2H), 7.42 (s, 1H), 7.38-7.33 (m, 3H), 7.11 (br. s, 1H), 6.97 (t, J=3.0 Hz, 2H), 6.73 (d, J=3.8 Hz, 1H), 4.48 (s, 2H), 3.18 (s, 3H).

Example 151A

2-{4-tert-Butoxyimino-2-pyrrolo[1,2-c]pyrimidin-3-yl-4H-chromen-4-yloxy}-N-(4-fluoro-phenyl)-N-methyl-acetamide To a solution of 2-{4-tert-Butoxyimino-2-pyrrolo[1,2-c]pyrimidin-3-yl-4H-chromen-6-yloxy}-N-(4-fluoro-phenyl)-acetamide (tert-butyl protected oxime of example 150) (220 mg; 0.44 mmol) in dimethylformamide (4 ml), was added at 0° C. NaH 60% in oil (21 mg; 0.53 mmol). After 1 hour at room temperature, Iodomethane (41 μl; 0.66 mmol) was added at 0° C. After stirring at room temperature for 18 hours, water was added at 0° C. and the resulting precipitate was filtered and purified by flash chromatography over silica gel (gradient dichloromethane/ethyl acetate: 0-4%) to yield the title compound (152 mg, 67%) as a yellow solid.

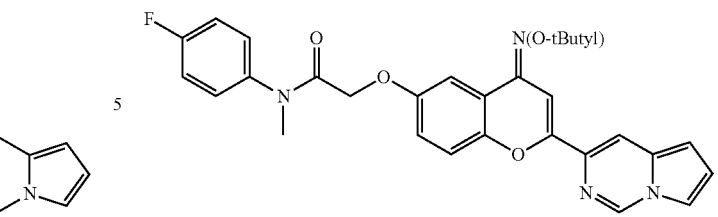

1H NMR: (300 MHz) CHCl$_3$-d$_1$ δ (ppm): 8.78 (s, 1H), 7.89 (s, 1H), 7.47 (s, 1H), 7.44 (d, 2.8 Hz, 1H), 7.33-7.29 (m, 3H), 7.18-7.12 (m, 3H), 6.97 (dd, J=8.8 Hz, J=2.8 Hz, 1H), 6.92 (t, J=3.8 Hz, 1H), 6.63 (d, J=3.8 Hz, 1H), 4.44 (s, 2H), 3.32 (s, 3H), 1.41 (s, 9H).

Example 152

N-(5-Fluoro-pyridin-2-yl)-2-{4-hydroxyimino-2-pyrrolo[1,2-c]pyrimidin-3-yl-4H-chromen-6-yloxy}-acetamide was prepared in 2% overall yield using the method described in example 147, starting from 6-hydroxy-2-pyrrolo[1,2-c]pyrimidin-3-yl-chromen-4-one O-tert-butyl-oxime (example 81A) and 2-Bromo-N-(5-fluoro-pyridin-2-yl)-acetamide (Bioorg. Med. Chem. 11 (2003) 2769-2782).

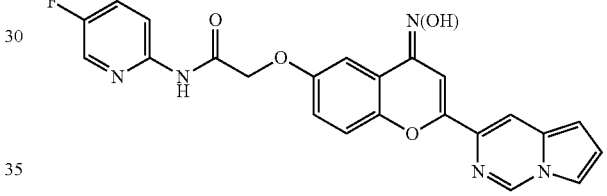

MS (ESI+): 446.0 [C$_{23}$H$_{16}$FN$_5$O$_4$+H]$^+$ (m/z).

1H NMR: (400 MHz) DMSO-d$_6$ δ (ppm): 11.00 (br. S, 1H), 10.80 (s, 1H), 9.27 (s, 1H), 8.42 (s, 1H), 8.19 (dd, 7.6 Hz, 1H), 8.10 (s, 1H), 7.87-7.80 (m, 2H), 7.50 (d, J=7.2 Hz, 1H), 7.48 (s, 1H), 7.39 (d, J=3.2 Hz, 1H), 7.25 (dd, J=8.8 Hz, J=2.8 Hz, 1H), 7.04 (d, J=3.6 Hz, 1H), 6.80 (s, 1H), 4.91 (s, 2H).

Example 153

2-Pyrrolo[1,2-c]pyrimidin-3-yl-5-trifluoromethyl-chromen-4-one oxime was prepared in 3% overall yield using methods A and C, starting from 6'-trifluoromethyl-2'-hydroxy-acetophenone and pyrrolo[1,2-c]pyrimidine-3-carboxylic acid methyl ester.

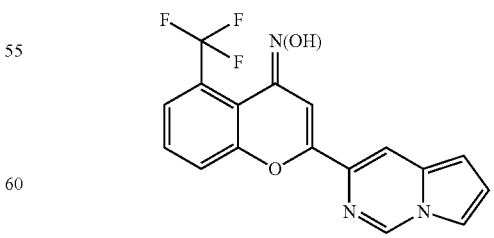

Mp: 255° C.-257° C.

MS (ESI+): 346.1 [C$_{17}$H$_{10}$F$_3$N$_3$O$_2$+H]$^+$ (m/z).

1H NMR: (300 MHz) DMSO-d$_6$ δ (ppm): 11.34 (s, 1H), 10.19 (s, 1H), 9.23 (s, 1H), 8.15 (s, 1H), 8.07 (d, J=8.3 Hz, 1H), 7.90 (s, 1H), 7.83 (s, 1H), 7.60 (d, J=8.3 Hz, 1H), 7.46 (s, 1H), 7.00 (t, J=3.2 Hz, 1H), 6.73 (d, J=3.8 Hz, 1H).

Example 154

2-(7-tert-Butyl-pyrrolo[1,2-c]pyrimidin-3-yl)-6-(2-morpholin-4-yl-ethoxy)-chromen-4-one oxime, hydrochloride is isolated as a by product from the reaction described in example 85.

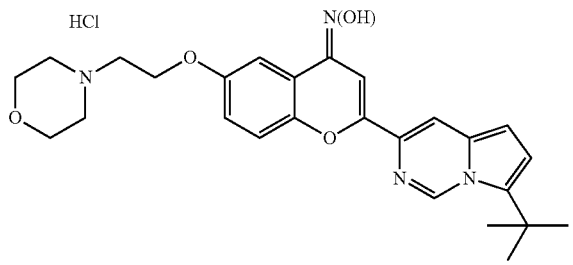

MS (ESI+): 463.0 [$C_{26}H_{30}N_4O_4$+H]$^+$ (m/z).
1H NMR: (400 MHz) DMSO-$d_6$ δ (ppm): 11.10 (br. s, 1H), 10.95 (br. s, 1H), 9.36 (s, 1H), 8.05 (s, 1H), 7.48-7.41 (m, 3H), 7.22 (dd, J=9.2 Hz, J=3.2 Hz, 1H), 6.78 (s, 1H), 6.72 (s, 1H), 4.48 (t, J=4.4 Hz, 2H), 3.81 (t, J=7.2 Hz, 2H), 3.59-3.50 (m, 4H), 3.25-3.17 (m, 4H), 1.44 (s, 9H).

Example 155

7-(2-Morpholin-4-yl-ethoxy)-2-thieno[2,3-c]pyridin-5-yl-chromen-4-one oxime, hydrochloride was prepared in 40% overall yield using the method described in example 142, starting from 4'-bromo-2'-hydroxy-acetophenone and Thieno[2,3-c]pyridine-5-carboxylic acid methyl ester.

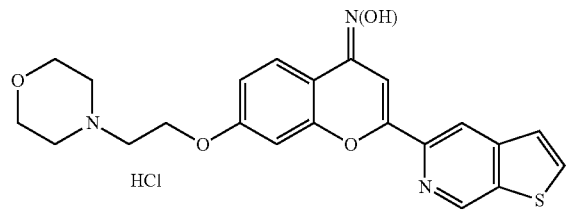

MS (ESI+): 424.0 [$C_{22}H_{21}N_3O_4S$+H]$^+$ (m/z).
1H NMR: (400 MHz) DMSO-$d_6$ δ (ppm): 10.99 (br. s, 1H), 10.88 (br. s, 1H), 9.36 (s, 1H), 8.51 (s, 1H), 8.20 (d, J=5.2 Hz, 1H), 7.73 (d, J=8.8 Hz, 1H), 7.64 (d, J=5.6 Hz, 1H), 7.28 (s, 1H), 6.65 (s, 1H), 6.59 (dd, J=8.8 Hz, J=2.4 Hz, 1H), 4.39 (m, 2H), 3.90 (d, J=11.6 Hz, 2H), 3.73 (t, J=12.0 Hz, 2H), 3.50 (s, 2H), 3.41 (d, J=12.4 Hz, 2H), 3.16-3.11 (m, 2H).

Example 156

5-(2-Morpholin-4-yl-ethoxy)-2-pyrrolo[1,2-c]pyrimidin-3-yl-chromen-4-one oxime, hydrochloride was prepared in 12% overall yield using methods A and C, starting from 2'-hydroxy-6'-(2-morpholino-4-yl-ethoxy)-acetophenone (example 156A) and pyrrolo[1,2-c]pyrimidine-3-carboxylic acid methyl ester. The hydrochloride salt of the title compound was isolated as a yellow solid after treatment with a 1.25 M solution of hydrogen chloride in isopropanol.

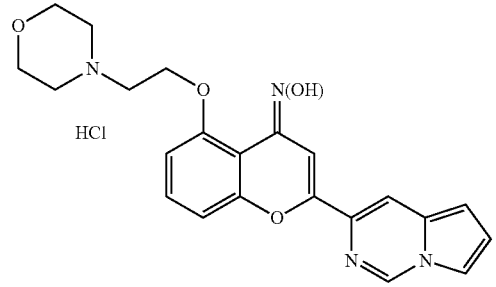

Mp: 200° C.-205° C.
MS (ESI+): 407.2 [$C_{22}H_{22}N_4O_4$+H]$^+$ (m/z).
1H NMR: (300 MHz) DMSO-$d_6$ δ (ppm): 10.09 (s, 1H), 9.24 (s, 1H), 8.11 (s, 1H), 7.85 (d, J=2.5 Hz, 1H), 7.63 (s, 1H), 7.55 (t, J=7.28 Hz, 1H), 7.20 (d, J=8.28 Hz, 1H), 7.05 (d, J=8.3 Hz, 1H), 7.00 (t, J=3.8 Hz, 1H), 6.78 (d, J=3.8 Hz, 1H), 4.56 (s, 2H), 3.91 (s, 4H), 3.61 (s, 2H), 3.47 (br. s, 4H).

Example 156A

2'-hydroxy-6'-(2-morpholino-4-yl-ethoxy)-acetophenone

In a sealed tube, to a solution of 6'-hydroxy-2'-methoxy-acetophenone (620 mg, 4.075 mmol) in butanone (20 ml) were added potassium carbonate (850 mg, 6.11 mmol) and 2-chloroethylmorpholine hydrochloride (800 mg, 4.28 mmol) and the mixture was stirred at 130° C. for 18 h. Water was added and the organics were extracted with ethylacetate, washed with brine, dried over sodium sulfate and concentrated to dryness. The residue was purified by flash chromatography over silica gel (gradient ethyl acetate/methanol: 0-2%) to yield 2'-methoxy-6'-(2-morpholino-4-yl-ethoxy)-acetophenone (1.0 g, 96%) as colorless oil. (1H NMR (300 MHz) CHCl$_3$-$d_1$ δ (ppm): 7.24 (t, J=8.5 Hz, 1H), 6.56 (d, J=8.5 Hz, 1H), 6.53 (d, J=8.5 Hz, 1H), 4.11 (t, J=5.7 Hz, 2H), 3.79 (s, 3H), 3.70 (m, 4H), 2.75 (t, J=5.8 Hz, 2H), 2.54 (m, 4H), 2.48 (s, 3H). To a solution of 2'-methoxy-6'-(2-morpholino-4-yl-ethoxy)-acetophenone (1.0 g, 3.58 mmol) in dichloromethane (50 ml) at 0° C. was added dropwise a 1M solution of boron tribromide in dichloromethane (14.0 ml, 14.0 mmol). The solution was stirred for 1 hour at this temperature and hydrolyzed with water. After 0.5 hour at room temperature the reaction mixture was cautiously neutralized with a saturated solution of sodium hydrogenocarbonate, and extracted with dichloromethane. The organic layer was washed with brine, dried over sodium sulfate and concentrated to dryness. The residue was purified by flash chromatography over silica gel (ethyl acetate/methanol: 0-4%) to yield 2'-hydroxy-6'-(2-morpholino-4-yl-ethoxy)-acetophenone (495 mg, 52%) as light yellow oil.

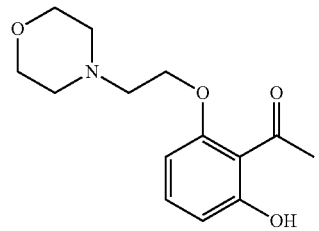 [SMILES: CC(=O)c1c(O)cccc1OCCN1CCOCC1]

1H NMR (300 MHz) CHCl₃-d₁ δ (ppm): 13.21 (s, 1H), 7.32 (t, J=8.5 Hz, 1H), 6.56 (d, J=8.5 Hz, 1H), 6.36 (d, J=8.5 Hz, 1H), 4.16 (t, J=5.7 Hz, 2H), 3.71 (m, 4H), 2.84 (t, J=5.8 Hz, 2H), 2.73 (s, 3H), 2.54 (m, 4H).

Example 157

5-(3-Morpholin-4-yl-propoxy)-2-pyrrolo[1,2-c]pyrimidin-3-yl-chromen-4-one oxime, hydrochloride was prepared in 2% overall yield using methods A and C, starting from 2'-hydroxy-6'-(3-morpholino-4-yl-propoxy)-acetophenone (example 157A) and pyrrolo[1,2-c]pyrimidine-3-carboxylic acid methyl ester.

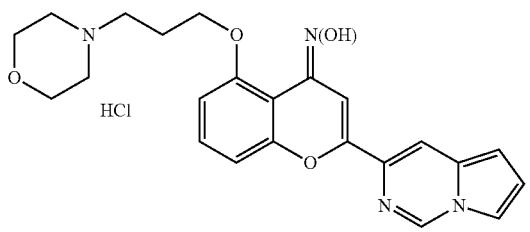

MS (ESI+): 421.0 [C₂₃H₂₄N₄O₄+H]⁺ (m/z).
1H NMR: (400 MHz) DMSO-d₆ δ (ppm): 10.09 (s, 1H), 9.24 (s, 1H), 8.11 (s, 1H), 7.85 (d, J=2.5 Hz, 1H), 7.63 (s, 1H), 7.55 (t, J=7.28 Hz, 1H), 7.20 (d, J=8.28 Hz, 1H), 7.05 (d, J=8.3 Hz, 1H), 7.00 (t, J=3.8 Hz, 1H), 6.78 (d, J=3.8 Hz, 1H), 4.19-3.93 (m, 8H), 3.25-3.04 (m, 4H), 2.24-2.20 (m, 2H).

Example 157A

2'-hydroxy-6'-(3-morpholino-4-yl-propoxy)-acetophenone

To a solution of 2',6'-dihydroxy-acetophenone (500 mg, 3.28 mmol) in dimethylformamide (20 ml) were added potassium carbonate (680 mg, 4.93 mmol) and 1-bromo-3-chloropropane (0.34 ml, 3.45 mmol) and the mixture was stirred at 70° C. for 4 h. Water was added and the organics were extracted with ethylacetate, washed with brine, dried over sodium sulfate and concentrated to dryness. The residue was purified by flash chromatography over silica gel (gradient cyclohexane/ethyl acetate: 0-15%) to yield 6'-(3-chloropropoxy)-2'-hydroxy-acetophenone (348 mg, 46%) as a pale yellow solid. To a solution of 6'-(3-chloropropoxy)-2'-hydroxy-acetophenone (345 mg, 1.50 mmol) in acetonitrile (15 ml) was added potassium carbonate (416 mg, 3.0 mmol) and morpholine (0.396 ml, 4.52 mmol). The mixture was stirred for 18 hours at room temperature then 60° C. for 3 days. Water was added and the organics were extracted with ethylacetate, washed with brine, dried over sodium sulfate and concentrated to dryness. The residue was purified by flash chromatography over silica gel (gradient ethyl acetate/methanol: 0-10%) to yield 2'-hydroxy-6'-(3-morpholino-4-yl-propoxy)-acetophenone (171 mg, 40%) as an orange oil that solidified.

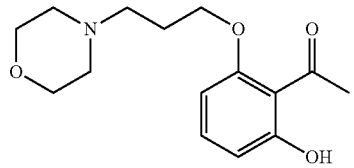 [SMILES: CC(=O)c1c(O)cccc1OCCCN1CCOCC1]

(1H NMR (300 MHz) CHCl₃-d₁ δ (ppm): 13.24 (s, 1H), 7.32 (t, J=8.3 Hz, 1H), 6.56 (d, J=8.4 Hz, 1H), 6.38 (d, J=8.4 Hz, 1H), 4.11 (t, J=6.4 Hz, 2H), 3.73 (m, 4H), 2.69 (s, 3H), 2.55 (t, J=6.2 Hz, 2H), 2.48 (m, 4H), 2.07 (quint., J=6.2 Hz, 2H).

Example 158

6-(2-Morpholin-4-yl-ethoxy)-2-thieno[2,3-c]pyridin-5-yl-chromen-4-one oxime, hydrochloride was prepared in 41% overall yield using the method described in example 127, starting from 5'-bromo-2'-hydroxy-acetophenone and Thieno[2,3-c]pyridine-5-carboxylic acid methyl ester.

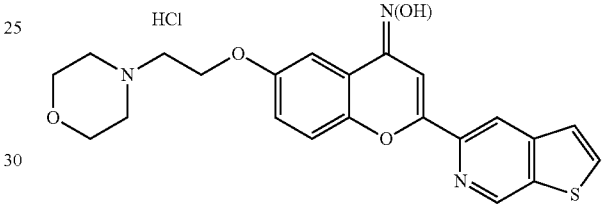

Mp: 258° C.-260° C.
MS (ESI+): 424.2 [C₂₂H₂₁N₃O₄S+H]⁺ (m/z).
1H NMR: (300 MHz) DMSO-d₆ δ (ppm): 11.24 (br. s, 1H), 11.05 (br. s, 1H), 9.39 (s, 1H), 8.52 (s, 1H), 8.26 (d, J=5.34 Hz, 1H), 7.71 (d, J=5.46, 1H), 7.69 (s, 1H), 7.51 (d, J=9.0 Hz, 1H), 7.43 (d, J=3.0 Hz, 1H), 7.23 (dd, J=9.1 Hz, J=3.0 Hz, 1H), 4.50 (m, 2H), 3.97 (d, J=10.4 Hz, 2H), 3.83 (t, J=11.7 Hz, 2H), 3.59-3.49 (m, 4H), 3.23-3.19 (m, 2H).

Example 159

6-(3-Pyridin-4-yl-propoxy)-2-pyrrolo[1,2-c]pyrimidin-3-yl-chromen-4-one oxime, hydrochloride was prepared in 10% overall yield using the method described in example 85, starting from 6-hydroxy-2-pyrrolo[1,2-c]pyrimidin-3-yl-chromen-4-one O-tert-butyl oxime (example 81A) and 4-(3-Chloro-propyl)-pyridine hydrochloride, prepared from 4-pyridine propanol (U.S. Pat. No. 6,362,336).

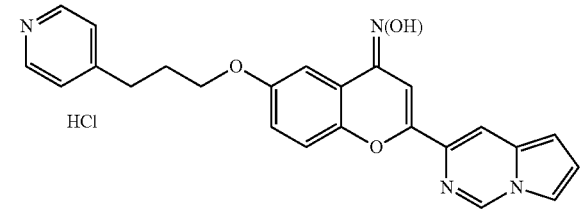

Mp: 210° C.-215° C.
MS (ESI+): 413.2 [C₂₄H₂₀N₄O₃+H]⁺ (m/z).
1H NMR: (300 MHz) DMSO-d₆ δ (ppm): 10.91 (br. s, 1H), 9.21 (s, 1H), 8.82 (d, J=2.8 Hz, 2H), 8.03-7.98 (m, 3H), 7.81 (d, J=2.5 Hz, 1H), 7.43 (s, 1H), 7.40 (d, J=9.1 Hz, 1H), 7.29

(d, J=3.0 Hz, 1H), 7.07 (dd, J=9.1 Hz, J=3.1 Hz, 1H), 6.97 (dd, J=3.7 Hz, J=2.8 Hz, 1H), 6.73 (d, J=3.8 Hz, 1H), 4.05 (t, J=6.2 Hz, 2H), 3.08 (t, J=7.3 Hz, 2H), 2.17 (quint., J=4.7 Hz, 2H).

Example 160

6-(2-Phenoxy-ethoxy)-2-pyrrolo[1,2-c]pyrimidin-3-yl-chromen-4-one oxime was prepared in 12% yield using method D (step 2), starting from 6-(2-Phenoxy-ethoxy)-2-pyrrolo[1,2-c]pyrimidin-3-yl-chromen-4-one O-tert-butyl oxime (example 160A).

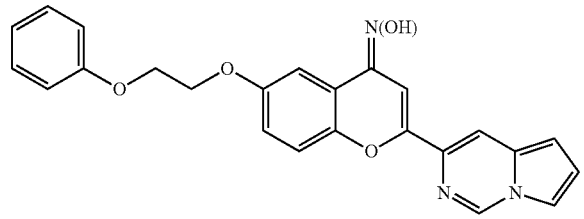

Mp: 210° C.-215° C.
HPLC (gradient 15%-75% MeOH/H$_2$O+0.05% TFA): >95%; RT=8.54 min.
MS (ESI+): 414.1 [C$_{24}$H$_{19}$N$_3$O$_2$+H]$^+$ (m/z).

Example 160A 6-(2-Phenoxy-ethoxy)-2-pyrrolo[1,2-c]pyrimidin-3-yl-chromen-4-one O-tert-butyl oxime

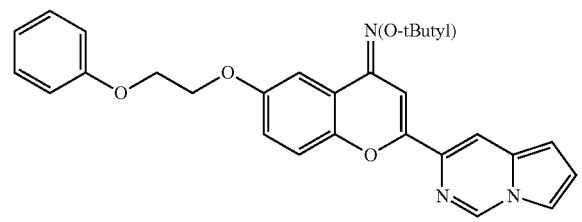

A mixture of 6-hydroxy-2-pyrrolo[1,2-c]pyrimidin-3-yl-chromen-4-one O-tert-butyl-oxime (example 81A) (150 mg, 0.43 mmol), cesium carbonate (280 mg, 0.85 mmol) and (2-Iodo-ethoxy)-benzene (413 mg, 3.87 mmol), in dimethylformamide (6 rill) was stirring at room temperature for 24 hours. The reaction mixture was diluted with water and extracted with ethyl acetate. The organic layers were washed with a saturated solution of ammonium chloride, water, brine, dried over sodium sulfate, filtered and concentrated. The residue was purified by flash chromatography over silica gel (gradient cyclohexane/ethyl acetate: 0-10%) to yield the title compound (77 mg, 38%) as a yellow solid.
1H NMR: (300 MHz) CHCl$_3$-d$_1$ δ (ppm): 8.80 (s, 1H), 7.91 (s, 1H), 7.61 (s, 1H), 7.50 (s, 1H), 7.45 (d, J=2.6 Hz, 1H), 7.33-7.28 (m, 2H), 7.22 (d, J=9.0 Hz, 1H), 7.04 (dd, J=9.0 Hz, J=3.0 Hz, 1H), 7.00-6.95 (m, 3H), 6.92 (dd, J=3.8 Hz, J=2.8 Hz 1H), 6.63 (d, J=3.8 Hz, 1H), 4.41-4.34 (m, 4H), 1.42 (s, 9H).

Example 161

6-[3-(4-Fluoro-phenoxy)-propoxy]-2-pyrrolo[1,2-c]pyrimidin-3-yl-chromen-4-one oxime was prepared in 74% yield using method D (step 2), starting from 6-[3-(4-Fluoro-phenoxy)-propoxy]-2-pyrrolo[1,2-c]pyrimidin-3-yl-chromen-4-one O-tert-butyl-oxime (example 161A).

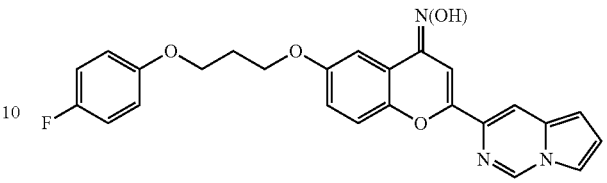

MS (ESI+): 446.0 [C$_{25}$H$_{20}$FN$_3$O$_4$+H]$^+$ (m/z).
1H NMR: (400 MHz) DMSO-d$_6$ δ (ppm): 10.93 (br. s, 1H), 9.21 (s, 1H), 8.04 (s, 1H), 7.82 (s, 1H), 7.44 (s, 1H), 7.41 (d, J=9.2 Hz, 1H), 7.33 (s, 1H), 7.15-7.09 (m, 3H), 7.00-6.96 (m, 3H), 7.74 (d, J=3.2 Hz, 1H), 4.18-4.11 (m, 4H), 2, 20-117 (m, 2H).

Example 161A

6-[3-(4-Fluoro-phenoxy)-propoxy]-2-pyrrolo[1,2-c]pyrimidin-3-yl-chromen-4-one O-tert-butyl-oxime A mixture of 6-(3-chloro-propoxy)-2-pyrrolo[1,2-c]pyrimidin-3-yl-chromen-4-one O-tert-butyl-oxime (example 101A) (125 mg, 0.29 mmol), potassium carbonate (120 mg, 0.87 mmol), potassium iodide (48 mg, 0.29 mmol) and 4-fluorophenol (65 mg, 0.58 mmol), in butanone (3.5 ml) was heated in a sealed tube at 130° C. for 18 hours. The reaction mixture was diluted with water and extracted with ethyl acetate. The organic layers were washed with, brine, dried over sodium sulfate, filtered and concentrated. The residue was purified by flash chromatography over silica gel (gradient cyclohexane/dichloromethane: 0-100%) to yield the title compound (100 mg, 69%) as a yellow solid.

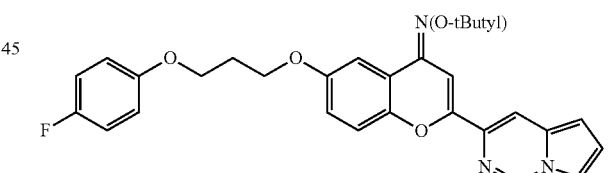

1H NMR: (300 MHz) CHCl$_3$-d$_1$ δ (ppm): 8.78 (s, 1H), 7.90 (s, 1H), 7.55 (d, J=2.8 Hz, 1H), 7.50 (s, 1H), 7.44 (d, J=2.6 Hz, 1H), 7.20 (d, J=8.8 Hz, 1H), 7.00-6.84 (m, 6H), 6.63 (d, J=3.8 Hz, 1H), 4.22 (t, J=6.0 Hz, 2H), 4.15 (t, J=6.0 Hz, 2H), 2.28 (quint., J=6.2 Hz, 2H), 1.42 (s, 9H).

Example 162

6-(3-Phenoxy-propoxy)-2-pyrrolo[1,2-c]pyrimidin-3-yl-chromen-4-one oxime was prepared in 24% overall yield using the method described in example 161, starting from 6-(3-chloro-propoxy)-2-pyrrolo[1,2-c]pyrimidin-3-yl-chromen-4-one O-tert-butyl oxime (example 101A) and phenol.

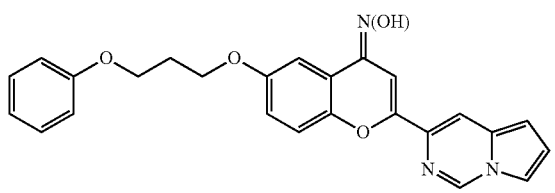

MS (ESI+): 428.1 [$C_{25}H_{21}FN_3O_4$+H]$^+$ (m/z).
Mixture 80:20 of E-Z isomers
1H NMR of the major Z isomer: (300 MHz) DMSO-$d_6$ δ (ppm): 10.90 (s, 1H), 9.21 (s, 1H), 8.04 (s, 1H), 7.81 (s, 1H), 7.43-7.25 (m, 5H), 7.13 (dd, J=9.1 Hz, J=3.0 Hz, 1H), 6.98-6.90 (m, 4H), 6.73 (d, J=3.8 Hz, 1H), 4.18-4.11 (m, 4H), 2.20-2.17 (m, 2H).

Example 163

6-[3-(3-Fluoro-phenoxy)-propoxy]-2-pyrrolo[1,2-c]pyrimidin-3-yl-chromen-4-one oxime was prepared in 46% overall yield using the method described in example 161, starting from 6-(3-chloro-propoxy)-2-pyrrolo[1,2-c]pyrimidin-3-yl-chromen-4-one O-tert-butyl oxime (example 101A) and 3-fluorophenol.

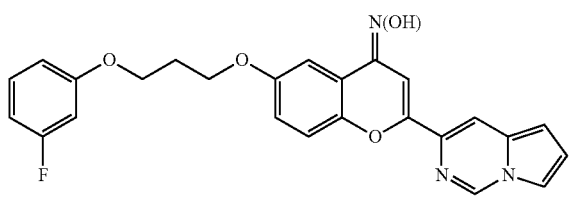

MS (ESI+): 446.0 [$C_{25}H_{20}FN_3O_4$+H]$^+$ (m/z).
1H NMR: (400 MHz) DMSO-$d_6$ δ (ppm): 10.93 (s, 1H), 9.21 (s, 1H), 8.04 (s, 1H), 7.81 (s, 1H), 7.44 (s, 1H), 7.41 (d, J=8.8 Hz, 1H), 7.34-7.30 (m, 2H), 7.13 (dd, J=9.2 Hz, J=3.0 Hz, 1H), 6.98 (dd, J=3.6 Hz, J=2.8 Hz, 1H), 6.87-6.73 (m, 4H), 4.18-4.11 (m, 4H), 2.23-2.17 (m, 2H).

Example 164

6-[3-(3,4-Difluoro-phenoxy)-propoxy]-2-pyrrolo[1,2-c]pyrimidin-3-yl-chromen-4-one oxime was prepared in 53% overall yield using the method described in example 161, starting from 6-(3-chloro-propoxy)-2-pyrrolo[1,2-c]pyrimidin-3-yl-chromen-4-one O-tert-butyl oxime (example 101A) and 3,4-difluorophenol.

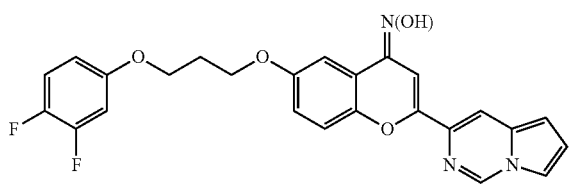

MS (ESI+): 464.1 [$C_{25}H_{19}F_2N_3O_4$+H]$^+$ (m/z).
1H NMR: (400 MHz) DMSO-$d_6$ δ (ppm): 10.93 (br. s, 1H), 9.21 (s, 1H), 8.04 (s, 1H), 7.81 (s, 1H), 7.44-7.30 (m, 4H), 7.16-7.07 (m, 2H), 6.98 (dd, J=3.6 Hz, J=2.8 Hz, 1H), 6.82-6.80 (m, 1H), 6.74 (d, J=3.6 Hz, 1H), 4.18-4.11 (m, 4H), 2.23-2.17 (m, 2H).

Example 165

6-(2-[1,4]Oxazepan-4-yl-ethoxy)-2-thieno[3,2-c]pyridin-6-yl-chromen-4-one oxime, hydrochloride was prepared in 18% yield using method D (step 2), and the procedure described in example 87A starting from 6-(2-chloro-ethoxy)-2-thieno[3,2-c]pyridin-6-yl-chromen-4-one oxime O-tert-butyl oxime (example 165A) and [1,4]oxazepane. The hydrochloride salt of the title compound was isolated as an orange solid after treatment with a 1.25 M solution of hydrogen chloride in isopropanol.

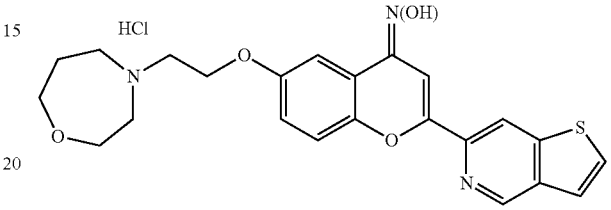

Mp: 223-226° C.
MS (ESI+): 438.2 [$C_{23}H_{23}N_3O_4S$+H]$^+$ (m/z).
1H NMR: (300 MHz) DMSO-$d_6$ δ (ppm): 11.11 (br. s, 1H), 10.83 (br. s, 1H), 9.27 (s, 1H), 8.78 (s, 1H), 8.05 (d, J=5.2 Hz, 1H), 7.73 (d, J=5.5 Hz, 1H), 7.69 (s, 1H), 7.51 (d, J=9.2 Hz, 1H), 7.41 (d, J=3.0 Hz, 1H), 7.24 (dd, J=9.0 Hz, J=3.0 Hz, 1H), 4.47 (m, 2H), 3.87 (m, 2H), 3.77 (m, 2H), 3.62 (m, 4H), 3.41 (m, 2H), 2.26 (m, 1H), 2.05 (m, 1H).

Example 165A 6-(2-chloro-ethoxy)-2-thieno[3,2-c]pyridin-6-yl-chromen-4-one oxime O-tert-butyl oxime was prepared in 41% yield using the method described in example 85A, starting from 6-hydroxy-2-thieno[3,2-c]pyridin-6-yl-chromen-4-one oxime O-tert-butyl-oxime (example 127B) in dimethylformamide.

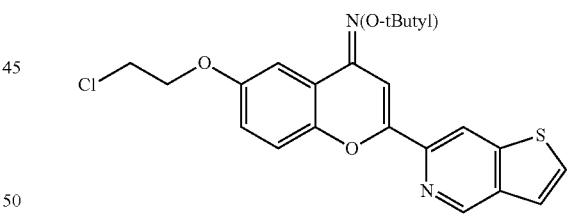

1H NMR: (300 MHz) CHCl$_3$-$d_1$ δ (ppm): 9.16 (s, 1H), 8.46 (s, 1H), 7.72 (s, 1H), 7.59 (d, J=5.5 Hz, 1H), 7.53 (d, J=3.0 Hz, 1H), 7.50 (d, J=5.5 Hz, 1H), 7.27 (m, 2H), 7.02 (dd, J=9.0 Hz, J=3.0 Hz, 1H), 4.31 (t, J=5.8 Hz, 2H), 3.85 (t, J=5.8 Hz, 2H), 1.42 (s, 9H).

Example 166

6-[2-(3,4-Dihydro-1H-isoquinolin-2-yl)-ethoxy]-2-thieno[3,2-c]pyridin-6-yl-chromen-4-one oxime, hydrochloride was prepared in 7.5% overall yield using the method described in example 165, starting from 6-(2-chloro-ethoxy)-2-thieno[3,2-c]pyridin-6-yl-chromen-4-one oxime O-tert-butyl oxime (example 165A) and 1,2,3,4-tetrahydro-isoquinoline.

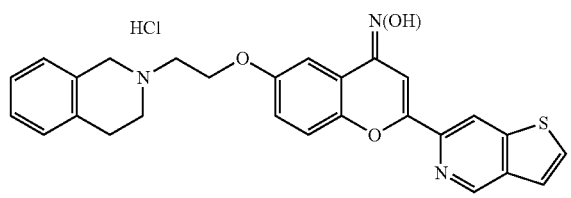

Mp: 234-237° C.
MS (ESI+): 470.2 [C$_{27}$H$_{23}$N$_3$O$_3$S+H]$^+$ (m/z).
1H NMR: (300 MHz) DMSO-d$_6$ δ (ppm): 11.03 (br. s, 2H), 9.27 (s, 1H), 8.80 (s, 1H), 8.06 (d, J=5.5 Hz, 1H), 7.73 (d, J=5.5 Hz, 1H), 7.70 (s, 1H), 7.52 (d, J=9.0 Hz, 1H), 7.45 (d, J=3.0 Hz, 1H), 7.30-7.20 (m, 5H), 4.40-4.80 (m, 2H), 3.85 (m, 1H), 3.70 (m, 2H), 3.60-3.20 (m, 2H), 3.10-3.00 (m, 1H), 1.90 (m, 2H).

Example 167

6-[2-(4-fluoro-piperidin-1-yl)-ethoxy]-2-thieno[3,2-c]pyridin-6-yl-chromen-4-one oxime, hydrochloride was prepared in 25% overall yield using the method described in example 165, starting from 6-(2-chloro-ethoxy)-2-thieno[3,2-c]pyridin-6-yl-chromen-4-one oxime O-tert-butyl oxime (example 165A) and 4-fluoropiperidine hydrochloride.

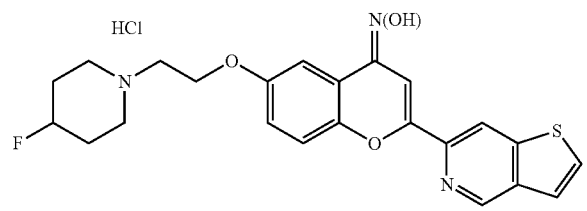

MS (ESI+): 440.1 [C$_{23}$H$_{22}$FN$_3$O$_3$S+H]$^+$ (m/z).
1H NMR: (400 MHz) DMSO-d$_6$ δ (ppm): 11.10 (br. s, 1H), 10.79 (br. s, 1H), 9.27 (s, 1H), 8.78 (s, 1H), 8.06 (d, J=3.9 Hz, 1H), 7.73 (d, J=3.9 Hz, 1H), 7.70 (s, 1H), 7.51 (d, J=6.6 Hz, 1H), 7.42 (s, 1H), 7.24 (d, J=6.9 Hz, 1H), 5.07, 5.95 (2×m, 1H), 4.45 (m, 2H), 3.65-3.45 (m, 4H), 3.35-3.10 (m, 2H), 2.30-2.00 (m, 4H).

Example 168

6-[2-(1,1-Dioxo-1-thiomorpholin-4-yl)-ethoxy]-2-thieno[3,2-c]pyridin-6-yl-chromen-4-one oxime, hydrochloride was prepared in 4% overall yield using the method described in example 165, starting from 6-(2-chloro-ethoxy)-2-thieno[3,2-c]pyridin-6-yl-chromen-4-one oxime O-tert-butyl oxime (example 165A) and thiomorpholine-1,1-dioxide.

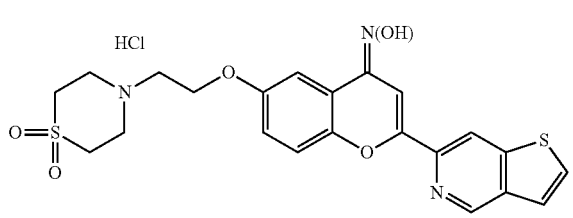

Mp: 195-197° C.
MS (ESI+): 472.2 [C$_{22}$H$_{21}$N$_3$O$_5$S$_2$+H]$^+$ (m/z).

1H NMR: (300 MHz) DMSO-d$_6$ δ (ppm): 11.05 (br. s, 1H), 9.25 (s, 1H), 8.76 (s, 1H), 8.05 (d, J=5.5 Hz, 1H), 7.72 (d, J=5.5 Hz, 1H), 7.68 (s, 1H), 7.50 (d, J=9.0 Hz, 1H), 7.40 (d, J=3.0 Hz, J=2.8 Hz, 1H), 7.23 (dd, J=9.0 Hz, J=3.0 Hz, 1H), 4.42 (m, 2H), 3.60 (m, 4H), 3.43 (m, 6H).

Example 169

6-(1-Pyrimidin-2-yl-piperidin-4-yloxy)-2-thieno[3,2-c]pyridin-6-yl-chromen-4-one oxime was prepared in 9% yield using method D (step 2), starting from 6-(1-Pyrimidin-2-yl-piperidin-4-yloxy)-2-thieno[3,2-c]pyridin-6-yl-chromen-4-one O-tert-butyl-oxime (example 169A).

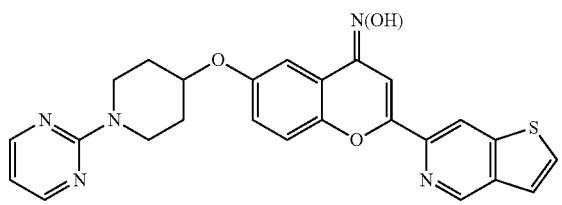

MS (ESI+): 472.1 [C$_{25}$H$_{21}$N$_5$O$_3$S+H]$^+$ (m/z).
1H NMR: (400 MHz) DMSO-d$_6$ δ (ppm): 11.20 (br. s, 1H), 9.28 (d, J=0.8 Hz, 1H), 8.82 (s, 1H), 8.43 (d, J=4.8 Hz, 2H), 8.06 (d, J=5.2 Hz, 1H), 7.74 (dd, J=5.2 Hz, J=0.8 Hz, 1H), 7.69 (s, 1H), 7.50 (d, J=9.2 Hz, 1H), 7.43 (d, J=3.2 Hz, 1H), 7.24 (dd, J=9.2 Hz, J=3.2 Hz, 1H), 6.71 (t, J=5.2 Hz, 1H), 4.72 (quint., J=4 Hz, 1H), 4.22-4.16 (m, 2H), 3.63-3.57 (m, 2H), 207-2.02 (m, 21-t), 1.68-1.65 (m, 2H).

Example 169A 6-(1-Pyrimidin-2-yl-piperidin-4-yloxy)-2-thieno[3,2-c]pyridin-6-yl-chromen-4-one O-tert-butyl-oxime was prepared using the procedure described in example 85A, starting from 6-Hydroxy-2-thieno[3,2-c]pyridin-6-yl-chromen-4-one O-tert-butyl-oxime (example 127B) and methanesulfonic acid 1-pyrimidin-2-yl-piperidin-4-yl ester (example 169B) in dimethylformamide.

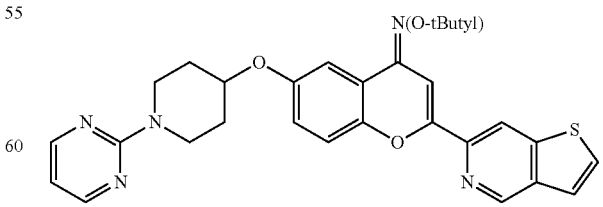

HPLC (gradient 5-95% ACN/H$_2$O+0.1% HCOOH): RT=6.63 min.
MS (ESI+): 528.3 [C$_{29}$H$_{29}$N$_5$O$_3$S+H]$^+$ (m/z).

Example 169B

Methanesulfonic acid 1-pyrimidin-2-yl-piperidin-4-yl ester

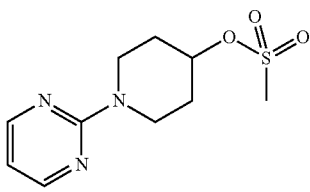 [SMILES: CS(=O)(=O)OC1CCN(c2ncccn2)CC1]

To a cooled solution of 1-Pyrimidin-2-yl-piperidin-4-ol (WO2008/8895 A1), (100 mg; 0.55 mmol) and triethylamine (233 μL, 1.67 mmol) in dry dichloromethane (1 mL), was added methanesulfonyl chloride (52 μL, 0.67 mmol). The reaction mixture was stirred at room temperature for 5 hours. Water was added. After extraction with dichloromethane, the combined organic extracts were dried over sodium sulfate and concentrated to afford a crude product that was used in the next step without further purification.

1H NMR: (300 MHz) CHCl$_3$-d$_1$ δ (ppm): 8.30 (d, J=4.7 Hz, 2H), 6.49 (t, J=4.7 Hz, 1H), 4.97 (m, 1H), 4.20 (m, 2H), 3.64 (m, 2H), 3.05 (s, 3H), 2.09 (m, 1.89 (m, 2H).

Example 170

6-(3,4,5,6-Tetrahydro-2H[1,2']bipyridinyl-4-yloxy)-2-thieno[3,2-c]pyridin-6-yl-chromen-4-one oxime was prepared in 6% overall yield using the method described in example 169, starting from 6-Hydroxy-2-thieno[3,2-c]pyridin-6-yl-chromen-4-one O-tert-butyl-oxime (example 127B) and methanesulfonic acid 3,4,5,6-tetrahydro-2H-[1,2]bipyridinyl-4-yl ester (example 170A).

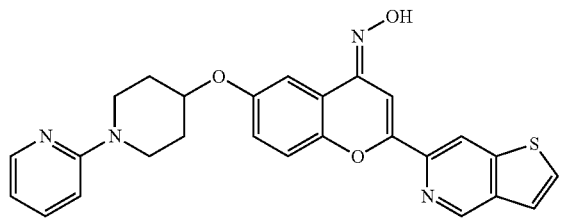 [SMILES: O/N=c1\cc(-c2cc3sccc3cn2)oc2ccc(OC3CCN(c4ccccn4)CC3)cc12]

MS (ESI+): 471.1 [C$_{26}$H$_{22}$N$_4$O$_3$S+H]$^+$ (m/z).

1H NMR: (400 MHz) DMSO-d$_6$ δ (ppm): 11.04 (br. s, 1H), 9.26 (d, J=0.8 Hz, 1H), 8.77 (s, 1H), 8.06-8.01 (m, 3H), 7.73 (dd, J=5.2 Hz, J=0.8 Hz, 1H), 7.69 (s, 1H), 7.50-7.42 (m, 3H), 7.25 (dd, J=8.8 Hz, J=2.8 Hz, 1H), 6.94 (t, J=6.8 Hz, 1H), 4.78 (quint., J=4 Hz, 1H), 3.92-3.91 (m, 2H), 3.71-3.65 (m, 2H), 2.13-2.11 (m, 2H), 1.83-1.81 (m, 2H).

Example 170A

Methanesulfonic acid 3,4,5,6-tetrahydro-2H-[1,2']bipyridinyl-4-yl ester was prepared in 48% overall yield using the method described in example 169B, starting from 3,4,5,6-Tetrahydro-2H-[1,2]bipyridinyl-4-ol (WO2008/62276 A2).

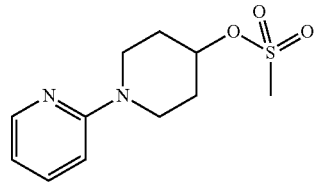 [SMILES: CS(=O)(=O)OC1CCN(c2ccccn2)CC1]

1H NMR: (300 MHz) CHCl$_3$-d$_1$ δ (ppm): 8.19-8.16 (m, 1H), 7.51-7.45 (m, 1H), 6.66 (dd, J=13.8 Hz, J=8.6 Hz, 1H), 6.63-6.60 (m, 1H), 4.96-4.92 (m, 1H), 3.96-3.88 (m, 2H), 3.45-3.36 (m, 2H), 3.11-3.07 (m, 2H), 3.04 (s, 3H), 2.12-2.04 (m, 2H), 1.98-1.89 (m, 2H).

Example 171

Human mGluR4 Positive Allosteric Modulator Evaluation Using Ca$^{++}$ Functional Assay Compounds of the present invention were tested successively for their agonist and positive allosteric modulator activities on human mGluR4 transiently over-expressed in HEK-293 cells. They exert agonist activity if, by themselves in absence of the endogenous glutamate, they are able to activate mGluR4; and they exert positive allosteric modulator activity if they increase the action of the endogenous glutamate.

Cell Culture and Transfection

HEK-293 cells were maintained in Modified Eagle's Medium supplemented with 10% Foetal Calf Serum, 1% Penicillin/Streptomycin and 1% non essential amino acids at 37° C./5% CO$_2$.

Cells were co-transfected by electroporation with two DNA plasmids encoding hmGluR4 and a chimeric G protein allowing redirection of the activation signal to intracellular calcium pathway. Cells were plated after transfection onto polyornithine coated, clear bottom, black-walled, 96-well plates and cultured for 24 h.

Calcium Assay EC$_{50}$ Determination

Receptor activity was detected by changes in intracellular calcium measured using the fluorescent Ca$^{2+}$ sensitive dye, Fluo4AM (Molecular Probes).

The day of the assay, medium was aspirated and replaced during 3 hours by medium without serum supplemented with 1% Glutamax, 1% Penicillin/Streptomycin and 1% non essential amino acids. Then, cells were washed with freshly prepared buffer B (HBSS 1×(PAA), Hepes 20 mM, MgSO$_4$-7H$_2$O 1 mM, Na$_2$CO$_3$ 3.3 mM, CaCl$_2$-2H$_2$O 1.3 mM, 0.5% BSA, Probenecid 2.5 mM) and loaded at 37° C. in 5% CO$_2$ for 1.5 hours with buffer B containing 1 μM Fluo4AM 0.1 mg/mL Pluronic Acid, 7 μg/mL Glutamate Pyruvate Transaminase and 2 mM sodium pyruvate. Afterwards cells were washed twice with buffer B and 50 μL of this buffer were added to each well. Addition of compounds and intracellular Ca$^{2+}$ measurements (excitation 485 nm, emission 525 nm) were performed by the fluorescence microplate reader FlexStation (Molecular Devices).

Agonist and positive allosteric modulator activities of compounds were consecutively evaluated on the same cells plate. Agonist activity was first tested during 60 s with the addition of compound alone on the cells. Then, the cells were stimulated by an EC$_{10}$ glutamate concentration and fluorescence recorded for additional 60 s. EC$_{10}$ glutamate concentration is the concentration giving 10% of the maximal glutamate response. Agonist and/or positive allosteric modulator activity(ies) were evaluated in comparison to basal signal evoked by $EC_{10}$ glutamate alone.

For $EC_{50}$ determination, a dose-response test was performed using 6 to 9 concentrations of each compound of the invention. Dose-response curves were fitted using the sigmoidal dose-response (variable slope) analysis in GraphPad Prism program (Graph Pad Inc) and $EC_{50}$ of agonist/positive allosteric modulator activity was calculated. Dose-response experiments were all performed in duplicate, two times independently.

Compounds of the present invention can either be mix agonists/positive allosteric modulators or pure positive allosteric modulators. Their $EC_{50}$ are preferably 5 µM or less, more preferably 1 µM or less.

The following lists represent the mean $EC_{50}$ obtained for selected compounds of the present invention:

Examples with an $EC_{50}<1$ µM: 1, 4, 5, 20, 23, 28, 37, 43, 51, 53, 61, 62, 63, 67, 69, 70, 73, 81, 83, 85, 91, 94, 96, 97, 98, 99, 101, 102, 103, 104, 105, 106, 107, 108, 109, 111, 112, 113, 114, 115, 116, 117, 118, 119, 123, 124, 125, 126, 127, 128, 129, 130, 131, 132, 133, 134, 135, 137, 138, 139, 140, 141, 142, 143, 146, 147, 148, 149, 150, 152, 156, 158, 159, 160, 161, 162, 163, 164.

Examples with an $EC_{50}<5$ µM: 2, 6, 10, 11, 15, 21, 22, 24, 26, 30, 31, 34, 36, 39, 41, 42, 44, 52, 54, 55, 56, 57, 58, 65, 66, 71, 76, 77, 78, 87, 88, 92, 93, 95, 121, 136, 144, 151, 153, 157.

Example 172

In-Vivo Evaluation in the Haldoperidol-Induced Catalepsy Model in the Mouse

Introduction

This method, which detects anti-Parkinsonian activity, follows that described by Pires et al. (*J Med and Biol Res* 38 1867-1872, 2005; Shiozaki et al., *Psychopharmacology* 147, 90-95, 1999)

Protocol

Catalepsy was assessed using the bar test in mice submitted to acute intra-peritoneal administration of Haloperidol 1 mg/kg. Mice (male Rj: NMRI mice, weighing 25-30 g at the beginning of the experiment) placed in group of 5 in Plexiglas cages, were injected with Haloperidol (1 mg/kg i.p.). Within 15 min after Haloperidol administration, mice were calm and showed slow spontaneous activity. The catalepsy response of one mouse was measured as the time the animal maintained an imposed posture with both forelimbs placed on a horizontal 0.9 cm diameter wire bar suspended 4 cm above a platform. The end point of catalepsy was considered to occur when both forelimbs were removed from the bar, the mouse climbed onto the bar or if the animal moved its head in an exploratory manner. A cut-off time of 180 seconds was applied. The degree of catalepsy was scored 45 min after Haloperidol administration and continued at 45 minutes intervals for a total of 270 minutes. Between determinations, the animals were returned to their home cages. The compound of Example 63, administered i.p. consecutively with haloperidol, was evaluated at 30 mg/kg and compared with a vehicle control group. The FIG. 1 shows the mean time of latency spent on the bar in each group of animals. At each time-point, the anticataleptic effect of compound of Example 63 was compared to vehicle-treated group using ANOVA test followed by the Dunnett's test.

Results

It can be clearly observed in FIG. 1 that the compound of Example 63 at the dose of 30 mg/kg administered i.p. consecutively with haloperidol exerts a significant anticataleptic activity.

Example 173

In-Vivo Evaluation in the Marble Burying Test in the Mouse

Introduction

The method, which detects anxiolytic/tranquilizing activity, follows that described by Broekkamp at al. (*Eur. J. Pharmacol.*, 126, 223-229, 1986). Mice exposed to novel object (marbles) will bury them in the sawdust floor covering. Anxiolytics decrease the number of marbles buried at non-sedative doses.

Protocol

Mice were individually placed in transparent plastic cages (33×21×18 cm) with 5 cm of sawdust on the floor and 25 marbles grouped in the centre of the cage. The cage was covered with an inverted plastic cage. Each test cage, together with the marbles, was impregnated with mouse odor beforehand by leaving 10 mice in the cage for 15 minutes. These mice then played no further role in the experiment. The number of marbles covered by sawdust (⅔ or more) was counted at the end of a 30 minute test. 12 mice were studied per group. The test was performed blind (apart from positive control). The compound of Example 85 was evaluated at 2 doses (100 and 300 mg/kg), administered p.o. 30 minutes before the test, and compared with vehicle control groups. Clobazam (8 mg/kg i.p.), administered 30 minutes before the test, was used as reference substance and was compared with the vehicle control group. Data were analyzed by comparing treated groups with control group using unpaired Student's t tests.

Results

Figure 2:
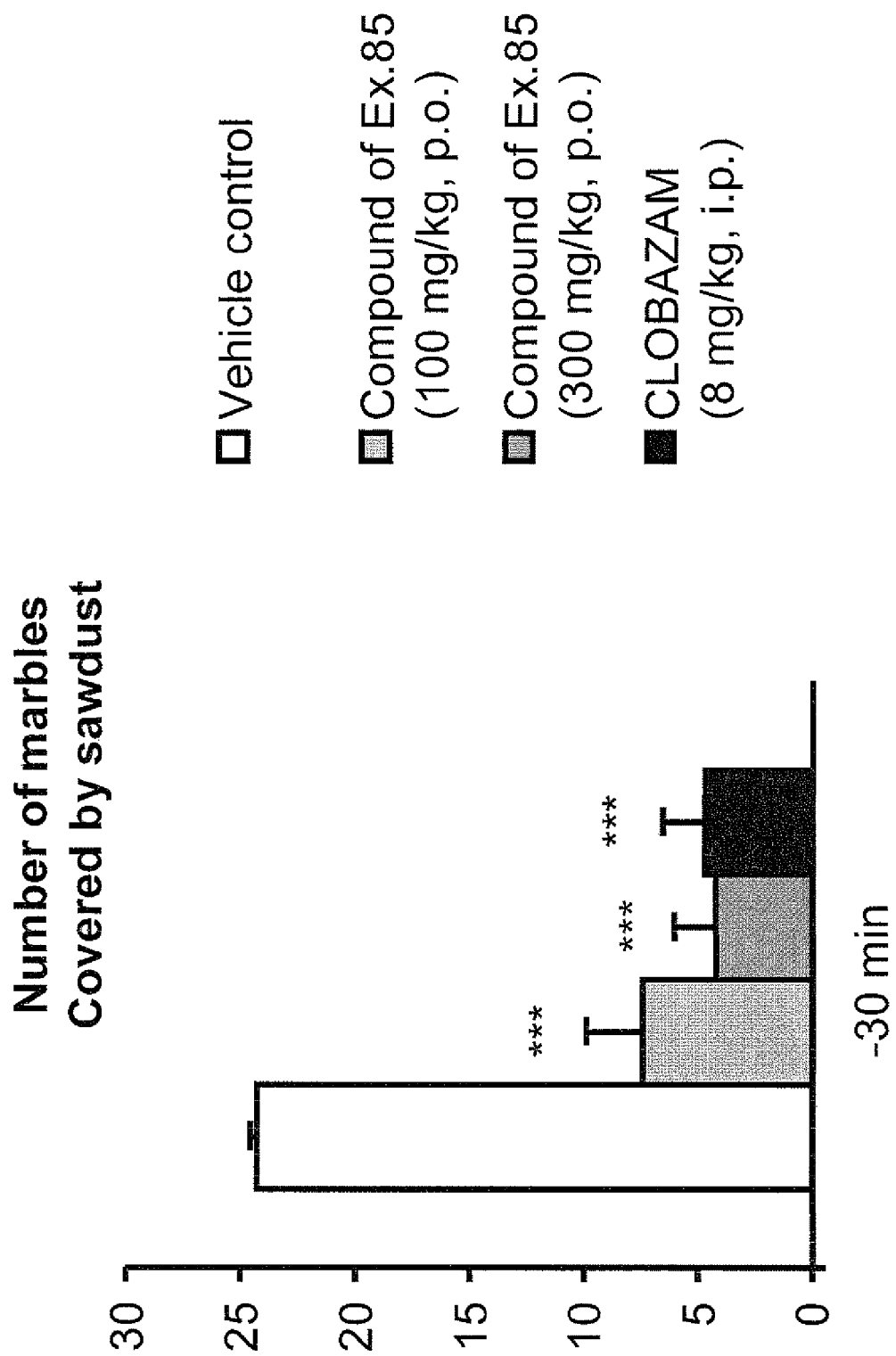
FIG. 2: Effect of the compound of Example 85 in the marble burying test in the mouse, administered p.o. at 100 or 300 mg/kg (see Example 173}. The figure shows the mean number of marbles burying in each group of animals, as also explained in Example 173.

The compound of Example 85 (100 and 300 mg/kg), administered p.o. 30 minutes before the test, markedly and dose-dependently decreased the number of marbles covered by sawdust, as compared with vehicle controls (−70% and −83%, respectively, p<0.001). The FIG. 2 shows the mean number of marbles burying in each group of animals.

The invention claimed is:
1. A compound of the general formula (I)

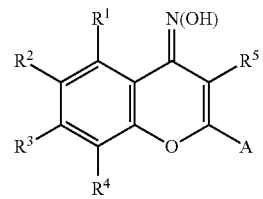

wherein:
$R^1$, $R^2$, $R^3$, and $R^4$ each independently represent a -L-R group, wherein:
L is selected from a bond, $C_1$-$C_{10}$ alkylene, $C_2$-$C_{10}$ alkenylene, or $C_2$-$C_{10}$ alkynylene, wherein said alkylene, said alkenylene or said alkynylene is optionally substituted with one or more groups independently selected from halogen, —$CF_3$, —CN, —OH, or —$NH_2$, and further wherein one or more —$CH_2$— units comprised in said alkylene, said alkenylene or said alkynylene are each optionally replaced by a group independently selected from: —O—, —NR$^{11}$—, —CO—, —S—, —SO—, or —SO$_2$—;

R is selected from hydrogen, C$_1$-C$_{10}$ alkyl, halogen, optionally substituted aryl, optionally substituted heteroaryl, optionally substituted cycloalkyl, optionally substituted heterocycloalkyl, —NR$^{11}$R$^{12}$, —OR$^{11}$, —SR$^{11}$, —SOR$^{11}$, —SO$_2$R$^{11}$, —CF$_3$, or —CN, wherein said optionally substituted aryl, said optionally substituted heteroaryl, said optionally substituted cycloalkyl, or said optionally substituted heterocycloalkyl may be substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl), —N(C$_1$-C$_4$ alkyl)(C$_1$-C$_4$ alkyl) wherein the two C$_1$-C$_4$ alkyl moieties of said —N(C$_1$-C$_4$ alkyl)(C$_1$-C$_4$ alkyl) are optionally mutually linked to form a ring together with the nitrogen atom which they are attached to, or -L$^1$-R$^{13}$;

R$^{11}$ and R$^{12}$ are each independently selected from hydrogen, optionally substituted C$_1$-C$_{10}$ alkyl, optionally substituted aryl, optionally substituted heteroaryl, optionally substituted cycloalkyl, optionally substituted heterocycloalkyl, or —CF$_3$, wherein said optionally substituted alkyl, said optionally substituted aryl, said optionally substituted heteroaryl, said optionally substituted cycloalkyl, or said optionally substituted heterocycloalkyl may be substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl), or —N(C$_1$-C$_4$ alkyl)(C$_1$-C$_4$ alkyl) wherein the two C$_1$-C$_4$ alkyl moieties of said —N(C$_1$-C$_4$ alkyl)(C$_1$-C$_4$ alkyl) are optionally mutually linked to form a ring together with the nitrogen atom which they are attached to;

L$^1$ is selected from a bond, C$_1$-C$_{10}$ alkylene, C$_2$-C$_{10}$ alkenylene, or C$_2$-C$_{10}$ alkynylene, wherein one or two —CH$_2$— units comprised in said alkylene, said alkenylene or said alkynylene are each optionally replaced by a group independently selected from —O—, —NH—, —N(C$_1$-C$_4$ alkyl)-, —CO—, —S—, —SO—, or —SO$_2$—;

R$^{13}$ is selected from hydrogen, C$_1$-C$_4$ alkyl, halogen, optionally substituted phenyl, optionally substituted heteroaryl, optionally substituted cycloalkyl, optionally substituted heterocycloalkyl, —NH$_2$, —NH(C$_1$-C$_4$ alkyl), —N(C$_1$-C$_4$ alkyl)(C$_1$-C$_4$ alkyl), —OH, —O(C$_1$-C$_4$ alkyl), —SH, —S(C$_1$-C$_4$ alkyl), —CF$_3$, or —CN, wherein said optionally substituted phenyl, said optionally substituted heteroaryl, said optionally substituted cycloalkyl, or said optionally substituted heterocycloalkyl may be substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl), or —N(C$_1$-C$_4$ alkyl)(C$_1$-C$_4$ alkyl) wherein the two C$_1$-C$_4$ alkyl moieties of said —N(C$_1$-C$_4$ alkyl)(C$_1$-C$_4$ alkyl) are optionally mutually linked to form a ring together with the nitrogen atom which they are attached to;

R$^5$ is selected from hydrogen, C$_1$-C$_4$ alkyl, halogen, —CF$_3$, —CN, —OH, —O(C$_1$-C$_4$ alkyl), —COOH, —COO(C$_1$-C$_4$ alkyl), —CONH$_2$, —CONH(C$_1$-C$_4$ alkyl), —CON(C$_1$-C$_4$ alkyl)(C$_1$-C$_4$ alkyl), wherein the two C$_1$-C$_4$ alkyl moieties of said —CON(C$_1$-C$_4$ alkyl)(C$_1$-C$_4$ alkyl) are optionally mutually linked to form a ring together with the nitrogen atom which they are attached to, —NH$_2$, —NH(C$_1$-C$_4$ alkyl), or —N(C$_1$-C$_4$ alkyl)(C$_1$-C$_4$ alkyl), wherein the two C$_1$-C$_4$ alkyl moieties of said —N(C$_1$-C$_4$ alkyl)(C$_1$-C$_4$ alkyl) are optionally mutually linked to form a ring together with the nitrogen atom which they are attached to;

A is a bicyclic moiety corresponding to formula (II):

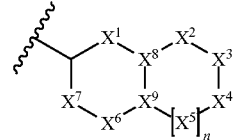

which may be saturated or unsaturated, and wherein:

n is 0 or 1;

X$^1$ to X$^6$ are each independently selected from N, N(R$^{x1}$), C(R$^{x2}$), C(R$^{x2}$)(R$^{x3}$), O, S, S(O), S(O)$_2$, or C(O);

X$^7$ is N or N(R$^{x1}$);

any of groups X$^1$ to X$^7$ containing a nitrogen atom may form an N-oxide group;

X$^8$ and X$^9$ are each independently selected from N, C, or C(R$^{x2}$);

each R$^{x1}$ is independently selected from hydrogen, C$_1$-C$_4$ alkyl, —OH, —O(C$_1$-C$_4$ alkyl), or —(C$_1$-C$_4$ alkylene)-phenyl; and each R$^{x2}$ and each R$^{x3}$ is independently selected from hydrogen, C$_1$-C$_4$ alkyl, halogen, —CF$_3$, —CN, —OH, —O(C$_1$-C$_4$ alkyl), —COOH, —COO(C$_1$-C$_4$ alkyl), —CONH$_2$, —CONH(C$_1$-C$_4$ alkyl), —CON(C$_1$-C$_4$ alkyl)(C$_1$-C$_4$ alkyl), —NH$_2$, —NH(C$_1$-C$_4$ alkyl), or —N(C$_1$-C$_4$ alkyl)(C$_1$-C$_4$ alkyl), wherein the two C$_1$-C$_4$ alkyl moieties of said —N(C$_1$-C$_4$ alkyl)(C$_1$-C$_4$ alkyl) or of said —CON(C$_1$-C$_4$ alkyl)(C$_1$-C$_4$ alkyl) are optionally mutually linked to form a ring together with the nitrogen atom which they are attached to;

or a pharmaceutically acceptable salt or solvate thereof.

2. The compound of claim 1, wherein L is a bond, C$_1$-C$_6$ alkylene, C$_2$-C$_6$ alkenylene, or C$_2$-C$_6$ alkynylene, wherein one or two —CH$_2$— units comprised in said alkylene, said alkenylene or said alkynylene are each optionally replaced by a group independently selected from —O—, —NR$^{11}$—, —CO—, or —S—.

3. The compound of claim 1, wherein R is selected from: hydrogen; optionally substituted aryl; optionally substituted heteroaryl having 5 or 6 ring atoms, wherein 1, 2, or 3 ring atoms are each independently selected from O, S, or N and the other ring atoms are carbon atoms; optionally substituted heterocycloalkyl having 3 to 10 ring atoms, wherein one or more ring atoms are each independently selected from O, S, or N and the other ring atoms are carbon atoms; —NH(C$_1$-C$_4$ alkyl); —N(C$_1$-C$_4$ alkyl)(C$_1$-C$_4$ alkyl); or —O(C$_1$-C$_4$ alkyl); wherein said optionally substituted aryl, said optionally substituted heteroaryl or said optionally substituted heterocycloalkyl may be substituted with one or more groups independently selected from C$_1$-C$_4$ alkyl, halogen, —CF$_3$, —CN, —OH, —O(C$_1$-C$_4$ alkyl), —NH$_2$, —NH(C$_1$-C$_4$ alkyl), —N(C$_1$-C$_4$ alkyl)(C$_1$-C$_4$ alkyl) wherein the two C$_1$-C$_4$ alkyl moieties of said —N(C$_1$-C$_4$ alkyl)(C$_1$-C$_4$ alkyl) are optionally mutually linked to form a ring together with the nitrogen atom which they are attached to, or -L$^1$-R$^{13}$.

4. The compound of claim 1, wherein R$^1$ and R$^4$ are each hydrogen, one of R$^2$ and R$^3$ is hydrogen, and the other one of R$^2$ and R$^3$ is selected from: hydrogen; C$_1$-C$_4$ alkyl; —(C$_1$-C$_3$ alkylene)-O—(C$_1$-C$_2$ alkyl); —(C$_2$-C$_4$ alkynylene)-phenyl; —OH; —O(C$_1$-C$_4$ alkyl); —O(C$_1$-C$_2$ alkylene)-O—(C$_1$-C$_2$ alkyl); —(C$_1$-C$_4$ alkylene)-morpholinyl; —O(C$_1$-C$_4$ alkylene)-phenyl; —O(C₁-C₄ alkylene)-imidazolyl; —O(C₁-C₄ alkylene)-pyrrolidinyl; —O(C₁-C₄ alkylene)-piperidinyl; —O(C₁-C₄ alkylene)-morpholinyl; —O(C₁-C₄ alkylene)-oxazepanyl; —O(C₁-C₄ alkylene)-(2-oxa-5-aza-bicyclo[2.2.1]hept-5-yl); —O(C₁-C₄ alkylene)-piperazinylene-(C₁-C₄ alkyl); or —O(C₁-C₄ alkylene)-diazepanylene-(C₁-C₄ alkyl); wherein the phenyl moiety, the imidazolyl moiety, the pyrrolidinyl moiety, the piperidinyl moiety, the morpholinyl moiety, the oxazepanyl moiety, the 2-oxa-5-aza-bicyclo[2.2.1]hept-5-yl moiety, the piperazinylene moiety, and the diazepanylene moiety are each optionally substituted with one or more groups independently selected from halogen, —CF₃, C₁-C₄ alkyl, —(C₁-C₄ alkylene)-OH, —(C₁-C₄ alkylene)-O—(C₁-C₄ alkyl), —OH, —O(C₁-C₄ alkyl), —O—(C₁-C₄ alkylene)-O—(C₁-C₄ alkyl), —NH₂, —NH(C₁-C₄ alkyl), or —N(C₁-C₄ alkyl)(C₁-C₄ alkyl) wherein the two C₁-C₄ alkyl moieties of said —N(C₁-C₄ alkyl)(C₁-C₄ alkyl) are optionally mutually linked to form a ring together with the nitrogen atom which they are attached to.

5. The compound of claim 1, wherein $R^5$ is hydrogen.

6. The compound of claim 1, wherein A is a bicyclic moiety corresponding to formula (II) as defined in claim 1, wherein the first ring of the bicyclic moiety, which ring is linked to the remainder of the compound of general formula (I), is aromatic.

7. The compound of claim 1, wherein A is one of the following groups:

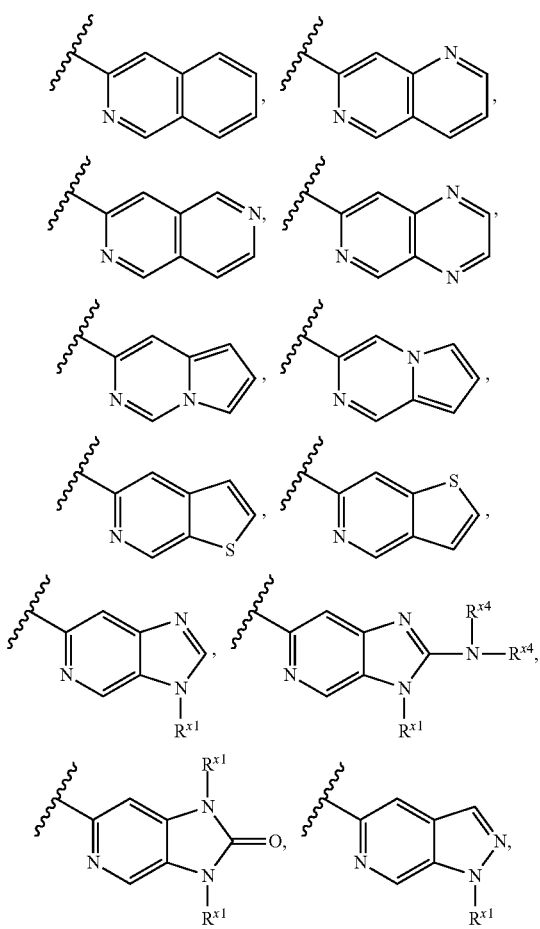

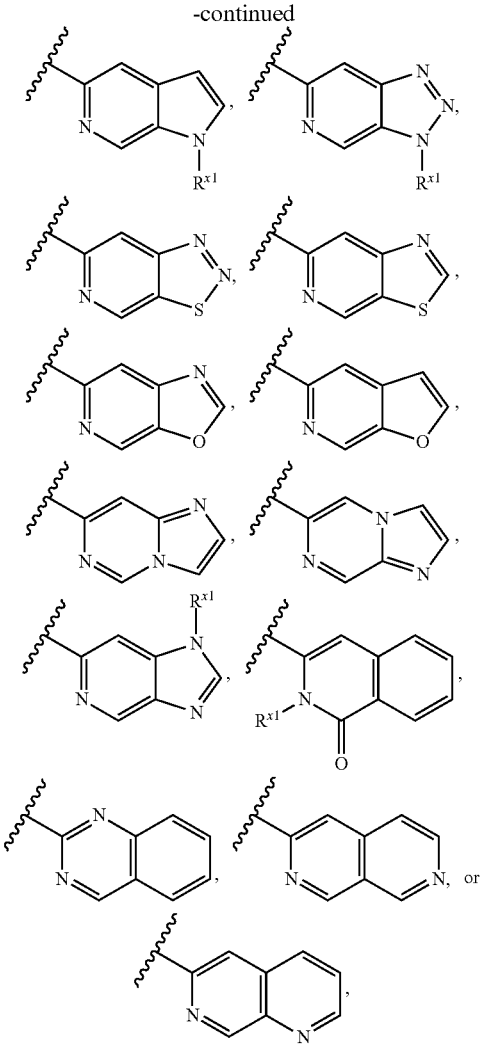

each of which may optionally be substituted on ring carbon atoms with one or more groups independently selected from C₁-C₄ alkyl, halogen, —CF₃, —CN, —OH, —O(C₁-C₄ alkyl), —NH₂, —NH(C₁-C₄ alkyl), or —N(C₁-C₄ alkyl)(C₁-C₄ alkyl) wherein the two C₁-C₄ alkyl moieties of said —N(C₁-C₄ alkyl)(C₁-C₄ alkyl) are optionally mutually linked to form a ring together with the nitrogen atom which they are attached to, wherein each $R^{x1}$ (if present) is independently selected from hydrogen, C₁-C₄ alkyl, —OH, or —O(C₁-C₄ alkyl), and further wherein each $R^{x4}$ (if present) is independently selected from hydrogen or C₁-C₄ alkyl, or the two groups $R^{x4}$ (if present) are each independently C₁-C₄ alkyl and are mutually linked to form a ring together with the nitrogen atom which they are attached to.

8. The compound of claim 1, wherein said compound is:
2-isoquinolin-3-yl-chromen-4-one oxime;
7-bromo-2-isoquinolin-3-yl-chromen-4-one oxime;
7-bromo-2-isoquinolin-3-yl-6-methyl-chromen-4-one oxime;
6-bromo-2-isoquinolin-3-yl-chromen-4-one oxime;
2-isoquinolin-3-yl-6-methyl-chromen-4-one oxime;
6-fluoro-2-isoquinolin-3-yl-chromen-4-one oxime;
6,8-difluoro-2-isoquinolin-3-yl-chromen-4-one oxime;
8-chloro-2-isoquinolin-3-yl-chromen-4-one oxime;
4-fluoro-2-isoquinolin-3-yl-chromen-4-one-(Z)-oxime;

2-isoquinolin-3-yl-6-trifluoromethoxy-chromen-4-one oxime;
2-isoquinolin-3-yl-6-trifluoromethyl-chromen-4-one oxime;
2-(7-fluoro-isoquinolin-3-yl)-chromen-4-one oxime;
2-(7-methoxy-isoquinolin-3-yl)-chromen-4-one oxime;
2-(6.7-dimethoxy-isoquinolin-3-yl)-chromen-4-one oxime;
2-(6-methyl-isoquinolin-3-yl)-chromen-4-one oxime;
2-(7-chloro-isoquinolin-3-yl)-chromen-4-one oxime;
2-(5-bromo-isoquinolin-3-yl)-chromen-4-one oxime;
2-(5-hydroxy-isoquinolin-3-yl)-chromen-4-one oxime;
2-(5-methoxy-isoquinolin-3-yl)-chromen-4-one oxime;
2-isoquinolin-3-yl-7-phenylethynyl-chromen-4-one oxime;
2-isoquinolin-3-yl-7((E)-styryl)-chromen-4-one oxime;
2-isoquinolin-3-yl-7-phenethyl-chromen-4-one oxime;
7-ethynyl-2-isoquinolin-3-yl-chromen-4-one oxime;
2-isoquinolin-3-yl-7-(pyridin-2-yl-ethynyl)-chromen-4-one oxime;
2-isoquinolin-3-yl-7-(pyridin-2-yl-ethynyl)-chromen-4-one oxime;
2-isoquinolin-3-yl-7-(pyridin-4-yl)ethynyl-chromen-4-one oxime;
7-(4-dimethylaminophenyl)ethynyl-2-isoquinolin-3-yl-chromen-4-one oxime;
2-isoquinolin-3-yl-7-(3-methoxyphenyl)ethynyl-chromen-4-one oxime;
7-(3-aminophenyl)ethynyl-2-isoquinolin-3-yl-chromen-4-one oxime;
7-(3-hydroxyphenyl)ethynyl-2-isoquinolin-3-yl-chromen-4-one oxime;
2-isoquinolin-3-yl-7-(4-methoxyphenyl)ethynyl-chromen-4-one oxime;
7-(2-chlorophenyl)ethynyl-2-isoquinolin-3-yl-chromen-4-one oxime;
7-(3-dimethylamino-prop-1-ynyl)-2-isoquinolin-3-yl-chromen-4-one oxime;
6-cyclopropyl-2-isoquinolin-3-yl-chromen-4-one oxime;
2-isoquinolin-3-yl-6-(pyrrolidin-1-yl)-chromen-4-one oxime;
2-isoquinolin-3-yl-6-(vinyl)-chromen-4-one oxime;
6-ethyl-2-isoquinolin-3-yl-chromen-4-one oxime;
6-cyano-2-isoquinolin-3-yl-chromen-4-one oxime;
6-dimethylamino-2-isoquinolin-3-yl-chromen-4-one oxime;
2-isoquinolin-3-yl-6-(morpholin-4-yl-methyl)-chromen-4-one oxime;
6-hydroxy-2-isoquinolin-3-yl-chromen-4-one oxime;
2-isoquinolin-3-yl-6-methoxy-chromen-4-one oxime;
2-isoquinolin-3-yl-6-(2-methoxy-ethoxy)-chromen-4-one oxime;
6-(2-dimethylamino-ethoxy)-2-isoquinolin-3-yl-chromen-4-one oxime;
2-isoquinolin-3-yl-6-[3-(4-methyl-piperazin-1-yl)-propylamino]-chromen-4-one oxime;
2-isoquinolin-3-yl-6-[2-(4-methyl-piperazin-1-yl)-ethoxy]-chromen-4-one oxime;
2-isoquinolin-3-yl-7-phenyl-chromen-4-one oxime;
7-(4-biphenyl)-2-isoquinolin-3-yl-chromen-4-one oxime;
2-isoquinolin-3-yl-7-[3-(4-methyl-piperazin-1-yl)-propylamino]-chromen-4-one oxime;
2-Isoquinolin-3-yl-7-{3-[2-(4-methyl-piperazin-1-yl)-ethoxy]-phenylethynyl}-chromen-4-one oxime;
2-Isoquinolin-3-yl-7-{3-methylaminophenylethynyl}-chromen-4-one oxime;
7-(4-Hydroxy-but-1-ynyl)-2-isoquinolin-3-yl-chromen-4-one oxime;
2-Isoquinolin-3-yl-7-[3-(2-methoxy-ethoxy)-phenylethynyl]-chromen-4-one oxime;
2-Isoquinolin-3-yl-7-[3-(2-methoxy-ethoxy)-prop-1-ynyl]-chromen-4-one oxime;
7-but-3-en-1-ynyl-2-Isoquinolin-3-yl-chromen-4-one oxime;
2-isoquinolin-3-yl-7-methoxy-chromen-4-one oxime;
2-isoquinolin-3-yl-7-(2-methoxy-ethoxy)-chromen-4-one oxime;
7-cyano-2-isoquinolin-3-yl-chromen-4-one oxime;
2-Isoquinolin-3-yl-7-[3-(4-methyl-piperazin-1-yl)-prop-1-ynyl]-chromen-4-one oxime;
2-(7-hydroxy-isoquinolin-3-yl)-chromen-4-one oxime;
2-[2,6]Naphthyridin-3-yl-chromen-4-one oxime;
2-[1,6]Naphthyridin-3-yl-chromen-4-one oxime;
2-Pyrrolo[1,2-c]pyrimidin-3-yl-chromen-4-one oxime;
2-(5,7-dimethyl-Pyrrolo[1,2-c]pyrimidin-3-yl)-chromen-4-one oxime;
2-(6-bromo-Pyrrolo[1,2-c]pyrimidin-3-yl)-chromen-4-one oxime;
6-bromo-2-Pyrrolo[1,2-c]pyrimidin-3-yl-chromen-4-one oxime;
6-methoxyethoxy-2-Pyrrolo[1,2-c]pyrimidin-3-yl-chromen-4-one oxime;
2-(1-Benzyl-1H-imidazo[4,5-c]pyridin-6-yl)-chromen-4-one oxime;
2-Thieno[2,3-c]pyridin-5-yl-chromen-4-one oxime;
2-Thieno[3,2-c]pyridin-6-yl-chromen-4-one oxime;
2-Isoquinolin-3-yl-3-methyl-chromen-4-one oxime;
3-{4-[(E)-Hydroxyimino]-4H-chromen-2-yl}-2H-isoquinolin-1-one;
2-Imidazo[1,2-c]pyrimidin-7-yl-chromen-4-one oxime;
2-(1H-Pyrrolo[2,3-c]pyridin-5-yl)-chromen-4-one oxime;
2-(1-Hydroxy-1H-pyrrolo[2,3-c]pyridin-5-yl)-chromen-4-one oxime;
2-(1-Methyl-1H-pyrrolo[2,3-c]pyridin-5-yl)-chromen-4-one oxime;
2-(1-Methoxy-1H-pyrrolo[2,3-c]pyridin-5-yl)-chromen-4-one oxime;
6-Hydroxy-2-pyrrolo[1,2-c]pyrimidin-3-yl-chromen-4-one oxime;
2-Thiazolo[5,4-c]pyridin-6-yl-chromen-4-one oxime;
6-(3-Methoxy-propyl)-2-pyrrolo[1,2-c]pyrimidin-3-yl-chromen-4-one oxime;
6-(3-Dimethylamino-propoxy)-2-pyrrolo[1,2-c]pyrimidin-3-yl-chromen-4-one oxime;
6-(3-Morpholin-4-yl-ethoxy)-2-pyrrolo[1,2-c]pyrimidin-3-yl-chromen-4-one oxime;
6-(2,3-Dihydroxy-propoxy)-2-pyrrolo[1,2-c]pyrimidin-3-yl-chromen-4-one oxime;
6-(2-Pyrrolidin-1-yl-ethoxy)-2-pyrrolo[1,2-c]pyrimidin-3-yl-chromen-4-one oxime;
6-(2-Piperidin-1-yl-ethoxy)-2-pyrrolo[1,2-c]pyrimidin-3-yl-chromen-4-one oxime;
6-(2-dimethylamino-ethoxy)-2-pyrrolo[1,2-c]pyrimidin-3-yl-chromen-4-one oxime;
6-(2-diethylamino-ethoxy)-2-pyrrolo[1,2-c]pyrimidin-3-yl-chromen-4-one oxime;
2-Pyrrolo[1,2-a]pyrazin-3-yl-chromen-4-one oxime;
6-[2-(2-methyl-pyrrolidin-1-yl)-ethoxy]-2-pyrrolo[1,2-c]pyrimidin-3-yl-chromen-4-one oxime;
6-[2-(4-methyl-piperazin-1-yl)-ethoxy]-2-pyrrolo[1,2-c]pyrimidin-3-yl-chromen-4-one oxime;
6-[2-(4-methyl-[1,4]diazepan-1-yl)-ethoxy]-2-pyrrolo[1,2-c]pyrimidin-3-yl-chromen-4-one oxime;

6-[2-((S)-2-hydroxymethylpyrrolidin-1-yl)-ethoxy]-2-pyrrolo[1,2-c]pyrimidin-3-yl-chromen-4-one oxime;
6-[2-((S)-2-methoxymethylpyrrolidin-1-yl)-ethoxy]-2-pyrrolo[1,2-c]pyrimidin-3-yl-chromen-4-one oxime;
6-[2-((R)-2-methoxymethylpyrrolidin-1-yl)-ethoxy]-2-pyrrolo[1,2-c]pyrimidin-3-yl-chromen-4-one oxime;
6-[2-(3-hydroxy-pyrrolidin-1-yl)-ethoxy]-2-pyrrolo[1,2-c]pyrimidin-3-yl-chromen-4-one oxime;
6-[2-(4-dimethylamino-piperidin-1-yl)-ethoxy]-2-pyrrolo[1,2-c]pyrimidin-3-yl-chromen-4-one oxime;
6-(2-cyclopentylamino-ethoxy)-2-pyrrolo[1,2-c]pyrimidin-3-yl-chromen-4-one oxime;
6-(3-morpholin-4-yl-propoxy)-2-pyrrolo[1,2-c]pyrimidin-3-yl-chromen-4-one oxime;
6-(4-morpholin-4-yl-butyl)-2-pyrrolo[1,2-c]pyrimidin-3-yl-chromen-4-one oxime;
6-(4,4-difluoro-piperidin-1-yl)-2-pyrrolo[1,2-c]pyrimidin-3-yl-chromen-4-one oxime;
6-{2-[bis-(2-methoxy-ethyl)-amino]-ethoxy}-2-pyrrolo[1,2-c]pyrimidin-3-yl-chromen-4-one oxime;
6-(2-Imidazol-1-yl-ethoxy)-2-pyrrolo[1,2-c]pyrimidin-3-yl-chromen-4-one oxime;
6-(3-morpholin-4-yl-propyl)-2-pyrrolo[1,2-c]pyrimidin-3-yl-chromen-4-one oxime;
6-((Z)-3-Morpholin-4-yl-propenyl))-2-pyrrolo[1,2-c]pyrimidin-3-yl-chromen-4-one oxime;
6-[2-(3-methoxy-piperidin-1-yl)-ethoxy]-2-pyrrolo[1,2-c]pyrimidin-3-yl-chromen-4-one oxime;
6-[2-(4-fluoro-phenyl)-ethoxy]-2-pyrrolo[1,2-c]pyrimidin-3-yl-chromen-4-one oxime;
2-quinazolin-2-yl-chromen-4-one oxime;
6-[(1S,4S)-2-(2-oxa-5-aza-bicyclo[2.2.1]hept-5-yl)-ethoxy]-2-pyrrolo[1,2-c]pyrimidin-3-yl-chromen-4-one oxime;
6-[2-(cis-2,6-dimethyl-morpholin-4-yl)-ethoxy]-2-pyrrolo[1,2-c]pyrimidin-3-yl-chromen-4-one oxime;
2-pyrrolo[1,2-c]pyrimidin-3-yl-6-[2-(4-trifluoromethyl-piperidin-1-yl)-ethoxy]-chromen-4-one oxime;
6-[2-(3,3-difluoro-piperidin-1-yl)-ethoxy]-2-pyrrolo[1,2-c]pyrimidin-3-yl-chromen-4-one oxime;
4-(hydroxyimino)-2-pyrrolo[1,2-c]pyrimidin-3-yl-4H-chromene-6-carboxylic acid (2-morpholin-4-yl-ethyl)-amide;
6-(2-[1,4]bipiperidinyl-1'-yl-ethoxy)-2-pyrrolo[1,2-c]pyrimidin-3-yl-chromen-4-one oxime;
6-(2-[1,4]oxazepan-4-yl-ethoxy)-2-pyrrolo[1,2-c]pyrimidin-3-yl-chromen-4-one oxime;
6-[2-(4-pyrrolidin-1-yl-piperidin-1-yl)-ethoxy]-2-pyrrolo[1,2-c]pyrimidin-3-yl-chromen-4-one oxime;
6-[2-(3,3-difluoro-pyrrolidin-1-yl)-ethoxy]-2-pyrrolo[1,2-c]pyrimidin-3-yl-chromen-4-one oxime;
7-[3-(3-dimethylamino-propoxy)-phenylethynyl]-2-pyrrolo[1,2-c]pyrimidin-3-yl-chromen-4-one oxime;
6-[2-(4-ethyl-piperazin-1-yl)-ethoxy]-2-pyrrolo[1,2-c]pyrimidin-3-yl-chromen-4-one oxime;
6-(2-amino-ethoxy)-2-pyrrolo[1,2-c]pyrimidin-3-yl-chromen-4-one oxime;
6-(2-Morpholin-4-yl-ethoxy)-2-(8aH-pyrrolo[1,2-a]pyrazin-3-yl)-chromen-4-one oxime;
6-[2-(4,4-Difluoro-piperidin-1-yl)-ethoxy]-2-pyrrolo[1,2-a]pyrazin-3-yl-chromen-4-one oxime;
6-(2-Imidazol-1-yl-ethoxy)-2-pyrrolo[1,2-a]pyrazin-3-yl-chromen-4-one oxime;
6-[2-(4-Fluoro-phenyl)-ethoxy]-2-pyrrolo[1,2-a]pyrazin-3-yl-chromen-4-one oxime;
6-(2-Morpholin-4-yl-ethoxy)-2-thieno[3,2-c]pyridin-6-yl-chromen-4-one oxime;
6-[2-(4,4-Difluoro-piperidin-1-yl)-ethoxy]-2-thieno[3,2-c]pyridin-6-yl-chromen-4-one oxime;
6-(2-imidazol-1-yl-ethoxy)-2-thieno[3,2-c]pyridin-6-yl-chromen-4-one oxime;
6-[2-(4-Fluoro-phenyl)-ethoxy]-2-thieno[3,2-c]pyridin-6-yl-chromen-4-one oxime;
6-[2-(3,3-Difluoro-piperidin-1-yl)-ethoxy]-2-thieno[3,2-c]pyridin-6-yl-chromen-4-one oxime;
6-[2-(2,6-Dimethyl-morpholin-4-yl)-ethoxy]-2-thieno[3,2-c]pyridin-6-yl-chromen-4-one oxime;
6-[2-(3,3-Difluoro-pyrrolidin-1-yl)-ethoxy]-2-thieno[3,2-c]pyridin-6-yl-chromen-4-one oxime;
6-(3-Pyridin-4-yl-propoxy)-2-thieno[3,2-c]pyridin-6-yl-chromen-4-one oxime;
6-(3-Pyridin-3-yl-propoxy)-2-thieno[3,2-c]pyridin-6-yl-chromen-4-one oxime;
6-(2-Pyridin-4-yl-ethoxy)-2-pyrrolo[1,2-c]pyrimidin-3-yl-chromen-4-one oxime;
2-Pyrrolo[1,2-c]pyrimidin-3-yl-6-[2-(4-trifluoromethyl-phenyl)-ethoxy]-chromen-4-one, oxime;
6-[2-(3-Fluoro-phenyl)-ethoxy]-2-pyrrolo[1,2-c]pyrimidin-3-yl-chromen-4-one, oxime;
5-Methoxy-2-pyrrolo[1,2-c]pyrimidin-3-yl-chromen-4-one oxime;
6-[2-(4-Chloro-phenyl)-ethoxy]-2-pyrrolo[1,2-c]pyrimidin-3-yl-chromen-4-one oxime;
2-Pyrrolo[1,2-c]pyrimidin-3-yl-6-[2-(3-trifluoromethyl-phenyl)-ethoxy]-chromen-4-one oxime;
7-(2-Morpholin-4-yl-ethoxy)-2-pyrrolo[1,2-c]pyrimidin-3-yl-chromen-4-one oxime;
7-(3-Morpholin-4-yl-propoxy)-2-pyrrolo[1,2-c]pyrimidin-3-yl-chromen-4-one oxime;
6-[(4-Fluoro-benzylamino)-methyl]-2-pyrrolo[1,2-c]pyrimidin-3-yl-chromen-4-one oxime;
6-{[2-(4-Fluoro-phenyl)-ethylamino]-methyl}-2-pyrrolo[1,2-c]pyrimidin-3-yl-chromen-4-one oxime;
6-Phenethyloxy-2-pyrrolo[1,2-c]pyrimidin-3-yl-chromen-4-one oxime;
6-[2-(Pyridin-4-yloxy)-ethoxy]-2-pyrrolo[1,2-c]pyrimidin-3-yl-chromen-4-one oxime;
6-[2-(Pyridin-3-yloxy)-ethoxy]-2-pyrrolo[1,2-c]pyrimidin-3-yl-chromen-4-one oxime;
6-[3-(Pyridin-3-yloxy)-propoxy]-2-pyrrolo[1,2-c]pyrimidin-3-yl-chromen-4-one oxime;
N-(4-Fluoro-phenyl)-2-{4-hydroxyimino-2-pyrrolo[1,2-c]pyrimidin-3-yl-4H-chromen-6-yloxy}-acetamide;
N-(4-Fluoro-phenyl)-2-{4-hydroxyimino-2-pyrrolo[1,2-c]pyrimidin-3-yl-4H-chromen-6-yloxy}-N-methyl-acetamide;
N-(5-Fluoro-pyridin-2-yl)-2-{4-hydroxyimino-2-pyrrolo[1,2-c]pyrimidin-3-yl-4H-chromen-6-yloxy}-acetamide;
2-Pyrrolo[1,2-c]pyrimidin-3-yl-5-trifluoromethyl-chromen-4-one oxime;
2-(7-tert-Butyl-pyrrolo[1,2-c]pyrimidin-3-yl)-6-(2-morpholin-4-yl-ethoxy)-chromen-4-one oxime;
7-(2-Morpholin-4-yl-ethoxy)-2-thieno[2,3-c]pyridin-5-yl-chromen-4-one oxime;
5-(2-Morpholin-4-yl-ethoxy)-2-pyrrolo[1,2-c]pyrimidin-3-yl-chromen-4-one oxime;
5-(3-Morpholin-4-yl-propoxy)-2-pyrrolo[1,2-c]pyrimidin-3-yl-chromen-4-one oxime;
6-(2-Morpholin-4-yl-ethoxy)-2-thieno[2,3-c]pyridin-5-yl-chromen-4-one oxime;
6-(3-Pyridin-4-yl-propoxy)-2-pyrrolo[1,2-c]pyrimidin-3-yl-chromen-4-one oxime;

6-(2-Phenoxy-ethoxy)-2-pyrrolo[1,2-c]pyrimidin-3-yl-chromen-4-one oxime;
6-[3-(4-Fluoro-phenoxy)-propoxy]-2-pyrrolo[1,2-c]pyrimidin-3-yl-chromen-4-one oxime;
6-(3-Phenoxy-propoxy)-2-pyrrolo[1,2-c]pyrimidin-3-yl-chromen-4-one oxime;
6-[3-(3-Fluoro-phenoxy)-propoxy]-2-pyrrolo[1,2-c]pyrimidin-3-yl-chromen-4-one oxime;
6-[3-(3,4-Difluoro-phenoxy)-propoxy]-2-pyrrolo[1,2-c]pyrimidin-3-yl-chromen-4-one oxime;
6-(2-[1,4]Oxazepan-4-yl-ethoxy)-2-thieno[3,2-c]pyridin-6-yl-chromen-4-one oxime;
6-[2-(3,4-Dihydro-1H-isoquinolin-2-yl)-ethoxy]-2-thieno[3,2-c]pyridin-6-yl-chromen-4-one oxime;
6-[2-(4-fluoro-piperidin-1-yl)-ethoxy]-2-thieno[3,2-c]pyridin-6-yl-chromen-4-one oxime;
6-[2-(1,1-Dioxo-1-thiomorpholin-4-yl)-ethoxy]-2-thieno[3,2-c]pyridin-6-yl-chromen-4-one oxime;
6-(1-Pyrimidin-2-yl-piperidin-4-yloxy)-2-thieno[3,2-c]pyridin-6-yl-chromen-4-one oxime; or
6-(3,4,5,6-Tetrahydro-2H-[1,2]bipyridinyl-4-yloxy)-2-thieno[3,2-c]pyridin-6-yl-chromen-4-one oxime; or
a pharmaceutically acceptable salt or solvate thereof.

9. The compound of claim 1, wherein three of $R^1$ to $R^4$ are hydrogen.

10. The compound of claim 9, $R^5$ is selected from hydrogen, $C_1$-$C_4$ alkyl, —O($C_1$-$C_4$ alkyl), —NH($C_1$-$C_4$ alkyl), or —N($C_1$-$C_4$ alkyl)($C_1$-$C_4$ alkyl), wherein the two $C_1$-$C_4$ alkyl moieties of said —N($C_1$-$C_4$ alkyl)($C_1$-$C_4$ alkyl) are optionally mutually linked to form a ring together with the nitrogen atom which they are attached to.

11. A pharmaceutical composition comprising the compound of claim 1 and a pharmaceutically acceptable excipient.

12. A method of treating a symptom of Parkinson's Disease or an anxiety disorder, the method comprising of the administration of the compound of claim 1 to a subject in need of such treatment.

13. A method of modulating a mGluR4 receptor, the method comprising the administration of the compound of claim 1 to a subject in need of such modulation.

14. The method of claim 13, wherein said condition which can be modulated by a mGluR4 receptor, is selected from: Parkinson's Disease, multiple sclerosis, anxiety disorders, schizophrenia, and diabetes.

15. The method of claim 14, wherein said anxiety disorders are selected from: panic disorders, phobias, obsessive-compulsive disorders, stress disorders, and generalized anxiety disorders.

16. The method of claim 12, whereby said compound is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route.

17. The method of claim 12, wherein said subject is a human.

\* \* \* \* \*